United States Patent
Patel et al.

(10) Patent No.: US 11,865,134 B2
(45) Date of Patent: Jan. 9, 2024

(54) TREATMENT OF INFLAMMATION WITH GLUCOCORTICOIDS AND ANGIOPOIETIN-LIKE 7 (ANGPTL7) INHIBITORS

(71) Applicant: Regeneron Pharmaceuticals, Inc., Tarrytown, NY (US)

(72) Inventors: Gaurang Patel, Tarrytown, NY (US); Ying Hu, Tarrytown, NY (US); Kavita Praveen, Tarrytown, NY (US); Giovanni Coppola, Tarrytown, NY (US); Goncalo Abecasis, Tarrytown, NY (US); Aris Baras, Tarrytown, NY (US); Carmelo Romano, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/678,792

(22) Filed: Feb. 23, 2022

(65) Prior Publication Data
US 2022/0370489 A1 Nov. 24, 2022

Related U.S. Application Data

(60) Provisional application No. 63/287,187, filed on Dec. 8, 2021, provisional application No. 63/251,175, filed on Oct. 1, 2021, provisional application No. 63/171,218, filed on Apr. 6, 2021, provisional application No. 63/154,576, filed on Feb. 26, 2021.

(51) Int. Cl.
| | |
|---|---|
| C07H 21/02 | (2006.01) |
| C07H 21/04 | (2006.01) |
| A61K 31/713 | (2006.01) |
| A61P 27/06 | (2006.01) |
| A61K 45/06 | (2006.01) |
| C12Q 1/6883 | (2018.01) |

(52) U.S. Cl.
CPC ............ *A61K 31/713* (2013.01); *A61K 45/06* (2013.01); *A61P 27/06* (2018.01); *C12Q 1/6883* (2013.01); *C12Q 2600/156* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 8,637,640 B2 | 1/2014 | Siekmann et al. |
| 8,642,737 B2 | 2/2014 | Siekmann et al. |
| 8,785,139 B2 | 7/2014 | Weber et al. |
| 8,809,501 B2 | 8/2014 | Siekmann et al. |
| 8,945,897 B2 | 2/2015 | Siekmann et al. |
| 8,951,982 B2 | 2/2015 | Jimenez et al. |
| 9,205,064 B2 | 12/2015 | Narain et al. |
| 9,238,837 B2 | 1/2016 | Schmidt-Ott et al. |
| 9,364,542 B2 | 6/2016 | Chang |
| 9,447,431 B2 | 9/2016 | Thess et al. |
| 9,492,555 B2 | 11/2016 | Haider et al. |
| 9,551,034 B2 | 1/2017 | Cowens et al. |
| 9,731,024 B2 | 8/2017 | Siekmann et al. |
| 9,795,683 B2 | 10/2017 | Jain et al. |
| 9,896,731 B2 | 2/2018 | Narain et al. |
| 10,111,968 B2 | 10/2018 | Thess et al. |
| 10,350,301 B2 | 7/2019 | Siekmann et al. |
| 10,351,915 B2 | 7/2019 | Narain et al. |
| 10,370,643 B2 | 8/2019 | Bernstein et al. |
| 10,414,793 B2 | 9/2019 | Haider et al. |
| 10,519,504 B2 | 12/2019 | Narain et al. |
| 2010/0028875 A1 | 2/2010 | Rhyu et al. |
| 2011/0020312 A1 | 1/2011 | Narain et al. |
| 2011/0027247 A1 | 2/2011 | Narain et al. |
| 2011/0123986 A1 | 5/2011 | Narain et al. |
| 2012/0010230 A1 | 1/2012 | MacDougall et al. |
| 2013/0022983 A1 | 1/2013 | Grifantini et al. |
| 2013/0310546 A1 | 11/2013 | Ray et al. |
| 2014/0107320 A1 | 4/2014 | Haider et al. |
| 2014/0187607 A1 | 7/2014 | Russell et al. |
| 2015/0023940 A1 | 1/2015 | Narain et al. |
| 2015/0025012 A1 | 1/2015 | MacDougall et al. |
| 2015/0174203 A1 | 6/2015 | Chen et al. |
| 2015/0299798 A1 | 10/2015 | de Reynies et al. |
| 2016/0120994 A1 | 5/2016 | Siekmann et al. |
| 2016/0145693 A1 | 5/2016 | Narain et al. |
| 2016/0271253 A1 | 9/2016 | Chang |
| 2017/0121780 A1 | 5/2017 | Cowens et al. |

(Continued)

FOREIGN PATENT DOCUMENTS

| | | |
|---|---|---|
| WO | 2012016131 | 2/2012 |
| WO | 2013147330 | 10/2013 |

(Continued)

OTHER PUBLICATIONS

Elbashir et al. (The EMBO Journal, vol. 20, No. 23, pp. 6877-6888, 2001).*
Non-Final Office Action dated Oct. 6, 2022 in related U.S. Appl. No. 17/031,523.
International Search Report and Written Opinion dated Jul. 14, 2022 for International Patent Application No. PCT/US2022/017533.
Karaki et al., "Antisense Oligonucleolides, A Novel Developing Targeting Therapy", Antisense Therapy, 2019, pp. 1-18.
Harborth et al., "Identification of essential genes in cultured mammalian cells using small interfering RNAs", J Cell Sci, 2001, 114(Pt 24), pp. 4557-4565.
Holen T et al., "Positional effects of short interfering RNAs targeting the human coagulation trigger Tissue Factor", Nucleic Acids Res, 2002, 30(8), pp. 1757-1766.

(Continued)

*Primary Examiner* — Amy H Bowman
(74) *Attorney, Agent, or Firm* — Armstrong Teasdale LLP

(57) ABSTRACT

The present disclosure provides methods of treating subjects having inflammation with an Angiopoietin-Like 7 (ANGPTL7) inhibitor and a glucocorticoid, methods of decreasing glucocorticoid-induced ophthalmic conditions in subjects, and methods of identifying subjects having an increased risk of developing glucocorticoid-induced ophthalmic conditions.

3 Claims, 4 Drawing Sheets
Specification includes a Sequence Listing.

(56) References Cited

U.S. PATENT DOCUMENTS

| | | |
|---|---|---|
| 2017/0137879 A1 | 5/2017 | Narain et al. |
| 2017/0368193 A1 | 12/2017 | Siekmann et al. |
| 2018/0177894 A1 | 6/2018 | Thess et al. |
| 2018/0185517 A1 | 7/2018 | Thess et al. |
| 2018/0200380 A1 | 7/2018 | Jain et al. |
| 2018/0237771 A1 | 8/2018 | Kim et al. |
| 2018/0334721 A1 | 11/2018 | Narain et al. |
| 2018/0340153 A1 | 11/2018 | Bean et al. |
| 2018/0340154 A1 | 11/2018 | Bean et al. |
| 2019/0010554 A1 | 1/2019 | Narain et al. |
| 2019/0091335 A1 | 3/2019 | Chang |
| 2019/0177391 A1 | 6/2019 | Chen et al. |
| 2019/0264173 A1 | 8/2019 | Studer et al. |
| 2019/0203186 A1 | 9/2019 | Bean et al. |
| 2019/0314516 A1 | 10/2019 | Siekmann et al. |
| 2019/0322989 A1 | 10/2019 | Bean et al. |
| 2019/0330593 A1 | 10/2019 | Bernstein et al. |
| 2019/0331666 A1 | 10/2019 | Studer et al. |
| 2020/0016202 A1 | 1/2020 | Kuchroo et al. |
| 2020/0017543 A1 | 1/2020 | Haider et al. |
| 2020/0399640 A1 | 12/2020 | Gottesman et al. |

FOREIGN PATENT DOCUMENTS

| | | |
|---|---|---|
| WO | 2013173543 | 11/2013 |
| WO | 2013173557 | 11/2013 |
| WO | 2014167529 | 10/2014 |
| WO | 2015132303 | 9/2015 |
| WO | 2018174861 | 9/2018 |
| WO | 2018175630 | 9/2018 |
| WO | 2018218299 | 12/2018 |
| WO | 2019140380 | 7/2019 |
| WO | 2019144052 | 7/2019 |
| WO | 2019197844 | 10/2019 |
| WO | 2020154268 | 7/2020 |
| WO | 2020242896 | 12/2020 |
| WO | 2022072356 | 4/2022 |

OTHER PUBLICATIONS

Reynolds et al., "Rational siRNA design for RNA interference", Nat Biotechnol, 2004, 22(3), pp. 326-330.

Ronchetti et al., "Defining the role of glucocorticoids in inflammation", Clinical Science, 2018, 132(14), pp. 1529-1543.

Baudouin et al., "Inflammation in Glaucoma: From the back to the front of the eye and beyond", Progress in Retinal and Eye Research, 2020, 83, pp. 1-26.

Qian et al., "Angiopoietin-Like Protein 7 Promotes an Inflammatory Phenotype in RAW264.7 Macrophages Through the P38 MAPK Signaling Pathway", Inflammation, 2016, 39(3), pp. 974-985.

Roberti et al., "Steroid-induced glaucoma: Epidemiology, pathophysiology, and clinical management", Survey of Ophthalmology, 2020, 65(4), pp. 458-473.

Fukuda et al., "Expression Profiling of Genes in Rheumatoid Fibroblast-like Synoviocytes Regulated by Fas Ligand Using cDNA Microarray Analysis", Arthritis & Rheumatology, 2019, 71(suppl-10), pp. 1.

Notice of Allowance dated Jul. 25, 2022 in related U.S. Appl. No. 17/318,023.

Non-final Office Action dated Aug. 25, 2022 in related U.S. Appl. No. 16/748,006.

Tanigawa et al., "Rare protein-altering variants in ANGPTL7 lower intraocular pressure and protect against glaucoma", PLoS Genetics, 2020, 16(5), e1008682, pp. 1-20.

Final Office Action dated Apr. 6, 2022 in related U.S. Appl. No. 17/318,023.

Toyono et al., "Angiopoietin-Like 7 Is an Anti-Angiogenic Protein Required to Prevent Vascularization of the Cornea", PLoS One, 2015, 10(1), pp. 1-13.

Weinreb et al., "Acute Effects of Dexamethasone on Intraocular Pressure in Glaucoma", Investigative Ophthalmology and Visual Science, 1985, 26, pp. 170-175.

Non-Final Office Action dated Dec. 28, 2021 in related U.S. Appl. No. 17/318,023.

Borras, "Gene therapy strategies in glaucoma and application for steroid-induced hypertension", Saudi Journal of Opthalmology, 2011, 25(4), pp. 353-362.

Buie et al., "Angiopoietin-like 7 (ANGPTL7) Modulates DEX Induction and Fibronectin (FN1) Fibrils Formation in the Human Trabecular Meshwork (HTM)—ARVO Annual Meeting Abstract", Investigative Ophthalmology & Visual Science, 2011, 52(14), pp. 4622.

Charlson et al., "The primary open-angle african american glaucoma genetics study: baseline demographics", Ophthalmology, 2015, 122, pp. 711-720.

Comes et al., "Evidence for a role of angiopoietin-like 7 (ANGPTL7) in extracellular matrix formation of the human trabecular meshwork: implications for glaucoma: ANGPTL7 in the human trabecular meshwork", Genes to Cells, 2010, 16(2), pp. 243-259.

Dewey et al., "Distribution and clinical impact of functional variants in 50,726 whole-exome sequences from the DiscovEHR Study", Science, 2016, 354(6319), pp. 1-13.

Deboever et al., "Bayesian model comparison for rare variant association studies for multiple phenotypes", BioRxiv, 2018, https://www.biorxiv.org/content/10.1101/257162v5.full.pdf.

Doench et al., "Optimized sgRNA design to maximize activity and minimize off-target effects of CRISPR-Cas9", Nature Biotechnology, 2016, 34(2), pp. 184-191.

Jaru-Ampornpan et al., "Screening Angiopoietin-Like 7 in Primary Congenital Glaucoma Patients—ARVO Annual Meeting Abstract", Investigative Ophthalmology & Visual Science, 2010, 51(13), pp. 2167.

Kuchtey et al., "Angiopoietin-like 7 secretion is induced by glaucoma stimuli and its concentration is elevated in glaucomatous aqueous humor", Investigative Ophthalmology & Visual Science, 2008, 49(8), pp. 3438-3448.

Rozsa et al., "Gene expression profile of human trabecular meshwork cells in response to long-term dexamethasone exposure", Molecular Vision, 2006, 12, pp. 125-141.

Tanigawa et al., "Rare protein-altering variants in ANGPTL7 lower intraocular pressure and protect against glaucoma", BioRxiv, 2019, https://www.biorxiv.org/content/10.1101/677443v2.full.pdf.

Usui et al., "To Protect Corneal Transparency against Diseases", Journal of Japanese Ophthalmological Society, 2016, 120, pp. 246-263.

Van Hout et al., "Whole exome sequencing and characterization of coding variation in 49,960 individuals in the UK Biobank", BioRxiv, 2019, doi: https://doi.org/10.1101/572347.

Willoughby et al., "Mutational Screening Of The Angiopoietin-like 7 Gene In High-tension Primary Open Angle Glaucoma", Investigative Ophthalmology & Visual Science, 2012, 53, pp. 4504.

Xiao et al., "Loss of Angiopoietin-like 7 diminishes the regeneration capacity of hematopoietic stem and progenitor cells", Journal of Hematology & Oncology, 2015, 8(1), pp. 7.

International Search Report and Written Opinion dated Aug. 11, 2020 for International Patent Application No. PCT/US2020/014373.

Notice of Allowance dated May 10, 2023 in related U.S. Appl. No. 16/748,006.

Advisory Action dated May 30, 2023 in related U.S. Appl. No. 17/031,523.

Ozcan et al., "Preclinical and clinical development of siRNA-based therapeutics", Adv Drug Deliv, 2015, 87, pp. 108-119.

Chan et al., "The complexity of antisense transcription revealed by the study of developing male germ cells", Genomics, 2006, 87, pp. 681-692.

Final Office Action dated Mar. 9, 2023 in related U.S. Appl. No. 16/748,006.

Final Office Action dated Mar. 17, 2023 in related U.S. Appl. No. 17/031,523.

Notice of Allowance dated Aug. 1, 2023 in related U.S. Appl. No. 17/031,523.

\* cited by examiner

TREATMENT OF INFLAMMATION WITH GLUCOCORTICOIDS AND ANGIOPOIETIN-LIKE 7 (ANGPTL7) INHIBITORS

REFERENCE TO SEQUENCE LISTING

This application includes a Sequence Listing submitted electronically as a text file named 18923806701SEQ, created on Feb. 22, 2022, with a size of 111 kilobytes. The Sequence Listing is incorporated herein by reference.

FIELD

The present disclosure relates generally to the treatment of subjects having inflammation with an Angiopoietin-Like 7 (ANGPTL7) inhibitor and a glucocorticoid, methods of decreasing glucocorticoid-induced ophthalmic conditions in subjects, and methods of identifying subjects having an increased risk of developing glucocorticoid-induced ophthalmic conditions.

BACKGROUND

Glucocorticoids (GCs) are one of the most commonly prescribed medications worldwide for the treatment of a plethora of diseases and conditions. Because of their broad-spectrum anti-inflammatory and immunosuppressive properties, the worldwide market for GC use is estimated to be greater than $10 billion per year. Approximately 1.2% of the United States population and 0.85% of the United Kingdom population are prescribed therapeutic GCs every year. GCs also remain the mainstay of treatment for a variety of ocular inflammatory diseases involving almost all tissues of the eye, such as eyelids, conjunctiva, cornea, sclera, uvea, retina, and optic nerve. The routes of GC administration in treatment of these disorders can be topical ocular, oral, systemic, intravitreal injection, implants, and periocular injections (including, for example, subconjunctival, sub-tenon, retrobulbar, and peribulbar). Prolonged GC therapy, however, can be associated with serious, unwanted GC-induced ophthalmic conditions, including development of posterior subcapsular cataracts, the development of GC-induced ocular hypertension (GC-OHT), and iatrogenic open-angle glaucoma. About 40% of individuals exposed to long-term steroids develop steroid-induced ocular hypertension and this risk can increase to about 90% in individuals who already have glaucoma. Thus, decreasing or preventing GC-induced ophthalmic conditions is desirable.

SUMMARY

The present disclosure provides methods of treating a subject undergoing treatment with a steroid, the methods comprising administering an ANGPTL7 inhibitor to the subject.

The present disclosure provides methods of treating a subject having inflammation, the methods comprising administering an ANGPTL7 inhibitor and a glucocorticoid to the subject.

The present disclosure also provides methods of treating a subject having rheumatoid arthritis, the methods comprising administering an ANGPTL7 inhibitor and a glucocorticoid to the subject.

The present disclosure also provides methods of treating a subject having Grave's disease, the methods comprising administering an ANGPTL7 inhibitor and a glucocorticoid to the subject.

The present disclosure also provides methods of treating a subject having ophthalmic inflammation, the methods comprising administering an ANGPTL7 inhibitor and a glucocorticoid to the subject.

The present disclosure provides methods of decreasing a steroid-induced ophthalmic condition in a subject treated with a steroid, the methods comprising administering an ANGPTL7 inhibitor to the subject.

The present disclosure also provides methods of decreasing a glucocorticoid-induced ophthalmic condition in a subject treated with a glucocorticoid, the methods comprising administering an ANGPTL7 inhibitor to the subject.

The present disclosure provides methods of treating a subject having inflammation and undergoing steroid treatment, the methods comprising administering an ANGPTL7 inhibitor to the subject.

The present disclosure also provides methods of treating a subject having inflammation and undergoing glucocorticoid treatment, the methods comprising administering an ANGPTL7 inhibitor to the subject.

The present disclosure also provides methods of treating a subject having rheumatoid arthritis and undergoing glucocorticoid treatment, the methods comprising administering an ANGPTL7 inhibitor to the subject.

The present disclosure also provides methods of treating a subject having Grave's disease and undergoing glucocorticoid treatment, the methods comprising administering an ANGPTL7 inhibitor to the subject.

The present disclosure also provides methods of treating a subject having ophthalmic inflammation and undergoing glucocorticoid treatment, the methods comprising administering an ANGPTL7 inhibitor to the subject.

The present disclosure also provides methods of treating a subject undergoing glucocorticoid treatment, wherein the subject is suffering from inflammation, the methods comprising: determining whether the subject has an ANGPTL7 predicted loss-of-function variant nucleic acid molecule encoding an ANGPTL7 polypeptide by: obtaining or having obtained a biological sample from the subject; and performing or having performed a sequence analysis on the biological sample to determine if the subject has a genotype comprising the ANGPTL7 predicted loss-of-function variant nucleic acid molecule; and administering or continuing to administer to a subject that is ANGPTL7 reference the glucocorticoid in a standard dosage amount, and administering an ANGPTL7 inhibitor to the subject; or administering or continuing to administer to a subject that is heterozygous for the ANGPTL7 predicted loss-of-function variant the glucocorticoid in an amount that is the same as or higher than a standard dosage amount, and administering an ANGPTL7 inhibitor to the subject; or administering or continuing to administer to a subject that is homozygous for the ANGPTL7 predicted loss-of-function variant the glucocorticoid in an amount that is the same as or higher than a standard dosage amount; wherein the presence of a genotype having the ANGPTL7 predicted loss-of-function variant nucleic acid molecule encoding the ANGPTL7 polypeptide indicates the subject has a decreased risk of developing a glucocorticoid-induced ophthalmic condition.

The present disclosure also provides methods of identifying a subject undergoing glucocorticoid treatment having an increased risk for developing a glucocorticoid-induced ophthalmic condition, the method comprising: determining or having determined the presence or absence of an ANGPTL7 predicted loss-of-function variant nucleic acid molecule encoding an ANGPTL7 polypeptide in a biological sample obtained from the subject; wherein: when the subject is ANGPTL7 reference, then the subject has an increased risk for developing the glucocorticoid-induced ophthalmic condition; and when the subject is heterozygous or homozygous for an ANGPTL7 predicted loss-of-function variant, then the subject does not have an increased risk for developing the glucocorticoid-induced ophthalmic condition.

The present disclosure also provides combinations of a glucocorticoid and an ANGPTL7 inhibitor for use in the treatment of inflammation in a subject identified as having: a genomic nucleic acid molecule having a nucleotide sequence encoding an ANGPTL7 polypeptide, wherein the nucleotide sequence comprises: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof; an mRNA molecule having a nucleotide sequence encoding an ANGPTL7 polypeptide, wherein the nucleotide sequence comprises: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof; or a cDNA molecule having a nucleotide sequence encoding an ANGPTL7 polypeptide, wherein the nucleotide sequence comprises: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof.

The present disclosure also provides combinations of a glucocorticoid and an ANGPTL7 inhibitor for use in the preparation of a medicament for treating inflammation in a subject identified as having: a genomic nucleic acid molecule having a nucleotide sequence encoding an ANGPTL7 polypeptide, wherein the nucleotide sequence comprises: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof; an mRNA molecule having a nucleotide sequence encoding an ANGPTL7 polypeptide, wherein the nucleotide sequence comprises: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof; or a cDNA molecule having a nucleotide sequence encoding an ANGPTL7 polypeptide, wherein the nucleotide sequence comprises: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof.

The present disclosure also provides ANGPTL7 inhibitors for use in decreasing or preventing a glucocorticoid-induced ophthalmic condition in a subject undergoing glucocorticoid treatment, wherein the subject is identified as being: a) ANGPTL7 reference for an ANGPTL7 genomic nucleic acid molecule, an ANGPTL7 mRNA molecule, or an ANGPTL7 cDNA molecule; or b) heterozygous for: i) a genomic nucleic acid molecule having a nucleotide sequence encoding an ANGPTL7 polypeptide, wherein the nucleotide sequence comprises: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof; ii) an mRNA molecule having a nucleotide sequence encoding an ANGPTL7 polypeptide, wherein the nucleotide sequence comprises: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof; or iii) a cDNA molecule having a nucleotide sequence encoding an ANGPTL7 polypeptide, wherein the nucleotide sequence comprises: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof.

The present disclosure also provides ANGPTL7 inhibitors for use in the preparation of a medicament for decreasing or preventing a glucocorticoid-induced ophthalmic condition in a subject undergoing glucocorticoid treatment, wherein the subject is identified as being: a) ANGPTL7 reference for an ANGPTL7 genomic nucleic acid molecule, an ANGPTL7 mRNA molecule, or an ANGPTL7 cDNA molecule; or b) heterozygous for: i) a genomic nucleic acid molecule having a nucleotide sequence encoding an ANGPTL7 polypeptide, wherein the nucleotide sequence comprises: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof; ii) an mRNA molecule having a nucleotide sequence encoding an ANGPTL7 polypeptide, wherein the nucleotide sequence comprises: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof; or iii) a cDNA molecule having a nucleotide sequence encoding an ANGPTL7 polypeptide, wherein the nucleotide sequence comprises: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof.

BRIEF DESCRIPTION OF THE DRAWINGS

The accompanying figures, which are incorporated in and constitute a part of this specification, illustrate several features of the present disclosure.

DESCRIPTION

Figure 1:
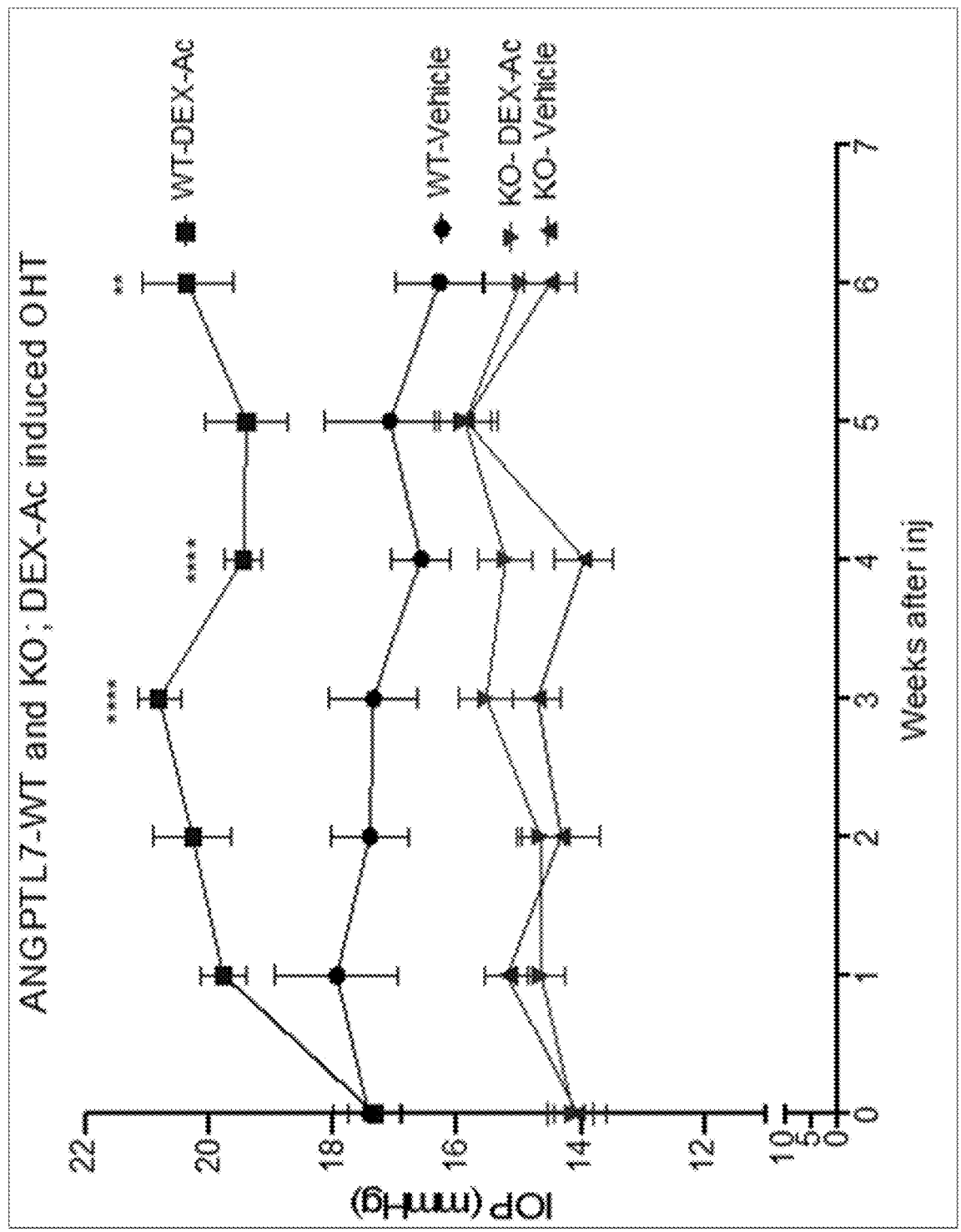
FIG. 1 shows inhibition of dexamethasone-21-acetate (DEX-Ac)-induced ocular hypertension in Angptl7 knockout (KO) mice.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or alternatively phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates (such as, for example, apes and monkeys). In some embodiments, the subject is a human. In some embodiments, the subject is a patient under the care of a physician.

The present disclosure demonstrates that inhibiting ANGPTL7 activity, such as in Angptl7 KO mice, surprisingly and unexpectedly suppresses the GC-mediated increase in ocular hypertension. Thus, it is believed that treatment of subjects undergoing glucocorticoid treatment of, for example, inflammation, with ANGPTL7 inhibitors can decrease or prevent undesirable glucocorticoid-induced ophthalmic conditions. It is believed that no ANGPTL7 inhibitors have any known association with decreasing or preventing undesirable glucocorticoid-induced ophthalmic conditions. Therefore, subjects that are ANGPTL7 reference that have an increased risk of developing glucocorticoid-induced ophthalmic conditions may be treated such that the glucocorticoid-induced ophthalmic conditions are prevented, the symptoms thereof are reduced, and/or development of symptoms is repressed. Accordingly, the present disclosure provides methods of leveraging the identification of ANGPTL7 reference subjects undergoing glucocorticoid treatment to identify or stratify risk in such subjects of developing glucocorticoid-induced ophthalmic conditions such that subjects at risk or subjects with active glucocorticoid-induced ophthalmic conditions may be treated accordingly.

For purposes of the present disclosure, any particular subject can be categorized as having one of three ANGPTL7 genotypes: i) ANGPTL7 reference; ii) heterozygous for an ANGPTL7 predicted loss-of-function variant; or iii) homozygous for an ANGPTL7 predicted loss-of-function variant. A subject is ANGPTL7 reference when the subject does not have a copy of an ANGPTL7 predicted loss-of-function variant nucleic acid molecule. A subject is heterozygous for an ANGPTL7 predicted loss-of-function variant when the subject has a single copy of an ANGPTL7 predicted loss-of-function variant nucleic acid molecule. As used herein, an ANGPTL7 predicted loss-of-function variant nucleic acid molecule is any ANGPTL7 nucleic acid molecule (such as, a genomic nucleic acid molecule, an mRNA molecule, or a cDNA molecule) encoding an ANGPTL7 polypeptide having a partial loss-of-function, a complete loss-of-function, a predicted partial loss-of-function, or a predicted complete loss-of-function. A subject who has an ANGPTL7 polypeptide having a partial loss-of-function (or predicted partial loss-of-function) is hypomorphic for ANGPTL7. The ANGPTL7 predicted loss-of-function variant nucleic acid molecule can be any nucleic acid molecule encoding an ANGPTL7 Arg177STOP, Gln175His, Phe161Ile, Trp188STOP, Lys192Gln, Arg340His, Arg220His, Asn302Lys, or Arg220Cys. In some embodiments, the ANGPTL7 predicted loss-of-function variant nucleic acid molecule encodes an ANGPTL7 Arg177STOP, Gln175His, Phe161Ile, Trp188STOP, or Lys192Gln. A subject is homozygous for an ANGPTL7 predicted loss-of-function variant when the subject has two copies of an ANGPTL7 predicted loss-of-function variant nucleic acid molecule.

For subjects that are genotyped or determined to be ANGPTL7 reference, such subjects have an increased risk of developing glucocorticoid-induced ophthalmic conditions such as, for example, ocular hypertension, increased intraocular pressure (IOP), pre-glaucoma, glaucoma, decreased corneal hysteresis, and posterior subcapsular cataracts, or any combination thereof. In some embodiments, the IOP is corneal-compensated intraocular pressure (IOPcc). In some embodiments, the IOP is Goldmann-correlated IOP (IOPg). For subjects that are genotyped or determined to be either ANGPTL7 reference or heterozygous for an ANGPTL7 predicted loss-of-function variant, such subjects can be treated with an ANGPTL7 inhibitor.

In any of the embodiments described herein, the glaucoma can be primary open-angle glaucoma, iatrogenic open-angle glaucoma, angle-closure glaucoma, normal-tension glaucoma, congenital glaucoma, neovascular glaucoma, steroid-induced glaucoma, or glaucoma related to ocular trauma.

In any of the embodiments described herein, the ANGPTL7 predicted loss-of-function variant nucleic acid molecule can be any ANGPTL7 nucleic acid molecule (such as, for example, genomic nucleic acid molecule, mRNA molecule, or cDNA molecule) encoding an ANGPTL7 polypeptide having a partial loss-of-function, a complete loss-of-function, a predicted partial loss-of-function, or a predicted complete loss-of-function. For example, the ANGPTL7 predicted loss-of-function variant nucleic acid molecule can be any nucleic acid molecule encoding ANGPTL7 Arg177STOP, Gln175His, Phe161Ile, Trp188STOP, Lys192Gln, Arg340His, Arg220His, Asn302Lys, or Arg220Cys. In some embodiments, the ANGPTL7 predicted loss-of-function variant nucleic acid molecule encodes ANGPTL7 Arg177STOP, Gln175His, Phe161Ile, Trp188STOP, or Lys192Gln.

In any of the embodiments described herein, the ANGPTL7 predicted loss-of-function polypeptide can be any ANGPTL7 polypeptide having a partial loss-of-function, a complete loss-of-function, a predicted partial loss-of-function, or a predicted complete loss-of-function. In any of the embodiments described herein, the ANGPTL7 predicted loss-of-function polypeptide can be any of the ANGPTL7 polypeptides described herein including, for example, ANGPTL7 Arg177STOP, Gln175His, Phe161Ile, Trp188STOP, Lys192Gln, Arg340His, Arg220His, Asn302Lys, or Arg220Cys. In some embodiments, the ANGPTL7 predicted loss-of-function polypeptide is ANGPTL7 Arg177STOP, Gln175His, Phe161Ile, Trp188STOP, or Lys192Gln.

In any of the embodiments described herein, the inflammation can be acute inflammation or chronic inflammation. In some embodiments, the acute inflammation is inflammation having a relatively short duration, lasting from about a few minutes to about one to two days. Acute inflammation can be characterized by increased blood flow, exudation of fluid and plasma proteins (edema), and emigration of leukocytes, predominantly neutrophils. In some embodiments, the chronic inflammation is inflammation having a longer duration, such as days to weeks or even longer, and is associated histologically with the presence of lymphocytes and macrophages and with proliferation of blood vessels and connective tissue. In any of the embodiments described herein, the inflammation is associated with rheumatoid arthritis, associated with Grave's disease, or is ophthalmic inflammation. In some embodiments, the inflammation is associated with rheumatoid arthritis. In some embodiments, the inflammation is associated with Grave's disease. In some embodiments, the inflammation is ophthalmic inflammation. In some embodiments, the ophthalmic inflammation is chosen from uveitis, juvenile idiopathic arthritis uveitis, scleritis, blepharitis, conjunctivitis, iritis, and episcleritis, or any combination thereof. In some embodiments, the ophthalmic inflammation is uveitis. In some embodiments, the ophthalmic inflammation is juvenile idiopathic arthritis uveitis. In some embodiments, the ophthalmic inflammation is scleritis. In some embodiments, the ophthalmic inflammation is blepharitis. In some embodiments, the ophthalmic inflammation is conjunctivitis. In some embodiments, the ophthalmic inflammation is iritis. In some embodiments, the ophthalmic inflammation is episcleritis.

In any of the embodiments described herein, the glucocorticoid-induced ophthalmic condition is chosen from ocular hypertension, increased intraocular pressure (IOP), pre-glaucoma, glaucoma, decreased corneal hysteresis, and posterior subcapsular cataracts, or any combination thereof. In some embodiments, the glucocorticoid-induced ophthalmic condition is ocular hypertension. In some embodiments, the glucocorticoid-induced ophthalmic condition is increased IOP. In some embodiments, the glucocorticoid-induced ophthalmic condition is pre-glaucoma. In some embodiments, the glucocorticoid-induced ophthalmic condition is glaucoma. In some embodiments, the glucocorticoid-induced ophthalmic condition is decreased corneal hysteresis. In some embodiments, the glucocorticoid-induced ophthalmic condition is posterior subcapsular cataracts.

The present disclosure provides methods of treating a subject undergoing treatment with a steroid, the methods comprising administering an ANGPTL7 inhibitor to the subject.

The present disclosure provides methods of treating a subject having inflammation, the methods comprising administering an ANGPTL7 inhibitor and a glucocorticoid to the subject.

The present disclosure provides methods of treating a subject having rheumatoid arthritis, the methods comprising administering an ANGPTL7 inhibitor and a glucocorticoid to the subject.

The present disclosure provides methods of treating a subject having Grave's disease, the methods comprising administering an ANGPTL7 inhibitor and a glucocorticoid to the subject.

The present disclosure provides methods of treating a subject having ophthalmic inflammation, the methods comprising administering an ANGPTL7) inhibitor and a glucocorticoid to the subject.

The present disclosure provides methods of decreasing a steroid-induced ophthalmic condition in a subject treated with a steroid, the methods comprising administering an ANGPTL7 inhibitor to the subject.

The present disclosure provides methods of decreasing a glucocorticoid-induced ophthalmic condition in a subject treated with a glucocorticoid, the methods comprising administering an ANGPTL7 inhibitor to the subject.

The present disclosure provides methods of treating a subject having inflammation and undergoing steroid treatment, the methods comprising administering an ANGPTL7 inhibitor to the subject.

The present disclosure provides methods of treating a subject having inflammation and undergoing glucocorticoid treatment, the methods comprising administering an ANGPTL7 inhibitor to the subject.

The present disclosure provides methods of treating a subject having rheumatoid arthritis and undergoing glucocorticoid treatment, the methods comprising administering an ANGPTL7 inhibitor to the subject.

The present disclosure provides methods of treating a subject having Grave's disease and undergoing glucocorticoid treatment, the methods comprising administering an ANGPTL7 inhibitor to the subject.

The present disclosure provides methods of treating a subject having ophthalmic inflammation and undergoing glucocorticoid treatment, the methods comprising administering an ANGPTL7 inhibitor to the subject.

In any of the methods described herein, the inflammation can be acute inflammation or chronic inflammation. In some embodiments, the inflammation is acute inflammation. In some embodiments, the inflammation is chronic inflammation. In some embodiments, the inflammation is associated with rheumatoid arthritis, associated with Grave's disease, or is ophthalmic inflammation. In some embodiments, the inflammation is associated with rheumatoid arthritis. In some embodiments, the inflammation is associated with Grave's disease. In some embodiments, the inflammation is ophthalmic inflammation. In some embodiments, the ophthalmic inflammation is chosen from uveitis, juvenile idiopathic arthritis uveitis, scleritis, blepharitis, conjunctivitis, iritis, episcleritis, diabetic macular edema, corneal injury inflammation, ocular surgery pain or inflammation, or any combination thereof. In some embodiments, the ophthalmic inflammation is uveitis. In some embodiments, the ophthalmic inflammation is juvenile idiopathic arthritis uveitis. In some embodiments, the ophthalmic inflammation is scleritis. In some embodiments, the ophthalmic inflammation is blepharitis. In some embodiments, the ophthalmic inflammation is conjunctivitis. In some embodiments, the ophthalmic inflammation is iritis. In some embodiments, the ophthalmic inflammation is episcleritis. In some embodiments, the ophthalmic inflammation is diabetic macular edema. In some embodiments, the ophthalmic inflammation is corneal injury inflammation. In some embodiments, the ophthalmic inflammation is associated with ocular surgery.

In any of the methods described herein, the subject can be undergoing treatment with a steroid or have undergone treatment with a steroid. In some embodiments, such subject can have any of the forms of inflammation described herein. Steroids are used after several ophthalmic procedures including, but not limited to, cataract extraction, YAG laser capsulotomy, descement stripping automated endothelial keratoplasty (DSAEK), lamellar keratoplasty, penetrating keratoplasty, laser in-situ keratomileusis (LASIK), photorefractive keratectomy (PRK), Pars Planar Vitrectomy (PPV), and intralesional injection. In some embodiments, the subject is undergoing or has undergone cataract extraction. In some embodiments, the subject is undergoing or has undergone YAG laser capsulotomy. In some embodiments, the subject is undergoing or has undergone DSAEK. In some embodiments, the subject is undergoing or has undergone lamellar keratoplasty. In some embodiments, the subject is undergoing or has undergone penetrating keratoplasty. In some embodiments, the subject is undergoing or has undergone LASIK. In some embodiments, the subject is undergoing or has undergone PRK. In some embodiments, the subject is undergoing or has undergone PPV. In some embodiments, the subject is undergoing or has undergone intralesional injection.

In any of the methods described herein, the glucocorticoid-induced ophthalmic condition is chosen from ocular hypertension, increased intraocular pressure (IOP), pre-glaucoma, glaucoma, decreased corneal hysteresis, and posterior subcapsular cataracts, or any combination thereof. In some embodiments, the glucocorticoid-induced ophthalmic condition is ocular hypertension. In some embodiments, the glucocorticoid-induced ophthalmic condition is increased IOP. In some embodiments, the glucocorticoid-induced ophthalmic condition is pre-glaucoma. In some embodiments, the glucocorticoid-induced ophthalmic condition is glaucoma. In some embodiments, the glucocorticoid-induced ophthalmic condition is decreased corneal hysteresis. In some embodiments, the glucocorticoid-induced ophthalmic condition is posterior subcapsular cataracts.

In any of the methods described herein, the glucocorticoid is chosen from prednisone, prednisolone, methylprednisolone, dexamethasone, betamethasone, triamcinolone, beclometasone, fludrocortisone acetate, deoxycorticosterone acetate (DOCA), aldosterone, budesonide, mometasone furoate, fluticasone propionate, hydrocortisone, cortisone acetate, and fluticasone furoate, difluprednate ophthalmic, fluorometholone, loteprednol etabonate, medrysone, rimexolone, fluocinolone acetonide, clobetasol, halobetasol, diflorasone, fluocinonide, flurandrenolide, Neo-Poly-Dex, tobramycin-dexamethasone, difluprednate, or any combination thereof. In some embodiments, the glucocorticoid is prednisone. In some embodiments, the glucocorticoid is prednisolone. In some embodiments, the glucocorticoid is methylprednisolone. In some embodiments, the glucocorticoid is dexamethasone. In some embodiments, the glucocorticoid is betamethasone. In some embodiments, the glucocorticoid is triamcinolone. In some embodiments, the glucocorticoid is beclomethasone. In some embodiments, the glucocorticoid is fludrocortisone acetate. In some embodiments, the glucocorticoid is DOCA. In some embodiments, the glucocorticoid is aldosterone. In some embodiments, the glucocorticoid is budesonide. In some embodiments, the glucocorticoid is mometasone furoate. In some embodiments, the glucocorticoid is fluticasone propionate. In some embodiments, the glucocorticoid is hydrocortisone. In some embodiments, the glucocorticoid is cortisone acetate. In some embodiments, the glucocorticoid is fluticasone furoate. In some embodiments, the glucocorticoid is difluprednate ophthalmic. In some embodiments, the glucocorticoid is fluorometholone. In some embodiments, the glucocorticoid is loteprednol etabonate. In some embodiments, the glucocorticoid is medrysone. In some embodiments, the glucocorticoid is rimexolone. In some embodiments, the glucocorticoid is fluocinolone acetonide. In some embodiments, the glucocorticoid is clobetasol. In some embodiments, the glucocorticoid is halobetasol. In some embodiments, the glucocorticoid is diflorasone. In some embodiments, the glucocorticoid is fluocinonide. In some embodiments, the glucocorticoid is flurandrenolide. In some embodiments, the glucocorticoid is Neo-Poly-Dex. In some embodiments, the glucocorticoid is tobramycin-dexamethasone. In some embodiments, the glucocorticoid is difluprednate.

In any of the methods described herein, the glucocorticoid treatment is treatment with prednisone, prednisolone, methylprednisolone, dexamethasone, betamethasone, triamcinolone, beclometasone, fludrocortisone acetate, DOCA, aldosterone, budesonide, mometasone furoate, fluticasone propionate, hydrocortisone, cortisone acetate, or fluticasone furoate, difluprednate ophthalmic, fluorometholone, loteprednol etabonate, medrysone, rimexolone, fluocinolone acetonide, clobetasol, halobetasol, diflorasone, fluocinonide, flurandrenolide, Neo-Poly-Dex, tobramycin-dexamethasone, difluprednate, or any combination thereof. In some embodiments, the glucocorticoid treatment is treatment with prednisone. In some embodiments, the glucocorticoid treatment is treatment with prednisolone. In some embodiments, the glucocorticoid treatment is treatment with methylprednisolone. In some embodiments, the glucocorticoid treatment is treatment with dexamethasone. In some embodiments, the glucocorticoid treatment is treatment with betamethasone. In some embodiments, the glucocorticoid treatment is treatment with triamcinolone. In some embodiments, the glucocorticoid treatment is treatment with beclomethasone. In some embodiments, the glucocorticoid treatment is treatment with fludrocortisone acetate. In some embodiments, the glucocorticoid treatment is treatment with DOCA. In some embodiments, the glucocorticoid treatment is treatment with aldosterone. In some embodiments, the glucocorticoid treatment is treatment with budesonide. In some embodiments, the glucocorticoid treatment is treatment with mometasone furoate. In some embodiments, the glucocorticoid treatment is treatment with fluticasone propionate. In some embodiments, the glucocorticoid treatment is treatment with hydrocortisone. In some embodiments, the glucocorticoid treatment is treatment with cortisone acetate. In some embodiments, the glucocorticoid treatment is treatment with fluticasone furoate. In some embodiments, the glucocorticoid treatment is treatment with difluprednate ophthalmic. In some embodiments, the glucocorticoid treatment is treatment with fluorometholone. In some embodiments, the glucocorticoid treatment is treatment with loteprednol etabonate. In some embodiments, the glucocorticoid treatment is treatment with medrysone. In some embodiments, the glucocorticoid treatment is treatment with rimexolone. In some embodiments, the glucocorticoid treatment is treatment with fluocinolone acetonide. In some embodiments, the glucocorticoid treatment is treatment with clobetasol. In some embodiments, the glucocorticoid treatment is treatment with halobetasol. In some embodiments, the glucocorticoid treatment is treatment with diflorasone. In some embodiments, the glucocorticoid treatment is treatment with fluocinonide. In some embodiments, the glucocorticoid treatment is treatment with flurandrenolide. In some embodiments, the glucocorticoid treatment is treatment with Neo-Poly-Dex. In some embodiments, the glucocorticoid treatment is treatment with tobramycin-dexamethasone. In some embodiments, the glucocorticoid treatment is treatment with difluprednate.

In some embodiments, the ANGPTL7 inhibitor comprises an inhibitory nucleic acid molecule. In some embodiments, the inhibitory nucleic acid molecule comprises an antisense molecule, a small interfering RNA (siRNA) molecule, or a short hairpin RNA (shRNA) molecule. In some embodiments, the inhibitory nucleic acid molecule comprises an antisense molecule. In some embodiments, the inhibitory nucleic acid molecule comprises an siRNA molecule. In some embodiments, the inhibitory nucleic acid molecule comprises an shRNA molecule. Such inhibitory nucleic acid molecules can be designed to target any region of an ANGPTL7 nucleic acid molecule, such as an mRNA molecule. In some embodiments, the inhibitory nucleic acid molecule hybridizes to a sequence within an ANGPTL7 genomic nucleic acid molecule or mRNA molecule and decreases expression of the ANGPTL7 polypeptide in a cell in the subject. In some embodiments, the ANGPTL7 inhibitor comprises an antisense RNA that hybridizes to an ANGPTL7 genomic nucleic acid molecule or mRNA molecule and decreases expression of the ANGPTL7 polypeptide in a cell in the subject. In some embodiments, the ANGPTL7 inhibitor comprises an siRNA that hybridizes to an ANGPTL7 genomic nucleic acid molecule or mRNA molecule and decreases expression of the ANGPTL7 polypeptide in a cell in the subject. In some embodiments, the ANGPTL7 inhibitor comprises an shRNA that hybridizes to an ANGPTL7 genomic nucleic acid molecule or mRNA molecule and decreases expression of the ANGPTL7 polypeptide in a cell in the subject.

In some embodiments, the antisense nucleic acid molecules comprise or consist of the nucleotide sequences shown in Table 1, Table 2, and Table 3.

TABLE 1

| Sequence | SEQ ID NO: |
|---|---|
| AGCUUGAGUCUCUGACAGGG | 166 |
| UUUUCUCUCUUUCCUUGCUC | 167 |
| CCUCGCCACUUUGUUGUUUU | 168 |
| GCCUCGCCACUUUGUUGUUU | 169 |
| GGCCUCGCCACUUUGUUGUU | 170 |
| GGGCCUCGCCACUUUGUUGU | 171 |
| AGGGCCUCGCCACUUUGUUG | 172 |
| GAGGGCCUCGCCACUUUGUU | 173 |
| UGAGGGCCUCGCCACUUUGU | 174 |
| UCUGAGGGCCUCGCCACUUU | 175 |
| UUUCACUCUGAGGGCCUCGC | 176 |
| CGCUUUCACUCUGAGGGCCU | 177 |
| UACGCUUUCACUCUGAGGGC | 178 |
| UUACGCUUUCACUCUGAGGG | 179 |
| CUUACGCUUUCACUCUGAGG | 180 |
| CCUUACGCUUUCACUCUGAG | 181 |
| AACCUUACGCUUUCACUCUG | 182 |
| GAACCUUACGCUUUCACUCU | 183 |
| UGACUGAACCUUACGCUUUC | 184 |
| CUGACUGAACCUUACGCUUU | 185 |
| GCUGACUGAACCUUACGCUU | 186 |
| GGCUGACUGAACCUUACGCU | 187 |
| AGGCUGACUGAACCUUACGC | 188 |
| GGUUUGGGUGAGGAAGGCUC | 189 |
| GGGUUUGGGUGAGGAAGGCU | 190 |
| UGUGGGUUUGGGUGAGGAAG | 191 |
| UUGUGGGUUUGGGUGAGGAA | 192 |
| UUUUGUGGGUUUGGGUGAGG | 193 |
| GAAAAUGCAGAGCCAGGUCA | 194 |
| CCACGAUGAAAAUGCAGAGC | 195 |
| GCCACGAUGAAAAUGCAGAG | 196 |
| AGGCCACGAUGAAAAUGCAG | 197 |
| AAAGGCCACGAUGAAAAUGC | 198 |
| ACAAAGGCCACGAUGAAAAU | 199 |
| UGACAAAGGCCACGAUGAAA | 200 |
| CUGACAAAGGCCACGAUGAA | 201 |
| GCUGACAAAGGCCACGAUGA | 202 |
| GGCUGACAAAGGCCACGAUG | 203 |
| ACGCUGGGUGGCUGACAAAG | 204 |

TABLE 1-continued

| Sequence | SEQ ID NO: |
|---|---|
| GUGCUUAGAGAGCUUCUGCA | 205 |
| UGUGCUUAGAGAGCUUCUGC | 206 |
| UUGUGCUUAGAGAGCUUCUG | 207 |
| UCUUGUGCUUAGAGAGCUUC | 208 |
| GUCUUGUGCUUAGAGAGCUU | 209 |
| UGUCUUGUGCUUAGAGAGCU | 210 |
| GUGUCUUGUGCUUAGAGAGC | 211 |
| GGUGUCUUGUGCUUAGAGAG | 212 |
| CUGGUGUCUUGUGCUUAGAG | 213 |
| GCUGGUGUCUUGUGCUUAGA | 214 |
| UGUGCUGGUGUCUUGUGCUU | 215 |
| CUGUGCUGGUGUCUUGUGCU | 216 |
| GGCUGUGCUGGUGUCUUGUG | 217 |
| CGCUUUGAGCUGUGGCUGUG | 218 |
| CCGCUUUGAGCUGUGGCUGU | 219 |
| ACCUCCUCACAGCAGUUGGC | 220 |
| UCACCUCCUCACAGCAGUUG | 221 |
| GUUGGCAACUUGGGCCUUGA | 222 |
| GGUUGGCAACUUGGGCCUUG | 223 |
| AGGUUGGCAACUUGGGCCUU | 224 |
| AAGGUUGGCAACUUGGGCCU | 225 |
| UAAGGUUGGCAACUUGGGCC | 226 |
| CUAAGGUUGGCAACUUGGGC | 227 |
| GCUAAGGUUGGCAACUUGGG | 228 |
| UGCUAAGGUUGGCAACUUGG | 229 |
| CUGCUAAGGUUGGCAACUUG | 230 |
| GCUGCUAAGGUUGGCAACUU | 231 |
| GGCUGCUAAGGUUGGCAACU | 232 |
| AGGCUGCUAAGGUUGGCAAC | 233 |
| CAGGCUGCUAAGGUUGGCAA | 234 |
| CAGUUCACUCAGCAGGCUGC | 235 |
| UCAGUUCACUCAGCAGGCUG | 236 |
| UUCAGUUCACUCAGCAGGCU | 237 |
| GUUCAGUUCACUCAGCAGGC | 238 |
| CUUGUUCAGUUCACUCAGCA | 239 |
| UCUUGUUCAGUUCACUCAGC | 240 |
| UUCUUGUUCAGUUCACUCAG | 241 |
| GUCCCUCCUCCUGCUUCUUGU | 242 |
| AUGACCACGCUGACCCAGUC | 243 |

TABLE 1-continued

| Sequence | SEQ ID NO: |
|---|---|
| UGCAUGACCACGCUGACCCA | 244 |
| ACCUGCAUGACCACGCUGAC | 245 |
| CACCUGCAUGACCACGCUGA | 246 |
| UCACCUGCAUGACCACGCUG | 247 |
| AUCACCUGCAUGACCACGCU | 248 |
| CUCCAUCACCUGCAUGACCA | 249 |
| CGCUUGCUGUUGCUCUCCAG | 250 |
| GCGCUUGCUGUUGCUCUCCA | 251 |
| CAUGCGCUUGCUGUUGCUCU | 252 |
| CCAUGCGCUUGCUGUUGCUC | 253 |
| UCCAUGCGCUUGCUGUUGCU | 254 |
| CUCCAUGCGCUUGCUGUUGC | 255 |
| ACUCCAUGCGCUUGCUGUUG | 256 |
| GACUCCAUGCGCUUGCUGUU | 257 |
| CGACUCCAUGCGCUUGCUGU | 258 |
| GGUUGUUCAUCUCGGAGUAC | 259 |
| UGGUUGUUCAUCUCGGAGUA | 260 |
| UUGGUUGUUCAUCUCGGAGU | 261 |
| GCAUGAUGUCAAUUUGGUUG | 262 |
| AGCUGCAUGAUGUCAAUUUG | 263 |
| AGUGACCGUCUGUGCUGCCU | 264 |
| UGAGUGACCGUCUGUGCUGC | 265 |
| CUGAGUGACCGUCUGUGCUG | 266 |
| UCUGAGUGACCGUCUGUGCU | 267 |
| ACUGGUCUCCUUACCUGCGG | 268 |
| GACUGGUCUCCUUACCUGCG | 269 |
| GGACUGGUCUCCUUACCUGC | 270 |
| GAAGCAGUGCUGUAGAUGGG | 271 |
| UGUAGAAGCAGUGCUGUAGA | 272 |
| AUGUAGAAGCAGUGCUGUAG | 273 |
| UAUGUAGAAGCAGUGCUGUA | 274 |
| AUAUGUAGAAGCAGUGCUGU | 275 |
| GAUAUGUAGAAGCAGUGCUG | 276 |
| GGAUAUGUAGAAGCAGUGCU | 277 |
| AGGAUAUGUAGAAGCAGUGC | 278 |
| CCAGGAUAUGUAGAAGCAGU | 279 |
| UGACCAGGAUAUGUAGAAGC | 280 |
| GAUGACCAGGAUAUGUAGAA | 281 |
| CUGAUGACCAGGAUAUGUAG | 282 |
| UCUGAUGACCAGGAUAUGUA | 283 |
| GUUCUGAUGACCAGGAUAUG | 284 |
| GGUUCUGAUGACCAGGAUAU | 285 |
| CAGUAGUGGUUCUGAUGACC | 286 |
| CCAGUAGUGGUUCUGAUGAC | 287 |
| CCCAGUAGUGGUUCUGAUGA | 288 |
| AGUGUACCCACAAAAGAGGC | 289 |
| AAGUGUACCCACAAAAGAGG | 290 |
| AAAGUGUACCCACAAAAGAG | 291 |
| GGAAAGUGUACCCACAAAAG | 292 |
| GGGAAAGUGUACCCACAAAA | 293 |
| AAGGGAAAGUGUACCCACAA | 294 |
| CUAAAGGGAAAGUGUACCCA | 295 |
| ACUAAAGGGAAAGUGUACCC | 296 |
| UACUAAAGGGAAAGUGUACC | 297 |
| AGGAAAUACUGCAUAAGCCU | 298 |
| GUGAAGGUGUUAGGUAAACU | 299 |
| CGUGAAGGUGUUAGGUAAAC | 300 |
| CCGUGAAGGUGUUAGGUAAA | 301 |
| CCCGUGAAGGUGUUAGGUAA | 302 |
| ACCCGUGAAGGUGUUAGGUA | 303 |
| GACCCGUGAAGGUGUUAGGU | 304 |
| AGACCCGUGAAGGUGUUAGG | 305 |
| GAGACCCGUGAAGGUGUUAG | 306 |
| AGAGACCCGUGAAGGUGUUA | 307 |
| AAGAGACCCGUGAAGGUGUU | 308 |
| AAAGAGACCCGUGAAGGUGU | 309 |
| AAAAGAGACCCGUGAAGGUG | 310 |
| UAAAAGAGACCCGUGAAGGU | 311 |
| AUAAAAGAGACCCGUGAAGG | 312 |
| GAUAAAAGAGACCCGUGAAG | 313 |
| GGAUAAAAGAGACCCGUGAA | 314 |
| UGGAUAAAAGAGACCCGUGA | 315 |
| GUGGAUAAAAGAGACCCGUG | 316 |
| UGUGGAUAAAAGAGACCCGU | 317 |
| ACACUGUGGAUAAAAGAG | 318 |
| GCUGAAACACUGUGGAUA | 319 |
| GGCUGAAACACUGUGGAU | 320 |
| UAGUAUCUCAGCACUCCAAG | 321 |

TABLE 1-continued

| Sequence | SEQ ID NO: |
|---|---|
| GUAGUAUCUCAGCACUCCAA | 322 |
| AUGUAGUAUCUCAGCACUCC | 323 |
| CAUGUAGUAUCUCAGCACUC | 324 |
| CCAUGUAGUAUCUCAGCACU | 325 |
| ACCAUGUAGUAUCUCAGCAC | 326 |
| AACCAUGUAGUAUCUCAGCA | 327 |
| AAACCAUGUAGUAUCUCAGC | 328 |
| CAAACCAUGUAGUAUCUCAG | 329 |
| GCAAACCAUGUAGUAUCUC | 330 |
| UUUGGGCAAACCAUGUAGUA | 331 |
| CUUUGGGCAAACCAUGUAGU | 332 |
| UGCUUCUAAGACUUGCUGGG | 333 |
| AACCCUGCUUCUAAGACUUG | 334 |
| GAACCCUGCUUCUAAGACUU | 335 |
| UGAACCCUGCUUCUAAGACU | 336 |
| UUGAACCCUGCUUCUAAGAC | 337 |
| GACUUGAACCCUGCUUCUAA | 338 |
| AGACUUGAACCCUGCUUCUA | 339 |
| AAGACUUGAACCCUGCUUCU | 340 |
| AAUCAGGAAGACUUGAACCC | 341 |
| CAAUCAGGAAGACUUGAACC | 342 |
| CCAAUCAGGAAGACUUGAAC | 343 |
| ACCAAUCAGGAAGACUUGAA | 344 |
| ACACCAAUCAGGAAGACUUG | 345 |
| UACACCAAUCAGGAAGACUU | 346 |
| CUACACCAAUCAGGAAGACU | 347 |
| GCUACACCAAUCAGGAAGAC | 348 |
| AGCUACACCAAUCAGGAAGA | 349 |
| GAGCUACACCAAUCAGGAAG | 350 |
| AGAGCUACACCAAUCAGGAA | 351 |
| CAGAGCUACACCAAUCAGGA | 352 |
| GCAGAGCUACACCAAUCAGG | 353 |
| UGGUGAGGAAGUAGCAGAGC | 354 |
| UUGGUGAGGAAGUAGCAGAG | 355 |
| CUUGGUGAGGAAGUAGCAGA | 356 |
| UCUUGGUGAGGAAGUAGCAG | 357 |
| CUCUUGGUGAGGAAGUAGCA | 358 |
| GCUCUUGGUGAGGAAGUAGC | 359 |
| UGUCAGCUCUUGGUGAGGAA | 360 |

TABLE 1-continued

| Sequence | SEQ ID NO: |
|---|---|
| CUGUCAGCUCUUGGUGAGGA | 361 |
| AGCCUGUCAGCUCUUGGUGA | 362 |
| UAUAGCCUGUCAGCUCUUGG | 363 |
| AUAUAGCCUGUCAGCUCUUG | 364 |
| AGAUAUAGCCUGUCAGCUCU | 365 |
| UCUUGAGAUAUAGCCUGUCA | 366 |
| UUCUUGAGAUAUAGCCUGUC | 367 |
| GGUGCUUCCUUGGAAUUUCU | 368 |
| AGUUUGGUGCUUCCUUGGAA | 369 |
| CAGUUUGGUGCUUCCUUGGA | 370 |
| UACAGUUUGGUGCUUCCUUG | 371 |
| GUUACAGUUUGGUGCUUCCU | 372 |
| UGUUACAGUUUGGUGCUUCC | 373 |
| CUGUUACAGUUUGGUGCUUC | 374 |
| GCUGUUACAGUUUGGUGCUU | 375 |
| AGCUGUUACAGUUUGGUGCU | 376 |
| CUUAGGAACACCAGAGAACU | 377 |
| UCUUAGGAACACCAGAGAAC | 378 |
| AUCUUAGGAACACCAGAGAA | 379 |
| AAUCUUAGGAACACCAGAGA | 380 |
| GUAAAUCUUAGGAACACCAG | 381 |
| UGGUAAAUCUUAGGAACACC | 382 |
| CUGGUAAAUCUUAGGAACAC | 383 |
| CCUGGUAAAUCUUAGGAACA | 384 |
| CAUUCCUGGUAAAUCUUAGG | 385 |
| GCUCAUUCCUGGUAAAUCUU | 386 |
| UGCUCAUUCCUGGUAAAUCU | 387 |
| AUGCUCAUUCCUGGUAAAUC | 388 |
| CGUUUACAGAGAGGACAC | 389 |
| UACGUUUACAGAGAGGAC | 390 |
| GUUACGUUUACAGAGAGG | 391 |
| AGUUACGUUUACAGAGAGAG | 392 |
| GAGUUACGUUUACAGAGAGA | 393 |
| AGAGUUACGUUUACAGAGAG | 394 |
| GAAGAGUUACGUUUACAGAG | 395 |
| GAGAAGAGUUACGUUUACAG | 396 |
| CCAAUGAGAAGAGUUACGUU | 397 |
| GCCAAUGAGAAGAGUUACGU | 398 |
| GAGCCAAUGAGAAGAGUUAC | 399 |

TABLE 1-continued

| Sequence | SEQ ID NO: |
|---|---|
| UGAGCCAAUGAGAAGAGUUA | 400 |
| CUACACUUAACUCUGAGCCA | 401 |
| UCUACACUUAACUCUGAGCC | 402 |
| CUCUACACUUAACUCUGAGC | 403 |
| UCUCUACACUUAACUCUGAG | 404 |
| UGUCUCUACACUUAACUCUG | 405 |
| CAUGGUUAUGUGUCUCUACA | 406 |
| GGACUCUUCACAUGGUUAUG | 407 |
| GGGACUCUUCACAUGGUUAU | 408 |
| AAGGGACUCUUCACAUGGUU | 409 |
| ACAAAGGGACUCUUCACAUG | 410 |
| AACACAAAGGGACUCUUCAC | 411 |
| GAACACAAAGGGACUCUUCA | 412 |
| UCCUGAACACAAAGGGACUC | 413 |
| CUUCCUGAACACAAAGGGAC | 414 |
| CAUCCUUCCUGAACACAAAG | 415 |
| GCAUCCUUCCUGAACACAAA | 416 |
| CCGCAUCCUUCCUGAACACA | 417 |
| AGCCGCAUCCUUCCUGAACA | 418 |
| GAGCCGCAUCCUUCCUGAAC | 419 |
| CCUGUAUUCGGAGAAAUUCA | 420 |
| UCCUGUAUUCGGAGAAAUUC | 421 |
| GAGCUGAGCUAACCAGAAAU | 422 |
| UGAGCUGAGCUAACCAGAAA | 423 |
| CUGAGCUGAGCUAACCAGAA | 424 |
| CCUGAGCUGAGCUAACCAGA | 425 |
| ACCUGAGCUGAGCUAACCAG | 426 |
| CCACCUGAGCUGAGCUAACC | 427 |
| CCCACCUGAGCUGAGCUAAC | 428 |
| UGUUGGCCCACCUGAGCUGA | 429 |
| AUGUUGGCCCACCUGAGCUG | 430 |
| UUCAUGUUGGCCCACCUGAG | 431 |
| AUUCAUGUUGGCCCACCUGA | 432 |
| AAAUUCAUGUUGGCCCACCU | 433 |
| UAAAUUCAUGUUGGCCCACC | 434 |
| GUAAAUUCAUGUUGGCCCAC | 435 |
| GUUGGUUCAGGUAACAGAAU | 436 |
| CCAUGCUUAGAAAGUGAUUG | 437 |
| AAGUCCAUGCUUAGAAAGUG | 438 |

TABLE 1-continued

| Sequence | SEQ ID NO: |
|---|---|
| GGAAGUCCAUGCUUAGAAAG | 439 |
| CGGAAGUCCAUGCUUAGAAA | 440 |
| CCGGAAGUCCAUGCUUAGAA | 441 |
| CCCGGAAGUCCAUGCUUAGA | 442 |
| UUUCUAAUCCCAAACUGAGG | 443 |
| CUUUCUAAUCCCAAACUGAG | 444 |
| CCUUUCUAAUCCCAAACUGA | 445 |
| ACCUUUCUAAUCCCAAACUG | 446 |
| AUGGCCUGAGAAUACCUUUC | 447 |
| AAUGGCCUGAGAAUACCUUU | 448 |
| AAAUGGCCUGAGAAUACCUU | 449 |
| AAAAUGGCCUGAGAAUACCU | 450 |
| UGGAAAAUGGCCUGAGAAUA | 451 |
| ACUUGUCUGGAAAAUGGCCU | 452 |
| CACUUGUCUGGAAAAUGGCC | 453 |
| UCACUUGUCUGGAAAAUGGC | 454 |
| GGACUCACUUGUCUGGAAAA | 455 |
| AAUCAGGACUCACUUGUCUG | 456 |
| AAAUCAGGACUCACUUGUCU | 457 |
| CAAAUCAGGACUCACUUGUC | 458 |
| CCAAAUCAGGACUCACUUGU | 459 |
| GACCAAAUCAGGACUCACUU | 460 |
| AGACCAAAUCAGGACUCACU | 461 |
| CAGACCAAAUCAGGACUCAC | 462 |
| CACAGACCAAAUCAGGACUC | 463 |
| UCACAGACCAAAUCAGGACU | 464 |
| CUCACAGACCAAAUCAGGAC | 465 |
| UCUCACAGACCAAAUCAGGA | 466 |
| AUCUCACAGACCAAAUCAGG | 467 |
| CAUCUCACAGACCAAAUCAG | 468 |
| GUUUCAUCUCACAGACCAAA | 469 |
| GGUUUCAUCUCACAGACCAA | 470 |
| CUGGUUUCAUCUCACAGACC | 471 |
| CAUGUCUGGUUUCAUCUCAC | 472 |
| GCAUGUCUGGUUUCAUCUCA | 473 |
| CGCAUGUCUGGUUUCAUCUC | 474 |
| UCCGCAUGUCUGGUUUCAUC | 475 |
| UUCCGCAUGUCUGGUUUCAU | 476 |
| CUUCCGCAUGUCUGGUUUCA | 477 |

TABLE 1-continued

| Sequence | SEQ ID NO: |
|---|---|
| UCUUCCGCAUGUCUGGUUUC | 478 |
| GUCUUCCGCAUGUCUGGUUU | 479 |
| GGUCUUCCGCAUGUCUGGUU | 480 |
| UGGUCUUCCGCAUGUCUGGU | 481 |
| CUGGUCUUCCGCAUGUCUGG | 482 |
| CCUGGUCUUCCGCAUGUCUG | 483 |
| GCCUGGUCUUCCGCAUGUCU | 484 |
| UGGCCUGGUCUUCCGCAUGU | 485 |
| UCUGUCUGGCCUGGUCUUCC | 486 |
| CUCUGUCUGGCCUGGUCUUC | 487 |
| CCUCUGUCUGGCCUGGUCUU | 488 |
| AUUCCUCUGUCUGGCCUGGU | 489 |
| GAUUCCUCUGUCUGGCCUGG | 490 |
| AGAUUCCUCUGUCUGGCCUG | 491 |
| UGGCACGGUCAGAUUCCUCU | 492 |
| GUGGCACGGUCAGAUUCCUC | 493 |
| AGUGGCACGGUCAGAUUCCU | 494 |
| AAGUGGCACGGUCAGAUUCC | 495 |
| GAAGUGGCACGGUCAGAUUC | 496 |
| GGAAGUGGCACGGUCAGAUU | 497 |
| AGGAAGUGGCACGGUCAGAU | 498 |
| CAGGAAGUGGCACGGUCAGA | 499 |
| AGCAGGAAGUGGCACGGUCA | 500 |
| GUUUGGAUGAGCAGGAAGUG | 501 |
| UGUUUGGAUGAGCAGGAAGU | 502 |
| CCUCCUGUUUGGAUGAGCAG | 503 |
| GCCUCCUGUUUGGAUGAGCA | 504 |
| AGCCUCCUGUUUGGAUGAGC | 505 |
| AAGCCUCCUGUUUGGAUGAG | 506 |
| AAAGCCUCCUGUUUGGAUGA | 507 |
| GAAAGCCUCCUGUUUGGAUG | 508 |
| UGAGAAAGCCUCCUGUUUGG | 509 |
| GUGAGAAAGCCUCCUGUUUG | 510 |
| GGUGAGAAAGCCUCCUGUUU | 511 |
| AUGGUGAGAAAGCCUCCUGU | 512 |
| CAGGAUGGUGAGAAAGCCUC | 513 |
| GCAGGAUGGUGAGAAAGCCU | 514 |
| UGGGAGAGCUGCACUUGACC | 515 |
| GUGGGAGAGCUGCACUUGAC | 516 |

TABLE 1-continued

| Sequence | SEQ ID NO: |
|---|---|
| GGUGGGAGAGCUGCACUUGA | 517 |
| UGGUGGGAGAGCUGCACUUG | 518 |
| CUGGUGGGAGAGCUGCACUU | 519 |
| AUGAUGUCCUGGGCAAGAAG | 520 |
| AAUGAUGUCCUGGGCAAGAA | 521 |
| GAAUGAUGUCCUGGGCAAGA | 522 |
| GGAAUGAUGUCCUGGGCAAG | 523 |
| GAAUAUAAGGGUAACUGAGC | 524 |
| GGGACUACCACUUAUAGAA | 525 |
| AGGGACUACCACUUAUAGA | 526 |
| UGAAAGCACCAACUUACUGC | 527 |
| GUGAAAGCACCAACUUACUG | 528 |
| CGUCUUAGUGGUGAAAGCAC | 529 |
| UCGUCUUAGUGGUGAAAGCA | 530 |
| UUCGUCUUAGUGGUGAAAGC | 531 |
| CAUUUCGUCUUAGUGGUGAA | 532 |
| UCAUUUCGUCUUAGUGGUGA | 533 |
| UUCAUUUCGUCUUAGUGGUG | 534 |
| CUUCAUUUCGUCUUAGUGGU | 535 |
| UCUUCAUUUCGUCUUAGUGG | 536 |
| AGGUAGAGUACGUGUGCCUU | 537 |
| GAGGUAGAGUACGUGUGCCU | 538 |
| GGAGGUAGAGUACGUGUGCC | 539 |
| GGGAGGUAGAGUACGUGUGC | 540 |
| AGGGAGGUAGAGUACGUGUG | 541 |
| AAGGGAGGUAGAGUACGUGU | 542 |
| AAAGGGAGGUAGAGUACGUG | 543 |
| GAAAGGGAGGUAGAGUACGU | 544 |
| CACAUAGGUUCUCUUGCAGA | 545 |
| AGGCACAUAGGUUCUCUUGC | 546 |
| GAGGCACAUAGGUUCUCUUG | 547 |
| CUGAGGCACAUAGGUUCUCU | 548 |
| UCUGAGGCACAUAGGUUCUC | 549 |
| GUCUGAGGCACAUAGGUUCU | 550 |
| UGUCUGAGGCACAUAGGUUC | 551 |
| UUGUCUGAGGCACAUAGGUU | 552 |
| UAGAGAGGAGCACCAAGAUG | 553 |
| UUAGAGAGGAGCACCAAGAU | 554 |
| CUUAGAGAGGAGCACCAAGA | 555 |

TABLE 1-continued

| Sequence | SEQ ID NO: |
|---|---|
| ACCUUAGAGAGGAGCACCAA | 556 |
| GACCUUAGAGAGGAGCACCA | 557 |
| GGACCUUAGAGAGGAGCACC | 558 |
| UGGGACCUUAGAGAGGAGCA | 559 |
| CUGGGACCUUAGAGAGGAGC | 560 |
| CACUGGGACCUUAGAGAGGA | 561 |
| GCACUGGGACCUUAGAGAGG | 562 |
| UGCACUGGGACCUUAGAGAG | 563 |
| ACUGCACUGGGACCUUAGAG | 564 |
| GACCACUGCACUGGGACCUU | 565 |
| UUGGUGACCACUGCACUGGG | 566 |
| CUUGGUGACCACUGCACUGG | 567 |
| UCUUGGUGACCACUGCACUG | 568 |
| UUCUUGGUGACCACUGCACU | 569 |
| UUUCUUGGUGACCACUGCAC | 570 |
| CUUUUCUUGGUGACCACUGC | 571 |
| GGUGCUUUUCUUGGUGACCA | 572 |
| GGGUGCUUUUCUUGGUGACC | 573 |
| AGCUUCCUGCCUGCUAUGUC | 574 |
| ACAGCCUUUUCUGAUAGGAU | 575 |
| GACAGCCUUUUCUGAUAGGA | 576 |
| GAAGAGACAGCCUUUUCUGA | 577 |
| GGAAGAGACAGCCUUUUCUG | 578 |
| AUAGUGGAAGAGACAGCCUU | 579 |
| GCAUAGUGGAAGAGACAGCC | 580 |
| AGCAUAGUGGAAGAGACAGC | 581 |
| GAGCAUAGUGGAAGAGACAG | 582 |
| AAGAGCAUAGUGGAAGAGAC | 583 |
| UAUGCAGGAUUUAAGCUCUG | 584 |
| UGGAGCUGCUACUUUAUGCA | 585 |
| AUGAGAGCAUCAGACUGGCC | 586 |
| AAUGAGAGCAUCAGACUGGC | 587 |
| CCUCCCAGAAGUUUUGUUAA | 588 |
| UCCUCCCAGAAGUUUUGUUA | 589 |
| UCAGAAGAACCUUUGAGGCC | 590 |
| ACACUCAGAAGAACCUUUGA | 591 |
| AACACUCAGAAGAACCUUUG | 592 |
| UAGCACCUCAAAACACUCAG | 593 |
| CUAGCACCUCAAAACACUCA | 594 |
| UGCCACCUGAGACCAUAAUU | 595 |
| ACUGCCACCUGAGACCAUAA | 596 |
| UACUGCCACCUGAGACCAUA | 597 |
| CAGAGAUGGUGGCUACUGCC | 598 |
| UCAGAGAUGGUGGCUACUGC | 599 |
| GUUCAGAGAUGGUGGCUACU | 600 |
| UGUUCAGAGAUGGUGGCUAC | 601 |
| UGUUGUUCAGAGAUGGUGGC | 602 |
| UUGUUGUUCAGAGAUGGUGG | 603 |
| GUUGUUGUUCAGAGAUGGUG | 604 |
| AUGUUUCCUGGUUGGUUGUU | 605 |
| UCUCAUAGAGUCUGGUUUUG | 606 |
| GAAUAUCUCAUAGAGUCUGG | 607 |
| GUCGUGAAUAUCUCAUAGAG | 608 |
| CAGUCGUGAAUAUCUCAUAG | 609 |
| CCACUAUAACAAAUCAGUCG | 610 |
| GCCACUAUAACAAAUCAGUC | 611 |
| CCGCCACUAUAACAAAUCAG | 612 |
| CAGACUUCUUAGACAGCCGC | 613 |
| UCAGACUUCUUAGACAGCCG | 614 |
| UUCAGACUUCUUAGACAGCC | 615 |
| AUUCAGACUUCUUAGACAGC | 616 |
| GUCAGAUAGAUUCAGACUUC | 617 |
| CUGUCAGAUAGAUUCAGACU | 618 |
| UCCUGUCAGAUAGAUUCAGA | 619 |
| CUCCUGUCAGAUAGAUUCAG | 620 |
| ACUCCUGUCAGAUAGAUUCA | 621 |
| UACUCCUGUCAGAUAGAUUC | 622 |
| GAUACUCCUGUCAGAUAGAU | 623 |
| AGAUACUCCUGUCAGAUAGA | 624 |
| CCACGUAACAGAUACUCCUG | 625 |
| GCCACGUAACAGAUACUCCU | 626 |
| GGCCACGUAACAGAUACUCC | 627 |
| GGGCCACGUAACAGAUACUC | 628 |
| AGGGCCACGUAACAGAUACU | 629 |
| GAGGGCCACGUAACAGAUAC | 630 |
| UGAGGGCCACGUAACAGAUA | 631 |
| AUGAGGGCCACGUAACAGAU | 632 |
| UAUGAGGGCCACGUAACAGA | 633 |

TABLE 1-continued

| Sequence | SEQ ID NO: |
|---|---|
| GUAUGAGGGCCACGUAACAG | 634 |
| UGUAUGAGGGCCACGUAACA | 635 |
| GUGUAUGAGGGCCACGUAAC | 636 |
| AGUGUAUGAGGGCCACGUAA | 637 |
| UACAGUGUAUGAGGGCCACG | 638 |
| UUACAGUGUAUGAGGGCCAC | 639 |
| GUUACAGUGUAUGAGGGCCA | 640 |
| AUGUUACAGUGUAUGAGGGC | 641 |
| AACAGGUGGUUUCAGGUUAA | 642 |
| ACGUUCCAACAGGUGGUUUC | 643 |
| GACGUUCCAACAGGUGGUUU | 644 |
| GGACGUUCCAACAGGUGGUU | 645 |
| GGGACGUUCCAACAGGUGGU | 646 |
| UGGGACGUUCCAACAGGUGG | 647 |
| GUGGGACGUUCCAACAGGUG | 648 |
| AGUGGGACGUUCCAACAGGU | 649 |
| UAGUGGGACGUUCCAACAGG | 650 |
| UUAGUGGGACGUUCCAACAG | 651 |
| AUUAGUGGGACGUUCCAACA | 652 |
| CAUUAGUGGGACGUUCCAAC | 653 |
| GCAUUAGUGGGACGUUCCAA | 654 |
| AGCAUUAGUGGGACGUUCCA | 655 |
| UAGCAUUAGUGGGACGUUCC | 656 |
| AUAGCAUUAGUGGGACGUUC | 657 |
| GAUAGCAUUAGUGGGACGUU | 658 |
| GGAUAGCAUUAGUGGGACGU | 659 |
| UGGAUAGCAUUAGUGGGACG | 660 |
| CUGGAUAGCAUUAGUGGGAC | 661 |
| CCUGGAUAGCAUUAGUGGGA | 662 |
| ACCUGGAUAGCAUUAGUGGG | 663 |
| CACCUGGAUAGCAUUAGUGG | 664 |
| UCACCUGGAUAGCAUUAGUG | 665 |
| UUCACCUGGAUAGCAUUAGU | 666 |
| CUUCACCUGGAUAGCAUUAG | 667 |
| CCUUCACCUGGAUAGCAUUA | 668 |
| CCCUUCACCUGGAUAGCAUU | 669 |
| AGCCCUUCACCUGGAUAGCA | 670 |
| AAGCCCUUCACCUGGAUAGC | 671 |
| GAAGCCCUUCACCUGGAUAG | 672 |

TABLE 1-continued

| Sequence | SEQ ID NO: |
|---|---|
| UACUAGCGGUGGAGCAGAGG | 673 |
| UUACUAGCGGUGGAGCAGAG | 674 |
| UUUACUAGCGGUGGAGCAGA | 675 |
| CUUUACUAGCGGUGGAGCAG | 676 |
| GCUUUACUAGCGGUGGAGCA | 677 |
| GGCUUUACUAGCGGUGGAGC | 678 |
| UGGCUUUACUAGCGGUGGAG | 679 |
| UUGGCUUUACUAGCGGUGGA | 680 |
| UUUGGCUUUACUAGCGGUGG | 681 |
| UUUUGGCUUUACUAGCGGUG | 682 |
| AUUUUGGCUUUACUAGCGGU | 683 |
| UAUUUUGGCUUUACUAGCGG | 684 |
| GUAUUUUGGCUUUACUAGCG | 685 |
| GGGUGUAUUUUGGCUUUACU | 686 |
| UUGGGAGAGGUGGAUAUGGG | 687 |
| UGCAUUUGGGAGAGGUGGAU | 688 |
| CAGUGUCUGCAUUUGGGAGA | 689 |
| UACCCAUCAGUGUCUGCAUU | 690 |
| AUUACCCAUCAGUGUCUGCA | 691 |
| AAUUACCCAUCAGUGUCUGC | 692 |
| CUACCCUGGGAUUCUCAGUG | 693 |
| UUCUACCCUGGGAUUCUCAG | 694 |
| UUUCUACCCUGGGAUUCUCA | 695 |
| AUUUCUACCCUGGGAUUCUC | 696 |
| UAUUUCUACCCUGGGAUUCU | 697 |
| UUAUUUCUACCCUGGGAUUC | 698 |
| CUUUAUUUCUACCCUGGGAU | 699 |
| AGCCUUUAUUUCUACCCUGG | 700 |
| ACUGAGCCUUUAUUUCUACC | 701 |
| GACUGAGCCUUUAUUUCUAC | 702 |
| GUUUAGAGACUGAGCCUUUA | 703 |
| UGUUUAGAGACUGAGCCUUU | 704 |
| GUGUUUAGAGACUGAGCCUU | 705 |
| GAGUGUUUAGAGACUGAGCC | 706 |
| UGAGUGUUUAGAGACUGAGC | 707 |
| UUGAGUGUUUAGAGACUGAG | 708 |
| AGUUGAGUGUUUAGAGACUG | 709 |
| GAGUUGAGUGUUUAGAGACU | 710 |
| UGAGUUGAGUGUUUAGAGAC | 711 |

TABLE 1-continued

| Sequence | SEQ ID NO: |
|---|---|
| UCUGAGUUGAGUGUUUAGAG | 712 |
| CCAUCUGAGUUGAGUGUUUA | 713 |
| UCCAUCUGAGUUGAGUGUUU | 714 |
| GCUCCAUCUGAGUUGAGUGU | 715 |
| ACCCAGUGGCUCCAUCUGAG | 716 |
| UUUAGACCCAGUGGCUCCAU | 717 |
| AUUUAGACCCAGUGGCUCCA | 718 |
| CAUUUAGACCCAGUGGCUCC | 719 |
| UGAGCAUUUAGACCCAGUGG | 720 |
| GUGAGCAUUUAGACCCAGUG | 721 |
| GGUGAGCAUUUAGACCCAGU | 722 |
| ACAGGGUGAGCAUUUAGACC | 723 |
| ACCACAGGGUGAGCAUUUAG | 724 |
| AAACCACAGGGUGAGCAUUU | 725 |
| GAACAAACCACAGGGUGAGC | 726 |
| AGAACAAACCACAGGGUGAG | 727 |
| AAGAGAACAAACCACAGGGU | 728 |
| GAGCAGUCGUAGAUGGCAUC | 729 |
| AGAGCAGUCGUAGAUGGCAU | 730 |
| AAGAGCAGUCGUAGAUGGCA | 731 |
| GAAGAGCAGUCGUAGAUGGC | 732 |
| GGAAGAGCAGUCGUAGAUGG | 733 |
| GGGAAGAGCAGUCGUAGAUG | 734 |
| AGGGAAGAGCAGUCGUAGAU | 735 |
| GAGGGAAGAGCAGUCGUAGA | 736 |
| GGUAGUUCUUCUGGUAGAGG | 737 |
| AGCUUAUACACUCCAGAGAU | 738 |
| GAAGUCAUCAGGAGGAAGCU | 739 |
| GGAAGUCAUCAGGAGGAAGC | 740 |
| GCCCAGGAAGUCAUCAGGAG | 741 |
| GCUGCCCAGGAAGUCAUCAG | 742 |
| AGUUCAGGGCUGCCCAGGAA | 743 |
| CUCACCUCCAGUUCAGGGCU | 744 |
| ACCUCACCUCCAGUUCAGGG | 745 |
| UAAUGACCUCACCUCCAGUU | 746 |
| GUAAUGACCUCACCUCCAGU | 747 |
| CUGUAAUGACCUCACCUCCA | 748 |
| UGACUGUAAUGACCUCACCU | 749 |
| CCAGUGACUGUAAUGACCUC | 750 |
| GACAGGUAUUAGGGCAUGGC | 751 |
| GGACAGGUAUUAGGGCAUGG | 752 |
| AGGACAGGUAUUAGGGCAUG | 753 |
| AAGGACAGGUAUUAGGGCAU | 754 |
| GGCCCUGUUGUUGUAGUCCC | 755 |
| UGGCCCUGUUGUUGUAGUCC | 756 |
| AUGGCCCUGUUGUUGUAGUC | 757 |
| AAUGGCCCUGUUGUUGUAGU | 758 |
| GAAUGGCCCUGUUGUUGUAG | 759 |
| GUGAAUGGCCCUGUUGUUGU | 760 |
| UGUGAAUGGCCCUGUUGUUG | 761 |
| ACUGUGAAUGGCCCUGUUGU | 762 |
| UUAAACUGUGAAUGGCCCUG | 763 |
| CAGCCGAAUUUUCCUUUCUU | 764 |
| CCCAGCCGAAUUUUCCUUUC | 765 |
| CCAUAGUGCUGGGAUUACAG | 766 |
| AAGUGAUCCACCUGCCUCGG | 767 |
| GAAGUGAUCCACCUGCCUCG | 768 |
| UGAAGUGAUCCACCUGCCUC | 769 |
| CUGAAGUGAUCCACCUGCCU | 770 |
| CCUGAAGUGAUCCACCUGCC | 771 |
| ACCUGAAGUGAUCCACCUGC | 772 |
| GGCCAGGCUGGUCUUAAACU | 773 |
| AGGGUUUCACCAUGUUGGCC | 774 |
| CAGGGUUUCACCAUGUUGGC | 775 |
| ACAGGGUUUCACCAUGUUGG | 776 |
| GACAGGGUUUCACCAUGUUG | 777 |
| AGACAGGGUUUCACCAUGUU | 778 |
| GAGACAGGGUUUCACCAUGU | 779 |
| AGAGACAGGGUUUCACCAUG | 780 |
| UAGAGACAGGGUUUCACCAU | 781 |
| GUAGAGACAGGGUUUCACCA | 782 |
| CACCAUGCCUGGCUAAUUUU | 783 |
| CCACCAUGCCUGGCUAAUUU | 784 |
| ACCACCAUGCCUGGCUAAUU | 785 |
| CACCACCAUGCCUGGCUAAU | 786 |
| CCACCACCAUGCCUGGCUAA | 787 |
| AACCUCUGCCUCCUGAGUUC | 788 |
| CAACCUCUGCCUCCUGAGUU | 789 |

TABLE 1-continued

| Sequence | SEQ ID NO: |
|---|---|
| GCAACCUCUGCCUCCUGAGU | 790 |
| UGCAACCUCUGCCUCCUGAG | 791 |
| CUGCAACCUCUGCCUCCUGA | 792 |
| ACUGCAACCUCUGCCUCCUG | 793 |
| CACUGCAACCUCUGCCUCCU | 794 |
| UCACUGCAACCUCUGCCUCC | 795 |
| CUCACUGCAACCUCUGCCUC | 796 |
| GCUCACUGCAACCUCUGCCU | 797 |
| UCGGCUCACUGCAACCUCUG | 798 |
| CUCGGCUCACUGCAACCUCU | 799 |
| UCUCGGCUCACUGCAACCUC | 800 |
| AUCUCGGCUCACUGCAACCU | 801 |
| GAUCUCGGCUCACUGCAACC | 802 |
| UGAUCUCGGCUCACUGCAAC | 803 |
| AGUGGCGUGAUCUCGGCUCA | 804 |
| AGUGCAGUGGCGUGAUCUCG | 805 |
| UAGUGCAGUGGCGUGAUCUC | 806 |
| AUAGUGCAGUGGCGUGAUCU | 807 |
| UAUAGUGCAGUGGCGUGAUC | 808 |
| UUAUAGUGCAGUGGCGUGAU | 809 |
| AUUAUAGUGCAGUGGCGUGA | 810 |
| GAUUAUAGUGCAGUGGCGUG | 811 |
| CAGAUUAUAGUGCAGUGGCG | 812 |
| GUCUCCCAGAUUAUAGUGCA | 813 |
| UGUCUCCCAGAUUAUAGUGC | 814 |
| UUGUCUCCCAGAUUAUAGUG | 815 |
| GCUUGUGUUUGAGUUUUCCU | 816 |
| UGCUUGUGUUUGAGUUUUCC | 817 |
| GGUGUUUGGUGUGUUUGCUU | 818 |
| CUGUGGUGUUUGGUGUGUUU | 819 |
| AGCUCUGUGGUGUUUGGUGU | 820 |
| AUAGCUCUGUGGUGUUUGGU | 821 |
| UUGCAUAGCUCUGUGGUGUU | 822 |
| UUUGCAUAGCUCUGUGGUGU | 823 |
| GUUUGCAUAGCUCUGUGGUG | 824 |
| GAGUGUUUGCAUAGCUCUGU | 825 |
| CUGAGUGUUUGCAUAGCUCU | 826 |
| ACUGAGUGUUUGCAUAGCUC | 827 |
| UGCAGGGCAUAAACUGAGUG | 828 |
| AGUGCAGGGCAUAAACUGAG | 829 |
| GAGUGCAGGGCAUAAACUGA | 830 |
| GGAGUGCAGGGCAUAAACUG | 831 |
| UGGAGUGCAGGGCAUAAACU | 832 |
| AUGCCUGGGUUUGGAGUGCA | 833 |
| GCCAAACAGAUGCCUGGGUU | 834 |
| AAUAGCUGUUCUAGGACAUG | 835 |
| GAAUAGCUGUUCUAGGACAU | 836 |
| CAAGGAAUAGCUGUUCUAGG | 837 |
| CCCAAGGAAUAGCUGUUCUA | 838 |
| CCUUCGUGUUUUCUUUUCUC | 839 |
| GCCUUCGUGUUUUCUUUUCU | 840 |
| UGCCUUCGUGUUUUCUUUUC | 841 |
| CUGCCUUCGUGUUUUCUUUU | 842 |
| GCUGCCUUCGUGUUUUCUUU | 843 |
| UGCUGCCUUCGUGUUUUCUU | 844 |
| AUGCUGCCUUCGUGUUUUCU | 845 |
| UUGAUGCUGCCUUCGUGUUU | 846 |
| UUUGAUGCUGCCUUCGUGUU | 847 |
| AUUUGAUGCUGCCUUCGUGU | 848 |
| AUAAUUUGAUGCUGCCUUCG | 849 |
| GAUAAUUUGAUGCUGCCUUC | 850 |
| CAGAUAAUUUGAUGCUGCCU | 851 |
| CCAGAUAAUUUGAUGCUGCC | 852 |
| UCCAGAUAAUUUGAUGCUGC | 853 |
| ACCAUGCCUGGGUGAAAAUC | 854 |
| GGAUUACAGGUGUGAGCCAC | 855 |
| GGGAUUACAGGUGUGAGCCA | 856 |
| UGGGAUUACAGGUGUGAGCC | 857 |
| UUGGGAUUACAGGUGUGAGC | 858 |
| CUUGGGAUUACAGGUGUGAG | 859 |
| ACUUGGGAUUACAGGUGUGA | 860 |
| AACUUGGGAUUACAGGUGUG | 861 |
| AAACUUGGGAUUACAGGUGU | 862 |
| AAAACUUGGGAUUACAGGUG | 863 |
| CCUCAGGUGAUUGUUCCGCC | 864 |
| ACCUCAGGUGAUUGUUCCGC | 865 |
| GACCUCAGGUGAUUGUUCCG | 866 |
| UGACCUCAGGUGAUUGUUCC | 867 |

TABLE 1-continued

| Sequence | SEQ ID NO: |
|---|---|
| CUGACCUCAGGUGAUUGUUC | 868 |
| CAGGCUGGUCUCAAAGUCCU | 869 |
| CCAGGCUGGUCUCAAAGUCC | 870 |
| GCCAGGCUGGUCUCAAAGUC | 871 |
| GGCCAGGCUGGUCUCAAAGU | 872 |
| AGUAGCUGGGACCAGAGUGC | 873 |
| UUCCAGUGAUUCUCCUGCCU | 874 |
| GUUCCAGUGAUUCUCCUGCC | 875 |
| AACCUCCACCUCCUGAGUUC | 876 |
| CAACCUCCACCUCCUGAGUU | 877 |
| GCAACCUCCACCUCCUGAGU | 878 |
| UGCAACCUCCACCUCCUGAG | 879 |
| CUGCAACCUCCACCUCCUGA | 880 |
| ACUGCAACCUCCACCUCCUG | 881 |
| CACUGCAACCUCCACCUCCU | 882 |
| UCACUGCAACCUCCACCUCC | 883 |
| CUCACUGCAACCUCCACCUC | 884 |
| GCUCACUGCAACCUCCACCU | 885 |
| UCGGCUCACUGCAACCUCCA | 886 |
| UCUCGGCUCACUGCAACCUC | 887 |
| AUCUCGGCUCACUGCAACCU | 888 |
| AAUCUCGGCUCACUGCAACC | 889 |
| CAAUCUCGGCUCACUGCAAC | 890 |
| GCAAUCUCGGCUCACUGCAA | 891 |
| GUGCAAUCUCGGCUCACUGC | 892 |
| GGUGCAAUCUCGGCUCACUG | 893 |
| UGGUGCAAUCUCGGCUCACU | 894 |
| GUGGUGCAAUCUCGGCUCAC | 895 |
| AGUGGUGCAAUCUCGGCUCA | 896 |
| CAGUGGUGCAAUCUCGGCUC | 897 |
| ACAGUGGUGCAAUCUCGGCU | 898 |
| UACAGUGGUGCAAUCUCGGC | 899 |
| GUACAGUGGUGCAAUCUCGG | 900 |
| AGUACAGUGGUGCAAUCUCG | 901 |
| GAGUACAGUGGUGCAAUCUC | 902 |
| UGCCCAGGCUAGAGUACAGU | 903 |
| UUGCCCAGGCUAGAGUACAG | 904 |
| AGAACGAUGCAAAUUGGGCC | 905 |
| AAGAACGAUGCAAAUUGGGC | 906 |

TABLE 1-continued

| Sequence | SEQ ID NO: |
|---|---|
| GAAGAACGAUGCAAAUUGGG | 907 |
| GGAAGAACGAUGCAAAUUGG | 908 |
| UGGAAGAACGAUGCAAAUUG | 909 |
| CUGGAAGAACGAUGCAAAUU | 910 |
| UCUGGAAGAACGAUGCAAAU | 911 |
| CUCUGGAAGAACGAUGCAAA | 912 |
| GCUCUGGAAGAACGAUGCAA | 913 |
| UGCUCUGGAAGAACGAUGCA | 914 |
| UUGCUCUGGAAGAACGAUGC | 915 |
| GCAUUGCUCUGGAAGAACGA | 916 |
| UGCAUUGCUCUGGAAGAACG | 917 |
| GUGCAUUGCUCUGGAAGAAC | 918 |
| UGGGUGGUGCAUUGCUCUGG | 919 |
| AGUCACACUGGCUCACUCGG | 920 |
| UGCACUCCCGCAGUCACACU | 921 |
| AGAGCCAGUAGAUGUGUGCA | 922 |
| UGCAGAGCCAGUAGAUGUGU | 923 |
| AACCUGUUCCUGUCCCUGCA | 924 |
| CAACCUGUUCCUGUCCCUGC | 925 |
| CCAACCUGUUCCUGUCCCUG | 926 |
| CCCAACCUGUUCCUGUCCCU | 927 |
| AAGAGGGCAGGCUUCCCAAC | 928 |
| AGGAGCAAGAGGGCAGGCUU | 929 |
| CAGAAGGCAGGAGCAAGAGG | 930 |
| CUCUGGUGAGGGACUUGCAG | 931 |
| ACUCUGGUGAGGGACUUGCA | 932 |
| UACUCUGGUGAGGGACUUGC | 933 |
| AUACUCUGGUGAGGGACUUG | 934 |
| GGGAUACUCUGGUGAGGGAC | 935 |
| CAGAACACCUGAAGCAGAGG | 936 |
| CCGCCUGAAGUCUCCAUGUC | 937 |
| UCCGCCUGAAGUCUCCAUGU | 938 |
| CUCCGCCUGAAGUCUCCAUG | 939 |
| CCUCCGCCUGAAGUCUCCAU | 940 |
| AGAAGGAGACAAGGCCACUU | 941 |
| UAGAAGGAGACAAGGCCACU | 942 |
| UCCCGGUAGAAGGAGACAAG | 943 |
| GUCCCGGUAGAAGGAGACAA | 944 |
| AGUCCCGGUAGAAGGAGACA | 945 |

TABLE 1-continued

| Sequence | SEQ ID NO: |
|---|---|
| CAGUCCCGGUAGAAGGAGAC | 946 |
| CCAGUCCCGGUAGAAGGAGA | 947 |
| UCCAGUCCCGGUAGAAGGAG | 948 |
| UUCCAGUCCCGGUAGAAGGA | 949 |
| UGCUUCCAGUCCCGGUAGAA | 950 |
| CUGCUUCCAGUCCCGGUAGA | 951 |
| CCUGCUUGUACUGCUUCCAG | 952 |
| CCCUGCUUGUACUGCUUCCA | 953 |
| GAUGCUGCCAAAGCCCUGCU | 954 |
| ACGGAUGCUGCCAAAGCCCU | 955 |
| CGGUGGAUGUGUUCGUUCCC | 956 |
| CCGGUGGAUGUGUUCGUUCC | 957 |
| GCCGGUGGAUGUGUUCGUUC | 958 |
| AGCCGGUGGAUGUGUUCGUU | 959 |
| GAGCCGGUGGAUGUGUUCGU | 960 |
| AGAGCCGGUGGAUGUGUUCG | 961 |
| GAGAGCCGGUGGAUGUGUUC | 962 |
| GGAGAGCCGGUGGAUGUGUU | 963 |
| UGGAGAGCCGGUGGAUGUGU | 964 |
| UCUGGAGAGCCGGUGGAUGU | 965 |
| UGUCUGGAGAGCCGGUGGAU | 966 |
| UGUGCUUACCUCCAUCUCUA | 967 |
| UUGUGCUUACCUCCAUCUCU | 968 |
| CCGGAGUUGUACGCGGUCAU | 969 |
| UCAGAAUAGGAAUGGCACCC | 970 |
| AUCAGAAUAGGAAUGGCACC | 971 |
| AAUCAGAAUAGGAAUGGCAC | 972 |
| GAAUCAGAAUAGGAAUGGCA | 973 |
| GCAGGAAAACCAUCACAAUG | 974 |
| UGCAGGAAAACCAUCACAAU | 975 |
| UUGCAGGAAAACCAUCACAA | 976 |
| UUACAACUUGCAGGAAAACC | 977 |
| CUCCAUUACAACUUGCAGGA | 978 |
| ACUCCAUUACAACUUGCAGG | 979 |
| AACUCCAUUACAACUUGCAG | 980 |
| CAACUCCAUUACAACUUGCA | 981 |
| CCUCAACUCCAUUACAACUU | 982 |
| UCCUCAACUCCAUUACAACU | 983 |
| UUCCUCAACUCCAUUACAAC | 984 |
| UCUACUCUGGCCUGGGUCUG | 985 |
| UGAAUUUGCUCUACUCUGGC | 986 |
| UUGAAUUUGCUCUACUCUGG | 987 |
| GUUGAAUUUGCUCUACUCUG | 988 |
| UCGGCCAGAGCAGAGACUAG | 989 |
| CUCGGCCAGAGCAGAGACUA | 990 |
| AAGGACCUCAUGCUCGGCCA | 991 |
| AAAGGACCUCAUGCUCGGCC | 992 |
| UAAAGGACCUCAUGCUCGGC | 993 |
| CUAAAGGACCUCAUGCUCGG | 994 |
| CCUAAAGGACCUCAUGCUCG | 995 |
| ACCUAAAGGACCUCAUGCUC | 996 |
| CACCUAAAGGACCUCAUGCU | 997 |
| GCACCUAAAGGACCUCAUGC | 998 |
| UGCACCUAAAGGACCUCAUG | 999 |
| UUGCACCUAAAGGACCUCAU | 1000 |
| AUUUGCACCUAAAGGACCUC | 1001 |
| GAUUUGCACCUAAAGGACCU | 1002 |
| AGAUUUGCACCUAAAGGACC | 1003 |
| AAGAUUUGCACCUAAAGGAC | 1004 |
| GUAAGAUUUGCACCUAAAGG | 1005 |
| GUGAGUGCUUUCAGACCUUC | 1006 |
| AGUGAGUGCUUUCAGACCUU | 1007 |
| UAGUGAGUGCUUUCAGACCU | 1008 |
| UAUAGUGAGUGCUUUCAGAC | 1009 |
| GAUAUAGUGAGUGCUUUCAG | 1010 |
| AGGAUAUAGUGAGUGCUUUC | 1011 |
| GAGGAUAUAGUGAGUGCUUU | 1012 |
| AGAGCUGCUGUAAGAGAAAC | 1013 |
| CAGAGCUGCUGUAAGAGAAA | 1014 |
| GAAUCCCACACAGAGCUGCU | 1015 |
| CUAUAUUCCUCACUUUCCUG | 1016 |
| GGCCUUGAUUAGUCUCUCUU | 1017 |
| UGGCCUUGAUUAGUCUCUCU | 1018 |
| AUGGCCUUGAUUAGUCUCUC | 1019 |
| UAUGGCCUUGAUUAGUCUCU | 1020 |
| AUAUGGCCUUGAUUAGUCUC | 1021 |
| GAACUUCUUUCCUGAUUCAC | 1022 |
| UCGAACUUCUUUCCUGAUUC | 1023 |

TABLE 1-continued

| Sequence | SEQ ID NO: |
|---|---|
| CUCGAACUUCUUUCCUGAUU | 1024 |
| GCUCGAACUUCUUUCCUGAU | 1025 |
| GGCUCGAACUUCUUUCCUGA | 1026 |
| AGGCUCGAACUUCUUUCCUG | 1027 |
| AAGGCUCGAACUUCUUUCCU | 1028 |
| CAAGGCUCGAACUUCUUUCC | 1029 |
| ACAAGGCUCGAACUUCUUUC | 1030 |
| AACAAGGCUCGAACUUCUUU | 1031 |
| AAACAAGGCUCGAACUUCUU | 1032 |
| AAAACAAGGCUCGAACUUCU | 1033 |
| GAAAACAAGGCUCGAACUUC | 1034 |
| AGAAAACAAGGCUCGAACUU | 1035 |
| AAUCAGAAAACAAGGCUCGA | 1036 |
| CCUGGGAAUCAGAAAACAAG | 1037 |
| ACCUCCAGUUUACUGUGUUA | 1038 |
| UUACCUCCAGUUUACUGUGU | 1039 |
| GUUUACCUCCAGUUUACUGU | 1040 |
| UGUUUACCUCCAGUUUACUG | 1041 |
| CUUGUUUACCUCCAGUUUAC | 1042 |
| AGUCCCAUAGCCAAACAUCU | 1043 |
| CAGUCCCAUAGCCAAACAUC | 1044 |
| ACAGUCCCAUAGCCAAACAU | 1045 |
| GACAGUCCCAUAGCCAAACA | 1046 |
| UGACAGUCCCAUAGCCAAAC | 1047 |
| CUGACAGUCCCAUAGCCAAA | 1048 |
| CCUGACAGUCCCAUAGCCAA | 1049 |
| UCUCCUGACAGUCCCAUAGC | 1050 |
| CUCUCCUGACAGUCCCAUAG | 1051 |
| UCUCUCCUGACAGUCCCAUA | 1052 |
| CCUUCUCUCCUGACAGUCCC | 1053 |
| GGCUCCAUUUCAUGCUGUCU | 1054 |
| AGGCUCCAUUUCAUGCUGUC | 1055 |
| GCAGGCUCCAUUUCAUGCUG | 1056 |
| GCAGCAGGCUCCAUUUCAUG | 1057 |
| AAGUGCAGCAGGCUCCAUUU | 1058 |
| AAAGUGCAGCAGGCUCCAUU | 1059 |
| GAAAGUGCAGCAGGCUCCAU | 1060 |
| AGAAAGUGCAGCAGGCUCCA | 1061 |
| AAGAAAGUGCAGCAGGCUCC | 1062 |
| UAAAGAAAGUGCAGCAGGCU | 1063 |
| UUAAAGAAAGUGCAGCAGGC | 1064 |
| CUUAAAGAAAGUGCAGCAGG | 1065 |
| GCCUUAAAGAAAGUGCAGCA | 1066 |
| AGCCUUAAAGAAAGUGCAGC | 1067 |
| AGCAGAGCCUUAAAGAAAGU | 1068 |
| GAGCAGAGCCUUAAAGAAAG | 1069 |
| AGGAGCAGAGCCUUAAAGAA | 1070 |
| GAGGAGCAGAGCCUUAAAGA | 1071 |
| AGGAGGAGCAGAGCCUUAAA | 1072 |
| UCAGGAGGAGCAGAGCCUUA | 1073 |
| UUGCCCUCCCAGUCCUGUCA | 1074 |
| ACUCAGCGUAGCGCAGGUUG | 1075 |
| UACUCAGCGUAGCGCAGGUU | 1076 |
| UAUACUCAGCGUAGCGCAGG | 1077 |
| CUAUACUCAGCGUAGCGCAG | 1078 |
| ACAAAGUGGCUAUACUCAGC | 1079 |
| AACAAAGUGGCUAUACUCAG | 1080 |
| CAUUGCCCAAAACAAAGUGG | 1081 |
| GUUGAGUUCAUUGCCCAAAA | 1082 |
| UGUUGAGUUCAUUGCCCAAA | 1083 |
| CUGUUGAGUUCAUUGCCCAA | 1084 |
| GCUGUUGAGUUCAUUGCCCA | 1085 |
| CGAUAGCUGUUGAGUUCAUU | 1086 |
| GGCGAUAGCUGUUGAGUUCA | 1087 |
| AGGCGAUAGCUGUUGAGUUC | 1088 |
| GAGGCGAUAGCUGUUGAGUU | 1089 |
| AGAGGCGAUAGCUGUUGAGU | 1090 |
| AAGAGGCGAUAGCUGUUGAG | 1091 |
| GAAGAGGCGAUAGCUGUUGA | 1092 |
| GGAAGAGGCGAUAGCUGUUG | 1093 |
| AGGAAGAGGCGAUAGCUGUU | 1094 |
| CAGGAAGAGGCGAUAGCUGU | 1095 |
| CCAGGAAGAGGCGAUAGCUG | 1096 |
| CCCAGGAAGAGGCGAUAGCU | 1097 |
| ACAUUGCCAGUGUAGUUCCC | 1098 |
| CACAUUGCCAGUGUAGUUCC | 1099 |
| CCACAUUGCCAGUGUAGUUC | 1100 |
| CCCACAUUGCCAGUGUAGUU | 1101 |

TABLE 1-continued

| Sequence | SEQ ID NO: |
|---|---|
| AUACUGGAGGGCGUCGUUCC | 1102 |
| GAUACUGGAGGGCGUCGUUC | 1103 |
| UGAUACUGGAGGGCGUCGUU | 1104 |
| AUGAUACUGGAGGGCGUCGU | 1105 |
| UAUGAUACUGGAGGGCGUCG | 1106 |
| UUGUUAUGAUACUGGAGGGC | 1107 |
| GUUGUUAUGAUACUGGAGGG | 1108 |
| UGUUGUUAUGAUACUGGAGG | 1109 |
| CUGUGUUGUUAUGAUACUGG | 1110 |
| GCUGUGUUGUUAUGAUACUG | 1111 |
| GGCUGUGUUGUUAUGAUACU | 1112 |
| AGGCUGUGUUGUUAUGAUAC | 1113 |
| GAAGGCUGUGUUGUUAUGAU | 1114 |
| UGAAGGCUGUGUUGUUAUGA | 1115 |
| CUGAAGGCUGUGUUGUUAUG | 1116 |
| GCUGAAGGCUGUGUUGUUAU | 1117 |
| UGCUGAAGGCUGUGUUGUUA | 1118 |
| UGUCCUUGUCCUUGGUGCUG | 1119 |
| UUGUCCUUGUCCUUGGUGCU | 1120 |
| GCAGUUGUCAUUGUCCUUGU | 1121 |
| CCAAGCAGUUGUCAUUGUCC | 1122 |
| UCCAAGCAGUUGUCAUUGUC | 1123 |
| UGUCCAAGCAGUUGUCAUUG | 1124 |
| UUGUCCAAGCAGUUGUCAUU | 1125 |
| CUUGUCCAAGCAGUUGUCAU | 1126 |
| ACUUGUCCAAGCAGUUGUCA | 1127 |
| CACUUGUCCAAGCAGUUGUC | 1128 |
| ACACUUGUCCAAGCAGUUGU | 1129 |
| CACACUUGUCCAAGCAGUUG | 1130 |
| GCACACUUGUCCAAGCAGUU | 1131 |
| UGCACACUUGUCCAAGCAGU | 1132 |
| CACCUUUGCGGAGCUGUGCA | 1133 |
| UCACCUUUGCGGAGCUGUGC | 1134 |
| CUCACCUUUGCGGAGCUGUG | 1135 |
| UCUCACCUUUGCGGAGCUGU | 1136 |
| AUCUCACCUUUGCGGAGCUG | 1137 |
| AAUCUCACCUUUGCGGAGCU | 1138 |
| AAAUCUCACCUUUGCGGAGC | 1139 |
| AGCUUGUACCUGAACUUCUC | 1140 |
| GAGCUUGUACCUGAACUUCU | 1141 |
| UGAGCUUGUACCUGAACUUC | 1142 |
| UAUGAGCUUGUACCUGAACU | 1143 |
| UUAUGAGCUUGUACCUGAAC | 1144 |
| GGAUUAUGAGCUUGUACCUG | 1145 |
| GGGAUUAUGAGCUUGUACCU | 1146 |
| UGGGAUUAUGAGCUUGUACC | 1147 |
| GUGGGAUUAUGAGCUUGUAC | 1148 |
| AGUGGGAUUAUGAGCUUGUA | 1149 |
| UCAAGUGGGAUUAUGAGCUU | 1150 |
| CUCUUUCUCCUCAAGUGGGA | 1151 |
| AACCGGAAUAUCAACUGUAC | 1152 |
| CAAAACCGGAAUAUCAACUG | 1153 |
| CCAAAACCGGAAUAUCAACU | 1154 |
| ACCAAAACCGGAAUAUCAAC | 1155 |
| GAAAGAAUACCAAAACCGGA | 1156 |
| GGGUCAGAAAGAAUACCAAA | 1157 |
| AGGGUCAGAAAGAAUACCAA | 1158 |
| ACCAGACAUCAGGUAAGGAG | 1159 |
| GACCAGACAUCAGGUAAGGA | 1160 |
| AGACCAGACAUCAGGUAAGG | 1161 |
| AUAGACCAGACAUCAGGUAA | 1162 |
| GAUAGACCAGACAUCAGGUA | 1163 |
| ACUGUGAUAGACCAGACAUC | 1164 |
| GACUGUGAUAGACCAGACAU | 1165 |
| UGACUGUGAUAGACCAGACA | 1166 |
| UUGACUGUGAUAGACCAGAC | 1167 |
| GUUGACUGUGAUAGACCAGA | 1168 |
| AGUUGACUGUGAUAGACCAG | 1169 |
| AAGUUGACUGUGAUAGACCA | 1170 |
| GCUAGUAAGUUGACUGUGAU | 1171 |
| UGCUAGUAAGUUGACUGUGA | 1172 |
| GUGCUAGUAAGUUGACUGUG | 1173 |
| AGUGCUAGUAAGUUGACUGU | 1174 |
| GACCCAGUGCUAGUAAGUUG | 1175 |
| AGACCCAGUGCUAGUAAGUU | 1176 |
| CAGACCCAGUGCUAGUAAGU | 1177 |
| ACAGACCCAGUGCUAGUAAG | 1178 |
| AACAGACCCAGUGCUAGUAA | 1179 |

TABLE 1-continued

| Sequence | SEQ ID NO: |
|---|---|
| AAACAGACCCAGUGCUAGUA | 1180 |
| GAAACAGACCCAGUGCUAGU | 1181 |
| CAUGAGAAACAGACCCAGUG | 1182 |
| GCCACCUGGCAUGAGAAACA | 1183 |
| AGCCACCUGGCAUGAGAAAC | 1184 |
| UAGCCACCUGGCAUGAGAAA | 1185 |
| AGUAGCCACCUGGCAUGAGA | 1186 |
| CAGUAGCCACCUGGCAUGAG | 1187 |
| GUUGUACCAGUAGCCACCUG | 1188 |
| AGUUGUACCAGUAGCCACCU | 1189 |
| CAGCAGUUGUACCAGUAGCC | 1190 |
| GCAGCAGUUGUACCAGUAGC | 1191 |
| GUGCAGCAGUUGUACCAGUA | 1192 |
| UGUGCAGCAGUUGUACCAGU | 1193 |
| CUGUGCAGCAGUUGUACCAG | 1194 |
| UCUGUGCAGCAGUUGUACCA | 1195 |
| GUCUGUGCAGCAGUUGUACC | 1196 |
| AGUCUGUGCAGCAGUUGUAC | 1197 |
| GAGUCUGUGCAGCAGUUGUA | 1198 |
| GGAGUCUGUGCAGCAGUUGU | 1199 |
| UUGGAGUCUGUGCAGCAGUU | 1200 |
| GUUGGAGUCUGUGCAGCAGU | 1201 |
| GAGGUUGGAGUCUGUGCAGC | 1202 |
| AUUGAGGUUGGAGUCUGUGC | 1203 |
| CAUUGAGGUUGGAGUCUGUG | 1204 |
| CCAUUGAGGUUGGAGUCUGU | 1205 |
| GUACACUCCAUUGAGGUUGG | 1206 |
| UAGUACACUCCAUUGAGGUU | 1207 |
| GGUAGUACACUCCAUUGAGG | 1208 |
| CGGUAGUACACUCCAUUGAG | 1209 |
| GCGGUAGUACACUCCAUUGA | 1210 |
| GGCGGUAGUACACUCCAUUG | 1211 |
| AGGCGGUAGUACACUCCAUU | 1212 |
| CAGGCGGUAGUACACUCCAU | 1213 |
| CCAGGCGGUAGUACACUCCA | 1214 |
| CUCACCCAGGCGGUAGUACA | 1215 |
| UGCUCACCCAGGCGGUAGUA | 1216 |
| GCUUAUUGUGCUCACCCAGG | 1217 |
| UGCUUAUUGUGCUCACCCAG | 1218 |

TABLE 1-continued

| Sequence | SEQ ID NO: |
|---|---|
| GUGCUUAUUGUGCUCACCCA | 1219 |
| CCAGGUGCUUAUUGUGCUCA | 1220 |
| UCCAGGUGCUUAUUGUGCUC | 1221 |
| CCAUCCAGGUGCUUAUUGUG | 1222 |
| GCCAUCCAGGUGCUUAUUGU | 1223 |
| UGCCAUCCAGGUGCUUAUUG | 1224 |
| AUGCCAUCCAGGUGCUUAUU | 1225 |
| GAUGCCAUCCAGGUGCUUAU | 1226 |
| UGAUGCCAUCCAGGUGCUUA | 1227 |
| ACCAGGUGAUGCCAUCCAGG | 1228 |
| UACCAGGUGAUGCCAUCCAG | 1229 |
| UAGGUAGAUCCAUGCCAGCC | 1230 |
| GUAGGUAGAUCCAUGCCAGC | 1231 |
| GAGUAGGUAGAUCCAUGCCA | 1232 |
| GGAGUAGGUAGAUCCAUGCC | 1233 |
| GGGAGUAGGUAGAUCCAUGC | 1234 |
| AGGGAGUAGGUAGAUCCAUG | 1235 |
| GAGGGAGUAGGUAGAUCCAU | 1236 |
| UGAGGGAGUAGGUAGAUCCA | 1237 |
| UUGAGGGAGUAGGUAGAUCC | 1238 |
| UUUGAGGGAGUAGGUAGAUC | 1239 |
| CGUUUGAGGGAGUAGGUAGA | 1240 |
| CCGUUUGAGGGAGUAGGUAG | 1241 |
| CCCGUUUGAGGGAGUAGGUA | 1242 |
| ACCCGUUUGAGGGAGUAGGU | 1243 |
| CACCCGUUUGAGGGAGUAGG | 1244 |
| CCACCCGUUUGAGGGAGUAG | 1245 |
| UCCACCCGUUUGAGGGAGUA | 1246 |
| AUCUCCACCCGUUUGAGGGA | 1247 |
| CAUCUCCACCCGUUUGAGGG | 1248 |
| UCAUCUCCACCCGUUUGAGG | 1249 |
| UUCAUCUCCACCCGUUUGAG | 1250 |
| UUUCAUCUCCACCCGUUUGA | 1251 |
| UUUUCAUCUCCACCCGUUUG | 1252 |
| AUUUUCAUCUCCACCCGUUU | 1253 |
| GGCGGAUUUUCAUCUCCACC | 1254 |
| GGCUUGAAGUCUUCGGGCG | 1255 |
| AAGGCUUGAAGUCUUCUGGG | 1256 |
| CCUUUUAAGGCUUGAAGUCU | 1257 |

TABLE 1-continued

| Sequence | SEQ ID NO: |
|---|---|
| CUCCUUUUAAGGCUUGAAGU | 1258 |
| CCUCCUUUUAAGGCUUGAAG | 1259 |
| ACGGCAGCCUCCUUUUAAGG | 1260 |
| CACGGCAGCCUCCUUUUAAG | 1261 |
| CUCCACGGCAGCCUCCUUUU | 1262 |
| UUUCUGUAUCCGUGCUCCAC | 1263 |
| AGUUUCUGUAUCCGUGCUCC | 1264 |
| CAGUUUCUGUAUCCGUGCUC | 1265 |
| CUCAGUUUCUGUAUCCGUGC | 1266 |
| UGUCUCAGUUUCUGUAUCCG | 1267 |
| UGCCCUCAUCCAGUCUCCAC | 1268 |
| AUCUGCCCUCAUCCAGUCUC | 1269 |
| CAUCUGCCCUCAUCCAGUCU | 1270 |
| UCAUCUGCCCUCAUCCAGUC | 1271 |
| CCUCAUCUGCCCUCAUCCAG | 1272 |
| CUAACACUCUCUUCCUGUCC | 1273 |
| UCUAACACUCUCUUCCUGUC | 1274 |
| UUCUAACACUCUCUUCCUGU | 1275 |
| UAUAGGCUGUUUCUCAGUCC | 1276 |
| CCUUGGAGACUUAUUCUUUC | 1277 |
| GCUCCUUGGAGACUUAUUCU | 1278 |
| UGCUCCUUGGAGACUUAUUC | 1279 |
| UUUUGUGCUCCUUGGAGACU | 1280 |
| UACUGUAACAUCCUUGGUAC | 1281 |
| GUUUACUGUAACAUCCUUGG | 1282 |
| AGGAUGUGGCAGGACCCAGU | 1283 |
| AAGGAUGUGGCAGGACCCAG | 1284 |
| GAAGGAUGUGGCAGGACCCA | 1285 |
| UGAGAAGGAUGUGGCAGGAC | 1286 |
| CAGUCUACCACCUUGAGAAG | 1287 |
| CACUCAGUCUACCACCUUGA | 1288 |
| GGAUCUUGGGCAGAGAGACC | 1289 |
| GGGAUCUUGGGCAGAGAGAC | 1290 |
| AGGGAUCUUGGGCAGAGAGA | 1291 |
| CAGGGAUCUUGGGCAGAGAG | 1292 |
| UGUCAGGGAUCUUGGGCAGA | 1293 |
| AUGUCAGGGAUCUUGGGCAG | 1294 |
| UAUGUCAGGGAUCUUGGGCA | 1295 |
| CUAUGUCAGGGAUCUUGGGC | 1296 |

TABLE 1-continued

| Sequence | SEQ ID NO: |
|---|---|
| GCUAUGUCAGGGAUCUUGGG | 1297 |
| UGCUAUGUCAGGGAUCUUGG | 1298 |
| CUGCUAUGUCAGGGAUCUUG | 1299 |
| AGCUACUGCUAUGUCAGGGA | 1300 |
| AAGCUACUGCUAUGUCAGGG | 1301 |
| AAGACAAGCUACUGCUAUGU | 1302 |
| CAUGUGGAAAAGACAAGCUA | 1303 |
| AUCAUGUGGAAAAGACAAGC | 1304 |
| GCCCUCACAUAGCCUAAGCC | 1305 |
| UUGCCCUCACAUAGCCUAAG | 1306 |
| UUUGCCCUCACAUAGCCUAA | 1307 |
| UUUUGCCCUCACAUAGCCUA | 1308 |
| GUUUUGCCCUCACAUAGCCU | 1309 |
| UGUUUUGCCCUCACAUAGCC | 1310 |
| GUGUUUUGCCCUCACAUAGC | 1311 |
| GAUUUGUGUUUUGCCCUCAC | 1312 |
| GGAUUUGUGUUUUGCCCUCA | 1313 |
| AAGGGAUUUGUGUUUUGCCC | 1314 |
| ACUCCUUUCUCUAACACUCA | 1315 |
| CACCUGCCUCCUUCACUCCU | 1316 |
| UACCAUUUCCCACCUGCCUC | 1317 |
| AUACCAUUUCCCACCUGCCU | 1318 |
| UCCAGCCUGGGUCAGUUCCA | 1319 |
| UGCAGUGCCCUGGAGUUUCC | 1320 |
| GAUGCAGUGCCCUGGAGUUU | 1321 |
| CAGAUGCAGUGCCCUGGAGU | 1322 |
| UGAUCGCCAGAUGCAGUGCC | 1323 |
| CUGAUCGCCAGAUGCAGUGC | 1324 |
| ACAUGACCAAGGCGAGCAGG | 1325 |
| UACAUGACCAAGGCGAGCAG | 1326 |
| GCUGGUGCUUCAUUCCUUUC | 1327 |
| CUGCUGGUGCUUCAUUCCUU | 1328 |
| CCUGCUGGUGCUUCAUUCCU | 1329 |
| ACUCUGUCCACCUCCUGCUG | 1330 |
| AGAGACUCUGUCCACCUCCU | 1331 |
| AUGAGAGACUCUGUCCACCU | 1332 |
| CAUCCAUGAGAGACUCUGUC | 1333 |
| GCAUCCAUGAGAGACUCUGU | 1334 |
| GGCAUCCAUGAGAGACUCUG | 1335 |

TABLE 1-continued

| Sequence | SEQ ID NO: |
|---|---|
| CCUUGAGCUUGUUUCUUACA | 1336 |
| UUCAACCAUUUCCUACAGAC | 1337 |
| CCAUCUACCUUCAGUUUUCA | 1338 |
| ACACCAUCUACCUUCAGUUU | 1339 |
| AACACCAUCUACCUUCAGUU | 1340 |
| UAACACCAUCUACCUUCAGU | 1341 |

TABLE 2

| Sequence | SEQ ID NO: |
|---|---|
| AGAAGGAGACAAGGCCACUU | 1342 |
| UAGAAGGAGACAAGGCCACU | 1343 |
| UCCCGGUAGAAGGAGACAAG | 1344 |
| GUCCCGGUAGAAGGAGACAA | 1345 |
| AGUCCCGGUAGAAGGAGACA | 1346 |
| CAGUCCCGGUAGAAGGAGAC | 1347 |
| CCAGUCCCGGUAGAAGGAGA | 1348 |
| UCCAGUCCCGGUAGAAGGAG | 1349 |
| UUCCAGUCCCGGUAGAAGGA | 1350 |
| UGCUUCCAGUCCCGGUAGAA | 1351 |
| CUGCUUCCAGUCCCGGUAGA | 1352 |
| CCUGCUUGUACUGCUUCCAG | 1353 |
| CCCUGCUUGUACUGCUUCCA | 1354 |
| GAUGCUGCCAAAGCCCUGCU | 1355 |
| ACGGAUGCUGCCAAAGCCCU | 1356 |
| CGGUGGAUGUGUUCGUUCCC | 1357 |
| CCGGUGGAUGUGUUCGUUCC | 1358 |
| GCCGGUGGAUGUGUUCGUUC | 1359 |
| AGCCGGUGGAUGUGUUCGUU | 1360 |
| GAGCCGGUGGAUGUGUUCGU | 1361 |
| AGAGCCGGUGGAUGUGUUCG | 1362 |
| GAGAGCCGGUGGAUGUGUUC | 1363 |
| GGAGAGCCGGUGGAUGUGUU | 1364 |
| UGGAGAGCCGGUGGAUGUGU | 1365 |
| UCUGGAGAGCCGGUGGAUGU | 1366 |
| UGUCUGGAGAGCCGGUGGAU | 1367 |
| UGUGCUUACCUCCAUCUCUA | 1368 |
| UUGUGCUUACCUCCAUCUCU | 1369 |
| CCGGAGUUGUACGCGGUCAU | 1370 |
| UCAGAAUAGGAAUGGCACCC | 1371 |

TABLE 2-continued

| Sequence | SEQ ID NO: |
|---|---|
| AUCAGAAUAGGAAUGGCACC | 1372 |
| AAUCAGAAUAGGAAUGGCAC | 1373 |
| GAAUCAGAAUAGGAAUGGCA | 1374 |
| GCAGGAAAACCAUCACAAUG | 1375 |
| UGCAGGAAAACCAUCACAAU | 1376 |
| UUGCAGGAAAACCAUCACAA | 1377 |
| UUACAACUUGCAGGAAAACC | 1378 |
| CUCCAUUACAACUUGCAGGA | 1379 |
| ACUCCAUUACAACUUGCAGG | 1380 |
| AACUCCAUUACAACUUGCAG | 1381 |
| CAACUCCAUUACAACUUGCA | 1382 |
| CCUCAACUCCAUUACAACUU | 1383 |
| UCCUCAACUCCAUUACAACU | 1384 |
| UUCCUCAACUCCAUUACAAC | 1385 |
| UCUACUCUGGCCUGGGUCUG | 1386 |
| UGAAUUUGCUCUACUCUGGC | 1387 |
| UUGAAUUUGCUCUACUCUGG | 1388 |
| GUUGAAUUUGCUCUACUCUG | 1389 |
| UCGGCCAGAGCAGAGACUAG | 1390 |
| CUCGGCCAGAGCAGAGACUA | 1391 |
| AAGGACCUCAUGCUCGGCCA | 1392 |
| AAAGGACCUCAUGCUCGGCC | 1393 |
| UAAAGGACCUCAUGCUCGGC | 1394 |
| CUAAAGGACCUCAUGCUCGG | 1395 |
| CCUAAAGGACCUCAUGCUCG | 1396 |
| ACCUAAAGGACCUCAUGCUC | 1397 |
| CACCUAAAGGACCUCAUGCU | 1398 |
| GCACCUAAAGGACCUCAUGC | 1399 |
| UGCACCUAAAGGACCUCAUG | 1400 |
| UUGCACCUAAAGGACCUCAU | 1401 |
| AUUUGCACCUAAAGGACCUC | 1402 |
| GAUUUGCACCUAAAGGACCU | 1403 |
| AGAUUUGCACCUAAAGGACC | 1404 |
| AAGAUUUGCACCUAAAGGAC | 1405 |
| GUAAGAUUUGCACCUAAAGG | 1406 |
| GUGAGUGCUUUCAGACCUUC | 1407 |
| AGUGAGUGCUUUCAGACCUU | 1408 |
| UAGUGAGUGCUUUCAGACCU | 1409 |
| UAUAGUGAGUGCUUUCAGAC | 1410 |

TABLE 2-continued

| Sequence | SEQ ID NO: |
|---|---|
| GAUAUAGUGAGUGCUUUCAG | 1411 |
| AGGAUAUAGUGAGUGCUUUC | 1412 |
| GAGGAUAUAGUGAGUGCUUU | 1413 |
| AGAGCUGCUGUAAGAGAAAC | 1414 |
| CAGAGCUGCUGUAAGAGAAA | 1415 |
| GAAUCCCACACAGAGCUGCU | 1416 |
| CUAUAUUCCUCACUUUCCUG | 1417 |
| GGCCUUGAUUAGUCUCUCUU | 1418 |
| UGGCCUUGAUUAGUCUCUCU | 1419 |
| AUGGCCUUGAUUAGUCUCUC | 1420 |
| UAUGGCCUUGAUUAGUCUCU | 1421 |
| AUAUGGCCUUGAUUAGUCUC | 1422 |
| GAACUUCUUUCCUGAUUCAC | 1423 |
| UCGAACUUCUUUCCUGAUUC | 1424 |
| CUCGAACUUCUUUCCUGAUU | 1425 |
| GCUCGAACUUCUUUCCUGAU | 1426 |
| GGCUCGAACUUCUUUCCUGA | 1427 |
| AGGCUCGAACUUCUUUCCUG | 1428 |
| AAGGCUCGAACUUCUUUCCU | 1429 |
| CAAGGCUCGAACUUCUUUCC | 1430 |
| ACAAGGCUCGAACUUCUUUC | 1431 |
| AACAAGGCUCGAACUUCUUU | 1432 |
| AAACAAGGCUCGAACUUCUU | 1433 |
| AAAACAAGGCUCGAACUUCU | 1434 |
| GAAAACAAGGCUCGAACUUC | 1435 |
| AGAAAACAAGGCUCGAACUU | 1436 |
| AAUCAGAAAACAAGGCUCGA | 1437 |
| CCUGGGAAUCAGAAAACAAG | 1438 |
| ACCUCCAGUUUACUGUGUUA | 1439 |
| UUACCUCCAGUUUACUGUGU | 1440 |
| GUUUACCUCCAGUUUACUGU | 1441 |
| UGUUUACCUCCAGUUUACUG | 1442 |
| CUUGUUUACCUCCAGUUUAC | 1443 |
| AGUCCCAUAGCCAAACAUCU | 1444 |
| CAGUCCCAUAGCCAAACAUC | 1445 |
| ACAGUCCCAUAGCCAAACAU | 1446 |
| GACAGUCCCAUAGCCAAACA | 1447 |
| UGACAGUCCCAUAGCCAAAC | 1448 |
| CUGACAGUCCCAUAGCCAAA | 1449 |
| CCUGACAGUCCCAUAGCCAA | 1450 |
| UCUCCUGACAGUCCCAUAGC | 1451 |
| CUCUCCUGACAGUCCCAUAG | 1452 |
| UCUCUCCUGACAGUCCCAUA | 1453 |
| CCUUCUCUCCUGACAGUCCC | 1454 |
| GGCUCCAUUUCAUGCUGUCU | 1455 |
| AGGCUCCAUUUCAUGCUGUC | 1456 |
| GCAGGCUCCAUUUCAUGCUG | 1457 |
| GCAGCAGGCUCCAUUUCAUG | 1458 |
| AAGUGCAGCAGGCUCCAUUU | 1459 |
| AAAGUGCAGCAGGCUCCAUU | 1460 |
| GAAAGUGCAGCAGGCUCCAU | 1461 |
| AGAAAGUGCAGCAGGCUCCA | 1462 |
| AAGAAAGUGCAGCAGGCUCC | 1463 |
| UAAAGAAAGUGCAGCAGGCU | 1464 |
| UUAAAGAAAGUGCAGCAGGC | 1465 |
| CUUAAAGAAAGUGCAGCAGG | 1466 |
| GCCUUAAAGAAAGUGCAGCA | 1467 |
| AGCCUUAAAGAAAGUGCAGC | 1468 |
| AGCAGAGCCUUAAAGAAAGU | 1469 |
| GAGCAGAGCCUUAAAGAAAG | 1470 |
| AGGAGCAGAGCCUUAAAGAA | 1471 |
| GAGGAGCAGAGCCUUAAAGA | 1472 |
| AGGAGGAGCAGAGCCUUAAA | 1473 |
| UCAGGAGGAGCAGAGCCUUA | 1474 |
| UUGCCCUCCCAGUCCUGUCA | 1475 |
| ACUCAGCGUAGCGCAGGUUG | 1476 |
| UACUCAGCGUAGCGCAGGUU | 1477 |
| UAUACUCAGCGUAGCGCAGG | 1478 |
| CUAUACUCAGCGUAGCGCAG | 1479 |
| ACAAAGUGGCUAUACUCAGC | 1480 |
| AACAAAGUGGCUAUACUCAG | 1481 |
| CAUUGCCCAAAACAAAGUGG | 1482 |
| GUUGAGUUCAUUGCCCAAAA | 1483 |
| UGUUGAGUUCAUUGCCCAAA | 1484 |
| CUGUUGAGUUCAUUGCCCAA | 1485 |
| GCUGUUGAGUUCAUUGCCCA | 1486 |
| CGAUAGCUGUUGAGUUCAUU | 1487 |
| GGCGAUAGCUGUUGAGUUCA | 1488 |

TABLE 2-continued

| Sequence | SEQ ID NO: |
| --- | --- |
| AGGCGAUAGCUGUUGAGUUC | 1489 |
| GAGGCGAUAGCUGUUGAGUU | 1490 |
| AGAGGCGAUAGCUGUUGAGU | 1491 |
| AAGAGGCGAUAGCUGUUGAG | 1492 |
| GAAGAGGCGAUAGCUGUUGA | 1493 |
| GGAAGAGGCGAUAGCUGUUG | 1494 |
| AGGAAGAGGCGAUAGCUGUU | 1495 |
| CAGGAAGAGGCGAUAGCUGU | 1496 |
| CCAGGAAGAGGCGAUAGCUG | 1497 |
| CCCAGGAAGAGGCGAUAGCU | 1498 |
| ACAUUGCCAGUGUAGUUCCC | 1499 |
| CACAUUGCCAGUGUAGUUCC | 1500 |
| CCACAUUGCCAGUGUAGUUC | 1501 |
| CCCACAUUGCCAGUGUAGUU | 1502 |
| AUACUGGAGGGCGUCGUUCC | 1503 |
| GAUACUGGAGGGCGUCGUUC | 1504 |
| UGAUACUGGAGGGCGUCGUU | 1505 |
| AUGAUACUGGAGGGCGUCGU | 1506 |
| UAUGAUACUGGAGGGCGUCG | 1507 |
| UUGUUAUGAUACUGGAGGGC | 1508 |
| GUUGUUAUGAUACUGGAGGG | 1509 |
| UGUUGUUAUGAUACUGGAGG | 1510 |
| CUGUGUUGUUAUGAUACUGG | 1511 |
| GCUGUGUUGUUAUGAUACUG | 1512 |
| GGCUGUGUUGUUAUGAUACU | 1513 |
| AGGCUGUGUUGUUAUGAUAC | 1514 |
| GAAGGCUGUGUUGUUAUGAU | 1515 |
| UGAAGGCUGUGUUGUUAUGA | 1516 |
| CUGAAGGCUGUGUUGUUAUG | 1517 |
| GCUGAAGGCUGUGUUGUUAU | 1518 |
| UGCUGAAGGCUGUGUUGUUA | 1519 |
| UGUCCUUGUCCUUGGUGCUG | 1520 |
| UUGUCCUUGUCCUUGGUGCU | 1521 |
| GCAGUUGUCAUUGUCCUUGU | 1522 |
| CCAAGCAGUUGUCAUUGUCC | 1523 |
| UCCAAGCAGUUGUCAUUGUC | 1524 |
| UGUCCAAGCAGUUGUCAUUG | 1525 |
| UUGUCCAAGCAGUUGUCAUU | 1526 |
| CUUGUCCAAGCAGUUGUCAU | 1527 |

TABLE 2-continued

| Sequence | SEQ ID NO: |
| --- | --- |
| ACUUGUCCAAGCAGUUGUCA | 1528 |
| CACUUGUCCAAGCAGUUGUC | 1529 |
| ACACUUGUCCAAGCAGUUGU | 1530 |
| CACACUUGUCCAAGCAGUUG | 1531 |
| GCACACUUGUCCAAGCAGUU | 1532 |
| UGCACACUUGUCCAAGCAGU | 1533 |
| CACCUUUGCGGAGCUGUGCA | 1534 |
| UCACCUUUGCGGAGCUGUGC | 1535 |
| CUCACCUUUGCGGAGCUGUG | 1536 |
| UCUCACCUUUGCGGAGCUGU | 1537 |
| AUCUCACCUUUGCGGAGCUG | 1538 |
| AAUCUCACCUUUGCGGAGCU | 1539 |
| AAAUCUCACCUUUGCGGAGC | 1540 |
| AGCUUGUACCUGAACUUCUC | 1541 |
| GAGCUUGUACCUGAACUUCU | 1542 |
| UGAGCUUGUACCUGAACUUC | 1543 |
| UAUGAGCUUGUACCUGAACU | 1544 |
| UUAUGAGCUUGUACCUGAAC | 1545 |
| GGAUUAUGAGCUUGUACCUG | 1546 |
| GGGAUUAUGAGCUUGUACCU | 1547 |
| UGGGAUUAUGAGCUUGUACC | 1548 |
| GUGGGAUUAUGAGCUUGUAC | 1549 |
| AGUGGGAUUAUGAGCUUGUA | 1550 |
| UCAAGUGGGAUUAUGAGCUU | 1551 |
| CUCUUUCUCCUCAAGUGGGA | 1552 |
| AACCGGAAUAUCAACUGUAC | 1553 |
| CAAAACCGGAAUAUCAACUG | 1554 |
| CCAAAACCGGAAUAUCAACU | 1555 |
| ACCAAAACCGGAAUAUCAAC | 1556 |
| GAAAGAAUACCAAAACCGGA | 1557 |
| GGGUCAGAAAGAAUACCAAA | 1558 |
| AGGGUCAGAAAGAAUACCAA | 1559 |
| ACCAGACAUCAGGUAAGGAG | 1560 |
| GACCAGACAUCAGGUAAGGA | 1561 |
| AGACCAGACAUCAGGUAAGG | 1562 |
| AUAGACCAGACAUCAGGUAA | 1563 |
| GAUAGACCAGACAUCAGGUA | 1564 |
| ACUGUGAUAGACCAGACAUC | 1565 |
| GACUGUGAUAGACCAGACAU | 1566 |

TABLE 2-continued

| Sequence | SEQ ID NO: |
|---|---|
| UGACUGUGAUAGACCAGACA | 1567 |
| UUGACUGUGAUAGACCAGAC | 1568 |
| GUUGACUGUGAUAGACCAGA | 1569 |
| AGUUGACUGUGAUAGACCAG | 1570 |
| AAGUUGACUGUGAUAGACCA | 1571 |
| GCUAGUAAGUUGACUGUGAU | 1572 |
| UGCUAGUAAGUUGACUGUGA | 1573 |
| GUGCUAGUAAGUUGACUGUG | 1574 |
| AGUGCUAGUAAGUUGACUGU | 1575 |
| GACCCAGUGCUAGUAAGUUG | 1576 |
| AGACCCAGUGCUAGUAAGUU | 1577 |
| CAGACCCAGUGCUAGUAAGU | 1578 |
| ACAGACCCAGUGCUAGUAAG | 1579 |
| AACAGACCCAGUGCUAGUAA | 1580 |
| AAACAGACCCAGUGCUAGUA | 1581 |
| GAAACAGACCCAGUGCUAGU | 1582 |
| CAUGAGAAACAGACCCAGUG | 1583 |
| GCCACCUGGCAUGAGAAACA | 1584 |
| AGCCACCUGGCAUGAGAAAC | 1585 |
| UAGCCACCUGGCAUGAGAAA | 1586 |
| AGUAGCCACCUGGCAUGAGA | 1587 |
| CAGUAGCCACCUGGCAUGAG | 1588 |
| GUUGUACCAGUAGCCACCUG | 1589 |
| AGUUGUACCAGUAGCCACCU | 1590 |
| CAGCAGUUGUACCAGUAGCC | 1591 |
| GCAGCAGUUGUACCAGUAGC | 1592 |
| GUGCAGCAGUUGUACCAGUA | 1593 |
| UGUGCAGCAGUUGUACCAGU | 1594 |
| CUGUGCAGCAGUUGUACCAG | 1595 |
| UCUGUGCAGCAGUUGUACCA | 1596 |
| GUCUGUGCAGCAGUUGUACC | 1597 |
| AGUCUGUGCAGCAGUUGUAC | 1598 |
| GAGUCUGUGCAGCAGUUGUA | 1599 |
| GGAGUCUGUGCAGCAGUUGU | 1600 |
| UUGGAGUCUGUGCAGCAGUU | 1601 |
| GUUGGAGUCUGUGCAGCAGU | 1602 |
| GAGGUUGGAGUCUGUGCAGC | 1603 |
| AUUGAGGUUGGAGUCUGUGC | 1604 |
| CAUUGAGGUUGGAGUCUGUG | 1605 |
| CCAUUGAGGUUGGAGUCUGU | 1606 |
| GUACACUCCAUUGAGGUUGG | 1607 |
| UAGUACACUCCAUUGAGGUU | 1608 |
| GGUAGUACACUCCAUUGAGG | 1609 |
| CGGUAGUACACUCCAUUGAG | 1610 |
| GCGGUAGUACACUCCAUUGA | 1611 |
| GGCGGUAGUACACUCCAUUG | 1612 |
| AGGCGGUAGUACACUCCAUU | 1613 |
| CAGGCGGUAGUACACUCCAU | 1614 |
| CCAGGCGGUAGUACACUCCA | 1615 |
| CUCACCCAGGCGGUAGUACA | 1616 |
| UGCUCACCCAGGCGGUAGUA | 1617 |
| GCUUAUUGUGCUCACCCAGG | 1618 |
| UGCUUAUUGUGCUCACCCAG | 1619 |
| GUGCUUAUUGUGCUCACCCA | 1620 |
| CCAGGUGCUUAUUGUGCUCA | 1621 |
| UCCAGGUGCUUAUUGUGCUC | 1622 |
| CCAUCCAGGUGCUUAUUGUG | 1623 |
| GCCAUCCAGGUGCUUAUUGU | 1624 |
| UGCCAUCCAGGUGCUUAUUG | 1625 |
| AUGCCAUCCAGGUGCUUAUU | 1626 |
| GAUGCCAUCCAGGUGCUUAU | 1627 |
| UGAUGCCAUCCAGGUGCUUA | 1628 |
| ACCAGGUGAUGCCAUCCAGG | 1629 |
| UACCAGGUGAUGCCAUCCAG | 1630 |
| UAGGUAGAUCCAUGCCAGCC | 1631 |
| GUAGGUAGAUCCAUGCCAGC | 1632 |
| GAGUAGGUAGAUCCAUGCCA | 1633 |
| GGAGUAGGUAGAUCCAUGCC | 1634 |
| GGGAGUAGGUAGAUCCAUGC | 1635 |
| AGGGAGUAGGUAGAUCCAUG | 1636 |
| GAGGGAGUAGGUAGAUCCAU | 1637 |
| UGAGGGAGUAGGUAGAUCCA | 1638 |
| UUGAGGGAGUAGGUAGAUCC | 1639 |
| UUUGAGGGAGUAGGUAGAUC | 1640 |
| CGUUUGAGGGAGUAGGUAGA | 1641 |
| CCGUUUGAGGGAGUAGGUAG | 1642 |
| CCCGUUUGAGGGAGUAGGUA | 1643 |
| ACCCGUUUGAGGGAGUAGGU | 1644 |

TABLE 2-continued

| Sequence | SEQ ID NO: |
|---|---|
| CACCCGUUUGAGGGAGUAGG | 1645 |
| CCACCCGUUUGAGGGAGUAG | 1646 |
| UCCACCCGUUUGAGGGAGUA | 1647 |
| AUCUCCACCCGUUUGAGGGA | 1648 |
| CAUCUCCACCCGUUUGAGGG | 1649 |
| UCAUCUCCACCCGUUUGAGG | 1650 |
| UUCAUCUCCACCCGUUUGAG | 1651 |
| UUUCAUCUCCACCCGUUUGA | 1652 |
| UUUUCAUCUCCACCCGUUUG | 1653 |
| AUUUUCAUCUCCACCCGUUU | 1654 |
| GGCGGAUUUUCAUCUCCACC | 1655 |
| GGCUUGAAGUCUUCUGGGCG | 1656 |
| AAGGCUUGAAGUCUUCUGGG | 1657 |
| CCUUUUAAGGCUUGAAGUCU | 1658 |
| CUCCUUUUAAGGCUUGAAGU | 1659 |
| CCUCCUUUUAAGGCUUGAAG | 1660 |
| ACGGCAGCCUCCUUUUAAGG | 1661 |
| CACGGCAGCCUCCUUUUAAG | 1662 |
| CUCCACGGCAGCCUCCUUUU | 1663 |
| UUUCUGUAUCCGUGCUCCAC | 1664 |
| AGUUUCUGUAUCCGUGCUCC | 1665 |
| CAGUUUCUGUAUCCGUGCUC | 1666 |
| CUCAGUUUCUGUAUCCGUGC | 1667 |
| UGUCUCAGUUUCUGUAUCCG | 1668 |
| UGCCCUCAUCCAGUCUCCAC | 1669 |
| AUCUGCCCUCAUCCAGUCUC | 1670 |
| CAUCUGCCCUCAUCCAGUCU | 1671 |
| UCAUCUGCCCUCAUCCAGUC | 1672 |
| CCUCAUCUGCCCUCAUCCAG | 1673 |
| CUAACACUCUCUUCCUGUCC | 1674 |
| UCUAACACUCUCUUCCUGUC | 1675 |
| UUCUAACACUCUCUUCCUGU | 1676 |
| UAUAGGCUGUUUCUCAGUCC | 1677 |
| CCUUGGAGACUUAUUCUUUC | 1678 |
| GCUCCUUGGAGACUUAUUCU | 1679 |
| UGCUCCUUGGAGACUUAUUC | 1680 |
| UUUUGUGCUCCUUGGAGACU | 1681 |

TABLE 3

| Sequence | SEQ ID NO: |
|---|---|
| AGCUUGAGUCUCUGACAGGG | 1682 |
| UUUUCUCUCUUUCCUUGCUC | 1683 |
| CCUCGCCACUUUGUUGUUUU | 1684 |
| GCCUCGCCACUUUGUUGUUU | 1685 |
| GGCCUCGCCACUUUGUUGUU | 1686 |
| GGGCCUCGCCACUUUGUUGU | 1687 |
| AGGGCCUCGCCACUUUGUUG | 1688 |
| GAGGGCCUCGCCACUUUGUU | 1689 |
| UGAGGGCCUCGCCACUUUGU | 1690 |
| UCUGAGGGCCUCGCCACUUU | 1691 |
| UUUCACUCUGAGGGCCUCGC | 1692 |
| CGCUUUCACUCUGAGGGCCU | 1693 |
| UACGCUUUCACUCUGAGGGC | 1694 |
| UUACGCUUUCACUCUGAGGG | 1695 |
| CUUACGCUUUCACUCUGAGG | 1696 |
| CCUUACGCUUUCACUCUGAG | 1697 |
| AACCUUACGCUUUCACUCUG | 1698 |
| GAACCUUACGCUUUCACUCU | 1699 |
| UGACUGAACCUUACGCUUUC | 1700 |
| CUGACUGAACCUUACGCUUU | 1701 |
| GCUGACUGAACCUUACGCUU | 1702 |
| GGCUGACUGAACCUUACGCU | 1703 |
| AGGCUGACUGAACCUUACGC | 1704 |
| GGUUUGGGUGAGGAAGGCUC | 1705 |
| GGGUUUGGGUGAGGAAGGCU | 1706 |
| UGUGGGUUUGGGUGAGGAAG | 1707 |
| UUGUGGGUUUGGGUGAGGAA | 1708 |
| UUUUGUGGGUUUGGGUGAGG | 1709 |
| GAAAAUGCAGAGCCAGGUCA | 1710 |
| CCACGAUGAAAAUGCAGAGC | 1711 |
| GCCACGAUGAAAAUGCAGAG | 1712 |
| AGGCCACGAUGAAAAUGCAG | 1713 |
| AAAGGCCACGAUGAAAAUGC | 1714 |
| ACAAAGGCCACGAUGAAAAU | 1715 |
| UGACAAAGGCCACGAUGAAA | 1716 |
| CUGACAAAGGCCACGAUGAA | 1717 |
| GCUGACAAAGGCCACGAUGA | 1718 |
| GGCUGACAAAGGCCACGAUG | 1719 |
| ACGCUGGGUGGCUGACAAAG | 1720 |

TABLE 3-continued

| Sequence | SEQ ID NO: |
|---|---|
| GUGCUUAGAGAGCUUCUGCA | 1721 |
| UGUGCUUAGAGAGCUUCUGC | 1722 |
| UUGUGCUUAGAGAGCUUCUG | 1723 |
| UCUUGUGCUUAGAGAGCUUC | 1724 |
| GUCUUGUGCUUAGAGAGCUU | 1725 |
| UGUCUUGUGCUUAGAGAGCU | 1726 |
| GUGUCUUGUGCUUAGAGAGC | 1727 |
| GGUGUCUUGUGCUUAGAGAG | 1728 |
| CUGGUGUCUUGUGCUUAGAG | 1729 |
| GCUGGUGUCUUGUGCUUAGA | 1730 |
| UGUGCUGGUGUCUUGUGCUU | 1731 |
| CUGUGCUGGUGUCUUGUGCU | 1732 |
| GGCUGUGCUGGUGUCUUGUG | 1733 |
| CGCUUUGAGCUGUGGCUGUG | 1734 |
| CCGCUUUGAGCUGUGGCUGU | 1735 |
| ACCUCCUCACAGCAGUUGGC | 1736 |
| UCACCUCCUCACAGCAGUUG | 1737 |
| GUUGGCAACUUGGGCCUUGA | 1738 |
| GGUUGGCAACUUGGGCCUUG | 1739 |
| AGGUUGGCAACUUGGGCCUU | 1740 |
| AAGGUUGGCAACUUGGGCCU | 1741 |
| UAAGGUUGGCAACUUGGGCC | 1742 |
| CUAAGGUUGGCAACUUGGGC | 1743 |
| GCUAAGGUUGGCAACUUGGG | 1744 |
| UGCUAAGGUUGGCAACUUGG | 1745 |
| CUGCUAAGGUUGGCAACUUG | 1746 |
| GCUGCUAAGGUUGGCAACUU | 1747 |
| GGCUGCUAAGGUUGGCAACU | 1748 |
| AGGCUGCUAAGGUUGGCAAC | 1749 |
| CAGGCUGCUAAGGUUGGCAA | 1750 |
| CAGUUCACUCAGCAGGCUGC | 1751 |
| UCAGUUCACUCAGCAGGCUG | 1752 |
| UUCAGUUCACUCAGCAGGCU | 1753 |
| GUUCAGUUCACUCAGCAGGC | 1754 |
| CUUGUUCAGUUCACUCAGCA | 1755 |
| UCUUGUUCAGUUCACUCAGC | 1756 |
| UUCUUGUUCAGUUCACUCAG | 1757 |
| GUCCCUCUCCUGCUUCUUGU | 1758 |
| AUGACCACGCUGACCCAGUC | 1759 |

TABLE 3-continued

| Sequence | SEQ ID NO: |
|---|---|
| UGCAUGACCACGCUGACCCA | 1760 |
| ACCUGCAUGACCACGCUGAC | 1761 |
| CACCUGCAUGACCACGCUGA | 1762 |
| UCACCUGCAUGACCACGCUG | 1763 |
| AUCACCUGCAUGACCACGCU | 1764 |
| CUCCAUCACCUGCAUGACCA | 1765 |
| CGCUUGCUGUUGCUCUCCAG | 1766 |
| GCGCUUGCUGUUGCUCUCCA | 1767 |
| CAUGCGCUUGCUGUUGCUCU | 1768 |
| CCAUGCGCUUGCUGUUGCUC | 1769 |
| UCCAUGCGCUUGCUGUUGCU | 1770 |
| CUCCAUGCGCUUGCUGUUGC | 1771 |
| ACUCCAUGCGCUUGCUGUUG | 1772 |
| GACUCCAUGCGCUUGCUGUU | 1773 |
| CGACUCCAUGCGCUUGCUGU | 1774 |
| GGUUGUUCAUCUCGGAGUAC | 1775 |
| UGGUUGUUCAUCUCGGAGUA | 1776 |
| UUGGUUGUUCAUCUCGGAGU | 1777 |
| GCAUGAUGUCAAUUUGGUUG | 1778 |
| AGCUGCAUGAUGUCAAUUUG | 1779 |
| AGUGACCGUCUGUGCUGCCU | 1780 |
| UGAGUGACCGUCUGUGCUGC | 1781 |
| CUGAGUGACCGUCUGUGCUG | 1782 |
| UCUGAGUGACCGUCUGUGCU | 1783 |
| UCUGCGGAGGUCUGAGUGAC | 1784 |
| AUCUGCGGAGGUCUGAGUGA | 1785 |
| CAUCUGCGGAGGUCUGAGUG | 1786 |
| GCAUCUGCGGAGGUCUGAGU | 1787 |
| UGGCAUCUGCGGAGGUCUGA | 1788 |
| AUGGCAUCUGCGGAGGUCUG | 1789 |
| GAUGGCAUCUGCGGAGGUCU | 1790 |
| GAGCAGUCGUAGAUGGCAUC | 1791 |
| AGAGCAGUCGUAGAUGGCAU | 1792 |
| AAGAGCAGUCGUAGAUGGCA | 1793 |
| GAAGAGCAGUCGUAGAUGGC | 1794 |
| GGAAGAGCAGUCGUAGAUGG | 1795 |
| GGGAAGAGCAGUCGUAGAUG | 1796 |
| AGGGAAGAGCAGUCGUAGAU | 1797 |
| GAGGGAAGAGCAGUCGUAGA | 1798 |

TABLE 3-continued

| Sequence | SEQ ID NO: |
|---|---|
| GGUAGUUCUUCUGGUAGAGG | 1799 |
| AGCUUAUACACUCCAGAGAU | 1800 |
| GAAGUCAUCAGGAGGAAGCU | 1801 |
| GGAAGUCAUCAGGAGGAAGC | 1802 |
| GCCCAGGAAGUCAUCAGGAG | 1803 |
| GCUGCCCAGGAAGUCAUCAG | 1804 |
| AGUUCAGGGCUGCCCAGGAA | 1805 |
| ACACCUCCAGUUCAGGGCUG | 1806 |
| AACACCUCCAGUUCAGGGCU | 1807 |
| CCGCCUGAAGUCUCCAUGUC | 1808 |
| UCCGCCUGAAGUCUCCAUGU | 1809 |
| CUCCGCCUGAAGUCUCCAUG | 1810 |
| CCUCCGCCUGAAGUCUCCAU | 1811 |
| AGAAGGAGACAAGGCCACUU | 1812 |
| UAGAAGGAGACAAGGCCACU | 1813 |
| UCCCGGUAGAAGGAGACAAG | 1814 |
| GUCCCGGUAGAAGGAGACAA | 1815 |
| AGUCCCGGUAGAAGGAGACA | 1816 |
| CAGUCCCGGUAGAAGGAGAC | 1817 |
| CCAGUCCCGGUAGAAGGAGA | 1818 |
| UCCAGUCCCGGUAGAAGGAG | 1819 |
| UUCCAGUCCCGGUAGAAGGA | 1820 |
| UGCUUCCAGUCCCGGUAGAA | 1821 |
| CUGCUUCCAGUCCCGGUAGA | 1822 |
| CCUGCUUGUACUGCUUCCAG | 1823 |
| CCCUGCUUGUACUGCUUCCA | 1824 |
| GAUGCUGCCAAAGCCCUGCU | 1825 |
| ACGGAUGCUGCCAAAGCCCU | 1826 |
| CGGUGGAUGUGUUCGUUCCC | 1827 |
| CCGGUGGAUGUGUUCGUUCC | 1828 |
| GCCGGUGGAUGUGUUCGUUC | 1829 |
| AGCCGGUGGAUGUGUUCGUU | 1830 |
| GAGCCGGUGGAUGUGUUCGU | 1831 |
| AGAGCCGGUGGAUGUGUUCG | 1832 |
| GAGAGCCGGUGGAUGUGUUC | 1833 |
| GGAGAGCCGGUGGAUGUGUU | 1834 |
| UGGAGAGCCGGUGGAUGUGU | 1835 |
| UCUGGAGAGCCGGUGGAUGU | 1836 |
| UGUCUGGAGAGCCGGUGGAU | 1837 |

TABLE 3-continued

| Sequence | SEQ ID NO: |
|---|---|
| CCAGUCCUCCAUCUCUACAC | 1838 |
| CCUCCCAGUCCUCCAUCUCU | 1839 |
| UUGCCCUCCCAGUCCUCCAU | 1840 |
| ACUCAGCGUAGCGCAGGUUG | 1841 |
| UACUCAGCGUAGCGCAGGUU | 1842 |
| UAUACUCAGCGUAGCGCAGG | 1843 |
| CUAUACUCAGCGUAGCGCAG | 1844 |
| ACAAAGUGGCUAUACUCAGC | 1845 |
| AACAAAGUGGCUAUACUCAG | 1846 |
| CAUUGCCCAAAACAAAGUGG | 1847 |
| GUUGAGUUCAUUGCCCAAAA | 1848 |
| UGUUGAGUUCAUUGCCCAAA | 1849 |
| CUGUUGAGUUCAUUGCCCAA | 1850 |
| GCUGUUGAGUUCAUUGCCCA | 1851 |
| CGAUAGCUGUUGAGUUCAUU | 1852 |
| GGCGAUAGCUGUUGAGUUCA | 1853 |
| AGGCGAUAGCUGUUGAGUUC | 1854 |
| GAGGCGAUAGCUGUUGAGUU | 1855 |
| AGAGGCGAUAGCUGUUGAGU | 1856 |
| AAGAGGCGAUAGCUGUUGAG | 1857 |
| GAAGAGGCGAUAGCUGUUGA | 1858 |
| GGAAGAGGCGAUAGCUGUUG | 1859 |
| AGGAAGAGGCGAUAGCUGUU | 1860 |
| CAGGAAGAGGCGAUAGCUGU | 1861 |
| CCAGGAAGAGGCGAUAGCUG | 1862 |
| CCCAGGAAGAGGCGAUAGCU | 1863 |
| ACAUUGCCAGUGUAGUUCCC | 1864 |
| CACAUUGCCAGUGUAGUUCC | 1865 |
| CCACAUUGCCAGUGUAGUUC | 1866 |
| CCCACAUUGCCAGUGUAGUU | 1867 |
| AUACUGGAGGGCGUCGUUCC | 1868 |
| GAUACUGGAGGGCGUCGUUC | 1869 |
| UGAUACUGGAGGGCGUCGUU | 1870 |
| AUGAUACUGGAGGGCGUCGU | 1871 |
| UAUGAUACUGGAGGGCGUCG | 1872 |
| UUGUUAUGAUACUGGAGGGC | 1873 |
| GUUGUUAUGAUACUGGAGGG | 1874 |
| UGUUGUUAUGAUACUGGAGG | 1875 |
| CUGUGUUGUUAUGAUACUGG | 1876 |

TABLE 3-continued

| Sequence | SEQ ID NO: |
|---|---|
| GCUGUGUUGUUAUGAUACUG | 1877 |
| GGCUGUGUUGUUAUGAUACU | 1878 |
| AGGCUGUGUUGUUAUGAUAC | 1879 |
| GAAGGCUGUGUUGUUAUGAU | 1880 |
| UGAAGGCUGUGUUGUUAUGA | 1881 |
| CUGAAGGCUGUGUUGUUAUG | 1882 |
| GCUGAAGGCUGUGUUGUUAU | 1883 |
| UGCUGAAGGCUGUGUUGUUA | 1884 |
| UGUCCUUGUCCUUGGUGCUG | 1885 |
| UUGUCCUUGUCCUUGGUGCU | 1886 |
| GCAGUUGUCAUUGUCCUUGU | 1887 |
| CCAAGCAGUUGUCAUUGUCC | 1888 |
| UCCAAGCAGUUGUCAUUGUC | 1889 |
| UGUCCAAGCAGUUGUCAUUG | 1890 |
| UUGUCCAAGCAGUUGUCAUU | 1891 |
| CUUGUCCAAGCAGUUGUCAU | 1892 |
| ACUUGUCCAAGCAGUUGUCA | 1893 |
| CACUUGUCCAAGCAGUUGUC | 1894 |
| ACACUUGUCCAAGCAGUUGU | 1895 |
| CACACUUGUCCAAGCAGUUG | 1896 |
| GCACACUUGUCCAAGCAGUU | 1897 |
| UGCACACUUGUCCAAGCAGU | 1898 |
| CACCUUUGCGGAGCUGUGCA | 1899 |
| AGCCACCUUUGCGGAGCUGU | 1900 |
| UAGCCACCUUUGCGGAGCUG | 1901 |
| GUAGCCACCUUUGCGGAGCU | 1902 |
| AGUAGCCACCUUUGCGGAGC | 1903 |
| CAGUAGCCACCUUUGCGGAG | 1904 |
| CCAGUAGCCACCUUUGCGGA | 1905 |
| ACCAGUAGCCACCUUUGCGG | 1906 |
| UACCAGUAGCCACCUUUGCG | 1907 |
| GUACCAGUAGCCACCUUUGC | 1908 |
| UGUACCAGUAGCCACCUUUG | 1909 |
| UUGUACCAGUAGCCACCUUU | 1910 |
| GUUGUACCAGUAGCCACCUU | 1911 |
| AGUUGUACCAGUAGCCACCU | 1912 |
| CAGCAGUUGUACCAGUAGCC | 1913 |
| GCAGCAGUUGUACCAGUAGC | 1914 |
| GUGCAGCAGUUGUACCAGUA | 1915 |
| UGUGCAGCAGUUGUACCAGU | 1916 |
| CUGUGCAGCAGUUGUACCAG | 1917 |
| UCUGUGCAGCAGUUGUACCA | 1918 |
| GUCUGUGCAGCAGUUGUACC | 1919 |
| AGUCUGUGCAGCAGUUGUAC | 1920 |
| GAGUCUGUGCAGCAGUUGUA | 1921 |
| GGAGUCUGUGCAGCAGUUGU | 1922 |
| UUGGAGUCUGUGCAGCAGUU | 1923 |
| GUUGGAGUCUGUGCAGCAGU | 1924 |
| GAGGUUGGAGUCUGUGCAGC | 1925 |
| AUUGAGGUUGGAGUCUGUGC | 1926 |
| CAUUGAGGUUGGAGUCUGUG | 1927 |
| CCAUUGAGGUUGGAGUCUGU | 1928 |
| GUACACUCCAUUGAGGUUGG | 1929 |
| UAGUACACUCCAUUGAGGUU | 1930 |
| GGUAGUACACUCCAUUGAGG | 1931 |
| CGGUAGUACACUCCAUUGAG | 1932 |
| GCGGUAGUACACUCCAUUGA | 1933 |
| GGCGGUAGUACACUCCAUUG | 1934 |
| AGGCGGUAGUACACUCCAUU | 1935 |
| CAGGCGGUAGUACACUCCAU | 1936 |
| CCAGGCGGUAGUACACUCCA | 1937 |
| CUCACCCAGGCGGUAGUACA | 1938 |
| UGCUCACCCAGGCGGUAGUA | 1939 |
| GCUUAUUGUGCUCACCCAGG | 1940 |
| UGCUUAUUGUGCUCACCCAG | 1941 |
| GUGCUUAUUGUGCUCACCCA | 1942 |
| CCAGGUGCUUAUUGUGCUCA | 1943 |
| UCCAGGUGCUUAUUGUGCUC | 1944 |
| CCAUCCAGGUGCUUAUUGUG | 1945 |
| GCCAUCCAGGUGCUUAUUGU | 1946 |
| UGCCAUCCAGGUGCUUAUUG | 1947 |
| AUGCCAUCCAGGUGCUUAUU | 1948 |
| GAUGCCAUCCAGGUGCUUAU | 1949 |
| UGAUGCCAUCCAGGUGCUUA | 1950 |
| ACCAGGUGAUGCCAUCCAGG | 1951 |
| UACCAGGUGAUGCCAUCCAG | 1952 |
| UAGGUAGAUCCAUGCCAGCC | 1953 |
| GUAGGUAGAUCCAUGCCAGC | 1954 |

TABLE 3-continued

| Sequence | SEQ ID NO: |
|---|---|
| GAGUAGGUAGAUCCAUGCCA | 1955 |
| GGAGUAGGUAGAUCCAUGCC | 1956 |
| GGGAGUAGGUAGAUCCAUGC | 1957 |
| AGGGAGUAGGUAGAUCCAUG | 1958 |
| GAGGGAGUAGGUAGAUCCAU | 1959 |
| UGAGGGAGUAGGUAGAUCCA | 1960 |
| UUGAGGGAGUAGGUAGAUCC | 1961 |
| UUUGAGGGAGUAGGUAGAUC | 1962 |
| CGUUUGAGGGAGUAGGUAGA | 1963 |
| CCGUUUGAGGGAGUAGGUAG | 1964 |
| CCCGUUUGAGGGAGUAGGUA | 1965 |
| ACCCGUUUGAGGGAGUAGGU | 1966 |
| CACCCGUUUGAGGGAGUAGG | 1967 |
| CCACCCGUUUGAGGGAGUAG | 1968 |
| UCCACCCGUUUGAGGGAGUA | 1969 |
| AUCUCCACCCGUUUGAGGGA | 1970 |
| CAUCUCCACCCGUUUGAGGG | 1971 |
| UCAUCUCCACCCGUUUGAGG | 1972 |
| UUCAUCUCCACCCGUUUGAG | 1973 |
| UUUCAUCUCCACCCGUUUGA | 1974 |
| UUUUCAUCUCCACCCGUUUG | 1975 |
| AUUUUCAUCUCCACCCGUUU | 1976 |
| GGCGGAUUUUCAUCUCCACC | 1977 |
| GGCUUGAAGUCUUCUGGGCG | 1978 |
| AAGGCUUGAAGUCUUCUGGG | 1979 |
| CCUUUUAAGGCUUGAAGUCU | 1980 |
| CUCCUUUUAAGGCUUGAAGU | 1981 |
| CCUCCUUUUAAGGCUUGAAG | 1982 |
| ACGGCAGCCUCCUUUUAAGG | 1983 |
| CACGGCAGCCUCCUUUUAAG | 1984 |
| CUCCACGGCAGCCUCCUUUU | 1985 |
| UUUCUGUAUCCGUGCUCCAC | 1986 |
| AGUUUCUGUAUCCGUGCUCC | 1987 |
| CAGUUUCUGUAUCCGUGCUC | 1988 |
| CUCAGUUUCUGUAUCCGUGC | 1989 |
| UGUCUCAGUUUCUGUAUCCG | 1990 |
| UGCCCUCAUCCAGUCUCCAC | 1991 |
| AUCUGCCCUCAUCCAGUCUC | 1992 |
| CAUCUGCCCUCAUCCAGUCU | 1993 |

| Sequence | SEQ ID NO: |
|---|---|
| UCAUCUGCCCUCAUCCAGUC | 1994 |
| CCUCAUCUGCCCUCAUCCAG | 1995 |
| CUAACACUCUCUUCCUGUCC | 1996 |
| UCUAACACUCUCUUCCUGUC | 1997 |
| UUCUAACACUCUCUUCCUGU | 1998 |
| UAUAGGCUGUUUCUCAGUCC | 1999 |
| CCUUGGAGACUUAUUCUUUC | 2000 |
| GCUCCUUGGAGACUUAUUCU | 2001 |
| UGCUCCUUGGAGACUUAUUC | 2002 |
| UUUUGUGCUCCUUGGAGACU | 2003 |
| UACUGUAACAUCCUUGGUAC | 2004 |
| GUUUACUGUAACAUCCUUGG | 2005 |
| AGGAUGUGGCAGGACCCAGU | 2006 |
| AAGGAUGUGGCAGGACCCAG | 2007 |
| GAAGGAUGUGGCAGGACCCA | 2008 |
| UGAGAAGGAUGUGGCAGGAC | 2009 |
| CAGUCUACCACCUUGAGAAG | 2010 |
| CACUCAGUCUACCACCUUGA | 2011 |
| GGAUCUUGGGCAGAGAGACC | 2012 |
| GGGAUCUUGGGCAGAGAGAC | 2013 |
| AGGGAUCUUGGGCAGAGAGA | 2014 |
| CAGGGAUCUUGGGCAGAGAG | 2015 |
| UGUCAGGGAUCUUGGGCAGA | 2016 |
| AUGUCAGGGAUCUUGGGCAG | 2017 |
| UAUGUCAGGGAUCUUGGGCA | 2018 |
| CUAUGUCAGGGAUCUUGGGC | 2019 |
| GCUAUGUCAGGGAUCUUGGG | 2020 |
| UGCUAUGUCAGGGAUCUUGG | 2021 |
| CUGCUAUGUCAGGGAUCUUG | 2022 |
| AGCUACUGCUAUGUCAGGGA | 2023 |
| AAGCUACUGCUAUGUCAGGG | 2024 |
| AAGACAAGCUACUGCUAUGU | 2025 |
| CAUGUGGAAAAGACAAGCUA | 2026 |
| AUCAUGUGGAAAAGACAAGC | 2027 |
| GCCCUCACAUAGCCUAAGCC | 2028 |
| UUGCCCUCACAUAGCCUAAG | 2029 |
| UUUGCCCUCACAUAGCCUAA | 2030 |
| UUUUGCCCUCACAUAGCCUA | 2031 |
| GUUUUGCCCUCACAUAGCCU | 2032 |

TABLE 3-continued

| Sequence | SEQ ID NO: |
|---|---|
| UGUUUUGCCCUCACAUAGCC | 2033 |
| GUGUUUUGCCCUCACAUAGC | 2034 |
| GAUUUGUGUUUUGCCCUCAC | 2035 |
| GGAUUUGUGUUUUGCCCUCA | 2036 |
| AAGGGAUUUGUGUUUUGCCC | 2037 |
| ACUCCUUUCUCUAACACUCA | 2038 |
| CACCUGCCUCCUUCACUCCU | 2039 |
| UACCAUUUCCCACCUGCCUC | 2040 |
| AUACCAUUUCCCACCUGCCU | 2041 |
| UCCAGCCUGGGUCAGUUCCA | 2042 |
| UGCAGUGCCCUGGAGUUUCC | 2043 |
| GAUGCAGUGCCCUGGAGUUU | 2044 |
| CAGAUGCAGUGCCCUGGAGU | 2045 |
| UGAUCGCCAGAUGCAGUGCC | 2046 |
| CUGAUCGCCAGAUGCAGUGC | 2047 |
| ACAUGACCAAGGCGAGCAGG | 2048 |
| UACAUGACCAAGGCGAGCAG | 2049 |
| GCUGGUGCUUCAUUCCUUUC | 2050 |
| CUGCUGGUGCUUCAUUCCUU | 2051 |
| CCUGCUGGUGCUUCAUUCCU | 2052 |
| ACUCUGUCCACCUCCUGCUG | 2053 |
| AGAGACUCUGUCCACCUCCU | 2054 |
| AUGAGAGACUCUGUCCACCU | 2055 |
| CAUCCAUGAGAGACUCUGUC | 2056 |
| GCAUCCAUGAGAGACUCUGU | 2057 |
| GGCAUCCAUGAGAGACUCUG | 2058 |
| CCUUGAGCUUGUUUCUUACA | 2059 |
| UUCAACCAUUUCCUACAGAC | 2060 |
| CCAUCUACCUUCAGUUUUCA | 2061 |
| ACACCAUCUACCUUCAGUUU | 2062 |
| AACACCAUCUACCUUCAGUU | 2063 |
| UAACACCAUCUACCUUCAGU | 2064 |

TABLE 4

| Sense Sequence | SEQ ID NO: | Antisense Sequence | SEQ ID NO: |
|---|---|---|---|
| AAAGGCUAGCAAAGAGCAA | 2065 | UUGCUCUUUGCUAGCCUUU | 2066 |
| AAGGCUAGCAAAGAGCAAG | 2067 | CUUGCUCUUUGCUAGCCUU | 2068 |
| AGGCUAGCAAAGAGCAAGG | 2069 | CCUUGCUCUUUGCUAGCCU | 2070 |
| GGCUAGCAAAGAGCAAGGA | 2071 | UCCUUGCUCUUUGCUAGCC | 2072 |
| GCUAGCAAAGAGCAAGGAA | 2073 | UUCCUUGCUCUUUGCUAGC | 2074 |
| CAAAGUGGCGAGGCCCUCA | 2075 | UGAGGGCUCGCCACUUUG | 2076 |
| AAAGUGGCGAGGCCCUCAG | 2077 | CUGAGGGCCUCGCCACUUU | 2078 |
| AAGUGGCGAGGCCCUCAGA | 2079 | UCUGAGGGCUCGCCACUU | 2080 |
| GCGAGGCCCUCAGAGUGAA | 2081 | UUCACUCUGAGGGCCUCGC | 2082 |
| AAAGCGUAAGGUUCAGUCA | 2083 | UGACUGAACCUUACGCUUU | 2084 |
| AAGAGCCUUCCUCACCCAA | 2085 | UUGGGUGAGGAAGGCUCUU | 2086 |
| AGAGCCUUCCUCACCCAAA | 2087 | UUUGGGUGAGGAAGGCUCU | 2088 |
| AAAAGCCUCUCUCAGCUGU | 2089 | ACAGCUGAGAGAGGCUUUU | 2090 |
| AAAGCCUCUCUCAGCUGUG | 2091 | CACAGCUGAGAGAGGCUUU | 2092 |
| UCAGCUGUGACCUGGCUCU | 2093 | AGAGCCAGGUCACAGCUGA | 2094 |
| UGACCUGGCUCUGCAUUUU | 2095 | AAAAUGCAGAGCCAGGUCA | 2096 |
| ACCUGGCUCUGCAUUUUCA | 2097 | UGAAAAUGCAGAGCCAGGU | 2098 |
| CCUGGCUCUGCAUUUUCAU | 2099 | AUGAAAAUGCAGAGCCAGG | 2100 |
| GCUCUGCAUUUUCAUCGUG | 2101 | CACGAUGAAAAUGCAGAGC | 2102 |
| CUCUGCAUUUUCAUCGUGG | 2103 | CCACGAUGAAAAUGCAGAG | 2104 |
| UCUGCAUUUUCAUCGUGGC | 2105 | GCCACGAUGAAAAUGCAGA | 2106 |
| CUGCAUUUUCAUCGUGGCC | 2107 | GGCCACGAUGAAAAUGCAG | 2108 |
| UGCAUUUUCAUCGUGGCCU | 2109 | AGGCCACGAUGAAAAUGCA | 2110 |
| GCAUUUUCAUCGUGGCCUU | 2111 | AAGGCCACGAUGAAAAUGC | 2112 |
| AUUUUCAUCGUGGCCUUUG | 2113 | CAAAGGCCACGAUGAAAAU | 2114 |
| UUUUCAUCGUGGCCUUUGU | 2115 | ACAAAGGCCACGAUGAAAA | 2116 |
| UUUCAUCGUGGCCUUUGUC | 2117 | GACAAAGGCCACGAUGAAA | 2118 |
| UUCAUCGUGGCCUUUGUCA | 2119 | UGACAAAGGCCACGAUGAA | 2120 |
| UCAUCGUGGCCUUUGUCAG | 2121 | CUGACAAAGGCCACGAUGA | 2122 |
| CAUCGUGGCCUUUGUCAGC | 2123 | GCUGACAAAGGCCACGAUG | 2124 |
| AUCGUGGCCUUUGUCAGCC | 2125 | GGCUGACAAAGGCCACGAU | 2126 |
| CCUUUGUCAGCCACCCAGC | 2127 | GCUGGGUGGCUGACAAAGG | 2128 |
| CUUUGUCAGCCACCCAGCG | 2129 | CGCUGGGUGGCUGACAAAG | 2130 |
| UUGUCAGCCACCCAGCGUG | 2131 | CACGCUGGGUGGCUGACAA | 2132 |
| GUGGCUGCAGAAGCUCUCU | 2133 | AGAGAGCUUCUGCAGCCAC | 2134 |
| UGGCUGCAGAAGCUCUCUA | 2135 | UAGAGAGCUUCUGCAGCCA | 2136 |
| GGCUGCAGAAGCUCUCUAA | 2137 | UUAGAGAGCUUCUGCAGCC | 2138 |
| GCUGCAGAAGCUCUCUAAG | 2139 | CUUAGAGAGCUUCUGCAGC | 2140 |

In some embodiments, the siRNA molecules comprise or consist of the nucleotide sequences (sense and antisense strands) shown in Table 4, Table 5, and Table 6.

TABLE 4-continued

| Sense Sequence | SEQ ID NO: | Antisense Sequence | SEQ ID NO: |
|---|---|---|---|
| CUGCAGAAGCUCUCUAAGC | 2141 | GCUUAGAGAGCUUCUGCAG | 2142 |
| UGCAGAAGCUCUCUAAGCA | 2143 | UGCUUAGAGAGCUUCUGCA | 2144 |
| GCAGAAGCUCUCUAAGCAC | 2145 | GUGCUUAGAGAGCUUCUGC | 2146 |
| CCAGCACAGCCACAGCUCA | 2147 | UGAGCUGUGGCUGUGCUGG | 2148 |
| CAGCACAGCCACAGCUCAA | 2149 | UUGAGCUGUGGCUGUGCUG | 2150 |
| GCACAGCCACAGCUCAAAG | 2151 | CUUUGAGCUGUGGCUGUGC | 2152 |
| CACAGCCACAGCUCAAAGC | 2153 | GCUUUGAGCUGUGGCUGUG | 2154 |
| ACAGCCACAGCUCAAAGCG | 2155 | CGCUUUGAGCUGUGGCUGU | 2156 |
| CAGCCACAGCUCAAAGCGG | 2157 | CCGCUUUGAGCUGUGGCUG | 2158 |
| AGCCACAGCUCAAAGCGGC | 2159 | GCCGCUUUGAGCUGUGGCU | 2160 |
| GGCCAACUGCUGUGAGGAG | 2161 | CUCCUCACAGCAGUUGGCC | 2162 |
| GCCAACUGCUGUGAGGAGG | 2163 | CCUCCUCACAGCAGUUGGC | 2164 |
| CCAACUGCUGUGAGGAGGU | 2165 | ACCUCCUCACAGCAGUUGG | 2166 |
| CAACUGCUGUGAGGAGGUG | 2167 | CACCUCCUCACAGCAGUUG | 2168 |
| AACUGCUGUGAGGAGGUGA | 2169 | UCACCUCCUCACAGCAGUU | 2170 |
| ACUGCUGUGAGGAGGUGAA | 2171 | UUCACCUCCUCACAGCAGU | 2172 |
| CUCAAGGCCCAAGUUGCCA | 2173 | UGGCAACUUGGGCCUUGAG | 2174 |
| GCCCAAGUUGCCAACCUUA | 2175 | UAAGGUUGGCAACUUGGGC | 2176 |
| CCCAAGUUGCCAACCUUAG | 2177 | CUAAGGUUGGCAACUUGGG | 2178 |
| CCAAGUUGCCAACCUUAGC | 2179 | GCUAAGGUUGGCAACUUGG | 2180 |
| CAAGUUGCCAACCUUAGCA | 2181 | UGCUAAGGUUGGCAACUUG | 2182 |
| AAGUUGCCAACCUUAGCAG | 2183 | CUGCUAAGGUUGGCAACUU | 2184 |
| AGUUGCCAACCUUAGCAGC | 2185 | GCUGCUAAGGUUGGCAACU | 2186 |
| GACUGGGUCAGCGUGGUCA | 2187 | UGACCACGCUGACCCAGUC | 2188 |
| ACUGGGUCAGCGUGGUCAU | 2189 | AUGACCACGCUGACCCAGU | 2190 |
| CUGGGUCAGCGUGGUCAUG | 2191 | CAUGACCACGCUGACCCAG | 2192 |
| UGGGUCAGCGUGGUCAUGC | 2193 | GCAUGACCACGCUGACCCA | 2194 |
| GGGUCAGCGUGGUCAUGCA | 2195 | UGCAUGACCACGCUGACCC | 2196 |
| CAGCGUGGUCAUGCAGGUG | 2197 | CACCUGCAUGACCACGCUG | 2198 |
| AGCGUGGUCAUGCAGGUGA | 2199 | UCACCUGCAUGACCACGCU | 2200 |
| GCGUGGUCAUGCAGGUGAU | 2201 | AUCACCUGCAUGACCACGC | 2202 |
| CGUGGUCAUGCAGGUGAUG | 2203 | CAUCACCUGCAUGACCACG | 2204 |
| AGCAAGCGCAUGGAGCGCG | 2205 | GCGACUCCAUGCGCUUGCU | 2206 |
| CAACCAAAUUGACAUCAUG | 2207 | CAUGAUGUCAAUUUGGUUG | 2208 |
| ACCAAAUUGACAUCAUGCA | 2209 | UGCAUGAUGUCAAUUUGGU | 2210 |
| UUGACAUCAUGCAGCUGCA | 2211 | UGCAGCUGCAUGAUGUCAA | 2212 |
| CAGGCAGCACAGACGGUCA | 2213 | UGACCGUCUGUGCUGCCUG | 2214 |
| AGGCAGCACAGACGGUCAC | 2215 | GUGACCGUCUGUGCUGCCU | 2216 |
| GGCAGCACAGACGGUCACU | 2217 | AGUGACCGUCUGUGCUGCC | 2218 |
| GCAGCACAGACGGUCACUC | 2219 | GAGUGACCGUCUGUGCUGC | 2220 |
| GUCACUCAGACCUCCGCAG | 2221 | CUGCGGAGGUCUGAGUGAC | 2222 |
| UCACUCAGACCUCCGCAGG | 2223 | CCUGCGGAGGUCUGAGUGA | 2224 |
| CCCAUCUACAGCACUGCUU | 2225 | AAGCAGUGCUGUAGAUGGG | 2226 |
| CCAUCUACAGCACUGCUUC | 2227 | GAAGCAGUGCUGUAGAUGG | 2228 |
| CAUCUACAGCACUGCUUCU | 2229 | AGAAGCAGUGCUGUAGAUG | 2230 |
| AUCUACAGCACUGCUUCUA | 2231 | UAGAAGCAGUGCUGUAGAU | 2232 |
| UCUACAGCACUGCUUCUAC | 2233 | GUAGAAGCAGUGCUGUAGA | 2234 |
| CUACAGCACUGCUUCUACA | 2235 | UGUAGAAGCAGUGCUGUAG | 2236 |
| ACUGCUUCUACAUAUCCUG | 2237 | CAGGAUAUGUAGAAGCAGU | 2238 |
| CUUCUACAUAUCCUGGUCA | 2239 | UGACCAGGAUAUGUAGAAG | 2240 |
| UUCUACAUAUCCUGGUCAU | 2241 | AUGACCAGGAUAUGUAGAA | 2242 |
| CUACAUAUCCUGGUCAUCA | 2243 | UGAUGACCAGGAUAUGUAG | 2244 |
| GGGCCUCUUUUGUGGGUAC | 2245 | GUACCCACAAAAGAGGCCC | 2246 |
| GCCUCUUUUGUGGGUACAC | 2247 | GUGUACCCACAAAAGAGGC | 2248 |
| CCUCUUUUGUGGGUACACU | 2249 | AGUGUACCCACAAAAGAGG | 2250 |
| CUCUUUUGUGGGUACACUU | 2251 | AAGUGUACCCACAAAAGAG | 2252 |
| GUGGGUACACUUUCCCUUU | 2253 | AAAGGGAAAGUGUACCCAC | 2254 |
| UGGGUACACUUUCCCUUUA | 2255 | UAAAGGGAAAGUGUACCCA | 2256 |
| GGGUACACUUUCCCUUUAG | 2257 | CUAAAGGGAAAGUGUACCC | 2258 |
| GGUACACUUUCCCUUUAGU | 2259 | ACUAAAGGGAAAGUGUACC | 2260 |
| GUACACUUUCCCUUUAGUA | 2261 | UACUAAAGGGAAAGUGUAC | 2262 |
| UACACUUUCCCUUUAGUAA | 2263 | UUACUAAAGGGAAAGUGUA | 2264 |
| ACACUUUCCCUUUAGUAAA | 2265 | UUUACUAAAGGGAAAGUGU | 2266 |
| AGGCUUAUGCAGUAUUUCC | 2267 | GGAAAUACUGCAUAAGCCU | 2268 |
| ACUUCUAAUGCUAUGUAAG | 2269 | CUUACAUAGCAUUAGAAGU | 2270 |
| CUUCUAAUGCUAUGUAAGU | 2271 | ACUUACAUAGCAUUAGAAG | 2272 |
| UGCUAUGUAAGUUUACCUA | 2273 | UAGGUAAACUUACAUAGCA | 2274 |
| GCUAUGUAAGUUUACCUAA | 2275 | UUAGGUAAACUUACAUAGC | 2276 |
| CUAUGUAAGUUUACCUAAC | 2277 | GUUAGGUAAACUUACAUAG | 2278 |
| ACACCUUCACGGGUCUCUU | 2279 | AAGAGACCCGUGAAGGUGU | 2280 |
| CACCUUCACGGGUCUCUUU | 2281 | AAAGAGACCCGUGAAGGUG | 2282 |
| ACCUUCACGGGUCUCUUUU | 2283 | AAAAGAGACCCGUGAAGGU | 2284 |
| CCUUCACGGGUCUCUUUUA | 2285 | UAAAAGAGACCCGUGAAGG | 2286 |
| CUUCACGGGUCUCUUUUAU | 2287 | AUAAAAGAGACCCGUGAAG | 2288 |
| UUCACGGGUCUCUUUUAUC | 2289 | GAUAAAAGAGACCCGUGAA | 2290 |
| UCACGGGUCUCUUUUAUCC | 2291 | GGAUAAAAGAGACCCGUGA | 2292 |

TABLE 4-continued

| Sense Sequence | SEQ ID NO: | Antisense Sequence | SEQ ID NO: |
|---|---|---|---|
| GGGUCUCUUUUAUCCACAC | 2293 | GUGUGGAUAAAAGAGACCC | 2294 |
| CACAGUGUUUCAGCCUACC | 2295 | GGUAGGCUGAAACACUGUG | 2296 |
| GAUACUACAUGGUUUGCCC | 2297 | GGGCAAACCAUGUAGUAUC | 2298 |
| AUACUACAUGGUUUGCCCA | 2299 | UGGGCAAACCAUGUAGUAU | 2300 |
| UACUACAUGGUUUGCCCAA | 2301 | UUGGGCAAACCAUGUAGUA | 2302 |
| ACUACAUGGUUUGCCCAAA | 2303 | UUUGGGCAAACCAUGUAGU | 2304 |
| AAGUCACCCAGCAAGUCUU | 2305 | AAGACUUGCUGGGUGACUU | 2306 |
| CACCCAGCAAGUCUUAGAA | 2307 | UUCUAAGACUUGCUGGGUG | 2308 |
| GUCUUAGAAGCAGGGUUCA | 2309 | UGAACCCUGCUUCUAAGAC | 2310 |
| CUUAGAAGCAGGGUUCAAG | 2311 | CUUGAACCCUGCUUCUAAG | 2312 |
| UUAGAAGCAGGGUUCAAGU | 2313 | ACUUGAACCCUGCUUCUAA | 2314 |
| UAGAAGCAGGGUUCAAGUC | 2315 | GACUUGAACCCUGCUUCUA | 2316 |
| AGAAGCAGGGUUCAAGUCU | 2317 | AGACUUGAACCCUGCUUCU | 2318 |
| GAAGCAGGGUUCAAGUCUU | 2319 | AAGACUUGAACCCUGCUUC | 2320 |
| AAGCAGGGUUCAAGUCUUC | 2321 | GAAGACUUGAACCCUGCUU | 2322 |
| GGUUCAAGUCUUCCUGAUU | 2323 | AAUCAGGAAGACUUGAACC | 2324 |
| GUUCAAGUCUUCCUGAUUG | 2325 | CAAUCAGGAAGACUUGAAC | 2326 |
| UUCAAGUCUUCCUGAUUGG | 2327 | CCAAUCAGGAAGACUUGAA | 2328 |
| UCAAGUCUUCCUGAUUGGU | 2329 | ACCAAUCAGGAAGACUUGA | 2330 |
| CAAGUCUUCCUGAUUGGUG | 2331 | CACCAAUCAGGAAGACUUG | 2332 |
| AAGUCUUCCUGAUUGGUGU | 2333 | ACACCAAUCAGGAAGACUU | 2334 |
| AGUCUUCCUGAUUGGUGUA | 2335 | UACACCAAUCAGGAAGACU | 2336 |
| GUCUUCCUGAUUGGUGUAG | 2337 | CUACACCAAUCAGGAAGAC | 2338 |
| UCCUGAUUGGUGUAGCUCU | 2339 | AGAGCUACACCAAUCAGGA | 2340 |
| CCUGAUUGGUGUAGCUCUG | 2341 | CAGAGCUACACCAAUCAGG | 2342 |
| CUCUGCUACUUCCUCACCA | 2343 | UGGUGAGGAAGUAGCAGAG | 2344 |
| UCUGCUACUUCCUCACCAA | 2345 | UUGGUGAGGAAGUAGCAGA | 2346 |
| CUGCUACUUCCUCACCAAG | 2347 | CUUGGUGAGGAAGUAGCAG | 2348 |
| UGCUACUUCCUCACCAAGA | 2349 | UCUUGGUGAGGAAGUAGCA | 2350 |
| GCUACUUCCUCACCAAGAG | 2351 | CUCUUGGUGAGGAAGUAGC | 2352 |
| CUACUUCCUCACCAAGAGC | 2353 | GCUCUUGGUGAGGAAGUAG | 2354 |
| ACUUCCUCACCAAGAGCUG | 2355 | CAGCUCUUGGUGAGGAAGU | 2356 |
| CUUCCUCACCAAGAGCUGA | 2357 | UCAGCUCUUGGUGAGGAAG | 2358 |
| UUCCUCACCAAGAGCUGAC | 2359 | GUCAGCUCUUGGUGAGGAA | 2360 |
| UCCUCACCAAGAGCUGACA | 2361 | UGUCAGCUCUUGGUGAGGA | 2362 |
| CCUCACCAAGAGCUGACAG | 2363 | CUGUCAGCUCUUGGUGAGG | 2364 |
| CUCACCAAGAGCUGACAGG | 2365 | CCUGUCAGCUCUUGGUGAG | 2366 |
| UCACCAAGAGCUGACAGGC | 2367 | GCCUGUCAGCUCUUGGUGA | 2368 |
| CACCAAGAGCUGACAGGCU | 2369 | AGCCUGUCAGCUCUUGGUG | 2370 |
| CCAAGAGCUGACAGGCUAU | 2371 | AUAGCCUGUCAGCUCUUGG | 2372 |
| CAAGAGCUGACAGGCUAUA | 2373 | UAUAGCCUGUCAGCUCUUG | 2374 |
| AAGAGCUGACAGGCUAUAU | 2375 | AUAUAGCCUGUCAGCUCUU | 2376 |
| AGAGCUGACAGGCUAUAUC | 2377 | GAUAUAGCCUGUCAGCUCU | 2378 |
| GAGCUGACAGGCUAUAUCU | 2379 | AGAUAUAGCCUGUCAGCUC | 2380 |
| AGCUGACAGGCUAUAUCUC | 2381 | GAGAUAUAGCCUGUCAGCU | 2382 |
| GCUGACAGGCUAUAUCUCA | 2383 | UGAGAUAUAGCCUGUCAGC | 2384 |
| CUGACAGGCUAUAUCUCAA | 2385 | UUGAGAUAUAGCCUGUCAG | 2386 |
| UGACAGGCUAUAUCUCAAG | 2387 | CUUGAGAUAUAGCCUGUCA | 2388 |
| GACAGGCUAUAUCUCAAGA | 2389 | UCUUGAGAUAUAGCCUGUC | 2390 |
| ACAGGCUAUAUCUCAAGAA | 2391 | UUCUUGAGAUAUAGCCUGU | 2392 |
| UCCUCUGGAAGCAAAGUUU | 2393 | AAACUUUGCUUCCAGAGGA | 2394 |
| CCUCUGGAAGCAAAGUUUU | 2395 | AAAACUUUGCUUCCAGAGG | 2396 |
| CUCUGGAAGCAAAGUUUUG | 2397 | CAAAACUUUGCUUCCAGAG | 2398 |
| ACAGUUCUCUGGUGUUCCU | 2399 | AGGAACACCAGAGAACUGU | 2400 |
| CAGUUCUCUGGUGUUCCUA | 2401 | UAGGAACACCAGAGAACUG | 2402 |
| AGUUCUCUGGUGUUCCUAA | 2403 | UUAGGAACACCAGAGAACU | 2404 |
| GUUCUCUGGUGUUCCUAAG | 2405 | CUUAGGAACACCAGAGAAC | 2406 |
| UUCUCUGGUGUUCCUAAGA | 2407 | UCUUAGGAACACCAGAGAA | 2408 |
| CUGGUGUUCCUAAGAUUUA | 2409 | UAAAUCUUAGGAACACCAG | 2410 |
| UGGUGUUCCUAAGAUUUAC | 2411 | GUAAAUCUUAGGAACACCA | 2412 |
| GGUGUUCCUAAGAUUUACC | 2413 | GGUAAAUCUUAGGAACACC | 2414 |
| GUGUUCCUAAGAUUUACCA | 2415 | UGGUAAAUCUUAGGAACAC | 2416 |
| UGUUCCUAAGAUUUACCAG | 2417 | CUGGUAAAUCUUAGGAACA | 2418 |
| GUUCCUAAGAUUUACCAGG | 2419 | CCUGGUAAAUCUUAGGAAC | 2420 |
| CCUAAGAUUUACCAGGAAU | 2421 | AUUCCUGGUAAAUCUUAGG | 2422 |
| CUAAGAUUUACCAGGAAUG | 2423 | CAUUCCUGGUAAAUCUUAG | 2424 |
| UUUACCAGGAAUGAGCAUU | 2425 | AAUGCUCAUUCCUGGUAAA | 2426 |
| CCAGGAAUGAGCAUUAAUG | 2427 | CAUUAAUGCUCAUUCCUGG | 2428 |
| CAGGAAUGAGCAUUAAUGG | 2429 | CCAUUAAUGCUCAUUCCUG | 2430 |
| AGGAAUGAGCAUUAAUGGA | 2431 | UCCAUUAAUGCUCAUUCCU | 2432 |
| GGAAUGAGCAUUAAUGGAA | 2433 | UUCCAUUAAUGCUCAUUCC | 2434 |
| GAAUGAGCAUUAAUGGAAU | 2435 | AUUCCAUUAAUGCUCAUUC | 2436 |
| GCAUUAAUGGAAUUUGUG | 2437 | CACAAAUUCCAUUAAUGC | 2438 |
| UUAAUGGAAUUUGUGUCC | 2439 | GGACACAAAUUCCAUUAA | 2440 |
| UAAUGGAAUUUGUGUCCU | 2441 | AGGACACAAAUUCCAUUA | 2442 |
| AAUGGAAUUUGUGUCCUC | 2443 | GAGGACACAAAUUCCAUU | 2444 |

TABLE 4-continued

| Sense Sequence | SEQ ID NO: | Antisense Sequence | SEQ ID NO: |
|---|---|---|---|
| AUGGAAUUUUGUGUCCUCU | 2445 | AGAGGACACAAAAUUCCAU | 2446 |
| GGAAUUUUGUGUCCUCUCU | 2447 | AGAGAGGACACAAAAUUCC | 2448 |
| GAAUUUUGUGUCCUCUCUC | 2449 | GAGAGAGGACACAAAAUUC | 2450 |
| UUUUGUGUCCUCUCUCUGU | 2451 | ACAGAGAGGACACAAAA | 2452 |
| UUUGUGUCCUCUCUCUGUA | 2453 | UACAGAGAGGACACAAA | 2454 |
| UGUGUCCUCUCUCUGUAAA | 2455 | UUUACAGAGAGGACACA | 2456 |
| AACGUAACUCUUCUCAUUG | 2457 | CAAUGAGAAGAGUUACGUU | 2458 |
| ACGUAACUCUUCUCAUUGG | 2459 | CCAAUGAGAAGAGUUACGU | 2460 |
| CGUAACUCUUCUCAUUGGC | 2461 | GCCAAUGAGAAGAGUUACG | 2462 |
| GUAACUCUUCUCAUUGGCU | 2463 | AGCCAAUGAGAAGAGUUAC | 2464 |
| UAACUCUUCUCAUUGGCUC | 2465 | GAGCCAAUGAGAAGAGUUA | 2466 |
| AACUCUUCUCAUUGGCUCA | 2467 | UGAGCCAAUGAGAAGAGUU | 2468 |
| ACUCUUCUCAUUGGCUCAG | 2469 | CUGAGCCAAUGAGAAGAGU | 2470 |
| CUCUUCUCAUUGGCUCAGA | 2471 | UCUGAGCCAAUGAGAAGAG | 2472 |
| UCUCAUUGGCUCAGAGUUA | 2473 | UAACUCUGAGCCAAUGAGA | 2474 |
| AUUGGCUCAGAGUUAAGUG | 2475 | CACUUAACUCUGAGCCAAU | 2476 |
| UUGGCUCAGAGUUAAGUGU | 2477 | ACACUUAACUCUGAGCCAA | 2478 |
| UGGCUCAGAGUUAAGUGUA | 2479 | UACACUUAACUCUGAGCCA | 2480 |
| GGCUCAGAGUUAAGUGUAG | 2481 | CUACACUUAACUCUGAGCC | 2482 |
| GCUCAGAGUUAAGUGUAGA | 2483 | UCUACACUUAACUCUGAGC | 2484 |
| CUCAGAGUUAAGUGUAGAG | 2485 | CUCUACACUUAACUCUGAG | 2486 |
| CAUAACCAUGUGAAGAGUC | 2487 | GACUCUUCACAUGGUUAUG | 2488 |
| AUAACCAUGUGAAGAGUCC | 2489 | GGACUCUUCACAUGGUUAU | 2490 |
| UAACCAUGUGAAGAGUCCC | 2491 | GGGACUCUUCACAUGGUUA | 2492 |
| AACCAUGUGAAGAGUCCCU | 2493 | AGGGACUCUUCACAUGGUU | 2494 |
| ACCAUGUGAAGAGUCCCUU | 2495 | AAGGGACUCUUCACAUGGU | 2496 |
| CCAUGUGAAGAGUCCCUUU | 2497 | AAAGGGACUCUUCACAUGG | 2498 |
| CAUGUGAAGAGUCCCUUUG | 2499 | CAAAGGGACUCUUCACAUG | 2500 |
| AUGUGAAGAGUCCCUUUGU | 2501 | ACAAAGGGACUCUUCACAU | 2502 |
| GUGAAGAGUCCCUUUGUGU | 2503 | ACACAAAGGGACUCUUCAC | 2504 |
| UGAAGAGUCCCUUUGUGUU | 2505 | AACACAAAGGGACUCUUCA | 2506 |
| AAGAGUCCCUUUGUGUUCA | 2507 | UGAACACAAAGGGACUCUU | 2508 |
| AGAGUCCCUUUGUGUUCAG | 2509 | CUGAACACAAAGGGACUCU | 2510 |
| GAGUCCCUUUGUGUUCAGG | 2511 | CCUGAACACAAAGGGACUC | 2512 |
| UGUUCAGGAAGGAUGCGGC | 2513 | GCCGCAUCCUUCCUGAACA | 2514 |
| GUUCAGGAAGGAUGCGGCU | 2515 | AGCCGCAUCCUUCCUGAAC | 2516 |
| UUCAGGAAGGAUGCGGCUC | 2517 | GAGCCGCAUCCUUCCUGAA | 2518 |
| GGAUGCGGCUCCUUAAGGU | 2519 | ACCUUAAGGAGCCGCAUCC | 2520 |
| GAUGCGGCUCCUUAAGGUU | 2521 | AACCUUAAGGAGCCGCAUC | 2522 |
| AUGCGGCUCCUUAAGGUUC | 2523 | GAACCUUAAGGAGCCGCAU | 2524 |
| UGCGGCUCCUUAAGGUUCC | 2525 | GGAACCUUAAGGAGCCGCA | 2526 |
| GCGGCUCCUUAAGGUUCCU | 2527 | AGGAACCUUAAGGAGCCGC | 2528 |
| CGGCUCCUUAAGGUUCCUC | 2529 | GAGGAACCUUAAGGAGCCG | 2530 |
| UCCUUAAGGUUCCUCAAUU | 2531 | AAUUGAGGAACCUUAAGGA | 2532 |
| CCUUAAGGUUCCUCAAUUG | 2533 | CAAUUGAGGAACCUUAAGG | 2534 |
| CUUAAGGUUCCUCAAUUGU | 2535 | ACAAUUGAGGAACCUUAAG | 2536 |
| UUAAGGUUCCUCAAUUGUG | 2537 | CACAAUUGAGGAACCUUAA | 2538 |
| GGUUCCUCAAUUGUGAUAC | 2539 | GUAUCACAAUUGAGGAACC | 2540 |
| GUUCCUCAAUUGUGAUACG | 2541 | CGUAUCACAAUUGAGGAAC | 2542 |
| UUCCUCAAUUGUGAUACGU | 2543 | ACGUAUCACAAUUGAGGAA | 2544 |
| UCCUCAAUUGUGAUACGUC | 2545 | GACGUAUCACAAUUGAGGA | 2546 |
| CCUCAAUUGUGAUACGUCU | 2547 | AGACGUAUCACAAUUGAGG | 2548 |
| CUCAAUUGUGAUACGUCUA | 2549 | UAGACGUAUCACAAUUGAG | 2550 |
| UCAAUUGUGAUACGUCUAU | 2551 | AUAGACGUAUCACAAUUGA | 2552 |
| CAAUUGUGAUACGUCUAUU | 2553 | AAUAGACGUAUCACAAUUG | 2554 |
| UUUUCCAUGGUCUAAAUG | 2555 | CAUUUAAGACCAUGGAAAA | 2556 |
| AAUGAAUUUCUCCGAAUAC | 2557 | GUAUUCGGAGAAAUUCAUU | 2558 |
| AUGAAUUUCUCCGAAUACA | 2559 | UGUAUUCGGAGAAAUUCAU | 2560 |
| UGAAUUUCUCCGAAUACAG | 2561 | CUGUAUUCGGAGAAAUUCA | 2562 |
| UUUCUCCGAAUACAGGAUU | 2563 | AAUCCUGUAUUCGGAGAAA | 2564 |
| UUCUCCGAAUACAGGAUUU | 2565 | AAAUCCUGUAUUCGGAGAA | 2566 |
| UCUCCGAAUACAGGAUUUU | 2567 | AAAAUCCUGUAUUCGGAGA | 2568 |
| AAUAUAGACUUAAUAGGCC | 2569 | GGCCUAUUAAGUCUAUAUU | 2570 |
| AUAUAGACUUAAUAGGCCA | 2571 | UGGCCUAUUAAGUCUAUAU | 2572 |
| UAUAGACUUAAUAGGCCAA | 2573 | UUGGCCUAUUAAGUCUAUA | 2574 |
| AUAGACUUAAUAGGCCAAA | 2575 | UUUGGCCUAUUAAGUCUAU | 2576 |
| UAGACUUAAUAGGCCAAAA | 2577 | UUUUGGCCUAUUAAGUCUA | 2578 |
| ACUUUAUUUCUGGUUAGC | 2579 | GCUAACCAGAAAUAAAGU | 2580 |
| CUUUUAUUUCUGGUUAGCU | 2581 | AGCUAACCAGAAAUAAAG | 2582 |
| UUUUAUUUCUGGUUAGCUC | 2583 | GAGCUAACCAGAAAUAAA | 2584 |
| UUUAUUUCUGGUUAGCUCA | 2585 | UGAGCUAACCAGAAAUAAA | 2586 |
| UUAUUUCUGGUUAGCUCAG | 2587 | CUGAGCUAACCAGAAAUAA | 2588 |
| UUCUGGUUAGCUCAGCUCA | 2589 | UGAGCUGAGCUAACCAGAA | 2590 |
| UCUGGUUAGCUCAGCUCAG | 2591 | CUGAGCUGAGCUAACCAGA | 2592 |
| CUGGUUAGCUCAGCUCAGG | 2593 | CCUGAGCUGAGCUAACCAG | 2594 |
| UGGUUAGCUCAGCUCAGGU | 2595 | ACCUGAGCUGAGCUAACCA | 2596 |

TABLE 4-continued

| Sense Sequence | SEQ ID NO: | Antisense Sequence | SEQ ID NO: |
|---|---|---|---|
| GGUUAGCUCAGCUCAGGUG | 2597 | CACCUGAGCUGAGCUAACC | 2598 |
| GUUAGCUCAGCUCAGGUGG | 2599 | CCACCUGAGCUGAGCUAAC | 2600 |
| UUAGCUCAGCUCAGGUGGG | 2601 | CCCACCUGAGCUGAGCUAA | 2602 |
| UAGCUCAGCUCAGGUGGGC | 2603 | GCCCACCUGAGCUGAGCUA | 2604 |
| ACAUGAAUUUACGGUUUAG | 2605 | CUAAACCGUAAAUUCAUGU | 2606 |
| CAUGAAUUUACGGUUUAGA | 2607 | UCUAAACCGUAAAUUCAUG | 2608 |
| AUGAAUUUACGGUUUAGAG | 2609 | CUCUAAACCGUAAAUUCAU | 2610 |
| GGAGCAUAUCCUAUAGACA | 2611 | UGUCUAUAGGAUAUGCUCC | 2612 |
| CAUAUCCUAUAGACAUGUC | 2613 | GACAUGUCUAUAGGAUAUG | 2614 |
| CAAAGACAUGAUCAGCUUC | 2615 | GAAGCUGAUCAUGUCUUUG | 2616 |
| AAAGACAUGAUCAGCUUCU | 2617 | AGAAGCUGAUCAUGUCUUU | 2618 |
| AAGACAUGAUCAGCUUCUA | 2619 | UAGAAGCUGAUCAUGUCUU | 2620 |
| AGACAUGAUCAGCUUCUAC | 2621 | GUAGAAGCUGAUCAUGUCU | 2622 |
| CAGCUUCUACUGACUAAGU | 2623 | ACUUAGUCAGUAGAAGCUG | 2624 |
| AGCUUCUACUGACUAAGUC | 2625 | GACUUAGUCAGUAGAAGCU | 2626 |
| GACUAAGUCAAUGGUUAAC | 2627 | GUUAACCAUUGACUUAGUC | 2628 |
| ACUAAGUCAAUGGUUAACC | 2629 | GGUUAACCAUUGACUUAGU | 2630 |
| AAUGGUUAACCUCAGCUCA | 2631 | UGAGCUGAGGUUAACCAUU | 2632 |
| GUAUCAAUCACUUUCUAAG | 2633 | CUUAGAAAGUGAUUGAUAC | 2634 |
| UAUCAAUCACUUUCUAAGC | 2635 | GCUUAGAAAGUGAUUGAUA | 2636 |
| AUCAAUCACUUUCUAAGCA | 2637 | UGCUUAGAAAGUGAUUGAU | 2638 |
| UCAAUCACUUUCUAAGCAU | 2639 | AUGCUUAGAAAGUGAUUGA | 2640 |
| CAAUCACUUUCUAAGCAUG | 2641 | CAUGCUUAGAAAGUGAUUG | 2642 |
| AAUCACUUUCUAAGCAUGG | 2643 | CCAUGCUUAGAAAGUGAUU | 2644 |
| AUCACUUUCUAAGCAUGGA | 2645 | UCCAUGCUUAGAAAGUGAU | 2646 |
| UCACUUUCUAAGCAUGGAC | 2647 | GUCCAUGCUUAGAAAGUGA | 2648 |
| CACUUUCUAAGCAUGGACU | 2649 | AGUCCAUGCUUAGAAAGUG | 2650 |
| ACUUUCUAAGCAUGGACUU | 2651 | AAGUCCAUGCUUAGAAAGU | 2652 |
| CUUUCUAAGCAUGGACUUC | 2653 | GAAGUCCAUGCUUAGAAAG | 2654 |
| UUUCUAAGCAUGGACUUCC | 2655 | GGAAGUCCAUGCUUAGAAA | 2656 |
| UUCUAAGCAUGGACUUCCG | 2657 | CGGAAGUCCAUGCUUAGAA | 2658 |
| UCUAAGCAUGGACUUCCGG | 2659 | CCGGAAGUCCAUGCUUAGA | 2660 |
| CUAAGCAUGGACUUCCGGG | 2661 | CCCGGAAGUCCAUGCUUAG | 2662 |
| CCUCAGUUUGGGAUUAGAA | 2663 | UUCUAAUCCCAAACUGAGG | 2664 |
| AAAGGUAUUCUCAGGCCAU | 2665 | AUGGCCUGAGAAUACCUUU | 2666 |
| AAGGUAUUCUCAGGCCAUU | 2667 | AAUGGCCUGAGAAUACCUU | 2668 |
| AGGUAUUCUCAGGCCAUUU | 2669 | AAAUGGCCUGAGAAUACCU | 2670 |
| GGUAUUCUCAGGCCAUUUU | 2671 | AAAAUGGCCUGAGAAUACC | 2672 |
| UAUUCUCAGGCCAUUUUCC | 2673 | GGAAAAUGGCCUGAGAAUA | 2674 |
| AUUCUCAGGCCAUUUUCCA | 2675 | UGGAAAAUGGCCUGAGAAU | 2676 |
| UUCUCAGGCCAUUUUCCAG | 2677 | CUGGAAAAUGGCCUGAGAA | 2678 |
| UCUCAGGCCAUUUUCCAGA | 2679 | UCUGGAAAAUGGCCUGAGA | 2680 |
| AAGUGAGUCCUGAUUUGGU | 2681 | ACCAAAUCAGGACUCACUU | 2682 |
| AGUGAGUCCUGAUUUGGUC | 2683 | GACCAAAUCAGGACUCACU | 2684 |
| GUGAGUCCUGAUUUGGUCU | 2685 | AGACCAAAUCAGGACUCAC | 2686 |
| GAGUCCUGAUUUGGUCUGU | 2687 | ACAGACCAAAUCAGGACUC | 2688 |
| AGUCCUGAUUUGGUCUGUG | 2689 | CACAGACCAAAUCAGGACU | 2690 |
| AACCAGACAUGCGGAAGAC | 2691 | GUCUUCCGCAUGUCUGGUU | 2692 |
| ACCAGACAUGCGGAAGACC | 2693 | GGUCUUCCGCAUGUCUGGU | 2694 |
| CCAGACAUGCGGAAGACCA | 2695 | UGGUCUUCCGCAUGUCUGG | 2696 |
| ACAUGCGGAAGACCAGGCC | 2697 | GGCCUGGUCUUCCGCAUGU | 2698 |
| CAUGCGGAAGACCAGGCCA | 2699 | UGGCCUGGUCUUCCGCAUG | 2700 |
| AUGCGGAAGACCAGGCCAG | 2701 | CUGGCCUGGUCUUCCGCAU | 2702 |
| UGCGGAAGACCAGGCCAGA | 2703 | UCUGGCCUGGUCUUCCGCA | 2704 |
| CGGAAGACCAGGCCAGACA | 2705 | UGUCUGGCCUGGUCUUCCG | 2706 |
| GGAAGACCAGGCCAGACAG | 2707 | CUGUCUGGCCUGGUCUUCC | 2708 |
| GAAGACCAGGCCAGACAGA | 2709 | UCUGUCUGGCCUGGUCUUC | 2710 |
| AAGACCAGGCCAGACAGAG | 2711 | CUCUGUCUGGCCUGGUCUU | 2712 |
| AGACCAGGCCAGACAGAGG | 2713 | CCUCUGUCUGGCCUGGUCU | 2714 |
| GACCAGGCCAGACAGAGGA | 2715 | UCCUCUGUCUGGCCUGGUC | 2716 |
| AGGCCAGACAGAGGAAUCU | 2717 | AGAUUCCUCUGUCUGGCCU | 2718 |
| AGAGGAAUCUGACCGUGCC | 2719 | GGCACGGUCAGAUUCCUCU | 2720 |
| GAGGAAUCUGACCGUGCCA | 2721 | UGGCACGGUCAGAUUCCUC | 2722 |
| AGGAAUCUGACCGUGCCAC | 2723 | GUGGCACGGUCAGAUUCCU | 2724 |
| GGAAUCUGACCGUGCCACU | 2725 | AGUGGCACGGUCAGAUUCC | 2726 |
| GAAUCUGACCGUGCCACUU | 2727 | AAGUGGCACGGUCAGAUUC | 2728 |
| AAUCUGACCGUGCCACUUC | 2729 | GAAGUGGCACGGUCAGAUU | 2730 |
| AUCUGACCGUGCCACUUCC | 2731 | GGAAGUGGCACGGUCAGAU | 2732 |
| UCUGACCGUGCCACUUCCU | 2733 | AGGAAGUGGCACGGUCAGA | 2734 |
| ACCGUGCCACUUCCUGCUC | 2735 | GAGCAGGAAGUGGCACGGU | 2736 |
| CGUGCCACUUCCUGCUCAU | 2737 | AUGAGCAGGAAGUGGCACG | 2738 |
| GCCACUUCCUGCUCAUCCA | 2739 | UGGAUGAGCAGGAAGUGGC | 2740 |
| CCACUUCCUGCUCAUCCAA | 2741 | UUGGAUGAGCAGGAAGUGG | 2742 |
| CACUUCCUGCUCAUCCAAA | 2743 | UUUGGAUGAGCAGGAAGUG | 2744 |
| ACAGGAGGCUUUCUCACCA | 2745 | UGGUGAGAAAGCCUCCUGU | 2746 |
| GGAGGCUUUCUCACCAUCC | 2747 | GGAUGGUGAGAAAGCCUCC | 2748 |

TABLE 4-continued

| Sense Sequence | SEQ ID NO: | Antisense Sequence | SEQ ID NO: |
|---|---|---|---|
| GAGGCUUUCUCACCAUCCU | 2749 | AGGAUGGUGAGAAAGCCUC | 2750 |
| AGGCUUUCUCACCAUCCUG | 2751 | CAGGAUGGUGAGAAAGCCU | 2752 |
| GGCUUUCUCACCAUCCUGC | 2753 | GCAGGAUGGUGAGAAAGCC | 2754 |
| GCUUUCUCACCAUCCUGCA | 2755 | UGCAGGAUGGUGAGAAAGC | 2756 |
| CUUUCUCACCAUCCUGCAA | 2757 | UUGCAGGAUGGUGAGAAAG | 2758 |
| UUUCUCACCAUCCUGCAAG | 2759 | CUUGCAGGAUGGUGAGAAA | 2760 |
| UUCUCACCAUCCUGCAAGG | 2761 | CCUUGCAGGAUGGUGAGAA | 2762 |
| UGCAGCUCUCCCACCAGGU | 2763 | ACCUGGUGGGAGAGCUGCA | 2764 |
| AGCUCUCCCACCAGGUCUC | 2765 | GAGACCUGGUGGGAGAGCU | 2766 |
| UCUUGCCCAGGACAUCAUU | 2767 | AAUGAUGUCCUGGGCAAGA | 2768 |
| CUUGCCCAGGACAUCAUUC | 2769 | GAAUGAUGUCCUGGGCAAG | 2770 |
| GGACAUCAUUCCUUAUUUU | 2771 | AAAAUAAGGAAUGAUGUCC | 2772 |
| UCAGUUACCCUUAUAUUCU | 2773 | AGAAUAUAAGGGUAACUGA | 2774 |
| CAGUUACCCUUAUAUUCUA | 2775 | UAGAAUAUAAGGGUAACUG | 2776 |
| AUUCUAUAAGUAGGUAGUC | 2777 | GACUACCUACUUAUAGAAU | 2778 |
| UUCUAUAAGUAGGUAGUCC | 2779 | GGACUACCUACUUAUAGAA | 2780 |
| UCUAUAAGUAGGUAGUCCC | 2781 | GGGACUACCUACUUAUAGA | 2782 |
| CUAUAAGUAGGUAGUCCCU | 2783 | AGGGACUACCUACUUAUAG | 2784 |
| UAUAAGUAGGUAGUCCCUU | 2785 | AAGGGACUACCUACUUAUA | 2786 |
| GCAGUAAGUUGGUGCUUUC | 2787 | GAAAGCACCAACUUACUGC | 2788 |
| CUUUCACCACUAAGACGAA | 2789 | UUCGUCUUAGUGGUGAAAG | 2790 |
| ACACGUACUCUACCUCCCU | 2791 | AGGGAGGUAGAGUACGUGU | 2792 |
| CACGUACUCUACCUCCCUU | 2793 | AAGGGAGGUAGAGUACGUG | 2794 |
| ACGUACUCUACCUCCCUUU | 2795 | AAAGGGAGGUAGAGUACGU | 2796 |
| CCCAAGGUGCUCUGCAAGA | 2797 | UCUUGCAGAGCACCUUGGG | 2798 |
| AACCUAUGUGCCUCAGACA | 2799 | UGUCUGAGGCACAUAGGUU | 2800 |
| UCCCAUCUGCCAUCUUGGU | 2801 | ACCAAGAUGGCAGAUGGGA | 2802 |
| CCCAUCUGCCAUCUUGGUG | 2803 | CACCAAGAUGGCAGAUGGG | 2804 |
| CCAUCUUGGUGCUCCUCUC | 2805 | GAGAGGAGCACCAAGAUGG | 2806 |
| AUCUUGGUGCUCCUCUCUA | 2807 | UAGAGAGGAGCACCAAGAU | 2808 |
| UCUUGGUGCUCCUCUCUAA | 2809 | UUAGAGAGGAGCACCAAGA | 2810 |
| CUUGGUGCUCCUCUCUAAG | 2811 | CUUAGAGAGGAGCACCAAG | 2812 |
| UUGGUGCUCCUCUCUAAGG | 2813 | CCUUAGAGAGGAGCACCAA | 2814 |
| UGGUGCUCCUCUCUAAGGU | 2815 | ACCUUAGAGAGGAGCACCA | 2816 |
| GGUGCUCCUCUCUAAGGUC | 2817 | GACCUUAGAGAGGAGCACC | 2818 |
| UGCUCCUCUCUAAGGUCCC | 2819 | GGGACCUUAGAGAGGAGCA | 2820 |
| GCUCCUCUCUAAGGUCCCA | 2821 | UGGGACCUUAGAGAGGAGC | 2822 |
| CUCUCUAAGGUCCCAGUGC | 2823 | GCACUGGGACCUUAGAGAG | 2824 |
| UCUCUAAGGUCCCAGUGCA | 2825 | UGCACUGGGACCUUAGAGA | 2826 |
| GGUCCCAGUGCAGUGGUCA | 2827 | UGACCACUGCACUGGGACC | 2828 |
| GUCCCAGUGCAGUGGUCAC | 2829 | GUGACCACUGCACUGGGAC | 2830 |
| UCCCAGUGCAGUGGUCACC | 2831 | GGUGACCACUGCACUGGGA | 2832 |
| CCCAGUGCAGUGGUCACCA | 2833 | UGGUGACCACUGCACUGGG | 2834 |
| CCAGUGCAGUGGUCACCAA | 2835 | UUGGUGACCACUGCACUGG | 2836 |
| CAGUGCAGUGGUCACCAAG | 2837 | CUUGGUGACCACUGCACUG | 2838 |
| AGUGCAGUGGUCACCAAGA | 2839 | UCUUGGUGACCACUGCACU | 2840 |
| GUGCAGUGGUCACCAAGAA | 2841 | UUCUUGGUGACCACUGCAC | 2842 |
| AGACAUAGCAGGCAGGAAG | 2843 | CUUCCUGCCUGCUAUGUCU | 2844 |
| ACAUAGCAGGCAGGAAGCU | 2845 | AGCUUCCUGCCUGCUAUGU | 2846 |
| CAUAGCAGGCAGGAAGCUU | 2847 | AAGCUUCCUGCCUGCUAUG | 2848 |
| AUAGCAGGCAGGAAGCUUC | 2849 | GAAGCUUCCUGCCUGCUAU | 2850 |
| UAGCAGGCAGGAAGCUUCU | 2851 | AGAAGCUUCCUGCCUGCUA | 2852 |
| GCAGGCAGGAAGCUUCUCU | 2853 | AGAGAAGCUUCCUGCCUGC | 2854 |
| GCCGCAGUCUCUGAAUCCU | 2855 | AGGAUUCAGAGACUGCGGC | 2856 |
| CCGCAGUCUCUGAAUCCUA | 2857 | UAGGAUUCAGAGACUGCGG | 2858 |
| CGCAGUCUCUGAAUCCUAU | 2859 | AUAGGAUUCAGAGACUGCG | 2860 |
| GCAGUCUCUGAAUCCUAUC | 2861 | GAUAGGAUUCAGAGACUGC | 2862 |
| CAGUCUCUGAAUCCUAUCA | 2863 | UGAUAGGAUUCAGAGACUG | 2864 |
| AAGGCUGUCUCUUCCACUA | 2865 | UAGUGGAAGAGACAGCCUU | 2866 |
| AGGCUGUCUCUUCCACUAU | 2867 | AUAGUGGAAGAGACAGCCU | 2868 |
| GGCUGUCUCUUCCACUAUG | 2869 | CAUAGUGGAAGAGACAGCC | 2870 |
| GCUGUCUCUUCCACUAUGC | 2871 | GCAUAGUGGAAGAGACAGC | 2872 |
| CUGUCUCUUCCACUAUGCU | 2873 | AGCAUAGUGGAAGAGACAG | 2874 |
| UGUCUCUUCCACUAUGCUC | 2875 | GAGCAUAGUGGAAGAGACA | 2876 |
| GUCUCUUCCACUAUGCUCU | 2877 | AGAGCAUAGUGGAAGAGAC | 2878 |
| UCUCUUCCACUAUGCUCUU | 2879 | AAGAGCAUAGUGGAAGAGA | 2880 |
| CUCUUCCACUAUGCUCUUU | 2881 | AAAGAGCAUAGUGGAAGAG | 2882 |
| CUUCCACUAUGCUCUUUGA | 2883 | UCAAAGAGCAUAGUGGAAG | 2884 |
| UUCCACUAUGCUCUUUGAU | 2885 | AUCAAAGAGCAUAGUGGAA | 2886 |
| UCCACUAUGCUCUUUGAUA | 2887 | UAUCAAAGAGCAUAGUGGA | 2888 |
| AGAAUACAGAGCUUAAAUC | 2889 | GAUUUAAGCUCUGUAUUCU | 2890 |
| UACAGAGCUUAAAUCCUGC | 2891 | GCAGGAUUUAAGCUCUGUA | 2892 |
| ACAGAGCUUAAAUCCUGCA | 2893 | UGCAGGAUUUAAGCUCUGU | 2894 |
| CAGAGCUUAAAUCCUGCAU | 2895 | AUGCAGGAUUUAAGCUCUG | 2896 |
| AGAGCUUAAAUCCUGCAUA | 2897 | UAUGCAGGAUUUAAGCUCU | 2898 |
| GAGCUUAAAUCCUGCAUAA | 2899 | UUAUGCAGGAUUUAAGCUC | 2900 |

TABLE 4-continued

| Sense Sequence | SEQ ID NO: | Antisense Sequence | SEQ ID NO: |
|---|---|---|---|
| AGCUUAAAUCCUGCAUAAA | 2901 | UUUAUGCAGGAUUUAAGCU | 2902 |
| GCUUAAAUCCUGCAUAAAG | 2903 | CUUUAUGCAGGAUUUAAGC | 2904 |
| UAAAUCCUGCAUAAAGUAG | 2905 | CUACUUUAUGCAGGAUUUA | 2906 |
| AAAUCCUGCAUAAAGUAGC | 2907 | GCUACUUUAUGCAGGAUUU | 2908 |
| AAUCCUGCAUAAAGUAGCA | 2909 | UGCUACUUUAUGCAGGAUU | 2910 |
| GCAUAAAGUAGCAGCUCCA | 2911 | UGGAGCUGCUACUUUAUGC | 2912 |
| AAGUAGCAGCUCCAUGGCC | 2913 | GGCCAUGGAGCUGCUACUU | 2914 |
| AGUAGCAGCUCCAUGGCCC | 2915 | GGGCCAUGGAGCUGCUACU | 2916 |
| GUAGCAGCUCCAUGGCCCU | 2917 | AGGGCCAUGGAGCUGCUAC | 2918 |
| UAGCAGCUCCAUGGCCCUA | 2919 | UAGGGCCAUGGAGCUGCUA | 2920 |
| AGCAGCUCCAUGGCCCUAG | 2921 | CUAGGGCCAUGGAGCUGCU | 2922 |
| GCAGCUCCAUGGCCCUAGA | 2923 | UCUAGGGCCAUGGAGCUGC | 2924 |
| CAGCUCCAUGGCCCUAGAG | 2925 | CUCUAGGGCCAUGGAGCUG | 2926 |
| AGCUCCAUGGCCCUAGAGU | 2927 | ACUCUAGGGCCAUGGAGCU | 2928 |
| GCUCCAUGGCCCUAGAGUA | 2929 | UACUCUAGGGCCAUGGAGC | 2930 |
| UCCAUGGCCCUAGAGUAAA | 2931 | UUUACUCUAGGGCCAUGGA | 2932 |
| CCAUGGCCCUAGAGUAAAA | 2933 | UUUUACUCUAGGGCCAUGG | 2934 |
| AACUGGCCAGUCUGAUGCU | 2935 | AGCAUCAGACUGGCCAGUU | 2936 |
| CUGGCCAGUCUGAUGCUCU | 2937 | AGAGCAUCAGACUGGCCAG | 2938 |
| UGGCCAGUCUGAUGCUCUC | 2939 | GAGAGCAUCAGACUGGCCA | 2940 |
| GGCCAGUCUGAUGCUCUCA | 2941 | UGAGAGCAUCAGACUGGCC | 2942 |
| GCCAGUCUGAUGCUCUCAU | 2943 | AUGAGAGCAUCAGACUGGC | 2944 |
| CCAGUCUGAUGCUCUCAUU | 2945 | AAUGAGAGCAUCAGACUGG | 2946 |
| CAGUCUGAUGCUCUCAUUU | 2947 | AAAUGAGAGCAUCAGACUG | 2948 |
| AGGAAGGCCUCAAAGGUUC | 2949 | GAACCUUUGAGGCCUUCCU | 2950 |
| GGAAGGCCUCAAAGGUUCU | 2951 | AGAACCUUUGAGGCCUUCC | 2952 |
| GAAGGCCUCAAAGGUUCUU | 2953 | AAGAACCUUUGAGGCCUUC | 2954 |
| AAGGCCUCAAAGGUUCUUC | 2955 | GAAGAACCUUUGAGGCCUU | 2956 |
| AGGCCUCAAAGGUUCUUCU | 2957 | AGAAGAACCUUUGAGGCCU | 2958 |
| GGCCUCAAAGGUUCUUCUG | 2959 | CAGAAGAACCUUUGAGGCC | 2960 |
| GCCUCAAAGGUUCUUCUGA | 2961 | UCAGAAGAACCUUUGAGGC | 2962 |
| GGUUCUUCUGAGUGUUUUG | 2963 | CAAAACACUCAGAAGAACC | 2964 |
| GUUCUUCUGAGUGUUUUGA | 2965 | UCAAAACACUCAGAAGAAC | 2966 |
| UUCUGAGUGUUUUGAGGUG | 2967 | CACCUCAAAACACUCAGAA | 2968 |
| UCUGAGUGUUUUGAGGUGC | 2969 | GCACCUCAAAACACUCAGA | 2970 |
| AGUGUUUUGAGGUGCUAGC | 2971 | GCUAGCACCUCAAAACACU | 2972 |
| GUGUUUUGAGGUGCUAGCU | 2973 | AGCUAGCACCUCAAAACAC | 2974 |
| UGUUUUGAGGUGCUAGCUG | 2975 | CAGCUAGCACCUCAAAACA | 2976 |
| GUUUUGAGGUGCUAGCUGG | 2977 | CCAGCUAGCACCUCAAAAC | 2978 |
| UUUUGAGGUGCUAGCUGGA | 2979 | UCCAGCUAGCACCUCAAAA | 2980 |
| GAGGUGCUAGCUGGAUGGA | 2981 | UCCAUCCAGCUAGCACCUC | 2982 |
| AGGUGCUAGCUGGAUGGAA | 2983 | UUCCAUCCAGCUAGCACCU | 2984 |
| GUGCUAGCUGGAUGGAAGG | 2985 | CCUUCCAUCCAGCUAGCAC | 2986 |
| UGCUAGCUGGAUGGAAGGG | 2987 | CCCUUCCAUCCAGCUAGCA | 2988 |
| CUAUCUCCCUUAAUUAUGG | 2989 | CCAUAAUUAAGGGAGAUAG | 2990 |
| UAUCUCCCUUAAUUAUGGU | 2991 | ACCAUAAUUAAGGGAGAUA | 2992 |
| AUCUCCCUUAAUUAUGGUC | 2993 | GACCAUAAUUAAGGGAGAU | 2994 |
| UCUCCCUUAAUUAUGGUCU | 2995 | AGACCAUAAUUAAGGGAGA | 2996 |
| CUCCCUUAAUUAUGGUCUC | 2997 | GAGACCAUAAUUAAGGGAG | 2998 |
| CCCUUAAUUAUGGUCUCAG | 2999 | CUGAGACCAUAAUUAAGGG | 3000 |
| CCUUAAUUAUGGUCUCAGG | 3001 | CCUGAGACCAUAAUUAAGG | 3002 |
| CUUAAUUAUGGUCUCAGGU | 3003 | ACCUGAGACCAUAAUUAAG | 3004 |
| UUAAUUAUGGUCUCAGGUG | 3005 | CACCUGAGACCAUAAUUAA | 3006 |
| UAAUUAUGGUCUCAGGUGG | 3007 | CCACCUGAGACCAUAAUUA | 3008 |
| AAUUAUGGUCUCAGGUGGC | 3009 | GCCACCUGAGACCAUAAUU | 3010 |
| AUUAUGGUCUCAGGUGGCA | 3011 | UGCCACCUGAGACCAUAAU | 3012 |
| UUAUGGUCUCAGGUGGCAG | 3013 | CUGCCACCUGAGACCAUAA | 3014 |
| UAUGGUCUCAGGUGGCAGU | 3015 | ACUGCCACCUGAGACCAUA | 3016 |
| AUGGUCUCAGGUGGCAGUA | 3017 | UACUGCCACCUGAGACCAU | 3018 |
| UGGUCUCAGGUGGCAGUAG | 3019 | CUACUGCCACCUGAGACCA | 3020 |
| GGUCUCAGGUGGCAGUAGC | 3021 | GCUACUGCCACCUGAGACC | 3022 |
| GUCUCAGGUGGCAGUAGCC | 3023 | GGCUACUGCCACCUGAGAC | 3024 |
| CAGUAGCCACCAUCUCUGA | 3025 | UCAGAGAUGGUGGCUACUG | 3026 |
| AGUAGCCACCAUCUCUGAA | 3027 | UUCAGAGAUGGUGGCUACU | 3028 |
| UCACGACUGAUUUGUUAUA | 3029 | UAUAACAAAUCAGUCGUGA | 3030 |
| CACGACUGAUUUGUUAUAG | 3031 | CUAUAACAAAUCAGUCGUG | 3032 |
| CGACUGAUUUGUUAUAGUG | 3033 | CACUAUAACAAAUCAGUCG | 3034 |
| GACUGAUUUGUUAUAGUGG | 3035 | CCACUAUAACAAAUCAGUC | 3036 |
| GCGGCUGCUAAGAAGUCU | 3037 | AGACUUCUUAGACAGCCGC | 3038 |
| CGGCUGUCUAAGAAGUCUG | 3039 | CAGACUUCUUAGACAGCCG | 3040 |
| GGCUGUCUAAGAAGUCUGA | 3041 | UCAGACUUCUUAGACAGCC | 3042 |
| GCUGUCUAAGAAGUCUGAA | 3043 | UUCAGACUUCUUAGACAGC | 3044 |
| UCUAAGAAGUCUGAAUCUA | 3045 | UAGAUUCAGACUUCUUAGA | 3046 |
| CUAAGAAGUCUGAAUCUAU | 3047 | AUAGAUUCAGACUUCUUAG | 3048 |
| UAAGAAGUCUGAAUCUAUC | 3049 | GAUAGAUUCAGACUUCUUA | 3050 |
| AAGAAGUCUGAAUCUAUCU | 3051 | AGAUAGAUUCAGACUUCUU | 3052 |

TABLE 4-continued

| Sense Sequence | SEQ ID NO: | Antisense Sequence | SEQ ID NO: |
|---|---|---|---|
| AGAAGUCUGAAUCUAUCUG | 3053 | CAGAUAGAUUCAGACUUCU | 3054 |
| GAAGUCUGAAUCUAUCUGA | 3055 | UCAGAUAGAUUCAGACUUC | 3056 |
| AAGUCUGAAUCUAUCUGAC | 3057 | GUCAGAUAGAUUCAGACUU | 3058 |
| AGUCUGAAUCUAUCUGACA | 3059 | UGUCAGAUAGAUUCAGACU | 3060 |
| GUCUGAAUCUAUCUGACAG | 3061 | CUGUCAGAUAGAUUCAGAC | 3062 |
| UCUGAAUCUAUCUGACAGG | 3063 | CCUGUCAGAUAGAUUCAGA | 3064 |
| CUGAAUCUAUCUGACAGGA | 3065 | UCCUGUCAGAUAGAUUCAG | 3066 |
| UGAAUCUAUCUGACAGGAG | 3067 | CUCCUGUCAGAUAGAUUCA | 3068 |
| GAAUCUAUCUGACAGGAGU | 3069 | ACUCCUGUCAGAUAGAUUC | 3070 |
| AAUCUAUCUGACAGGAGUA | 3071 | UACUCCUGUCAGAUAGAUU | 3072 |
| AUCUAUCUGACAGGAGUAU | 3073 | AUACUCCUGUCAGAUAGAU | 3074 |
| UCUAUCUGACAGGAGUAUC | 3075 | GAUACUCCUGUCAGAUAGA | 3076 |
| CUAUCUGACAGGAGUAUCU | 3077 | AGAUACUCCUGUCAGAUAG | 3078 |
| UAUCUGACAGGAGUAUCUG | 3079 | CAGAUACUCCUGUCAGAUA | 3080 |
| CAGGAGUAUCUGUUACGUG | 3081 | CACGUAACAGAUACUCCUG | 3082 |
| AGGAGUAUCUGUUACGUGG | 3083 | CCACGUAACAGAUACUCCU | 3084 |
| GGAGUAUCUGUUACGUGGC | 3085 | GCCACGUAACAGAUACUCC | 3086 |
| GAGUAUCUGUUACGUGGCC | 3087 | GGCCACGUAACAGAUACUC | 3088 |
| AGUAUCUGUUACGUGGCCC | 3089 | GGGCCACGUAACAGAUACU | 3090 |
| GUAUCUGUUACGUGGCCCU | 3091 | AGGGCCACGUAACAGAUAC | 3092 |
| UAUCUGUUACGUGGCCCUC | 3093 | GAGGGCCACGUAACAGAUA | 3094 |
| AUCUGUUACGUGGCCCUCA | 3095 | UGAGGGCCACGUAACAGAU | 3096 |
| UCUGUUACGUGGCCCUCAU | 3097 | AUGAGGGCCACGUAACAGA | 3098 |
| CUGUUACGUGGCCCUCAUA | 3099 | UAUGAGGGCCACGUAACAG | 3100 |
| UGUUACGUGGCCCUCAUAC | 3101 | GUAUGAGGGCCACGUAACA | 3102 |
| CGUGGCCCUCAUACACUGU | 3103 | ACAGUGUAUGAGGGCCACG | 3104 |
| GUGGCCCUCAUACACUGUA | 3105 | UACAGUGUAUGAGGGCCAC | 3106 |
| UGGCCCUCAUACACUGUAA | 3107 | UUACAGUGUAUGAGGGCCA | 3108 |
| GGCCCUCAUACACUGUAAC | 3109 | GUUACAGUGUAUGAGGGCC | 3110 |
| ACAUUCUAGAAUUCAUGG | 3111 | CCAUGAAUUCUAGAAAUGU | 3112 |
| CAUUUCUAGAAUUCAUGGC | 3113 | GCCAUGAAUUCUAGAAAUG | 3114 |
| AUUUCUAGAAUUCAUGGCC | 3115 | GGCCAUGAAUUCUAGAAAU | 3116 |
| UUUCUAGAAUUCAUGGCCC | 3117 | GGGCCAUGAAUUCUAGAAA | 3118 |
| UUCUAGAAUUCAUGGCCCA | 3119 | UGGGCCAUGAAUUCUAGAA | 3120 |
| UCUAGAAUUCAUGGCCCAG | 3121 | CUGGGCCAUGAAUUCUAGA | 3122 |
| CUAGAAUUCAUGGCCCAGC | 3123 | GCUGGGCCAUGAAUUCUAG | 3124 |
| UAGAAUUCAUGGCCCAGCU | 3125 | AGCUGGGCCAUGAAUUCUA | 3126 |
| AGAAUUCAUGGCCCAGCUA | 3127 | UAGCUGGGCCAUGAAUUCU | 3128 |
| GAAUUCAUGGCCCAGCUAU | 3129 | AUAGCUGGGCCAUGAAUUC | 3130 |
| AAUUCAUGGCCCAGCUAUA | 3131 | UAUAGCUGGGCCAUGAAUU | 3132 |
| AUUCAUGGCCCAGCUAUAG | 3133 | CUAUAGCUGGGCCAUGAAU | 3134 |
| UUCAUGGCCCAGCUAUAGC | 3135 | GCUAUAGCUGGGCCAUGAA | 3136 |
| UCAUGGCCCAGCUAUAGCA | 3137 | UGCUAUAGCUGGGCCAUGA | 3138 |
| CAUGGCCCAGCUAUAGCAG | 3139 | CUGCUAUAGCUGGGCCAUG | 3140 |
| AUGGCCCAGCUAUAGCAGA | 3141 | UCUGCUAUAGCUGGGCCAU | 3142 |
| CCCAGCUAUAGCAGAAUAA | 3143 | UUAUUCUGCUAUAGCUGGG | 3144 |
| AACGUCCCACUAAUGCUAU | 3145 | AUAGCAUUAGUGGGACGUU | 3146 |
| ACGUCCCACUAAUGCUAUC | 3147 | GAUAGCAUUAGUGGGACGU | 3148 |
| CGUCCCACUAAUGCUAUCC | 3149 | GGAUAGCAUUAGUGGGACG | 3150 |
| CCACUAAUGCUAUCCAGGU | 3151 | ACCUGGAUAGCAUUAGUGG | 3152 |
| CACUAAUGCUAUCCAGGUG | 3153 | CACCUGGAUAGCAUUAGUG | 3154 |
| ACUAAUGCUAUCCAGGUGA | 3155 | UCACCUGGAUAGCAUUAGU | 3156 |
| CUAAUGCUAUCCAGGUGAA | 3157 | UUCACCUGGAUAGCAUUAG | 3158 |
| UAAUGCUAUCCAGGUGAAG | 3159 | CUUCACCUGGAUAGCAUUA | 3160 |
| AUCCAGGUGAAGGGCUUCC | 3161 | GGAAGCCCUUCACCUGGAU | 3162 |
| CCUCUGCUCCACCGCUAGU | 3163 | ACUAGCGGUGGAGCAGAGG | 3164 |
| CUCUGCUCCACCGCUAGUA | 3165 | UACUAGCGGUGGAGCAGAG | 3166 |
| UCUGCUCCACCGCUAGUAA | 3167 | UUACUAGCGGUGGAGCAGA | 3168 |
| CUGCUCCACCGCUAGUAAA | 3169 | UUUACUAGCGGUGGAGCAG | 3170 |
| UGCUCCACCGCUAGUAAAG | 3171 | CUUUACUAGCGGUGGAGCA | 3172 |
| GCUCCACCGCUAGUAAAGC | 3173 | GCUUUACUAGCGGUGGAGC | 3174 |
| CUCCACCGCUAGUAAAGCC | 3175 | GGCUUUACUAGCGGUGGAG | 3176 |
| UCCACCGCUAGUAAAGCCA | 3177 | UGGCUUUACUAGCGGUGGA | 3178 |
| CCACCGCUAGUAAAGCCAA | 3179 | UUGGCUUUACUAGCGGUGG | 3180 |
| CACCGCUAGUAAAGCCAAA | 3181 | UUUGGCUUUACUAGCGGUG | 3182 |
| ACCGCUAGUAAAGCCAAAA | 3183 | UUUUGGCUUUACUAGCGGU | 3184 |
| CCGCUAGUAAAGCCAAAAU | 3185 | AUUUUGGCUUUACUAGCGG | 3186 |
| CGCUAGUAAAGCCAAAAUA | 3187 | UAUUUUGGCUUUACUAGCG | 3188 |
| GCUAGUAAAGCCAAAAUAC | 3189 | GUAUUUUGGCUUUACUAGC | 3190 |
| CUAGUAAAGCCAAAAUACA | 3191 | UGUAUUUUGGCUUUACUAG | 3192 |
| AUACCACCUCUCCCAAAU | 3193 | AUUUGGGAGAGGUGGAUAU | 3194 |
| UAUCCACCUCUCCCAAAUG | 3195 | CAUUUGGGAGAGGUGGAUA | 3196 |
| UCUCCCAAAUGCAGACACU | 3197 | AGUGUCUGCAUUUGGGAGA | 3198 |
| CUCCCAAAUGCAGACACUG | 3199 | CAGUGUCUGCAUUUGGGAG | 3200 |
| UCCCAAAUGCAGACACUGA | 3201 | UCAGUGUCUGCAUUUGGGA | 3202 |
| CCCAAAUGCAGACACUGAU | 3203 | AUCAGUGUCUGCAUUUGGG | 3204 |

TABLE 4-continued

| Sense Sequence | SEQ ID NO: | Antisense Sequence | SEQ ID NO: |
|---|---|---|---|
| CAAAUGCAGACACUGAUGG | 3205 | CCAUCAGUGUCUGCAUUUG | 3206 |
| AAAUGCAGACACUGAUGGG | 3207 | CCCAUCAGUGUCUGCAUUU | 3208 |
| AAUGCAGACACUGAUGGGU | 3209 | ACCCAUCAGUGUCUGCAUU | 3210 |
| AUGCAGACACUGAUGGGUA | 3211 | UACCCAUCAGUGUCUGCAU | 3212 |
| UGCAGACACUGAUGGGUAA | 3213 | UUACCCAUCAGUGUCUGCA | 3214 |
| GCAGACACUGAUGGGUAAU | 3215 | AUUACCCAUCAGUGUCUGC | 3216 |
| CAGACACUGAUGGGUAAUU | 3217 | AAUUACCCAUCAGUGUCUG | 3218 |
| AGACACUGAUGGGUAAUUA | 3219 | UAAUUACCCAUCAGUGUCU | 3220 |
| GACACUGAUGGGUAAUUAA | 3221 | UUAAUUACCCAUCAGUGUC | 3222 |
| ACACUGAUGGGUAAUUAAC | 3223 | GUUAAUUACCCAUCAGUGU | 3224 |
| AUAAAGGCUCAGUCUCUAA | 3225 | UUAGAGACUGAGCCUUUAU | 3226 |
| UAAAGGCUCAGUCUCUAAA | 3227 | UUUAGAGACUGAGCCUUUA | 3228 |
| CUCAACUCAGAUGGAGCCA | 3229 | UGGCUCCAUCUGAGUUGAG | 3230 |
| UCAACUCAGAUGGAGCCAC | 3231 | GUGGCUCCAUCUGAGUUGA | 3232 |
| CAACUCAGAUGGAGCCACU | 3233 | AGUGGCUCCAUCUGAGUUG | 3234 |
| AGAUGGAGCCACUGGGUCU | 3235 | AGACCCAGUGGCUCCAUCU | 3236 |
| GAUGGAGCCACUGGGUCUA | 3237 | UAGACCCAGUGGCUCCAUC | 3238 |
| AUGGAGCCACUGGGUCUAA | 3239 | UUAGACCCAGUGGCUCCAU | 3240 |
| UGGAGCCACUGGGUCUAAA | 3241 | UUUAGACCCAGUGGCUCCA | 3242 |
| GGAGCCACUGGGUCUAAAU | 3243 | AUUUAGACCCAGUGGCUCC | 3244 |
| GAGCCACUGGGUCUAAAUG | 3245 | CAUUUAGACCCAGUGGCUC | 3246 |
| AGCCACUGGGUCUAAAUGC | 3247 | GCAUUUAGACCCAGUGGCU | 3248 |
| GCCACUGGGUCUAAAUGCU | 3249 | AGCAUUUAGACCCAGUGGC | 3250 |
| CCACUGGGUCUAAAUGCUC | 3251 | GAGCAUUUAGACCCAGUGG | 3252 |
| CACUGGGUCUAAAUGCUCA | 3253 | UGAGCAUUUAGACCCAGUG | 3254 |
| ACUGGGUCUAAAUGCUCAC | 3255 | GUGAGCAUUUAGACCCAGU | 3256 |
| CUGGGUCUAAAUGCUCACC | 3257 | GGUGAGCAUUUAGACCCAG | 3258 |
| GGUCUAAAUGCUCACCCUG | 3259 | CAGGGUGAGCAUUUAGACC | 3260 |
| GUCUAAAUGCUCACCCUGU | 3261 | ACAGGGUGAGCAUUUAGAC | 3262 |
| UCUAAAUGCUCACCCUGUG | 3263 | CACAGGGUGAGCAUUUAGA | 3264 |
| CUAAAUGCUCACCCUGUGG | 3265 | CCACAGGGUGAGCAUUUAG | 3266 |
| GAUGCCAUCUACGACUGCU | 3267 | AGCAGUCGUAGAUGGCAUC | 3268 |
| AUGCCAUCUACGACUGCUC | 3269 | GAGCAGUCGUAGAUGGCAU | 3270 |
| UGCCAUCUACGACUGCUCU | 3271 | AGAGCAGUCGUAGAUGGCA | 3272 |
| GCCAUCUACGACUGCUCUU | 3273 | AAGAGCAGUCGUAGAUGGC | 3274 |
| CCAUCUACGACUGCUCUUC | 3275 | GAAGAGCAGUCGUAGAUGG | 3276 |
| CUACGACUGCUCUUCCCUC | 3277 | GAGGGAAGAGCAGUCGUAG | 3278 |
| UACGACUGCUCUUCCCUCU | 3279 | AGAGGGAAGAGCAGUCGUA | 3280 |
| AUCUCUGGAGUGUAUAAGC | 3281 | GCUUAUACACUCCAGAGAU | 3282 |
| CUGGAGUGUAUAAGCUUCC | 3283 | GGAAGCUUAUACACUCCAG | 3284 |
| UGGAGUGUAUAAGCUUCCU | 3285 | AGGAAGCUUAUACACUCCA | 3286 |
| GGAGUGUAUAAGCUUCCUC | 3287 | GAGGAAGCUUAUACACUCC | 3288 |
| GUAUAAGCUUCCUCCUGAU | 3289 | AUCAGGAGGAAGCUUAUAC | 3290 |
| UAUAAGCUUCCUCCUGAUG | 3291 | CAUCAGGAGGAAGCUUAUA | 3292 |
| AUAAGCUUCCUCCUGAUGA | 3293 | UCAUCAGGAGGAAGCUUAU | 3294 |
| AAGCUUCCUCCUGAUGACU | 3295 | AGUCAUCAGGAGGAAGCUU | 3296 |
| AGCUUCCUCCUGAUGACUU | 3297 | AAGUCAUCAGGAGGAAGCU | 3298 |
| GCUUCCUCCUGAUGACUUC | 3299 | GAAGUCAUCAGGAGGAAGC | 3300 |
| CUUCCUCCUGAUGACUUCC | 3301 | GGAAGUCAUCAGGAGGAAG | 3302 |
| UUCCUCCUGAUGACUUCCU | 3303 | AGGAAGUCAUCAGGAGGAA | 3304 |
| ACUUCCUGGGCAGCCCUGA | 3305 | UCAGGGCUGCCCAGGAAGU | 3306 |
| ACUGGAGGUGAGGUCAUUA | 3307 | UAAUGACCUCACCUCCAGU | 3308 |
| CUGGAGGUGAGGUCAUUAC | 3309 | GUAAUGACCUCACCUCCAG | 3310 |
| UGGAGGUGAGGUCAUUACA | 3311 | UGUAAUGACCUCACCUCCA | 3312 |
| GGAGGUGAGGUCAUUACAG | 3313 | CUGUAAUGACCUCACCUCC | 3314 |
| GAGGUGAGGUCAUUACAGU | 3315 | ACUGUAAUGACCUCACCUC | 3316 |
| AGGUGAGGUCAUUACAGUC | 3317 | GACUGUAAUGACCUCACCU | 3318 |
| GGUGAGGUCAUUACAGUCA | 3319 | UGACUGUAAUGACCUCACC | 3320 |
| UCAUUACAGUCACUGGCCA | 3321 | UGGCCAGUGACUGUAAUGA | 3322 |
| CAUUACAGUCACUGGCCAU | 3323 | AUGGCCAGUGACUGUAAUG | 3324 |
| AUUACAGUCACUGGCCAUG | 3325 | CAUGGCCAGUGACUGUAAU | 3326 |
| UACAGUCACUGGCCAUGCC | 3327 | GGCAUGGCCAGUGACUGUA | 3328 |
| ACAGUCACUGGCCAUGCCC | 3329 | GGGCAUGGCCAGUGACUGU | 3330 |
| CAGUCACUGGCCAUGCCCU | 3331 | AGGGCAUGGCCAGUGACUG | 3332 |
| GUCACUGGCCAUGCCCUAA | 3333 | UUAGGGCAUGGCCAGUGAC | 3334 |
| UCACUGGCCAUGCCCUAAU | 3335 | AUUAGGGCAUGGCCAGUGA | 3336 |
| CACUGGCCAUGCCCUAAUA | 3337 | UAUUAGGGCAUGGCCAGUG | 3338 |
| ACUGGCCAUGCCCUAAUAC | 3339 | GUAUUAGGGCAUGGCCAGU | 3340 |
| CUGGCCAUGCCCUAAUACC | 3341 | GGUAUUAGGGCAUGGCCAG | 3342 |
| UGGCCAUGCCCUAAUACCU | 3343 | AGGUAUUAGGGCAUGGCCA | 3344 |
| GCCAUGCCCUAAUACCUGU | 3345 | ACAGGUAUUAGGGCAUGGC | 3346 |
| CCAUGCCCUAAUACCUGUC | 3347 | GACAGGUAUUAGGGCAUGG | 3348 |
| CAUGCCCUAAUACCUGUCC | 3349 | GGACAGGUAUUAGGGCAUG | 3350 |
| AUGCCCUAAUACCUGUCCU | 3351 | AGGACAGGUAUUAGGGCAU | 3352 |
| UGCCCUAAUACCUGUCCUU | 3353 | AAGGACAGGUAUUAGGGCA | 3354 |
| GCCCUAAUACCUGUCCUUC | 3355 | GAAGGACAGGUAUUAGGGC | 3356 |

TABLE 4-continued

| Sense Sequence | SEQ ID NO: | Antisense Sequence | SEQ ID NO: |
|---|---|---|---|
| CCCUAAUACCUGUCCUUCA | 3357 | UGAAGGACAGGUAUUAGGG | 3358 |
| CUAAUACCUGUCCUUCACC | 3359 | GGUGAAGGACAGGUAUUAG | 3360 |
| UAAUACCUGUCCUUCACCC | 3361 | GGGUGAAGGACAGGUAUUA | 3362 |
| ACAGGGCCAUUCACAGUUU | 3363 | AAACUGUGAAUGGCCCUGU | 3364 |
| CAGGGCCAUUCACAGUUUA | 3365 | UAAACUGUGAAUGGCCCUG | 3366 |
| AGGGCCAUUCACAGUUUAA | 3367 | UUAAACUGUGAAUGGCCCU | 3368 |
| GGGCCAUUCACAGUUUAAA | 3369 | UUUAAACUGUGAAUGGCCC | 3370 |
| GGCCAUUCACAGUUUAAAG | 3371 | CUUUAAACUGUGAAUGGCC | 3372 |
| CCAUUCACAGUUUAAAGAA | 3373 | UUCUUUAAACUGUGAAUGG | 3374 |
| CUGUAAUCCCAGCACUAUG | 3375 | CAUAGUGCUGGGAUUACAG | 3376 |
| UGUAAUCCCAGCACUAUGG | 3377 | CCAUAGUGCUGGGAUUACA | 3378 |
| ACUAUGGGAGGCCGAGGCA | 3379 | UGCCUCGGCCUCCCAUAGU | 3380 |
| CCGAGGCAGGUGGAUCACU | 3381 | AGUGAUCCACCUGCCUCGG | 3382 |
| CGAGGCAGGUGGAUCACUU | 3383 | AAGUGAUCCACCUGCCUCG | 3384 |
| GAGGCAGGUGGAUCACUUC | 3385 | GAAGUGAUCCACCUGCCUC | 3386 |
| AGGCAGGUGGAUCACUUCA | 3387 | UGAAGUGAUCCACCUGCCU | 3388 |
| GGCAGGUGGAUCACUUCAG | 3389 | CUGAAGUGAUCCACCUGCC | 3390 |
| GCAGGUGGAUCACUUCAGG | 3391 | CCUGAAGUGAUCCACCUGC | 3392 |
| CAGGUGGAUCACUUCAGGU | 3393 | ACCUGAAGUGAUCCACCUG | 3394 |
| GUUUAAGACCAGCCUGGCC | 3395 | GGCCAGGCUGGUCUUAAAC | 3396 |
| UUUAAGACCAGCCUGGCCA | 3397 | UGGCCAGGCUGGUCUUAAA | 3398 |
| UUAAGACCAGCCUGGCCAA | 3399 | UUGGCCAGGCUGGUCUUAA | 3400 |
| UAAGACCAGCCUGGCCAAC | 3401 | GUUGGCCAGGCUGGUCUUA | 3402 |
| AAAAUUAGCCAGGCAUGGU | 3403 | ACCAUGCCUGGCUAAUUUU | 3404 |
| AAAUUAGCCAGGCAUGGUG | 3405 | CACCAUGCCUGGCUAAUUU | 3406 |
| AAUUAGCCAGGCAUGGUGG | 3407 | CCACCAUGCCUGGCUAAUU | 3408 |
| AUUAGCCAGGCAUGGUGGU | 3409 | ACCACCAUGCCUGGCUAAU | 3410 |
| UUAGCCAGGCAUGGUGGUG | 3411 | CACCACCAUGCCUGGCUAA | 3412 |
| UAGCCAGGCAUGGUGGUGG | 3413 | CCACCACCAUGCCUGGCUA | 3414 |
| AACUCAGGAGGCAGAGGUU | 3415 | AACCUCUGCCUCCUGAGUU | 3416 |
| ACUCAGGAGGCAGAGGUUG | 3417 | CAACCUCUGCCUCCUGAGU | 3418 |
| CUCAGGAGGCAGAGGUUGC | 3419 | GCAACCUCUGCCUCCUGAG | 3420 |
| UCAGGAGGCAGAGGUUGCA | 3421 | UGCAACCUCUGCCUCCUGA | 3422 |
| CAGGAGGCAGAGGUUGCAG | 3423 | CUGCAACCUCUGCCUCCUG | 3424 |
| GAGGUUGCAGUGAGCCGAG | 3425 | CUCGGCUCACUGCAACCUC | 3426 |
| AUCACGCCACUGCACUAUA | 3427 | UAUAGUGCAGUGGCGUGAU | 3428 |
| UCACGCCACUGCACUAUAA | 3429 | UUAUAGUGCAGUGGCGUGA | 3430 |
| CACGCCACUGCACUAUAAU | 3431 | AUUAUAGUGCAGUGGCGUG | 3432 |
| ACGCCACUGCACUAUAAUC | 3433 | GAUUAUAGUGCAGUGGCGU | 3434 |
| CGCCACUGCACUAUAAUCU | 3435 | AGAUUAUAGUGCAGUGGCG | 3436 |
| GCCACUGCACUAUAAUCUG | 3437 | CAGAUUAUAGUGCAGUGGC | 3438 |
| ACCCAGGCAUCUGUUUGGC | 3439 | GCCAAACAGAUGCCUGGGU | 3440 |
| CCCAGGCAUCUGUUUGGCC | 3441 | GGCCAAACAGAUGCCUGGG | 3442 |
| CCAGGCAUCUGUUUGGCCC | 3443 | GGGCCAAACAGAUGCCUGG | 3444 |
| CCCUUCAAAUCAUUAUCAG | 3445 | CUGAUAAUGAUUUGAAGGG | 3446 |
| CCUUCAAAUCAUUAUCAGU | 3447 | ACUGAUAAUGAUUUGAAGG | 3448 |
| CUUCAAAUCAUUAUCAGUC | 3449 | GACUGAUAAUGAUUUGAAG | 3450 |
| ACAUAGAUCAGAUCAUUCU | 3451 | AGAAUGAUCUGAUCUAUGU | 3452 |
| CAUAGAUCAGAUCAUUCUU | 3453 | AAGAAUGAUCUGAUCUAUG | 3454 |
| UCAGAUCAUUCUUAUAACC | 3455 | GGUUAUAAGAAUGAUCUGA | 3456 |
| CAGAUCAUUCUUAUAACCA | 3457 | UGGUUAUAAGAAUGAUCUG | 3458 |
| AUAACCACCACAUAACUUA | 3459 | UAAGUUAUGUGGUGGUUAU | 3460 |
| UAACCACCACAUAACUUAG | 3461 | CUAAGUUAUGUGGUGGUUA | 3462 |
| AACCACCACAUAACUUAGU | 3463 | ACUAAGUUAUGUGGUGGUU | 3464 |
| ACCACCACAUAACUUAGUU | 3465 | AACUAAGUUAUGUGGUGGU | 3466 |
| CCACCACAUAACUUAGUUU | 3467 | AAACUAAGUUAUGUGGUGG | 3468 |
| CACCACAUAACUUAGUUUA | 3469 | UAAACUAAGUUAUGUGGUG | 3470 |
| ACACGAAGGCAGCAUCAAA | 3471 | UUUGAUGCUGCCUUCGUGU | 3472 |
| CACGAAGGCAGCAUCAAAU | 3473 | AUUUGAUGCUGCCUUCGUG | 3474 |
| ACGAAGGCAGCAUCAAAUU | 3475 | AAUUUGAUGCUGCCUUCGU | 3476 |
| CGAAGGCAGCAUCAAAUUA | 3477 | UAAUUUGAUGCUGCCUUCG | 3478 |
| GAAGGCAGCAUCAAAUUAU | 3479 | AUAAUUUGAUGCUGCCUUC | 3480 |
| AAGGCAGCAUCAAAUUAUC | 3481 | GAUAAUUUGAUGCUGCCUU | 3482 |
| AGGCAGCAUCAAAUUAUCU | 3483 | AGAUAAUUUGAUGCUGCCU | 3484 |
| GGCAGCAUCAAAUUAUCUG | 3485 | CAGAUAAUUUGAUGCUGCC | 3486 |
| AAUUAUCUGGAUUUUCACC | 3487 | GGUGAAAAUCCAGAUAAUU | 3488 |
| AUUAUCUGGAUUUUCACCC | 3489 | GGGUGAAAAUCCAGAUAAU | 3490 |
| UUAUCUGGAUUUUCACCCA | 3491 | UGGGUGAAAAUCCAGAUAA | 3492 |
| AUUUUCACCCAGGCAUGGU | 3493 | ACCAUGCCUGGGUGAAAAU | 3494 |
| ACCCAGGCAUGGUGGCUCA | 3495 | UGAGCCACCAUGCCUGGGU | 3496 |
| CCAGGCAUGGUGGCUCACA | 3497 | UGUGAGCCACCAUGCCUGG | 3498 |
| CAGGCAUGGUGGCUCACAC | 3499 | GUGUGAGCCACCAUGCCUG | 3500 |
| GUGGCUCACACCUGUAAUC | 3501 | GAUUACAGGUGUGAGCCAC | 3502 |
| UGGCUCACACCUGUAAUCC | 3503 | GGAUUACAGGUGUGAGCCA | 3504 |
| GGCUCACACCUGUAAUCCC | 3505 | GGGAUUACAGGUGUGAGCC | 3506 |
| CACACCUGUAAUCCCAAGU | 3507 | ACUUGGGAUUACAGGUGUG | 3508 |

TABLE 4-continued

| Sense Sequence | SEQ ID NO: | Antisense Sequence | SEQ ID NO: |
|---|---|---|---|
| ACACCUGUAAUCCCAAGUU | 3509 | AACUUGGGAUUACAGGUGU | 3510 |
| CACCUGUAAUCCCAAGUUU | 3511 | AAACUUGGGAUUACAGGUG | 3512 |
| ACCUGUAAUCCCAAGUUUU | 3513 | AAAACUUGGGAUUACAGGU | 3514 |
| GGCACUCUGGUCCCAGCUA | 3515 | UAGCUGGGACCAGAGUGCC | 3516 |
| GCACUCUGGUCCCAGCUAC | 3517 | GUAGCUGGGACCAGAGUGC | 3518 |
| CACUCUGGUCCCAGCUACU | 3519 | AGUAGCUGGGACCAGAGUG | 3520 |
| ACUCUGGUCCCAGCUACUA | 3521 | UAGUAGCUGGGACCAGAGU | 3522 |
| AACUCAGGAGGUGGAGGUU | 3523 | AACCUCCACCUCCUGAGUU | 3524 |
| ACUCAGGAGGUGGAGGUUG | 3525 | CAACCUCCACCUCCUGAGU | 3526 |
| CUCAGGAGGUGGAGGUUGC | 3527 | GCAACCUCCACCUCCUGAG | 3528 |
| UCAGGAGGUGGAGGUUGCA | 3529 | UGCAACCUCCACCUCCUGA | 3530 |
| CAGGAGGUGGAGGUUGCAG | 3531 | CUGCAACCUCCACCUCCUG | 3532 |
| GAGGUUGCAGUGAGCCGAG | 3533 | CUCGGCUCACUGCAACCUC | 3534 |
| AGAUUGCACCACUGUACUC | 3535 | GAGUACAGUGGUGCAAUCU | 3536 |
| ACUGUACUCUAGCCUGGGC | 3537 | GCCCAGGCUAGAGUACAGU | 3538 |
| CUGUACUCUAGCCUGGGCA | 3539 | UGCCCAGGCUAGAGUACAG | 3540 |
| UGUACUCUAGCCUGGGCAA | 3541 | UUGCCCAGGCUAGAGUACA | 3542 |
| UCCCUCCAAGCUUCAUGUG | 3543 | CACAUGAAGCUUGGAGGGA | 3544 |
| CCCUCCAAGCUUCAUGUGC | 3545 | GCACAUGAAGCUUGGAGGG | 3546 |
| CCUCCAAGCUUCAUGUGCA | 3547 | UGCACAUGAAGCUUGGAGG | 3548 |
| CUCCAAGCUUCAUGUGCAC | 3549 | GUGCACAUGAAGCUUGGAG | 3550 |
| GGCCCAAUUUGCAUCGUUC | 3551 | GAACGAUGCAAAUUGGGCC | 3552 |
| GCCCAAUUUGCAUCGUUCU | 3553 | AGAACGAUGCAAAUUGGGC | 3554 |
| CCCAAUUUGCAUCGUUCUU | 3555 | AAGAACGAUGCAAAUUGGG | 3556 |
| CCAAUUUGCAUCGUUCUUC | 3557 | GAAGAACGAUGCAAAUUGG | 3558 |
| UUUGCAUCGUUCUUCCAGA | 3559 | UCUGGAAGAACGAUGCAAA | 3560 |
| CAUCGUUCUUCCAGAGCAA | 3561 | UUGCUCUGGAAGAACGAUG | 3562 |
| AUCGUUCUUCCAGAGCAAU | 3563 | AUUGCUCUGGAAGAACGAU | 3564 |
| UCGUUCUUCCAGAGCAAUG | 3565 | CAUUGCUCUGGAAGAACGA | 3566 |
| CGUUCUUCCAGAGCAAUGC | 3567 | GCAUUGCUCUGGAAGAACG | 3568 |
| CUUCCAGAGCAAUGCACCA | 3569 | UGGUGCAUUGCUCUGGAAG | 3570 |
| UUCCAGAGCAAUGCACCAC | 3571 | GUGGUGCAUUGCUCUGGAA | 3572 |
| CCCGAGUGAGCCAGUGUGA | 3573 | UCACACUGGCUCACUCGGG | 3574 |
| CCGAGUGAGCCAGUGUGAC | 3575 | GUCACACUGGCUCACUCGG | 3576 |
| CGAGUGAGCCAGUGUGACU | 3577 | AGUCACACUGGCUCACUCG | 3578 |
| AGUGUGACUGCGGGAGUGC | 3579 | GCACUCCCGCAGUCACACU | 3580 |
| GUGUGACUGCGGGAGUGCA | 3581 | UGCACUCCCGCAGUCACAC | 3582 |
| UGUGACUGCGGGAGUGCAC | 3583 | GUGCACUCCCGCAGUCACA | 3584 |
| GUGACUGCGGGAGUGCACA | 3585 | UGUGCACUCCCGCAGUCAC | 3586 |
| UGACUGCGGGAGUGCACAC | 3587 | GUGUGCACUCCCGCAGUCA | 3588 |
| UCUACUGGCUCUGCAGGGA | 3589 | UCCCUGCAGAGCCAGUAGA | 3590 |
| UACUGGCUCUGCAGGGACA | 3591 | UGUCCCUGCAGAGCCAGUA | 3592 |
| AGGUUGGGAAGCCUGCCCU | 3593 | AGGGCAGGCUUCCCAACCU | 3594 |
| GUUGGGAAGCCUGCCCUCU | 3595 | AGAGGGCAGGCUUCCCAAC | 3596 |
| UUGGGAAGCCUGCCCUCUU | 3597 | AAGAGGGCAGGCUUCCCAA | 3598 |
| GAAGCCUGCCCUCUUGCUC | 3599 | GAGCAAGAGGGCAGGCUUC | 3600 |
| AAGCCUGCCCUCUUGCUCC | 3601 | GGAGCAAGAGGGCAGGCUU | 3602 |
| CUCUUGCUCCUGCCUUCUG | 3603 | CAGAAGGCAGGAGCAAGAG | 3604 |
| UCUUGCUCCUGCCUUCUGC | 3605 | GCAGAAGGCAGGAGCAAGA | 3606 |
| UUGCUCCUGCCUUCUGCCC | 3607 | GGGCAGAAGGCAGGAGCAA | 3608 |
| CCCUGCAAGUCCCUCACCA | 3609 | UGGUGAGGGACUUGCAGGG | 3610 |
| CCUGCAAGUCCCUCACCAG | 3611 | CUGGUGAGGGACUUGCAGG | 3612 |
| AAGUCCCUCACCAGAGUAU | 3613 | AUACUCUGGUGAGGGACUU | 3614 |
| AGUCCCUCACCAGAGUAUC | 3615 | GAUACUCUGGUGAGGGACU | 3616 |
| GUCCCUCACCAGAGUAUCC | 3617 | GGAUACUCUGGUGAGGGAC | 3618 |
| UCCCUCACCAGAGUAUCCC | 3619 | GGGAUACUCUGGUGAGGGA | 3620 |
| CCCUCUGCUUCAGGUGUUC | 3621 | GAACACCUGAAGCAGAGGG | 3622 |
| CCUCUGCUUCAGGUGUUCU | 3623 | AGAACACCUGAAGCAGAGG | 3624 |
| CUCUGCUUCAGGUGUUCUG | 3625 | CAGAACACCUGAAGCAGAG | 3626 |
| AGACUUCAGGCGGAGGCUG | 3627 | CAGCCUCCGCCUGAAGUCU | 3628 |
| ACUUCAGGCGGAGGCUGGA | 3629 | UCCAGCCUCCGCCUGAAGU | 3630 |
| GCGGAGGCUGGACCAUCAU | 3631 | AUGAUGGUCCAGCCUCCGC | 3632 |
| CGGAGGCUGGACCAUCAUC | 3633 | GAUGAUGGUCCAGCCUCCG | 3634 |
| GGAGGCUGGACCAUCAUCC | 3635 | GGAUGAUGGUCCAGCCUCC | 3636 |
| AAGUGGCCUUGUCUCCUUC | 3637 | GAAGGAGACAAGGCCACUU | 3638 |
| AGUGGCCUUGUCUCCUUCU | 3639 | AGAAGGAGACAAGGCCACU | 3640 |
| GUGGCCUUGUCUCCUUCUA | 3641 | UAGAAGGAGACAAGGCCAC | 3642 |
| CUUGUCUCCUUCUACCGGG | 3643 | CCCGGUAGAAGGAGACAAG | 3644 |
| UUGUCUCCUUCUACCGGGA | 3645 | UCCCGGUAGAAGGAGACAA | 3646 |
| UGUCUCCUUCUACCGGGAC | 3647 | GUCCCGGUAGAAGGAGACA | 3648 |
| GUCUCCUUCUACCGGGACU | 3649 | AGUCCCGGUAGAAGGAGAC | 3650 |
| UUCUACCGGGACUGGAAGC | 3651 | GCUUCCAGUCCCGGUAGAA | 3652 |
| UCUACCGGGACUGGAAGCA | 3653 | UGCUUCCAGUCCCGGUAGA | 3654 |
| CUACCGGGACUGGAAGCAG | 3655 | CUGCUUCCAGUCCCGGUAG | 3656 |
| AGCAGGGCUUUGGCAGCAU | 3657 | AUGCUGCCAAAGCCCUGCU | 3658 |
| AGGGCUUUGGCAGCAUCCG | 3659 | CGGAUGCUGCCAAAGCCCU | 3660 |

TABLE 4-continued

| Sense Sequence | SEQ ID NO: | Antisense Sequence | SEQ ID NO: |
|---|---|---|---|
| GGGCUUUGGCAGCAUCCGU | 3661 | ACGGAUGCUGCCAAAGCCC | 3662 |
| GGCUUUGGCAGCAUCCGUG | 3663 | CACGGAUGCUGCCAAAGCC | 3664 |
| CAUCCACCGGCUCUCCAGA | 3665 | UCUGGAGAGCCGGUGGAUG | 3666 |
| AUCCACCGGCUCUCCAGAC | 3667 | GUCUGGAGAGCCGGUGGAU | 3668 |
| UCCACCGGCUCUCCAGACA | 3669 | UGUCUGGAGAGCCGGUGGA | 3670 |
| CUGGACCAGUGCCACCACA | 3671 | UGUGGUGGCACUGGUCCAG | 3672 |
| GGGUGCCAUUCCUAUUCUG | 3673 | CAGAAUAGGAAUGGCACCC | 3674 |
| GGUGCCAUUCCUAUUCUGA | 3675 | UCAGAAUAGGAAUGGCACC | 3676 |
| GUGCCAUUCCUAUUCUGAU | 3677 | AUCAGAAUAGGAAUGGCAC | 3678 |
| UGCCAUUCCUAUUCUGAUU | 3679 | AAUCAGAAUAGGAAUGGCA | 3680 |
| AUUCCUAUUCUGAUUCAAG | 3681 | CUUGAAUCAGAAUAGGAAU | 3682 |
| UGUAUAUUCAUUGUGAUGG | 3683 | CCAUCACAAUGAAUAUACA | 3684 |
| GUAUAUUCAUUGUGAUGGU | 3685 | ACCAUCACAAUGAAUAUAC | 3686 |
| AUUCAUUGUGAUGGUUUUC | 3687 | GAAAACCAUCACAAUGAAU | 3688 |
| UUCAUUGUGAUGGUUUUCC | 3689 | GGAAAACCAUCACAAUGAA | 3690 |
| UGUGAUGGUUUUCCUGCAA | 3691 | UUGCAGGAAAACCAUCACA | 3692 |
| GUGAUGGUUUUCCUGCAAG | 3693 | CUUGCAGGAAAACCAUCAC | 3694 |
| UGAUGGUUUUCCUGCAAGU | 3695 | ACUUGCAGGAAAACCAUCA | 3696 |
| AUGGUUUUCCUGCAAGUUG | 3697 | CAACUUGCAGGAAAACCAU | 3698 |
| GGUUUUCCUGCAAGUUGUA | 3699 | UACAACUUGCAGGAAAACC | 3700 |
| GUUUUCCUGCAAGUUGUAA | 3701 | UUACAACUUGCAGGAAAAC | 3702 |
| UUUUCCUGCAAGUUGUAAU | 3703 | AUUACAACUUGCAGGAAAA | 3704 |
| UUUCCUGCAAGUUGUAAUG | 3705 | CAUUACAACUUGCAGGAAA | 3706 |
| UUCCUGCAAGUUGUAAUGG | 3707 | CCAUUACAACUUGCAGGAA | 3708 |
| UCCUGCAAGUUGUAAUGGA | 3709 | UCCAUUACAACUUGCAGGA | 3710 |
| CAAGUUGUAAUGGAGUUGA | 3711 | UCAACUCCAUUACAACUUG | 3712 |
| AAGUUGUAAUGGAGUUGAG | 3713 | CUCAACUCCAUUACAACUU | 3714 |
| AGUUGUAAUGGAGUUGAGG | 3715 | CCUCAACUCCAUUACAACU | 3716 |
| GUUGUAAUGGAGUUGAGGA | 3717 | UCCUCAACUCCAUUACAAC | 3718 |
| CUGCAGGUGGGACAGGAAG | 3719 | CUUCCUGUCCCACCUGCAG | 3720 |
| GCAGGUGGGACAGGAAGAG | 3721 | CUCUUCCUGUCCCACCUGC | 3722 |
| CAGGUGGGACAGGAAGAGG | 3723 | CCUCUUCCUGUCCCACCUG | 3724 |
| AGGUGGGACAGGAAGAGGC | 3725 | GCCUCUUCCUGUCCCACCU | 3726 |
| GGGACAGGAAGAGGCCAGA | 3727 | UCUGGCCUCUUCCUGUCCC | 3728 |
| GGACAGGAAGAGGCCAGAC | 3729 | GUCUGGCCUCUUCCUGUCC | 3730 |
| GACAGGAAGAGGCCAGACC | 3731 | GGUCUGGCCUCUUCCUGUC | 3732 |
| CAGACCCAGGCCAGAGUAG | 3733 | CUACUCUGGCCUGGGUCUG | 3734 |
| AGACCCAGGCCAGAGUAGA | 3735 | UCUACUCUGGCCUGGGUCU | 3736 |
| GACCCAGGCCAGAGUAGAG | 3737 | CUCUACUCUGGCCUGGGUC | 3738 |
| CCCAGGCCAGAGUAGAGCA | 3739 | UGCUCUACUCUGGCCUGGG | 3740 |
| CAGGCCAGAGUAGAGCAAA | 3741 | UUUGCUCUACUCUGGCCUG | 3742 |
| GCCAGAGUAGAGCAAAUUC | 3743 | GAAUUUGCUCUACUCUGGC | 3744 |
| CCAGAGUAGAGCAAAUUCA | 3745 | UGAAUUUGCUCUACUCUGG | 3746 |
| CAGAGUAGAGCAAAUUCAA | 3747 | UUGAAUUUGCUCUACUCUG | 3748 |
| AGAGUAGAGCAAAUUCAAC | 3749 | GUUGAAUUUGCUCUACUCU | 3750 |
| ACACUAGUCUCUGCUCUGG | 3751 | CCAGAGCAGAGACUAGUGU | 3752 |
| CACUAGUCUCUGCUCUGGC | 3753 | GCCAGAGCAGAGACUAGUG | 3754 |
| CUAGUCUCUGCUCUGGCCG | 3755 | CGGCCAGAGCAGAGACUAG | 3756 |
| UAGUCUCUGCUCUGGCCGA | 3757 | UCGGCCAGAGCAGAGACUA | 3758 |
| AGUCUCUGCUCUGGCCGAG | 3759 | CUCGGCCAGAGCAGAGACU | 3760 |
| CUCUGGCCGAGCAUGAGGU | 3761 | ACCUCAUGCUCGGCCAGAG | 3762 |
| UCUGGCCGAGCAUGAGGUC | 3763 | GACCUCAUGCUCGGCCAGA | 3764 |
| UGGCCGAGCAUGAGGUCCU | 3765 | AGGACCUCAUGCUCGGCCA | 3766 |
| GGCCGAGCAUGAGGUCCUU | 3767 | AAGGACCUCAUGCUCGGCC | 3768 |
| GCCGAGCAUGAGGUCCUUU | 3769 | AAAGGACCUCAUGCUCGGC | 3770 |
| CCGAGCAUGAGGUCCUUUA | 3771 | UAAAGGACCUCAUGCUCGG | 3772 |
| CGAGCAUGAGGUCCUUUAG | 3773 | CUAAAGGACCUCAUGCUCG | 3774 |
| GAGCAUGAGGUCCUUUAGG | 3775 | CCUAAAGGACCUCAUGCUC | 3776 |
| AGCAUGAGGUCCUUUAGGU | 3777 | ACCUAAAGGACCUCAUGCU | 3778 |
| GCAUGAGGUCCUUUAGGUG | 3779 | CACCUAAAGGACCUCAUGC | 3780 |
| CAUGAGGUCCUUUAGGUGC | 3781 | GCACCUAAAGGACCUCAUG | 3782 |
| AUGAGGUCCUUUAGGUGCA | 3783 | UGCACCUAAAGGACCUCAU | 3784 |
| UGAGGUCCUUUAGGUGCAA | 3785 | UUGCACCUAAAGGACCUCA | 3786 |
| GAGGUCCUUUAGGUGCAAA | 3787 | UUUGCACCUAAAGGACCUC | 3788 |
| AGGUCCUUUAGGUGCAAAU | 3789 | AUUUGCACCUAAAGGACCU | 3790 |
| GGUCCUUUAGGUGCAAAUC | 3791 | GAUUUGCACCUAAAGGACC | 3792 |
| GUCCUUUAGGUGCAAAUCU | 3793 | AGAUUUGCACCUAAAGGAC | 3794 |
| UCCUUUAGGUGCAAAUCUU | 3795 | AAGAUUUGCACCUAAAGGA | 3796 |
| CCUUUAGGUGCAAAUCUUA | 3797 | UAAGAUUUGCACCUAAAGG | 3798 |
| CUUUAGGUGCAAAUCUUAC | 3799 | GUAAGAUUUGCACCUAAAG | 3800 |
| UUUAGGUGCAAAUCUUACU | 3801 | AGUAAGAUUUGCACCUAAA | 3802 |
| GCAAAUCUUACUGAUACUG | 3803 | CAGUAUCAGUAAGAUUUGC | 3804 |
| UCUUACUGAUACUGUUUGG | 3805 | CCAAACAGUAUCAGUAAGA | 3806 |
| AAAGCACUCACUAUAUCCU | 3807 | AGGAUAUAGUGAGUGCUUU | 3808 |
| AAGCACUCACUAUAUCCUC | 3809 | GAGGAUAUAGUGAGUGCUU | 3810 |
| ACUCACUAUAUCCUCAUGU | 3811 | ACAUGAGGAUAUAGUGAGU | 3812 |

TABLE 4-continued

| Sense Sequence | SEQ ID NO: | Antisense Sequence | SEQ ID NO: |
|---|---|---|---|
| UCACUAUAUCCUCAUGUUU | 3813 | AAACAUGAGGAUAUAGUGA | 3814 |
| UAUCCUCAUGUUUCUCUUA | 3815 | UAAGAGAAACAUGAGGAUA | 3816 |
| AUCCUCAUGUUUCUCUUAC | 3817 | GUAAGAGAAACAUGAGGAU | 3818 |
| UCCUCAUGUUUCUCUUACA | 3819 | UGUAAGAGAAACAUGAGGA | 3820 |
| CUCAUGUUUCUCUUACAGC | 3821 | GCUGUAAGAGAAACAUGAG | 3822 |
| UCAUGUUUCUCUUACAGCA | 3823 | UGCUGUAAGAGAAACAUGA | 3824 |
| UUCUCUUACAGCAGCUCUG | 3825 | CAGAGCUGCUGUAAGAGAA | 3826 |
| GCAGCUCUGUGUGGGAUUC | 3827 | GAAUCCCACACAGAGCUGC | 3828 |
| ACAUAGCUGCACCUUAUAA | 3829 | UUAUAAGGUGCAGCUAUGU | 3830 |
| CAUAGCUGCACCUUAUAAG | 3831 | CUUAUAAGGUGCAGCUAUG | 3832 |
| AUAGCUGCACCUUAUAAGC | 3833 | GCUUAUAAGGUGCAGCUAU | 3834 |
| UAGCUGCACCUUAUAAGCA | 3835 | UGCUUAUAAGGUGCAGCUA | 3836 |
| AGACUAAUCAAGGCCAUAU | 3837 | AUAUGGCCUUGAUUAGUCU | 3838 |
| GACUAAUCAAGGCCAUAUG | 3839 | CAUAUGGCCUUGAUUAGUC | 3840 |
| ACUAAUCAAGGCCAUAUGG | 3841 | CCAUAUGGCCUUGAUUAGU | 3842 |
| CUAAUCAAGGCCAUAUGGU | 3843 | ACCAUAUGGCCUUGAUUAG | 3844 |
| UAAUCAAGGCCAUAUGGUG | 3845 | CACCAUAUGGCCUUGAUUA | 3846 |
| AAUCAAGGCCAUAUGGUGA | 3847 | UCACCAUAUGGCCUUGAUU | 3848 |
| AUCAAGGCCAUAUGGUGAA | 3849 | UUCACCAUAUGGCCUUGAU | 3850 |
| UCAAGGCCAUAUGGUGAAU | 3851 | AUUCACCAUAUGGCCUUGA | 3852 |
| CAAGGCCAUAUGGUGAAUC | 3853 | GAUUCACCAUAUGGCCUUG | 3854 |
| AAGGCCAUAUGGUGAAUCA | 3855 | UGAUUCACCAUAUGGCCUU | 3856 |
| AAAGAAGUUCGAGCCUUGU | 3857 | ACAAGGCUCGAACUUCUUU | 3858 |
| AAGAAGUUCGAGCCUUGUU | 3859 | AACAAGGCUCGAACUUCUU | 3860 |
| AGAAGUUCGAGCCUUGUUU | 3861 | AAACAAGGCUCGAACUUCU | 3862 |
| GAAGUUCGAGCCUUGUUUU | 3863 | AAAACAAGGCUCGAACUUC | 3864 |
| AAGUUCGAGCCUUGUUUUC | 3865 | GAAAACAAGGCUCGAACUU | 3866 |
| AGUUCGAGCCUUGUUUUCU | 3867 | AGAAAACAAGGCUCGAACU | 3868 |
| GUUCGAGCCUUGUUUUCUG | 3869 | CAGAAAACAAGGCUCGAAC | 3870 |
| UUCGAGCCUUGUUUUCUGA | 3871 | UCAGAAAACAAGGCUCGAA | 3872 |
| UCGAGCCUUGUUUUCUGAU | 3873 | AUCAGAAAACAAGGCUCGA | 3874 |
| CGAGCCUUGUUUUCUGAUU | 3875 | AAUCAGAAAACAAGGCUCG | 3876 |
| UUCUGAUUCCCAGGUUAAC | 3877 | GUUAACCUGGGAAUCAGAA | 3878 |
| AAAAGAUGUUUGGCUAUGG | 3879 | CCAUAGCCAAACAUCUUUU | 3880 |
| AAAGAUGUUUGGCUAUGGG | 3881 | CCCAUAGCCAAACAUCUUU | 3882 |
| AAGAUGUUUGGCUAUGGGA | 3883 | UCCCAUAGCCAAACAUCUU | 3884 |
| AGAUGUUUGGCUAUGGGAC | 3885 | GUCCCAUAGCCAAACAUCU | 3886 |
| GAUGUUUGGCUAUGGGACU | 3887 | AGUCCCAUAGCCAAACAUC | 3888 |
| UUUGGCUAUGGGACUGUCA | 3889 | UGACAGUCCCAUAGCCAAA | 3890 |
| UUGGCUAUGGGACUGUCAG | 3891 | CUGACAGUCCCAUAGCCAA | 3892 |
| UGGCUAUGGGACUGUCAGG | 3893 | CCUGACAGUCCCAUAGCCA | 3894 |
| GAGCCUGCUGCACUUUCUU | 3895 | AAGAAAGUGCAGCAGGCUC | 3896 |
| CUGCUGCACUUUCUUUAAG | 3897 | CUUAAAGAAAGUGCAGCAG | 3898 |
| UGCUGCACUUUCUUUAAGG | 3899 | CCUUAAAGAAAGUGCAGCA | 3900 |
| GCUGCACUUUCUUUAAGGC | 3901 | GCCUUAAAGAAAGUGCAGC | 3902 |
| UGCACUUUCUUUAAGGCUC | 3903 | GAGCCUUAAAGAAAGUGCA | 3904 |
| GCACUUUCUUUAAGGCUCU | 3905 | AGAGCCUUAAAGAAAGUGC | 3906 |
| CACUUUCUUUAAGGCUCUG | 3907 | CAGAGCCUUAAAGAAAGUG | 3908 |
| UUCUUUAAGGCUCUGCUCC | 3909 | GGAGCAGAGCCUUAAAGAA | 3910 |
| GCUCUGCUCCUCCUGACAG | 3911 | CUGUCAGGAGGAGCAGAGC | 3912 |
| AGGACUGGGAGGGCAACCU | 3913 | AGGUUGCCCUCCCAGUCCU | 3914 |
| GCAACCUGCGCUACGCUGA | 3915 | UCAGCGUAGCGCAGGUUGC | 3916 |
| CAACCUGCGCUACGCUGAG | 3917 | CUCAGCGUAGCGCAGGUUG | 3918 |
| CUGCGCUACGCUGAGUAUA | 3919 | UAUACUCAGCGUAGCGCAG | 3920 |
| UGCGCUACGCUGAGUAUAG | 3921 | CUAUACUCAGCGUAGCGCA | 3922 |
| CUACGCUGAGUAUAGCCAC | 3923 | GUGGCUAUACUCAGCGUAG | 3924 |
| UACGCUGAGUAUAGCCACU | 3925 | AGUGGCUAUACUCAGCGUA | 3926 |
| CACUUUGUUUGGGCAAUG | 3927 | CAUUGCCCAAAACAAAGUG | 3928 |
| AACUACACUGGCAAUGUGG | 3929 | CCACAUUGCCAGUGUAGUU | 3930 |
| ACUACACUGGCAAUGUGGG | 3931 | CCCACAUUGCCAGUGUAGU | 3932 |
| AACGACGCCCUCCAGUAUC | 3933 | GAUACUGGAGGGCGUCGUU | 3934 |
| ACGACGCCCUCCAGUAUCA | 3935 | UGAUACUGGAGGGCGUCGU | 3936 |
| CGACGCCCUCCAGUAUCAU | 3937 | AUGAUACUGGAGGGCGUCG | 3938 |
| GACGCCCUCCAGUAUCAUA | 3939 | UAUGAUACUGGAGGGCGUC | 3940 |
| ACGCCCUCCAGUAUCAUAA | 3941 | UUAUGAUACUGGAGGGCGU | 3942 |
| CGCCCUCCAGUAUCAUAAC | 3943 | GUUAUGAUACUGGAGGGCG | 3944 |
| CAAGUGUGCACAGCUCCGC | 3945 | GCGGAGCUGUGCACACUUG | 3946 |
| AAGUGUGCACAGCUCCGCA | 3947 | UGCGGAGCUGUGCACACUU | 3948 |
| AGUGUGCACAGCUCCGCAA | 3949 | UUGCGGAGCUGUGCACACU | 3950 |
| UGCACAGCUCCGCAAAGGU | 3951 | ACCUUUGCGGAGCUGUGCA | 3952 |
| GCACAGCUCCGCAAAGGUG | 3953 | CACCUUUGCGGAGCUGUGC | 3954 |
| CACAGCUCCGCAAAGGUGA | 3955 | UCACCUUUGCGGAGCUGUG | 3956 |
| ACAGCUCCGCAAAGGUGAG | 3957 | CUCACCUUUGCGGAGCUGU | 3958 |
| CAAGCUCAUAAUCCCACUU | 3959 | AAGUGGGAUUAUGAGCUUG | 3960 |
| CAUAAUCCCACUUGAGGAG | 3961 | CUCCUCAAGUGGGAUUAUG | 3962 |
| ACUGUACAGUUGAUAUUCC | 3963 | GGAAUAUCAACUGUACAGU | 3964 |

TABLE 4-continued

| Sense Sequence | SEQ ID NO: | Antisense Sequence | SEQ ID NO: |
|---|---|---|---|
| CUGUACAGUUGAUAUUCCG | 3965 | CGGAAUAUCAACUGUACAG | 3966 |
| UGUACAGUUGAUAUUCCGG | 3967 | CCGGAAUAUCAACUGUACA | 3968 |
| GUACAGUUGAUAUUCCGGU | 3969 | ACCGGAAUAUCAACUGUAC | 3970 |
| UACAGUUGAUAUUCCGGUU | 3971 | AACCGGAAUAUCAACUGUA | 3972 |
| ACAGUUGAUAUUCCGGUUU | 3973 | AAACCGGAAUAUCAACUGU | 3974 |
| CAGUUGAUAUUCCGGUUUU | 3975 | AAAACCGGAAUAUCAACUG | 3976 |
| AGUUGAUAUUCCGGUUUUG | 3977 | CAAAACCGGAAUAUCAACU | 3978 |
| GUUGAUAUUCCGGUUUUGG | 3979 | CCAAAACCGGAAUAUCAAC | 3980 |
| UUGAUAUUCCGGUUUUGGU | 3981 | ACCAAAACCGGAAUAUCAA | 3982 |
| UGAUAUUCCGGUUUUGGUA | 3983 | UACCAAAACCGGAAUAUCA | 3984 |
| GAUAUUCCGGUUUUGGUAU | 3985 | AUACCAAAACCGGAAUAUC | 3986 |
| AUAUUCCGGUUUUGGUAUU | 3987 | AAUACCAAAACCGGAAUAU | 3988 |
| UAUUCCGGUUUUGGUAUUC | 3989 | GAAUACCAAAACCGGAAUA | 3990 |
| AUUCCGGUUUUGGUAUUCU | 3991 | AGAAUACCAAAACCGGAAU | 3992 |
| UUCCGGUUUUGGUAUUCUU | 3993 | AAGAAUACCAAAACCGGAA | 3994 |
| GGUUUUGGUAUUCUUUCUG | 3995 | CAGAAAGAAUACCAAAACC | 3996 |
| UUUUGGUAUUCUUUCUGAC | 3997 | GUCAGAAAGAAUACCAAAA | 3998 |
| GGUAUUCUUUCUGACCCUG | 3999 | CAGGGUCAGAAAGAAUACC | 4000 |
| AACUCCUUACCUGAUGUCU | 4001 | AGACAUCAGGUAAGGAGUU | 4002 |
| ACUCCUUACCUGAUGUCUG | 4003 | CAGACAUCAGGUAAGGAGU | 4004 |
| CUCCUUACCUGAUGUCUGG | 4005 | CCAGACAUCAGGUAAGGAG | 4006 |
| UCCUUACCUGAUGUCUGGU | 4007 | ACCAGACAUCAGGUAAGGA | 4008 |
| CCUUACCUGAUGUCUGGUC | 4009 | GACCAGACAUCAGGUAAGG | 4010 |
| CUUACCUGAUGUCUGGUCU | 4011 | AGACCAGACAUCAGGUAAG | 4012 |
| UUACCUGAUGUCUGGUCUA | 4013 | UAGACCAGACAUCAGGUAA | 4014 |
| UACCUGAUGUCUGGUCUAU | 4015 | AUAGACCAGACAUCAGGUA | 4016 |
| ACCUGAUGUCUGGUCUAUC | 4017 | GAUAGACCAGACAUCAGGU | 4018 |
| GAUGUCUGGUCUAUCACAG | 4019 | CUGUGAUAGACCAGACAUC | 4020 |
| AUGUCUGGUCUAUCACAGU | 4021 | ACUGUGAUAGACCAGACAU | 4022 |
| UGUCUGGUCUAUCACAGUC | 4023 | GACUGUGAUAGACCAGACA | 4024 |
| GUCUGGUCUAUCACAGUCA | 4025 | UGACUGUGAUAGACCAGAC | 4026 |
| UCUGGUCUAUCACAGUCAA | 4027 | UUGACUGUGAUAGACCAGA | 4028 |
| CUGGUCUAUCACAGUCAAC | 4029 | GUUGACUGUGAUAGACCAG | 4030 |
| UGGUCUAUCACAGUCAACU | 4031 | AGUUGACUGUGAUAGACCA | 4032 |
| CUAUCACAGUCAACUUACU | 4033 | AGUAAGUUGACUGUGAUAG | 4034 |
| UAUCACAGUCAACUUACUA | 4035 | UAGUAAGUUGACUGUGAUA | 4036 |
| ACAGUCAACUUACUAGCAC | 4037 | GUGCUAGUAAGUUGACUGU | 4038 |
| AACUUACUAGCACUGGGUC | 4039 | GACCCAGUGCUAGUAAGUU | 4040 |
| ACUUACUAGCACUGGGUCU | 4041 | AGACCCAGUGCUAGUAAGU | 4042 |
| CUUACUAGCACUGGGUCUG | 4043 | CAGACCCAGUGCUAGUAAG | 4044 |
| UUACUAGCACUGGGUCUGU | 4045 | ACAGACCCAGUGCUAGUAA | 4046 |
| UACUAGCACUGGGUCUGUU | 4047 | AACAGACCCAGUGCUAGUA | 4048 |
| ACUAGCACUGGGUCUGUUU | 4049 | AAACAGACCCAGUGCUAGU | 4050 |
| CUGGGUCUGUUUCUCAUGC | 4051 | GCAUGAGAAACAGACCCAG | 4052 |
| UGGGUCUGUUUCUCAUGCC | 4053 | GGCAUGAGAAACAGACCCA | 4054 |
| GGGUCUGUUUCUCAUGCCA | 4055 | UGGCAUGAGAAACAGACCC | 4056 |
| GGUCUGUUUCUCAUGCCAG | 4057 | CUGGCAUGAGAAACAGACC | 4058 |
| UGUUUCUCAUGCCAGGUGG | 4059 | CCACCUGGCAUGAGAAACA | 4060 |
| GUUUCUCAUGCCAGGUGGC | 4061 | GCCACCUGGCAUGAGAAAC | 4062 |
| UUUCUCAUGCCAGGUGGCU | 4063 | AGCCACCUGGCAUGAGAAA | 4064 |
| UUCUCAUGCCAGGUGGCUA | 4065 | UAGCCACCUGGCAUGAGAA | 4066 |
| UCUCAUGCCAGGUGGCUAC | 4067 | GUAGCCACCUGGCAUGAGA | 4068 |
| CUCAUGCCAGGUGGCUACU | 4069 | AGUAGCCACCUGGCAUGAG | 4070 |
| CAACUGCUGCACAGACUCC | 4071 | GGAGUCUGUGCAGCAGUUG | 4072 |
| CACAGACUCCAACCUCAAU | 4073 | AUUGAGGUUGGAGUCUGUG | 4074 |
| ACAGACUCCAACCUCAAUG | 4075 | CAUUGAGGUUGGAGUCUGU | 4076 |
| CAGACUCCAACCUCAAUGG | 4077 | CCAUUGAGGUUGGAGUCUG | 4078 |
| CCAACCUCAAUGGAGUGUA | 4079 | UACACUCCAUUGAGGUUGG | 4080 |
| CAACCUCAAUGGAGUGUAC | 4081 | GUACACUCCAUUGAGGUUG | 4082 |
| AACCUCAAUGGAGUGUACU | 4083 | AGUACACUCCAUUGAGGUU | 4084 |
| ACCUCAAUGGAGUGUACUA | 4085 | UAGUACACUCCAUUGAGGU | 4086 |
| CCUCAAUGGAGUGUACUAC | 4087 | GUAGUACACUCCAUUGAGG | 4088 |
| CUCAAUGGAGUGUACUACC | 4089 | GGUAGUACACUCCAUUGAG | 4090 |
| UCAAUGGAGUGUACUACCG | 4091 | CGGUAGUACACUCCAUUGA | 4092 |
| CAAUGGAGUGUACUACCGC | 4093 | GCGGUAGUACACUCCAUUG | 4094 |
| AAUGGAGUGUACUACCGCC | 4095 | GGCGGUAGUACACUCCAUU | 4096 |
| AUGGAGUGUACUACCGCCU | 4097 | AGGCGGUAGUACACUCCAU | 4098 |
| UGGAGUGUACUACCGCCUG | 4099 | CAGGCGGUAGUACACUCCA | 4100 |
| GGAGUGUACUACCGCCUGG | 4101 | CCAGGCGGUAGUACACUCC | 4102 |
| GAGUGUACUACCGCCUGGG | 4103 | CCCAGGCGGUAGUACACUC | 4104 |
| AGUGUACUACCGCCUGGGU | 4105 | ACCCAGGCGGUAGUACACU | 4106 |
| GUACUACCGCCUGGGUGAG | 4107 | CUCACCCAGGCGGUAGUAC | 4108 |
| UACUACCGCCUGGGUGAGC | 4109 | GCUCACCCAGGCGGUAGUA | 4110 |
| ACUACCGCCUGGGUGAGCA | 4111 | UGCUCACCCAGGCGGUAGU | 4112 |
| CAAUAGCACCUGGAUGGC | 4113 | GCCAUCCAGGUGCUUAUUG | 4114 |
| AAUAAGCACCUGGAUGGCA | 4115 | UGCCAUCCAGGUGCUUAUU | 4116 |

TABLE 4-continued

| Sense Sequence | SEQ ID NO: | Antisense Sequence | SEQ ID NO: |
|---|---|---|---|
| AUAAGCACCUGGAUGGCAU | 4117 | AUGCCAUCCAGGUGCUUAU | 4118 |
| UAAGCACCUGGAUGGCAUC | 4119 | GAUGCCAUCCAGGUGCUUA | 4120 |
| AAGCACCUGGAUGGCAUCA | 4121 | UGAUGCCAUCCAGGUGCUU | 4122 |
| AGCACCUGGAUGGCAUCAC | 4123 | GUGAUGCCAUCCAGGUGCU | 4124 |
| GCACCUGGAUGGCAUCACC | 4125 | GGUGAUGCCAUCCAGGUGC | 4126 |
| CACCUGGAUGGCAUCACCU | 4127 | AGGUGAUGCCAUCCAGGUG | 4128 |
| UGGAUGGCAUCACCUGGUA | 4129 | UACCAGGUGAUGCCAUCCA | 4130 |
| UGGCAUGGAUCUACCUACU | 4131 | AGUAGGUAGAUCCAUGCCA | 4132 |
| GGCAUGGAUCUACCUACUC | 4133 | GAGUAGGUAGAUCCAUGCC | 4134 |
| GCAUGGAUCUACCUACUCC | 4135 | GGAGUAGGUAGAUCCAUGC | 4136 |
| CAUGGAUCUACCUACUCCC | 4137 | GGGAGUAGGUAGAUCCAUG | 4138 |
| AUGGAUCUACCUACUCCCU | 4139 | AGGGAGUAGGUAGAUCCAU | 4140 |
| UGGAUCUACCUACUCCCUC | 4141 | GAGGGAGUAGGUAGAUCCA | 4142 |
| GGAUCUACCUACUCCCUCA | 4143 | UGAGGGAGUAGGUAGAUCC | 4144 |
| GAUCUACCUACUCCCUCAA | 4145 | UUGAGGGAGUAGGUAGAUC | 4146 |
| AUCUACCUACUCCCUCAAA | 4147 | UUUGAGGGAGUAGGUAGAU | 4148 |
| CGCCCAGAAGACUUCAAGC | 4149 | GCUUGAAGUCUUCUGGGCG | 4150 |
| GCCCAGAAGACUUCAAGCC | 4151 | GGCUUGAAGUCUUCUGGGC | 4152 |
| CCCAGAAGACUUCAAGCCU | 4153 | AGGCUUGAAGUCUUCUGGG | 4154 |
| CCAGAAGACUUCAAGCCUU | 4155 | AAGGCUUGAAGUCUUCUGG | 4156 |
| CAGAAGACUUCAAGCCUUA | 4157 | UAAGGCUUGAAGUCUUCUG | 4158 |
| GAAGACUUCAAGCCUUAAA | 4159 | UUUAAGGCUUGAAGUCUUC | 4160 |
| AAGACUUCAAGCCUUAAAA | 4161 | UUUUAAGGCUUGAAGUCUU | 4162 |
| AGACUUCAAGCCUUAAAAG | 4163 | CUUUUAAGGCUUGAAGUCU | 4164 |
| GACUUCAAGCCUUAAAAGG | 4165 | CCUUUUAAGGCUUGAAGUC | 4166 |
| ACUUCAAGCCUUAAAAGGA | 4167 | UCCUUUUAAGGCUUGAAGU | 4168 |
| CUUCAAGCCUUAAAAGGAG | 4169 | CUCCUUUUAAGGCUUGAAG | 4170 |
| UUCAAGCCUUAAAAGGAGG | 4171 | CCUCCUUUUAAGGCUUGAA | 4172 |
| CCUUAAAAGGAGGCUGCCG | 4173 | CGGCAGCCUCCUUUUAAGG | 4174 |
| CUUAAAAGGAGGCUGCCGU | 4175 | ACGGCAGCCUCCUUUUAAG | 4176 |
| UUAAAAGGAGGCUGCCGUG | 4177 | CACGGCAGCCUCCUUUUAA | 4178 |
| UAAAAGGAGGCUGCCGUGG | 4179 | CCACGGCAGCCUCCUUUUA | 4180 |
| AAAAGGAGGCUGCCGUGGA | 4181 | UCCACGGCAGCCUCCUUUU | 4182 |
| AAAGGAGGCUGCCGUGGAG | 4183 | CUCCACGGCAGCCUCCUUU | 4184 |
| GUGGAGCACGGAUACAAGA | 4185 | UUCUGUAUCCGUGCUCCAC | 4186 |
| ACUGGAUGAGGGCAGAUGA | 4187 | UCAUCUGCCCUCAUCCAGU | 4188 |
| CUGGAUGAGGGCAGAUGAG | 4189 | CUCAUCUGCCCUCAUCCAG | 4190 |
| GGAUGAGGGCAGAUGAGGA | 4191 | UCCUCAUCUGCCCUCAUCC | 4192 |
| AUGAGGGCAGAUGAGGACA | 4193 | UGUCCUCAUCUGCCCUCAU | 4194 |
| UGAGGGCAGAUGAGGACAG | 4195 | CUGUCCUCAUCUGCCCUCA | 4196 |
| AGGGCAGAUGAGGACAGGA | 4197 | UCCUGUCCUCAUCUGCCCU | 4198 |
| GGCAGAUGAGGACAGGAAG | 4199 | CUUCCUGUCCUCAUCUGCC | 4200 |
| CAGAUGAGGACAGGAAGAG | 4201 | CUCUUCCUGUCCUCAUCUG | 4202 |
| GAAUAAGCUCCAAGGAGC | 4203 | GCUCCUUGGAGACUAUUC | 4204 |
| AAUAAGUCUCCAAGGAGCA | 4205 | UGCUCCUUGGAGACUUAUU | 4206 |
| AUAAGUCUCCAAGGAGCAC | 4207 | GUGCUCCUUGGAGACUUAU | 4208 |
| GUACCAAGGAUGUUACAGU | 4209 | ACUGUAACAUCCUUGGUAC | 4210 |
| UACCAAGGAUGUUACAGUA | 4211 | UACUGUAACAUCCUUGGUA | 4212 |
| ACCAAGGAUGUUACAGUAA | 4213 | UUACUGUAACAUCCUUGGU | 4214 |
| CCAAGGAUGUUACAGUAAA | 4215 | UUUACUGUAACAUCCUUGG | 4216 |
| CUGGGUCCUGCCACAUCCU | 4217 | AGGAUGUGGCAGGACCCAG | 4218 |
| UGGGUCCUGCCACAUCCUU | 4219 | AAGGAUGUGGCAGGACCCA | 4220 |
| GGGUCCUGCCACAUCCUUC | 4221 | GAAGGAUGUGGCAGGACCC | 4222 |
| GGUCCUGCCACAUCCUUCU | 4223 | AGAAGGAUGUGGCAGGACC | 4224 |
| UCCUGCCACAUCCUUCUCA | 4225 | UGAGAAGGAUGUGGCAGGA | 4226 |
| CCUGCCACAUCCUUCUCAA | 4227 | UUGAGAAGGAUGUGGCAGG | 4228 |
| CUGCCACAUCCUUCUCAAG | 4229 | CUUGAGAAGGAUGUGGCAG | 4230 |
| CUUCUCAAGGUGGUAGACU | 4231 | AGUCUACCACCUUGAGAAG | 4232 |
| AGGUGGUAGACUGAGUGGG | 4233 | CCCACUCAGUCUACCACCU | 4234 |
| GGUCUCUCUGCCCAAGAUC | 4235 | GAUCUUGGGCAGAGAGACC | 4236 |
| GUCUCUCUGCCCAAGAUCC | 4237 | GGAUCUUGGGCAGAGAGAC | 4238 |
| UCUCUCUGCCCAAGAUCCC | 4239 | GGGAUCUUGGGCAGAGAGA | 4240 |
| UCUGCCCAAGAUCCCUGAC | 4241 | GUCAGGGAUCUUGGGCAGA | 4242 |
| CUGCCCAAGAUCCCUGACA | 4243 | UGUCAGGGAUCUUGGGCAG | 4244 |
| UGCCCAAGAUCCCUGACAU | 4245 | AUGUCAGGGAUCUUGGGCA | 4246 |
| GCCCAAGAUCCCUGACAUA | 4247 | UAUGUCAGGGAUCUUGGGC | 4248 |
| CCCAAGAUCCCUGACAUAG | 4249 | CUAUGUCAGGGAUCUUGGG | 4250 |
| AUCCCUGACAUAGCAGUAG | 4251 | CUACUGCUAUGUCAGGGAU | 4252 |
| CCCUGACAUAGCAGUAGCU | 4253 | AGCUACUGCUAUGUCAGGG | 4254 |
| CCUGACAUAGCAGUAGCUU | 4255 | AAGCUACUGCUAUGUCAGG | 4256 |
| CUGACAUAGCAGUAGCUUG | 4257 | CAAGCUACUGCUAUGUCAG | 4258 |
| UGACAUAGCAGUAGCUUGU | 4259 | ACAAGCUACUGCUAUGUCA | 4260 |
| ACAUAGCAGUAGCUUGUCU | 4261 | AGACAAGCUACUGCUAUGU | 4262 |
| CAUAGCAGUAGCUUGUCUU | 4263 | AAGACAAGCUACUGCUAUG | 4264 |
| GCAGUAGCUUGUCUUUUCC | 4265 | GGAAAAGACAAGCUACUGC | 4266 |
| CAGUAGCUUGUCUUUUCCA | 4267 | UGGAAAAGACAAGCUACUG | 4268 |

TABLE 4-continued

| Sense Sequence | SEQ ID NO: | Antisense Sequence | SEQ ID NO: |
|---|---|---|---|
| AGUAGCUUGUCUUUUCCAC | 4269 | GUGGAAAAGACAAGCUACU | 4270 |
| GUAGCUUGUCUUUUCCACA | 4271 | UGUGGAAAAGACAAGCUAC | 4272 |
| CUUGUCUUUUCCACAUGAU | 4273 | AUCAUGUGGAAAAGACAAG | 4274 |
| UUGUCUUUUCCACAUGAUU | 4275 | AAUCAUGUGGAAAAGACAA | 4276 |
| CUUUUCCACAUGAUUUGUC | 4277 | GACAAAUCAUGUGGAAAAG | 4278 |
| UUUUCCACAUGAUUUGUCU | 4279 | AGACAAAUCAUGUGGAAAA | 4280 |
| UUUCCACAUGAUUUGUCUG | 4281 | CAGACAAAUCAUGUGGAAA | 4282 |
| UUCCACAUGAUUUGUCUGU | 4283 | ACAGACAAAUCAUGUGGAA | 4284 |
| GCUUAGGCUAUGUGAGGGC | 4285 | GCCCUCACAUAGCCUAAGC | 4286 |
| AGGCUAUGUGAGGGCAAAA | 4287 | UUUUGCCCUCACAUAGCCU | 4288 |
| AGGAGUGAAGGAGGCAGGU | 4289 | ACCUGCCUCCUUCACUCCU | 4290 |
| GGAGUGAAGGAGGCAGGUG | 4291 | CACCUGCCUCCUUCACUCC | 4292 |
| GAGUGAAGGAGGCAGGUGG | 4293 | CCACCUGCCUCCUUCACUC | 4294 |
| AAUUAUCUUGAGUCUACAC | 4295 | GUGUAGACUCAAGAUAAUU | 4296 |
| ACUCCAGGGCACUGCAUCU | 4297 | AGAUGCAGUGCCCUGGAGU | 4298 |
| CUCCAGGGCACUGCAUCUG | 4299 | CAGAUGCAGUGCCCUGGAG | 4300 |
| AGGGCACUGCAUCUGGCGA | 4301 | UCGCCAGAUGCAGUGCCCU | 4302 |
| GGGCACUGCAUCUGGCGAU | 4303 | AUCGCCAGAUGCAGUGCCC | 4304 |
| GGCACUGCAUCUGGCGAUC | 4305 | GAUCGCCAGAUGCAGUGCC | 4306 |
| GCACUGCAUCUGGCGAUCA | 4307 | UGAUCGCCAGAUGCAGUGC | 4308 |
| CCCUGCUCGCCUUGGUCAU | 4309 | AUGACCAAGGCGAGCAGGG | 4310 |
| CCUGCUCGCCUUGGUCAUG | 4311 | CAUGACCAAGGCGAGCAGG | 4312 |
| CUGCUCGCCUUGGUCAUGU | 4313 | ACAUGACCAAGGCGAGCAG | 4314 |
| UGCUCGCCUUGGUCAUGUA | 4315 | UACAUGACCAAGGCGAGCA | 4316 |
| AUGAAGCACCAGCAGGAGG | 4317 | CCUCCUGCUGGUGCUUCAU | 4318 |
| UGAAGCACCAGCAGGAGGU | 4319 | ACCUCCUGCUGGUGCUUCA | 4320 |
| CAGCAGGAGGUGGACAGAG | 4321 | CUCUGUCCACCUCCUGCUG | 4322 |
| AGCAGGAGGUGGACAGAGU | 4323 | ACUCUGUCCACCUCCUGCU | 4324 |
| GCAGGAGGUGGACAGAGUC | 4325 | GACUCUGUCCACCUCCUGC | 4326 |
| CAGGAGGUGGACAGAGUCU | 4327 | AGACUCUGUCCACCUCCUG | 4328 |
| GGAGGUGGACAGAGUCUCU | 4329 | AGAGACUCUGUCCACCUCC | 4330 |
| AGGUGGACAGAGUCUCUCA | 4331 | UGAGAGACUCUGUCCACCU | 4332 |
| UGGACAGAGUCUCUCAUGG | 4333 | CCAUGAGAGACUCUGUCCA | 4334 |
| GGACAGAGUCUCUCAUGGA | 4335 | UCCAUGAGAGACUCUGUCC | 4336 |
| GACAGAGUCUCUCAUGGAU | 4337 | AUCCAUGAGAGACUCUGUC | 4338 |
| ACAGAGUCUCUCAUGGAUG | 4339 | CAUCCAUGAGAGACUCUGU | 4340 |
| GGAGCUUCCUUUUAAAUUU | 4341 | AAAUUUAAAAGGAAGCUCC | 4342 |
| AACUGAAGGUAGAUGGUGU | 4343 | ACACCAUCUACCUUCAGUU | 4344 |
| ACUGAAGGUAGAUGGUGUU | 4345 | AACACCAUCUACCUUCAGU | 4346 |
| CUGAAGGUAGAUGGUGUUA | 4347 | UAACACCAUCUACCUUCAG | 4348 |
| UGAAGGUAGAUGGUGUUAU | 4349 | AUAACACCAUCUACCUUCA | 4350 |
| GAAGGUAGAUGGUGUUAUA | 4351 | UAUAACACCAUCUACCUUC | 4352 |
| GUAGAUGGUGUUAUAGUUA | 4353 | UAACUAUAACACCAUCUAC | 4354 |
| UGUAAAUAAGCAUCUCACU | 4355 | AGUGAGAUGCUUAUUUACA | 4356 |
| AUAAGCAUCUCACUUUGUA | 4357 | UACAAAGUGAGAUGCUUAU | 4358 |

TABLE 5

| Sense Sequence | SEQ ID NO: | Antisense Sequence | SEQ ID NO: |
|---|---|---|---|
| AAGUGGCCUUGUCUCCUUC | 4359 | GAAGGAGACAAGGCCACUU | 4360 |
| AGUGGCCUUGUCUCCUUCU | 4361 | AGAAGGAGACAAGGCCACU | 4362 |
| GUGGCCUUGUCUCCUUCUA | 4363 | UAGAAGGAGACAAGGCCAC | 4364 |
| CUUGUCUCCUUCUACCGGG | 4365 | CCCGGUAGAAGGAGACAAG | 4366 |
| UUGUCUCCUUCUACCGGGA | 4367 | UCCCGGUAGAAGGAGACAA | 4368 |
| UGUCUCCUUCUACCGGGAC | 4369 | GUCCCGGUAGAAGGAGACA | 4370 |
| GUCUCCUUCUACCGGGACU | 4371 | AGUCCCGGUAGAAGGAGAC | 4372 |
| UUCUACCGGGACUGGAAGC | 4373 | GCUUCCAGUCCCGGUAGAA | 4374 |
| UCUACCGGGACUGGAAGCA | 4375 | UGCUUCCAGUCCCGGUAGA | 4376 |
| CUACCGGGACUGGAAGCAG | 4377 | CUGCUUCCAGUCCCGGUAG | 4378 |
| AGCAGGGCUUUGGCAGCAU | 4379 | AUGCUGCCAAAGCCCUGCU | 4380 |
| AGGGCUUUGGCAGCAUCCG | 4381 | CGGAUGCUGCCAAAGCCCU | 4382 |
| GGGCUUUGGCAGCAUCCGU | 4383 | ACGGAUGCUGCCAAAGCCC | 4384 |
| GGCUUUGGCAGCAUCCGUG | 4385 | CACGGAUGCUGCCAAAGCC | 4386 |
| CAUCCACCGGCUCUCCAGA | 4387 | UCUGGAGAGCCGGUGGAUG | 4388 |
| AUCCACCGGCUCUCCAGAC | 4389 | GUCUGGAGAGCCGGUGGAU | 4390 |
| UCCACCGGCUCUCCAGACA | 4391 | UGUCUGGAGAGCCGGUGGA | 4392 |
| CUGGACCAGUGCCACCACA | 4393 | UGUGGUGGCACUGGUCCAG | 4394 |
| GGGUGCCAUUCCUAUUCUG | 4395 | CAGAAUAGGAAUGGCACCC | 4396 |
| GGUGCCAUUCCUAUUCUGA | 4397 | UCAGAAUAGGAAUGGCACC | 4398 |
| GUGCCAUUCCUAUUCUGAU | 4399 | AUCAGAAUAGGAAUGGCAC | 4400 |
| UGCCAUUCCUAUUCUGAUU | 4401 | AAUCAGAAUAGGAAUGGCA | 4402 |
| AUUCCUAUUCUGAUUCAAG | 4403 | CUUGAAUCAGAAUAGGAAU | 4404 |
| UGUAUUCAUUGUGAUGG | 4405 | CCAUCACAAUGAAUAUACA | 4406 |
| GUAUUCAUUGUGAUGGU | 4407 | ACCAUCACAAUGAAUAUAC | 4408 |
| AUUCAUUGUGAUGGUUUUC | 4409 | GAAAACCAUCACAAUGAAU | 4410 |
| UUCAUUGUGAUGGUUUUCC | 4411 | GGAAAACCAUCACAAUGAA | 4412 |

TABLE 5-continued

| Sense Sequence | SEQ ID NO: | Antisense Sequence | SEQ ID NO: |
|---|---|---|---|
| UGUGAUGGUUUUCCUGCAA | 4413 | UUGCAGGAAAACCAUCACA | 4414 |
| GUGAUGGUUUUCCUGCAAG | 4415 | CUUGCAGGAAAACCAUCAC | 4416 |
| UGAUGGUUUUCCUGCAAGU | 4417 | ACUUGCAGGAAAACCAUCA | 4418 |
| AUGGUUUUCCUGCAAGUUG | 4419 | CAACUUGCAGGAAAACCAU | 4420 |
| GGUUUUCCUGCAAGUUGUA | 4421 | UACAACUUGCAGGAAAACC | 4422 |
| GUUUUCCUGCAAGUUGUAA | 4423 | UUACAACUUGCAGGAAAAC | 4424 |
| UUUUCCUGCAAGUUGUAAU | 4425 | AUUACAACUUGCAGGAAAA | 4426 |
| UUUCCUGCAAGUUGUAAUG | 4427 | CAUUACAACUUGCAGGAAA | 4428 |
| UUCCUGCAAGUUGUAAUGG | 4429 | CCAUUACAACUUGCAGGAA | 4430 |
| UCCUGCAAGUUGUAAUGGA | 4431 | UCCAUUACAACUUGCAGGA | 4432 |
| CAAGUUGUAAUGGAGUUGA | 4433 | UCAACUCCAUUACAACUUG | 4434 |
| AAGUUGUAAUGGAGUUGAG | 4435 | CUCAACUCCAUUACAACUU | 4436 |
| AGUUGUAAUGGAGUUGAGG | 4437 | CCUCAACUCCAUUACAACU | 4438 |
| GUUGUAAUGGAGUUGAGGA | 4439 | UCCUCAACUCCAUUACAAC | 4440 |
| CUGCAGGUGGGACAGGAAG | 4441 | CUUCCUGUCCCACCUGCAG | 4442 |
| GCAGGUGGGACAGGAAGAG | 4443 | CUCUUCCUGUCCCACCUGC | 4444 |
| CAGGUGGGACAGGAAGAGG | 4445 | CCUCUUCCUGUCCCACCUG | 4446 |
| AGGUGGGACAGGAAGAGGC | 4447 | GCCUCUUCCUGUCCCACCU | 4448 |
| GGGACAGGAAGAGGCCAGA | 4449 | UCUGGCCUCUUCCUGUCCC | 4450 |
| GGACAGGAAGAGGCCAGAC | 4451 | GUCUGGCCUCUUCCUGUCC | 4452 |
| GACAGGAAGAGGCCAGACC | 4453 | GGUCUGGCCUCUUCCUGUC | 4454 |
| CAGACCCAGGCCAGAGUAG | 4455 | CUACUCUGGCCUGGGUCUG | 4456 |
| AGACCCAGGCCAGAGUAGA | 4457 | UCUACUCUGGCCUGGGUCU | 4458 |
| GACCCAGGCCAGAGUAGAG | 4459 | CUCUACUCUGGCCUGGGUC | 4460 |
| CCCAGGCCAGAGUAGAGCA | 4461 | UGCUCUACUCUGGCCUGGG | 4462 |
| CAGGCCAGAGUAGAGCAAA | 4463 | UUUGCUCUACUCUGGCCUG | 4464 |
| GCCAGAGUAGAGCAAAUUC | 4465 | GAAUUUGCUCUACUCUGGC | 4466 |
| CCAGAGUAGAGCAAAUUCA | 4467 | UGAAUUUGCUCUACUCUGG | 4468 |
| CAGAGUAGAGCAAAUUCAA | 4469 | UUGAAUUUGCUCUACUCUG | 4470 |
| AGAGUAGAGCAAAUUCAAC | 4471 | GUUGAAUUUGCUCUACUCU | 4472 |
| ACACUAGUCUCUGCUCUGG | 4473 | CCAGAGCAGAGACUAGUGU | 4474 |
| CACUAGUCUCUGCUCUGGC | 4475 | GCCAGAGCAGAGACUAGUG | 4476 |
| CUAGUCUCUGCUCUGGCCG | 4477 | CGGCCAGAGCAGAGACUAG | 4478 |
| UAGUCUCUGCUCUGGCCGA | 4479 | UCGGCCAGAGCAGAGACUA | 4480 |
| AGUCUCUGCUCUGGCCGAG | 4481 | CUCGGCCAGAGCAGAGACU | 4482 |
| CUCUGGCCGAGCAUGAGGU | 4483 | ACCUCAUGCUCGGCCAGAG | 4484 |
| UCUGGCCGAGCAUGAGGUC | 4485 | GACCUCAUGCUCGGCCAGA | 4486 |
| UGGCCGAGCAUGAGGUCCU | 4487 | AGGACCUCAUGCUCGGCCA | 4488 |
| GGCCGAGCAUGAGGUCCUU | 4489 | AAGGACCUCAUGCUCGGCC | 4490 |
| GCCGAGCAUGAGGUCCUUU | 4491 | AAAGGACCUCAUGCUCGGC | 4492 |
| CCGAGCAUGAGGUCCUUUA | 4493 | UAAAGGACCUCAUGCUCGG | 4494 |
| CGAGCAUGAGGUCCUUUAG | 4495 | CUAAAGGACCUCAUGCUCG | 4496 |
| GAGCAUGAGGUCCUUUAGG | 4497 | CCUAAAGGACCUCAUGCUC | 4498 |
| AGCAUGAGGUCCUUUAGGU | 4499 | ACCUAAAGGACCUCAUGCU | 4500 |
| GCAUGAGGUCCUUUAGGUG | 4501 | CACCUAAAGGACCUCAUGC | 4502 |
| CAUGAGGUCCUUUAGGUGC | 4503 | GCACCUAAAGGACCUCAUG | 4504 |
| AUGAGGUCCUUUAGGUGCA | 4505 | UGCACCUAAAGGACCUCAU | 4506 |
| UGAGGUCCUUUAGGUGCAA | 4507 | UUGCACCUAAAGGACCUCA | 4508 |
| GAGGUCCUUUAGGUGCAAA | 4509 | UUUGCACCUAAAGGACCUC | 4510 |
| AGGUCCUUUAGGUGCAAAU | 4511 | AUUUGCACCUAAAGGACCU | 4512 |
| GGUCCUUUAGGUGCAAAUC | 4513 | GAUUUGCACCUAAAGGACC | 4514 |
| GUCCUUUAGGUGCAAAUCU | 4515 | AGAUUUGCACCUAAAGGAC | 4516 |
| UCCUUUAGGUGCAAAUCUU | 4517 | AAGAUUUGCACCUAAAGGA | 4518 |
| CCUUUAGGUGCAAAUCUUA | 4519 | UAAGAUUUGCACCUAAAGG | 4520 |
| CUUUAGGUGCAAAUCUUAC | 4521 | GUAAGAUUUGCACCUAAAG | 4522 |
| UUUAGGUGCAAAUCUUACU | 4523 | AGUAAGAUUUGCACCUAAA | 4524 |
| GCAAAUCUUACUGAUACUG | 4525 | CAGUAUCAGUAAGAUUUGC | 4526 |
| UCUUACUGAUACUGUUGG | 4527 | CCAAACAGUAUCAGUAAGA | 4528 |
| AAAGCACUCACUAUAUCCU | 4529 | AGGAUAUAGUGAGUGCUUU | 4530 |
| AAGCACUCACUAUAUCCUC | 4531 | GAGGAUAUAGUGAGUGCUU | 4532 |
| ACUCACUAUAUCCUCAUGU | 4533 | ACAUGAGGAUAUAGUGAGU | 4534 |
| UCACUAUAUCCUCAUGUUU | 4535 | AAACAUGAGGAUAUAGUGA | 4536 |
| UAUCCUCAUGUUUCUCUUA | 4537 | UAAGAGAAACAUGAGGAUA | 4538 |
| AUCCUCAUGUUUCUCUUAC | 4539 | GUAAGAGAAACAUGAGGAU | 4540 |
| UCCUCAUGUUUCUCUUACA | 4541 | UGUAAGAGAAACAUGAGGA | 4542 |
| CUCAUGUUUCUCUUACAGC | 4543 | GCUGUAAGAGAAACAUGAG | 4544 |
| UCAUGUUUCUCUUACAGCA | 4545 | UGCUGUAAGAGAAACAUGA | 4546 |
| UUCUCUUACAGCAGCUCUG | 4547 | CAGAGCUGCUGUAAGAGAA | 4548 |
| GCAGCUCUGUGUGGGAUUC | 4549 | GAAUCCCACACAGAGCUGC | 4550 |
| ACAUAGCUGCACCUUAUAA | 4551 | UUAUAAGGUGCAGCUAUGU | 4552 |
| CAUAGCUGCACCUUAUAAG | 4553 | CUUAUAAGGUGCAGCUAUG | 4554 |
| AUAGCUGCACCUUAUAAGC | 4555 | GCUUAUAAGGUGCAGCUAU | 4556 |
| UAGCUGCACCUUAUAAGCA | 4557 | UGCUUAUAAGGUGCAGCUA | 4558 |
| AGACUAAUCAAGGCCAUAU | 4559 | AUAUGGCCUUGAUUAGUCU | 4560 |
| GACUAAUCAAGGCCAUAUG | 4561 | CAUAUGGCCUUGAUUAGUC | 4562 |
| ACUAAUCAAGGCCAUAUGG | 4563 | CCAUAUGGCCUUGAUUAGU | 4564 |

TABLE 5-continued

| Sense Sequence | SEQ ID NO: | Antisense Sequence | SEQ ID NO: |
|---|---|---|---|
| CUAAUCAAGGCCAUAUGGU | 4565 | ACCAUAUGGCCUUGAUUAG | 4566 |
| UAAUCAAGGCCAUAUGGUG | 4567 | CACCAUAUGGCCUUGAUUA | 4568 |
| AAUCAAGGCCAUAUGGUGA | 4569 | UCACCAUAUGGCCUUGAUU | 4570 |
| AUCAAGGCCAUAUGGUGAA | 4571 | UUCACCAUAUGGCCUUGAU | 4572 |
| UCAAGGCCAUAUGGUGAAU | 4573 | AUUCACCAUAUGGCCUUGA | 4574 |
| CAAGGCCAUAUGGUGAAUC | 4575 | GAUUCACCAUAUGGCCUUG | 4576 |
| AAGGCCAUAUGGUGAAUCA | 4577 | UGAUUCACCAUAUGGCCUU | 4578 |
| AAAGAAGUUCGAGCCUUGU | 4579 | ACAAGGCUCGAACUUCUUU | 4580 |
| AAGAAGUUCGAGCCUUGUU | 4581 | AACAAGGCUCGAACUUCUU | 4582 |
| AGAAGUUCGAGCCUUGUUU | 4583 | AAACAAGGCUCGAACUUCU | 4584 |
| GAAGUUCGAGCCUUGUUUU | 4585 | AAAACAAGGCUCGAACUUC | 4586 |
| AAGUUCGAGCCUUGUUUUC | 4587 | GAAAACAAGGCUCGAACUU | 4588 |
| AGUUCGAGCCUUGUUUUCU | 4589 | AGAAAACAAGGCUCGAACU | 4590 |
| GUUCGAGCCUUGUUUUCUG | 4591 | CAGAAAACAAGGCUCGAAC | 4592 |
| UUCGAGCCUUGUUUUCUGA | 4593 | UCAGAAAACAAGGCUCGAA | 4594 |
| UCGAGCCUUGUUUUCUGAU | 4595 | AUCAGAAAACAAGGCUCGA | 4596 |
| CGAGCCUUGUUUUCUGAUU | 4597 | AAUCAGAAAACAAGGCUCG | 4598 |
| UUCUGAUUCCCAGGUUAAC | 4599 | GUUAACCUGGGAAUCAGAA | 4600 |
| AAAAGAUGUUUGGCUAUGG | 4601 | CCAUAGCCAAACAUCUUUU | 4602 |
| AAAGAUGUUUGGCUAUGGG | 4603 | CCCAUAGCCAAACAUCUUU | 4604 |
| AAGAUGUUUGGCUAUGGGA | 4605 | UCCCAUAGCCAAACAUCUU | 4606 |
| AGAUGUUUGGCUAUGGGAC | 4607 | GUCCCAUAGCCAAACAUCU | 4608 |
| GAUGUUUGGCUAUGGGACU | 4609 | AGUCCCAUAGCCAAACAUC | 4610 |
| UUUGGCUAUGGGACUGUCA | 4611 | UGACAGUCCCAUAGCCAAA | 4612 |
| UUGGCUAUGGGACUGUCAG | 4613 | CUGACAGUCCCAUAGCCAA | 4614 |
| UGGCUAUGGGACUGUCAGG | 4615 | CCUGACAGUCCCAUAGCCA | 4616 |
| GAGCCUGCUGCACUUUCUU | 4617 | AAGAAAGUGCAGCAGGCUC | 4618 |
| CUGCUGCACUUUCUUUAAG | 4619 | CUUAAAGAAAGUGCAGCAG | 4620 |
| UGCUGCACUUUCUUUAAGG | 4621 | CCUUAAAGAAAGUGCAGCA | 4622 |
| GCUGCACUUUCUUUAAGGC | 4623 | GCCUUAAAGAAAGUGCAGC | 4624 |
| UGCACUUUCUUUAAGGCUC | 4625 | GAGCCUUAAAGAAAGUGCA | 4626 |
| GCACUUUCUUUAAGGCUCU | 4627 | AGAGCCUUAAAGAAAGUGC | 4628 |
| CACUUUCUUUAAGGCUCUG | 4629 | CAGAGCCUUAAAGAAAGUG | 4630 |
| UUCUUUAAGGCUCUGCUCC | 4631 | GGAGCAGAGCCUUAAAGAA | 4632 |
| GCUCUGCUCCUCCUGACAG | 4633 | CUGUCAGGAGGAGCAGAGC | 4634 |
| AGGACUGGGAGGGCAACCU | 4635 | AGGUUGCCCUCCCAGUCCU | 4636 |
| GCAACCUGCGCUACGCUGA | 4637 | UCAGCGUAGCGCAGGUUGC | 4638 |
| CAACCUGCGCUACGCUGAG | 4639 | CUCAGCGUAGCGCAGGUUG | 4640 |
| CUGCGCUACGCUGAGUAUA | 4641 | UAUACUCAGCGUAGCGCAG | 4642 |
| UGCGCUACGCUGAGUAUAG | 4643 | CUAUACUCAGCGUAGCGCA | 4644 |
| CUACGCUGAGUAUAGCCAC | 4645 | GUGGCUAUACUCAGCGUAG | 4646 |
| UACGCUGAGUAUAGCCACU | 4647 | AGUGGCUAUACUCAGCGUA | 4648 |
| CACUUUGUUUUGGGCAAUG | 4649 | CAUUGCCCAAAACAAAGUG | 4650 |
| AACUACACUGGCAAUGUGG | 4651 | CCACAUUGCCAGUGUAGUU | 4652 |
| ACUACACUGGCAAUGUGGG | 4653 | CCCACAUUGCCAGUGUAGU | 4654 |
| AACGACGCCCUCCAGUAUC | 4655 | GAUACUGGAGGGCGUCGUU | 4656 |
| ACGACGCCCUCCAGUAUCA | 4657 | UGAUACUGGAGGGCGUCGU | 4658 |
| CGACGCCCUCCAGUAUCAU | 4659 | AUGAUACUGGAGGGCGUCG | 4660 |
| GACGCCCUCCAGUAUCAUA | 4661 | UAUGAUACUGGAGGGCGUC | 4662 |
| ACGCCCUCCAGUAUCAUAA | 4663 | UUAUGAUACUGGAGGGCGU | 4664 |
| CGCCCUCCAGUAUCAUAAC | 4665 | GUUAUGAUACUGGAGGGCG | 4666 |
| CAAGUGUGCACAGCUCCGC | 4667 | GCGGAGCUGUGCACACUUG | 4668 |
| AAGUGUGCACAGCUCCGCA | 4669 | UGCGGAGCUGUGCACACUU | 4670 |
| AGUGUGCACAGCUCCGCAA | 4671 | UUGCGGAGCUGUGCACACU | 4672 |
| UGCACAGCUCCGCAAAGGU | 4673 | ACCUUUGCGGAGCUGUGCA | 4674 |
| GCACAGCUCCGCAAAGGUG | 4675 | CACCUUUGCGGAGCUGUGC | 4676 |
| CACAGCUCCGCAAAGGUGA | 4677 | UCACCUUUGCGGAGCUGUG | 4678 |
| ACAGCUCCGCAAAGGUGAG | 4679 | CUCACCUUUGCGGAGCUGU | 4680 |
| CAAGCUCAUAAUCCCACUU | 4681 | AAGUGGGAUUAUGAGCUUG | 4682 |
| CAUAAUCCCACUUGAGGAG | 4683 | CUCCUCAAGUGGGAUUAUG | 4684 |
| ACUGUACAGUUGAUAUUCC | 4685 | GGAAUAUCAACUGUACAGU | 4686 |
| CUGUACAGUUGAUAUUCCG | 4687 | CGGAAUAUCAACUGUACAG | 4688 |
| UGUACAGUUGAUAUUCCGG | 4689 | CCGGAAUAUCAACUGUACA | 4690 |
| GUACAGUUGAUAUUCCGGU | 4691 | ACCGGAAUAUCAACUGUAC | 4692 |
| UACAGUUGAUAUUCCGGUU | 4693 | AACCGGAAUAUCAACUGUA | 4694 |
| ACAGUUGAUAUUCCGGUUU | 4695 | AAACCGGAAUAUCAACUGU | 4696 |
| CAGUUGAUAUUCCGGUUUU | 4697 | AAAACCGGAAUAUCAACUG | 4698 |
| AGUUGAUAUUCCGGUUUUG | 4699 | CAAAACCGGAAUAUCAACU | 4700 |
| GUUGAUAUUCCGGUUUUGG | 4701 | CCAAAACCGGAAUAUCAAC | 4702 |
| UUGAUAUUCCGGUUUUGGU | 4703 | ACCAAAACCGGAAUAUCAA | 4704 |
| UGAUAUUCCGGUUUUGGUA | 4705 | UACCAAAACCGGAAUAUCA | 4706 |
| GAUAUUCCGGUUUUGGUAU | 4707 | AUACCAAAACCGGAAUAUC | 4708 |
| AUAUUCCGGUUUUGGUAUU | 4709 | AAUACCAAAACCGGAAUAU | 4710 |
| UAUUCCGGUUUUGGUAUUC | 4711 | GAAUACCAAAACCGGAAUA | 4712 |
| AUUCCGGUUUUGGUAUUCU | 4713 | AGAAUACCAAAACCGGAAU | 4714 |
| UUCCGGUUUUGGUAUUCUU | 4715 | AAGAAUACCAAAACCGGAA | 4716 |

TABLE 5-continued

| Sense Sequence | SEQ ID NO: | Antisense Sequence | SEQ ID NO: |
| --- | --- | --- | --- |
| GGUUUUGGUAUUCUUUCUG | 4717 | CAGAAAGAAUACCAAAACC | 4718 |
| UUUUGGUAUUCUUUCUGAC | 4719 | GUCAGAAAGAAUACCAAAA | 4720 |
| GGUAUUCUUUCUGACCCUG | 4721 | CAGGGUCAGAAAGAAUACC | 4722 |
| AACUCCUUACCUGAUGUCU | 4723 | AGACAUCAGGUAAGGAGUU | 4724 |
| ACUCCUUACCUGAUGUCUG | 4725 | CAGACAUCAGGUAAGGAGU | 4726 |
| CUCCUUACCUGAUGUCUGG | 4727 | CCAGACAUCAGGUAAGGAG | 4728 |
| UCCUUACCUGAUGUCUGGU | 4729 | ACCAGACAUCAGGUAAGGA | 4730 |
| CCUUACCUGAUGUCUGGUC | 4731 | GACCAGACAUCAGGUAAGG | 4732 |
| CUUACCUGAUGUCUGGUCU | 4733 | AGACCAGACAUCAGGUAAG | 4734 |
| UUACCUGAUGUCUGGUCUA | 4735 | UAGACCAGACAUCAGGUAA | 4736 |
| UACCUGAUGUCUGGUCUAU | 4737 | AUAGACCAGACAUCAGGUA | 4738 |
| ACCUGAUGUCUGGUCUAUC | 4739 | GAUAGACCAGACAUCAGGU | 4740 |
| GAUGUCUGGUCUAUCACAG | 4741 | CUGUGAUAGACCAGACAUC | 4742 |
| AUGUCUGGUCUAUCACAGU | 4743 | ACUGUGAUAGACCAGACAU | 4744 |
| UGUCUGGUCUAUCACAGUC | 4745 | GACUGUGAUAGACCAGACA | 4746 |
| GUCUGGUCUAUCACAGUCA | 4747 | UGACUGUGAUAGACCAGAC | 4748 |
| UCUGGUCUAUCACAGUCAA | 4749 | UUGACUGUGAUAGACCAGA | 4750 |
| CUGGUCUAUCACAGUCAAC | 4751 | GUUGACUGUGAUAGACCAG | 4752 |
| UGGUCUAUCACAGUCAACU | 4753 | AGUUGACUGUGAUAGACCA | 4754 |
| CUAUCACAGUCAACUUACU | 4755 | AGUAAGUUGACUGUGAUAG | 4756 |
| UAUCACAGUCAACUUACUA | 4757 | UAGUAAGUUGACUGUGAUA | 4758 |
| ACAGUCAACUUACUAGCAC | 4759 | GUGCUAGUAAGUUGACUGU | 4760 |
| AACUUACUAGCACUGGGUC | 4761 | GACCCAGUGCUAGUAAGUU | 4762 |
| ACUUACUAGCACUGGGUCU | 4763 | AGACCCAGUGCUAGUAAGU | 4764 |
| CUUACUAGCACUGGGUCUG | 4765 | CAGACCCAGUGCUAGUAAG | 4766 |
| UUACUAGCACUGGGUCUGU | 4767 | ACAGACCCAGUGCUAGUAA | 4768 |
| UACUAGCACUGGGUCUGUU | 4769 | AACAGACCCAGUGCUAGUA | 4770 |
| ACUAGCACUGGGUCUGUUU | 4771 | AAACAGACCCAGUGCUAGU | 4772 |
| CUGGGUCUGUUUCUCAUGC | 4773 | GCAUGAGAAACAGACCCAG | 4774 |
| UGGGUCUGUUUCUCAUGCC | 4775 | GGCAUGAGAAACAGACCCA | 4776 |
| GGGUCUGUUUCUCAUGCCA | 4777 | UGGCAUGAGAAACAGACCC | 4778 |
| GGUCUGUUUCUCAUGCCAG | 4779 | CUGGCAUGAGAAACAGACC | 4780 |
| UGUUUCUCAUGCCAGGUGG | 4781 | CCACCUGGCAUGAGAAACA | 4782 |
| GUUUCUCAUGCCAGGUGGC | 4783 | GCCACCUGGCAUGAGAAAC | 4784 |
| UUUCUCAUGCCAGGUGGCU | 4785 | AGCCACCUGGCAUGAGAAA | 4786 |
| UUCUCAUGCCAGGUGGCUA | 4787 | UAGCCACCUGGCAUGAGAA | 4788 |
| UCUCAUGCCAGGUGGCUAC | 4789 | GUAGCCACCUGGCAUGAGA | 4790 |
| CUCAUGCCAGGUGGCUACU | 4791 | AGUAGCCACCUGGCAUGAG | 4792 |
| CAACUGCUGCACAGACUCC | 4793 | GGAGUCUGUGCAGCAGUUG | 4794 |
| CACAGACUCCAACCUCAAU | 4795 | AUUGAGGUUGGAGUCUGUG | 4796 |
| ACAGACUCCAACCUCAAUG | 4797 | CAUUGAGGUUGGAGUCUGU | 4798 |
| CAGACUCCAACCUCAAUGG | 4799 | CCAUUGAGGUUGGAGUCUG | 4800 |
| CCAACCUCAAUGGAGUGUA | 4801 | UACACUCCAUUGAGGUUGG | 4802 |
| CAACCUCAAUGGAGUGUAC | 4803 | GUACACUCCAUUGAGGUUG | 4804 |
| AACCUCAAUGGAGUGUACU | 4805 | AGUACACUCCAUUGAGGUU | 4806 |
| ACCUCAAUGGAGUGUACUA | 4807 | UAGUACACUCCAUUGAGGU | 4808 |
| CCUCAAUGGAGUGUACUAC | 4809 | GUAGUACACUCCAUUGAGG | 4810 |
| CUCAAUGGAGUGUACUACC | 4811 | GGUAGUACACUCCAUUGAG | 4812 |
| UCAAUGGAGUGUACUACCG | 4813 | CGGUAGUACACUCCAUUGA | 4814 |
| CAAUGGAGUGUACUACCGC | 4815 | GCGGUAGUACACUCCAUUG | 4816 |
| AAUGGAGUGUACUACCGCC | 4817 | GGCGGUAGUACACUCCAUU | 4818 |
| AUGGAGUGUACUACCGCCU | 4819 | AGGCGGUAGUACACUCCAU | 4820 |
| UGGAGUGUACUACCGCCUG | 4821 | CAGGCGGUAGUACACUCCA | 4822 |
| GGAGUGUACUACCGCCUGG | 4823 | CCAGGCGGUAGUACACUCC | 4824 |
| GAGUGUACUACCGCCUGGG | 4825 | CCCAGGCGGUAGUACACUC | 4826 |
| AGUGUACUACCGCCUGGGU | 4827 | ACCCAGGCGGUAGUACACU | 4828 |
| GUACUACCGCCUGGGUGAG | 4829 | CUCACCCAGGCGGUAGUAC | 4830 |
| UACUACCGCCUGGGUGAGC | 4831 | GCUCACCCAGGCGGUAGUA | 4832 |
| ACUACCGCCUGGGUGAGCA | 4833 | UGCUCACCCAGGCGGUAGU | 4834 |
| CAAUAAGCACCUGGAUGGC | 4835 | GCCAUCCAGGUGCUUAUUG | 4836 |
| AAUAAGCACCUGGAUGGCA | 4837 | UGCCAUCCAGGUGCUUAUU | 4838 |
| AUAAGCACCUGGAUGGCAU | 4839 | AUGCCAUCCAGGUGCUUAU | 4840 |
| UAAGCACCUGGAUGGCAUC | 4841 | GAUGCCAUCCAGGUGCUUA | 4842 |
| AAGCACCUGGAUGGCAUCA | 4843 | UGAUGCCAUCCAGGUGCUU | 4844 |
| AGCACCUGGAUGGCAUCAC | 4845 | GUGAUGCCAUCCAGGUGCU | 4846 |
| GCACCUGGAUGGCAUCACC | 4847 | GGUGAUGCCAUCCAGGUGC | 4848 |
| CACCUGGAUGGCAUCACCU | 4849 | AGGUGAUGCCAUCCAGGUG | 4850 |
| UGGAUGGCAUCACCUGGUA | 4851 | UACCAGGUGAUGCCAUCCA | 4852 |
| UGGCAUGGAUCUACCUACU | 4853 | AGUAGGUAGAUCCAUGCCA | 4854 |
| GGCAUGGAUCUACCUACUC | 4855 | GAGUAGGUAGAUCCAUGCC | 4856 |
| GCAUGGAUCUACCUACUCC | 4857 | GGAGUAGGUAGAUCCAUGC | 4858 |
| CAUGGAUCUACCUACUCCC | 4859 | GGGAGUAGGUAGAUCCAUG | 4860 |
| AUGGAUCUACCUACUCCCU | 4861 | AGGGAGUAGGUAGAUCCAU | 4862 |
| UGGAUCUACCUACUCCCUC | 4863 | GAGGGAGUAGGUAGAUCCA | 4864 |
| GGAUCUACCUACUCCCUCA | 4865 | UGAGGGAGUAGGUAGAUCC | 4866 |
| GAUCUACCUACUCCCUCAA | 4867 | UUGAGGGAGUAGGUAGAUC | 4868 |

TABLE 5-continued

| Sense Sequence | SEQ ID NO: | Antisense Sequence | SEQ ID NO: |
| --- | --- | --- | --- |
| AUCUACCUACUCCCUCAAA | 4869 | UUUGAGGGAGUAGGUAGAU | 4870 |
| CGCCCAGAAGACUUCAAGC | 4871 | GCUUGAAGUCUUCUGGGCG | 4872 |
| GCCCAGAAGACUUCAAGCC | 4873 | GGCUUGAAGUCUUCUGGGC | 4874 |
| CCCAGAAGACUUCAAGCCU | 4875 | AGGCUUGAAGUCUUCUGGG | 4876 |
| CCAGAAGACUUCAAGCCUU | 4877 | AAGGCUUGAAGUCUUCUGG | 4878 |
| CAGAAGACUUCAAGCCUUA | 4879 | UAAGGCUUGAAGUCUUCUG | 4880 |
| GAAGACUUCAAGCCUUAAA | 4881 | UUUAAGGCUUGAAGUCUUC | 4882 |
| AAGACUUCAAGCCUUAAAA | 4883 | UUUUAAGGCUUGAAGUCUU | 4884 |
| AGACUUCAAGCCUUAAAAG | 4885 | CUUUUAAGGCUUGAAGUCU | 4886 |
| GACUUCAAGCCUUAAAAGG | 4887 | CCUUUUAAGGCUUGAAGUC | 4888 |
| ACUUCAAGCCUUAAAAGGA | 4889 | UCCUUUUAAGGCUUGAAGU | 4890 |
| CUUCAAGCCUUAAAAGGAG | 4891 | CUCCUUUUAAGGCUUGAAG | 4892 |
| UUCAAGCCUUAAAAGGAGG | 4893 | CCUCCUUUUAAGGCUUGAA | 4894 |
| CCUUAAAAGGAGGCUGCCG | 4895 | CGGCAGCCUCCUUUUAAGG | 4896 |
| CUUAAAAGGAGGCUGCCGU | 4897 | ACGGCAGCCUCCUUUUAAG | 4898 |
| UUAAAAGGAGGCUGCCGUG | 4899 | CACGGCAGCCUCCUUUUAA | 4900 |
| UAAAAGGAGGCUGCCGUGG | 4901 | CCACGGCAGCCUCCUUUUA | 4902 |
| AAAAGGAGGCUGCCGUGGA | 4903 | UCCACGGCAGCCUCCUUUU | 4904 |
| AAAGGAGGCUGCCGUGGAG | 4905 | CUCCACGGCAGCCUCCUUU | 4906 |
| GUGGAGCACGGAUACAAGA | 4907 | UUCUGUAUCCGUGCUCCAC | 4908 |
| ACUGGAUGAGGGCAGAUGA | 4909 | UCAUCUGCCCUCAUCCAGU | 4910 |
| CUGGAUGAGGGCAGAUGAG | 4911 | CUCAUCUGCCCUCAUCCAG | 4912 |
| GGAUGAGGGCAGAUGAGGA | 4913 | UCCUCAUCUGCCCUCAUCC | 4914 |
| AUGAGGGCAGAUGAGGACA | 4915 | UGUCCUCAUCUGCCCUCAU | 4916 |
| UGAGGGCAGAUGAGGACAG | 4917 | CUGUCCUCAUCUGCCCUCA | 4918 |
| AGGGCAGAUGAGGACAGGA | 4919 | UCCUGUCCUCAUCUGCCCU | 4920 |
| GGCAGAUGAGGACAGGAAG | 4921 | CUUCCUGUCCUCAUCUGCC | 4922 |
| CAGAUGAGGACAGGAAGAG | 4923 | CUCUUCCUGUCCUCAUCUG | 4924 |
| GAAUAAGUCUCCAAGGAGC | 4925 | GCUCCUUGGAGACUUAUUC | 4926 |
| AAUAAGUCUCCAAGGAGCA | 4927 | UGCUCCUUGGAGACUUAUU | 4928 |
| AUAAGUCUCCAAGGAGCAC | 4929 | GUGCUCCUUGGAGACUUAU | 4930 |

TABLE 6

| Sense Sequence | SEQ ID NO: | Antisense Sequence | SEQ ID NO: |
| --- | --- | --- | --- |
| AAAGGCUAGCAAAGAGCAA | 4931 | UUGCUCUUUGCUAGCCUUU | 4932 |
| AAGGCUAGCAAAGAGCAAG | 4933 | CUUGCUCUUUGCUAGCCUU | 4934 |

TABLE 6-continued

| Sense Sequence | SEQ ID NO: | Antisense Sequence | SEQ ID NO: |
| --- | --- | --- | --- |
| AGGCUAGCAAAGAGCAAGG | 4935 | CCUUGCUCUUUGCUAGCCU | 4936 |
| GGCUAGCAAAGAGCAAGGA | 4937 | UCCUUGCUCUUUGCUAGCC | 4938 |
| GCUAGCAAAGAGCAAGGAA | 4939 | UUCCUUGCUCUUUGCUAGC | 4940 |
| CAAAGUGGCGAGGCCCUCA | 4941 | UGAGGGCCUCGCCACUUUG | 4942 |
| AAAGUGGCGAGGCCCUCAG | 4943 | CUGAGGGCCUCGCCACUUU | 4944 |
| AAGUGGCGAGGCCCUCAGA | 4945 | UCUGAGGGCCUCGCCACUU | 4946 |
| GCGAGGCCCUCAGAGUGAA | 4947 | UUCACUCUGAGGGCCUCGC | 4948 |
| AAAGCGUAAGGUUCAGUCA | 4949 | UGACUGAACCUUACGCUUU | 4950 |
| AAGAGCCUUCCUCACCCAA | 4951 | UUGGGUGAGGAAGGCUCUU | 4952 |
| AGAGCCUUCCUCACCCAAA | 4953 | UUUGGGUGAGGAAGGCUCU | 4954 |
| AAAAGCCUCUCUCAGCUGU | 4955 | ACAGCUGAGAGAGGCUUUU | 4956 |
| AAAGCCUCUCUCAGCUGUG | 4957 | CACAGCUGAGAGAGGCUUU | 4958 |
| UCAGCUGUGACCUGGCUCU | 4959 | AGAGCCAGGUCACAGCUGA | 4960 |
| UGACCUGGCUCUGCAUUUU | 4961 | AAAAUGCAGAGCCAGGUCA | 4962 |
| ACCUGGCUCUGCAUUUUCA | 4963 | UGAAAAUGCAGAGCCAGGU | 4964 |
| CCUGGCUCUGCAUUUUCAU | 4965 | AUGAAAAUGCAGAGCCAGG | 4966 |
| GCUCUGCAUUUUCAUCGUG | 4967 | CACGAUGAAAAUGCAGAGC | 4968 |
| CUCUGCAUUUUCAUCGUGG | 4969 | CCACGAUGAAAAUGCAGAG | 4970 |
| UCUGCAUUUUCAUCGUGGC | 4971 | GCCACGAUGAAAAUGCAGA | 4972 |
| CUGCAUUUUCAUCGUGGCC | 4973 | GGCCACGAUGAAAAUGCAG | 4974 |
| UGCAUUUUCAUCGUGGCCU | 4975 | AGGCCACGAUGAAAAUGCA | 4976 |
| GCAUUUUCAUCGUGGCCUU | 4977 | AAGGCCACGAUGAAAAUGC | 4978 |
| AUUUUCAUCGUGGCCUUUG | 4979 | CAAAGGCCACGAUGAAAAU | 4980 |
| UUUUCAUCGUGGCCUUUGU | 4981 | ACAAAGGCCACGAUGAAAA | 4982 |
| UUUCAUCGUGGCCUUUGUC | 4983 | GACAAAGGCCACGAUGAAA | 4984 |
| UUCAUCGUGGCCUUUGUCA | 4985 | UGACAAAGGCCACGAUGAA | 4986 |
| UCAUCGUGGCCUUUGUCAG | 4987 | CUGACAAAGGCCACGAUGA | 4988 |
| CAUCGUGGCCUUUGUCAGC | 4989 | GCUGACAAAGGCCACGAUG | 4990 |
| AUCGUGGCCUUUGUCAGCC | 4991 | GGCUGACAAAGGCCACGAU | 4992 |
| CCUUUGUCAGCCACCCAGC | 4993 | GCUGGGUGGCUGACAAAGG | 4994 |
| CUUUGUCAGCCACCCAGCG | 4995 | CGCUGGGUGGCUGACAAAG | 4996 |
| UUGUCAGCCACCCAGCGUG | 4997 | CACGCUGGGUGGCUGACAA | 4998 |
| GUGGCUGCAGAAGCUCUCU | 4999 | AGAGAGCUUCUGCAGCCAC | 5000 |
| UGGCUGCAGAAGCUCUCUA | 5001 | UAGAGAGCUUCUGCAGCCA | 5002 |
| GGCUGCAGAAGCUCUCUAA | 5003 | UUAGAGAGCUUCUGCAGCC | 5004 |
| GCUGCAGAAGCUCUCUAAG | 5005 | CUUAGAGAGCUUCUGCAGC | 5006 |
| CUGCAGAAGCUCUCUAAGC | 5007 | GCUUAGAGAGCUUCUGCAG | 5008 |
| UGCAGAAGCUCUCUAAGCA | 5009 | UGCUUAGAGAGCUUCUGCA | 5010 |

TABLE 6-continued

| Sense Sequence | SEQ ID NO: | Antisense Sequence | SEQ ID NO: |
|---|---|---|---|
| GCAGAAGCUCUCUAAGCAC | 5011 | GUGCUUAGAGAGCUUCUGC | 5012 |
| CCAGCACAGCCACAGCUCA | 5013 | UGAGCUGUGGCUGUGCUGG | 5014 |
| CAGCACAGCCACAGCUCAA | 5015 | UUGAGCUGUGGCUGUGCUG | 5016 |
| GCACAGCCACAGCUCAAAG | 5017 | CUUUGAGCUGUGGCUGUGC | 5018 |
| CACAGCCACAGCUCAAAGC | 5019 | GCUUUGAGCUGUGGCUGUG | 5020 |
| ACAGCCACAGCUCAAAGCG | 5021 | CGCUUUGAGCUGUGGCUGU | 5022 |
| CAGCCACAGCUCAAAGCGG | 5023 | CCGCUUUGAGCUGUGGCUG | 5024 |
| AGCCACAGCUCAAAGCGGC | 5025 | GCCGCUUUGAGCUGUGGCU | 5026 |
| GGCCAACUGCUGUGAGGAG | 5027 | CUCCUCACAGCAGUUGGCC | 5028 |
| GCCAACUGCUGUGAGGAGG | 5029 | CCUCCUCACAGCAGUUGGC | 5030 |
| CCAACUGCUGUGAGGAGGU | 5031 | ACCUCCUCACAGCAGUUGG | 5032 |
| CAACUGCUGUGAGGAGGUG | 5033 | CACCUCCUCACAGCAGUUG | 5034 |
| AACUGCUGUGAGGAGGUGA | 5035 | UCACCUCCUCACAGCAGUU | 5036 |
| ACUGCUGUGAGGAGGUGAA | 5037 | UUCACCUCCUCACAGCAGU | 5038 |
| CUCAAGGCCCAAGUUGCCA | 5039 | UGGCAACUUGGGCCUUGAG | 5040 |
| GCCCAAGUUGCCAACCUUA | 5041 | UAAGGUUGGCAACUUGGGC | 5042 |
| CCCAAGUUGCCAACCUUAG | 5043 | CUAAGGUUGGCAACUUGGG | 5044 |
| CCAAGUUGCCAACCUUAGC | 5045 | GCUAAGGUUGGCAACUUGG | 5046 |
| CAAGUUGCCAACCUUAGCA | 5047 | UGCUAAGGUUGGCAACUUG | 5048 |
| AAGUUGCCAACCUUAGCAG | 5049 | CUGCUAAGGUUGGCAACUU | 5050 |
| AGUUGCCAACCUUAGCAGC | 5051 | GCUGCUAAGGUUGGCAACU | 5052 |
| GACUGGGUCAGCGUGGUCA | 5053 | UGACCACGCUGACCCAGUC | 5054 |
| ACUGGGUCAGCGUGGUCAU | 5055 | AUGACCACGCUGACCCAGU | 5056 |
| CUGGGUCAGCGUGGUCAUG | 5057 | CAUGACCACGCUGACCCAG | 5058 |
| UGGGUCAGCGUGGUCAUGC | 5059 | GCAUGACCACGCUGACCCA | 5060 |
| GGGUCAGCGUGGUCAUGCA | 5061 | UGCAUGACCACGCUGACCC | 5062 |
| CAGCGUGGUCAUGCAGGUG | 5063 | CACCUGCAUGACCACGCUG | 5064 |
| AGCGUGGUCAUGCAGGUGA | 5065 | UCACCUGCAUGACCACGCU | 5066 |
| GCGUGGUCAUGCAGGUGAU | 5067 | AUCACCUGCAUGACCACGC | 5068 |
| CGUGGUCAUGCAGGUGAUG | 5069 | CAUCACCUGCAUGACCACG | 5070 |
| AGCAAGCGCAUGGAGCGC | 5071 | GCGACUCCAUGCGCUUGCU | 5072 |
| CAACCAAAUUGACAUCAUG | 5073 | CAUGAUGUCAAUUUGGUUG | 5074 |
| ACCAAAUUGACAUCAUGCA | 5075 | UGCAUGAUGUCAAUUUGGU | 5076 |
| UUGACAUCAUGCAGCUGCA | 5077 | UGCAGCUGCAUGAUGUCAA | 5078 |
| CAGGCAGCACAGACGGUCA | 5079 | UGACCGUCUGUGCUGCCUG | 5080 |
| AGGCAGCACAGACGGUCAC | 5081 | GUGACCGUCUGUGCUGCCU | 5082 |
| GGCAGCACAGACGGUCACU | 5083 | AGUGACCGUCUGUGCUGCC | 5084 |
| GCAGCACAGACGGUCACUC | 5085 | GAGUGACCGUCUGUGCUGC | 5086 |
| GUCACUCAGACCUCCGCAG | 5087 | CUGCGGAGGUCUGAGUGAC | 5088 |
| UCACUCAGACCUCCGCAGA | 5089 | UCUGCGGAGGUCUGAGUGA | 5090 |
| CACUCAGACCUCCGCAGAU | 5091 | AUCUGCGGAGGUCUGAGUG | 5092 |
| ACUCAGACCUCCGCAGAUG | 5093 | CAUCUGCGGAGGUCUGAGU | 5094 |
| CUCAGACCUCCGCAGAUGC | 5095 | GCAUCUGCGGAGGUCUGAG | 5096 |
| UCAGACCUCCGCAGAUGCC | 5097 | GGCAUCUGCGGAGGUCUGA | 5098 |
| CAGACCUCCGCAGAUGCCA | 5099 | UGGCAUCUGCGGAGGUCUG | 5100 |
| GAUGCCAUCUACGACUGCU | 5101 | AGCAGUCGUAGAUGGCAUC | 5102 |
| AUGCCAUCUACGACUGCUC | 5103 | GAGCAGUCGUAGAUGGCAU | 5104 |
| UGCCAUCUACGACUGCUCU | 5105 | AGAGCAGUCGUAGAUGGCA | 5106 |
| GCCAUCUACGACUGCUCUU | 5107 | AAGAGCAGUCGUAGAUGGC | 5108 |
| CCAUCUACGACUGCUCUUC | 5109 | GAAGAGCAGUCGUAGAUGG | 5110 |
| CUACGACUGCUCUUCCCUC | 5111 | GAGGGAAGAGCAGUCGUAG | 5112 |
| UACGACUGCUCUUCCCUCU | 5113 | AGAGGGAAGAGCAGUCGUA | 5114 |
| AUCUCUGGAGUGUAUAAGC | 5115 | GCUUAUACACUCCAGAGAU | 5116 |
| CUGGAGUGUAUAAGCUUCC | 5117 | GGAAGCUUAUACACUCCAG | 5118 |
| UGGAGUGUAUAAGCUUCCU | 5119 | AGGAAGCUUAUACACUCCA | 5120 |
| GGAGUGUAUAAGCUUCCUC | 5121 | GAGGAAGCUUAUACACUCC | 5122 |
| GUAUAAGCUUCCUCCUGAU | 5123 | AUCAGGAGGAAGCUUAUAC | 5124 |
| UAUAAGCUUCCUCCUGAUG | 5125 | CAUCAGGAGGAAGCUUAUA | 5126 |
| AUAAGCUUCCUCCUGAUGA | 5127 | UCAUCAGGAGGAAGCUUAU | 5128 |
| AAGCUUCCUCCUGAUGACU | 5129 | AGUCAUCAGGAGGAAGCUU | 5130 |
| AGCUUCCUCCUGAUGACUU | 5131 | AAGUCAUCAGGAGGAAGCU | 5132 |
| GCUUCCUCCUGAUGACUUC | 5133 | GAAGUCAUCAGGAGGAAGC | 5134 |
| CUUCCUCCUGAUGACUUCC | 5135 | GGAAGUCAUCAGGAGGAAG | 5136 |
| UUCCUCCUGAUGACUUCCU | 5137 | AGGAAGUCAUCAGGAGGAA | 5138 |
| ACUCCUGGGCAGCCCUGA | 5139 | UCAGGGCUGCCCAGGAAGU | 5140 |
| AGACUUCAGGCGGAGGCUG | 5141 | CAGCCUCCGCCUGAAGUCU | 5142 |
| ACUUCAGGCGGAGGCUGGA | 5143 | UCCAGCCUCCGCCUGAAGU | 5144 |
| GCGGAGGCUGGACCAUCAU | 5145 | AUGAUGGUCCAGCCUCCGC | 5146 |
| CGGAGGCUGGACCAUCAUC | 5147 | GAUGAUGGUCCAGCCUCCG | 5148 |
| GGAGGCUGGACCAUCAUCC | 5149 | GGAUGAUGGUCCAGCCUCC | 5150 |
| AAGUGGCCUUGUCUCCUUC | 5151 | GAAGGAGACAAGGCCACUU | 5152 |
| AGUGGCCUUGUCUCCUUCU | 5153 | AGAAGGAGACAAGGCCACU | 5154 |
| GUGGCCUUGUCUCCUUCUA | 5155 | UAGAAGGAGACAAGGCCAC | 5156 |
| CUUGUCUCCUUCUACCGGG | 5157 | CCCGGUAGAAGGAGACAAG | 5158 |
| UUGUCUCCUUCUACCGGGA | 5159 | UCCCGGUAGAAGGAGACAA | 5160 |
| UGUCUCCUUCUACCGGGAC | 5161 | GUCCCGGUAGAAGGAGACA | 5162 |

TABLE 6-continued

| Sense Sequence | SEQ ID NO: | Antisense Sequence | SEQ ID NO: |
|---|---|---|---|
| GUCUCCUUCUACCGGGACU | 5163 | AGUCCCGGUAGAAGGAGAC | 5164 |
| UUCUACCGGGACUGGAAGC | 5165 | GCUUCCAGUCCCGGUAGAA | 5166 |
| UCUACCGGGACUGGAAGCA | 5167 | UGCUUCCAGUCCCGGUAGA | 5168 |
| CUACCGGGACUGGAAGCAG | 5169 | CUGCUUCCAGUCCCGGUAG | 5170 |
| AGCAGGGCUUUGGCAGCAU | 5171 | AUGCUGCCAAAGCCCUGCU | 5172 |
| AGGGCUUUGGCAGCAUCCG | 5173 | CGGAUGCUGCCAAAGCCCU | 5174 |
| GGGCUUUGGCAGCAUCCGU | 5175 | ACGGAUGCUGCCAAAGCCC | 5176 |
| GGCUUUGGCAGCAUCCGUG | 5177 | CACGGAUGCUGCCAAAGCC | 5178 |
| CAUCCACCGGCUCUCCAGA | 5179 | UCUGGAGAGCCGGUGGAUG | 5180 |
| AUCCACCGGCUCUCCAGAC | 5181 | GUCUGGAGAGCCGGUGGAU | 5182 |
| UCCACCGGCUCUCCAGACA | 5183 | UGUCUGGAGAGCCGGUGGA | 5184 |
| AGGACUGGGAGGGCAACCU | 5185 | AGGUUGCCCUCCCAGUCCU | 5186 |
| GCAACCUGCGCUACGCUGA | 5187 | UCAGCGUAGCGCAGGUUGC | 5188 |
| CAACCUGCGCUACGCUGAG | 5189 | CUCAGCGUAGCGCAGGUUG | 5190 |
| CUGCGCUACGCUGAGUAUA | 5191 | UAUACUCAGCGUAGCGCAG | 5192 |
| UGCGCUACGCUGAGUAUAG | 5193 | CUAUACUCAGCGUAGCGCA | 5194 |
| CUACGCUGAGUAUAGCCAC | 5195 | GUGGCUAUACUCAGCGUAG | 5196 |
| UACGCUGAGUAUAGCCACU | 5197 | AGUGGCUAUACUCAGCGUA | 5198 |
| CACUUUGUUUUGGGCAAUG | 5199 | CAUUGCCCAAAACAAAGUG | 5200 |
| AACUACACUGGCAAUGUGG | 5201 | CCACAUUGCCAGUGUAGUU | 5202 |
| ACUACACUGGCAAUGUGGG | 5203 | CCCACAUUGCCAGUGUAGU | 5204 |
| AACGACGCCCUCCAGUAUC | 5205 | GAUACUGGAGGGCGUCGUU | 5206 |
| ACGACGCCCUCCAGUAUCA | 5207 | UGAUACUGGAGGGCGUCGU | 5208 |
| CGACGCCCUCCAGUAUCAU | 5209 | AUGAUACUGGAGGGCGUCG | 5210 |
| GACGCCCUCCAGUAUCAUA | 5211 | UAUGAUACUGGAGGGCGUC | 5212 |
| ACGCCCUCCAGUAUCAUAA | 5213 | UUAUGAUACUGGAGGGCGU | 5214 |
| CGCCCUCCAGUAUCAUAAC | 5215 | GUUAUGAUACUGGAGGGCG | 5216 |
| CAAGUGUGCACAGCUCCGC | 5217 | GCGGAGCUGUGCACACUUG | 5218 |
| AAGUGUGCACAGCUCCGCA | 5219 | UGCGGAGCUGUGCACACUU | 5220 |
| AGUGUGCACAGCUCCGCAA | 5221 | UUGCGGAGCUGUGCACACU | 5222 |
| UGCACAGCUCCGCAAAGGU | 5223 | ACCUUUGCGGAGCUGUGCA | 5224 |
| GCACAGCUCCGCAAAGGUG | 5225 | CACCUUUGCGGAGCUGUGC | 5226 |
| CACAGCUCCGCAAAGGUGG | 5227 | CCACCUUUGCGGAGCUGUG | 5228 |
| ACAGCUCCGCAAAGGUGGC | 5229 | GCCACCUUUGCGGAGCUGU | 5230 |
| CAGCUCCGCAAAGGUGGCU | 5231 | AGCCACCUUUGCGGAGCUG | 5232 |
| AGCUCCGCAAAGGUGGCUA | 5233 | UAGCCACCUUUGCGGAGCU | 5234 |
| GCUCCGCAAAGGUGGCUAC | 5235 | GUAGCCACCUUUGCGGAGC | 5236 |
| CUCCGCAAAGGUGGCUACU | 5237 | AGUAGCCACCUUUGCGGAG | 5238 |
| GCAAAGGUGGCUACUGGUA | 5239 | UACCAGUAGCCACCUUUGC | 5240 |
| CAAAGGUGGCUACUGGUAC | 5241 | GUACCAGUAGCCACCUUUG | 5242 |
| AAAGGUGGCUACUGGUACA | 5243 | UGUACCAGUAGCCACCUUU | 5244 |
| CAACUGCUGCACAGACUCC | 5245 | GGAGUCUGUGCAGCAGUUG | 5246 |
| CACAGACUCCAACCUCAAU | 5247 | AUUGAGGUUGGAGUCUGUG | 5248 |
| ACAGACUCCAACCUCAAUG | 5249 | CAUUGAGGUUGGAGUCUGU | 5250 |
| CAGACUCCAACCUCAAUGG | 5251 | CCAUUGAGGUUGGAGUCUG | 5252 |
| CCAACCUCAAUGGAGUGUA | 5253 | UACACUCCAUUGAGGUUGG | 5254 |
| CAACCUCAAUGGAGUGUAC | 5255 | GUACACUCCAUUGAGGUUG | 5256 |
| AACCUCAAUGGAGUGUACU | 5257 | AGUACACUCCAUUGAGGUU | 5258 |
| ACCUCAAUGGAGUGUACUA | 5259 | UAGUACACUCCAUUGAGGU | 5260 |
| CCUCAAUGGAGUGUACUAC | 5261 | GUAGUACACUCCAUUGAGG | 5262 |
| CUCAAUGGAGUGUACUACC | 5263 | GGUAGUACACUCCAUUGAG | 5264 |
| UCAAUGGAGUGUACUACCG | 5265 | CGGUAGUACACUCCAUUGA | 5266 |
| CAAUGGAGUGUACUACCGC | 5267 | GCGGUAGUACACUCCAUUG | 5268 |
| AAUGGAGUGUACUACCGCC | 5269 | GGCGGUAGUACACUCCAUU | 5270 |
| AUGGAGUGUACUACCGCCU | 5271 | AGGCGGUAGUACACUCCAU | 5272 |
| UGGAGUGUACUACCGCCUG | 5273 | CAGGCGGUAGUACACUCCA | 5274 |
| GGAGUGUACUACCGCCUGG | 5275 | CCAGGCGGUAGUACACUCC | 5276 |
| GAGUGUACUACCGCCUGGG | 5277 | CCCAGGCGGUAGUACACUC | 5278 |
| AGUGUACUACCGCCUGGGU | 5279 | ACCCAGGCGGUAGUACACU | 5280 |
| GUACUACCGCCUGGGUGAG | 5281 | CUCACCCAGGCGGUAGUAC | 5282 |
| UACUACCGCCUGGGUGAGC | 5283 | GCUCACCCAGGCGGUAGUA | 5284 |
| ACUACCGCCUGGGUGAGCA | 5285 | UGCUCACCCAGGCGGUAGU | 5286 |
| CAAUAAGCACCUGGAUGGC | 5287 | GCCAUCCAGGUGCUUAUUG | 5288 |
| AAUAAGCACCUGGAUGGCA | 5289 | UGCCAUCCAGGUGCUUAUU | 5290 |
| AUAAGCACCUGGAUGGCAU | 5291 | AUGCCAUCCAGGUGCUUAU | 5292 |
| UAAGCACCUGGAUGGCAUC | 5293 | GAUGCCAUCCAGGUGCUUA | 5294 |
| AAGCACCUGGAUGGCAUCA | 5295 | UGAUGCCAUCCAGGUGCUU | 5296 |
| AGCACCUGGAUGGCAUCAC | 5297 | GUGAUGCCAUCCAGGUGCU | 5298 |
| GCACCUGGAUGGCAUCACC | 5299 | GGUGAUGCCAUCCAGGUGC | 5300 |
| CACCUGGAUGGCAUCACCU | 5301 | AGGUGAUGCCAUCCAGGUG | 5302 |
| UGGAUGGCAUCACCUGGUA | 5303 | UACCAGGUGAUGCCAUCCA | 5304 |
| UGGCAUGGAUCUACCUACU | 5305 | AGUAGGUAGAUCCAUGCCA | 5306 |
| GGCAUGGAUCUACCUACUC | 5307 | GAGUAGGUAGAUCCAUGCC | 5308 |
| GCAUGGAUCUACCUACUCC | 5309 | GGAGUAGGUAGAUCCAUGC | 5310 |
| CAUGGAUCUACCUACUCCC | 5311 | GGGAGUAGGUAGAUCCAUG | 5312 |
| AUGGAUCUACCUACUCCCU | 5313 | AGGGAGUAGGUAGAUCCAU | 5314 |

TABLE 6-continued

| Sense Sequence | SEQ ID NO: | Antisense Sequence | SEQ ID NO: |
|---|---|---|---|
| UGGAUCUACCUACUCCCUC | 5315 | GAGGGAGUAGGUAGAUCCA | 5316 |
| GGAUCUACCUACUCCCUCA | 5317 | UGAGGGAGUAGGUAGAUCC | 5318 |
| GAUCUACCUACUCCCUCAA | 5319 | UUGAGGGAGUAGGUAGAUC | 5320 |
| AUCUACCUACUCCCUCAAA | 5321 | UUUGAGGGAGUAGGUAGAU | 5322 |
| CGCCCAGAAGACUUCAAGC | 5323 | GCUUGAAGUCUUCUGGGCG | 5324 |
| GCCCAGAAGACUUCAAGCC | 5325 | GGCUUGAAGUCUUCUGGGC | 5326 |
| CCCAGAAGACUUCAAGCCU | 5327 | AGGCUUGAAGUCUUCUGGG | 5328 |
| CCAGAAGACUUCAAGCCUU | 5329 | AAGGCUUGAAGUCUUCUGG | 5330 |
| CAGAAGACUUCAAGCCUUA | 5331 | UAAGGCUUGAAGUCUUCUG | 5332 |
| GAAGACUUCAAGCCUUAAA | 5333 | UUUAAGGCUUGAAGUCUUC | 5334 |
| AAGACUUCAAGCCUUAAAA | 5335 | UUUUAAGGCUUGAAGUCUU | 5336 |
| AGACUUCAAGCCUUAAAAG | 5337 | CUUUUAAGGCUUGAAGUCU | 5338 |
| GACUUCAAGCCUUAAAAGG | 5339 | CCUUUUAAGGCUUGAAGUC | 5340 |
| ACUUCAAGCCUUAAAAGGA | 5341 | UCCUUUUAAGGCUUGAAGU | 5342 |
| CUUCAAGCCUUAAAAGGAG | 5343 | CUCCUUUUAAGGCUUGAAG | 5344 |
| UUCAAGCCUUAAAAGGAGG | 5345 | CCUCCUUUUAAGGCUUGAA | 5346 |
| CCUUAAAAGGAGGCUGCCG | 5347 | CGGCAGCCUCCUUUUAAGG | 5348 |
| CUUAAAAGGAGGCUGCCGU | 5349 | ACGGCAGCCUCCUUUUAAG | 5350 |
| UUAAAAGGAGGCUGCCGUG | 5351 | CACGGCAGCCUCCUUUUAA | 5352 |
| UAAAAGGAGGCUGCCGUGG | 5353 | CCACGGCAGCCUCCUUUUA | 5354 |
| AAAAGGAGGCUGCCGUGGA | 5355 | UCCACGGCAGCCUCCUUUU | 5356 |
| AAAGGAGGCUGCCGUGGAG | 5357 | CUCCACGGCAGCCUCCUUU | 5358 |
| GUGGAGCACGGAUACAGAA | 5359 | UUCUGUAUCCGUGCUCCAC | 5360 |
| ACUGGAUGAGGGCAGAUGA | 5361 | UCAUCUGCCCUCAUCCAGU | 5362 |
| CUGGAUGAGGGCAGAUGAG | 5363 | CUCAUCUGCCCUCAUCCAG | 5364 |
| GGAUGAGGGCAGAUGAGGA | 5365 | UCCUCAUCUGCCCUCAUCC | 5366 |
| AUGAGGGCAGAUGAGGACA | 5367 | UGUCCUCAUCUGCCCUCAU | 5368 |
| UGAGGGCAGAUGAGGACAG | 5369 | CUGUCCUCAUCUGCCCUCA | 5370 |
| AGGGCAGAUGAGGACAGGA | 5371 | UCCUGUCCUCAUCUGCCCU | 5372 |
| GGCAGAUGAGGACAGGAAG | 5373 | CUUCCUGUCCUCAUCUGCC | 5374 |
| CAGAUGAGGACAGGAAGAG | 5375 | CUCUUCCUGUCCUCAUCUG | 5376 |
| GAAUAAGUCUCCAAGGAGC | 5377 | GCUCCUUGGAGACUUAUUC | 5378 |
| AAUAAGUCUCCAAGGAGCA | 5379 | UGCUCCUUGGAGACUUAUU | 5380 |
| AUAAGUCUCCAAGGAGCAC | 5381 | GUGCUCCUUGGAGACUUAU | 5382 |
| GUACCAAGGAUGUUACAGU | 5383 | ACUGUAACAUCCUUGGUAC | 5384 |
| UACCAAGGAUGUUACAGUA | 5385 | UACUGUAACAUCCUUGGUA | 5386 |
| ACCAAGGAUGUUACAGUAA | 5387 | UUACUGUAACAUCCUUGGU | 5388 |
| CCAAGGAUGUUACAGUAAA | 5389 | UUUACUGUAACAUCCUUGG | 5390 |
| CUGGGUCCUGCCACAUCCU | 5391 | AGGAUGUGGCAGGACCCAG | 5392 |
| UGGGUCCUGCCACAUCCUU | 5393 | AAGGAUGUGGCAGGACCCA | 5394 |
| GGGUCCUGCCACAUCCUUC | 5395 | GAAGGAUGUGGCAGGACCC | 5396 |
| GGUCCUGCCACAUCCUUCU | 5397 | AGAAGGAUGUGGCAGGACC | 5398 |
| UCCUGCCACAUCCUUCUCA | 5399 | UGAGAAGGAUGUGGCAGGA | 5400 |
| CCUGCCACAUCCUUCUCAA | 5401 | UUGAGAAGGAUGUGGCAGG | 5402 |
| CUGCCACAUCCUUCUCAAG | 5403 | CUUGAGAAGGAUGUGGCAG | 5404 |
| CUUCUCAAGGUGGUAGACU | 5405 | AGUCUACCACCUUGAGAAG | 5406 |
| AGGUGGUAGACUGAGUGGG | 5407 | CCCACUCAGUCUACCACCU | 5408 |
| GGUCUCUCUGCCCAAGAUC | 5409 | GAUCUUGGGCAGAGAGACC | 5410 |
| GUCUCUCUGCCCAAGAUCC | 5411 | GGAUCUUGGGCAGAGAGAC | 5412 |
| UCUCUCUGCCCAAGAUCCC | 5413 | GGGAUCUUGGGCAGAGAGA | 5414 |
| UCUGCCCAAGAUCCCUGAC | 5415 | GUCAGGGAUCUUGGGCAGA | 5416 |
| CUGCCCAAGAUCCCUGACA | 5417 | UGUCAGGGAUCUUGGGCAG | 5418 |
| UGCCCAAGAUCCCUGACAU | 5419 | AUGUCAGGGAUCUUGGGCA | 5420 |
| GCCCAAGAUCCCUGACAUA | 5421 | UAUGUCAGGGAUCUUGGGC | 5422 |
| CCCAAGAUCCCUGACAUAG | 5423 | CUAUGUCAGGGAUCUUGGG | 5424 |
| AUCCCUGACAUAGCAGUAG | 5425 | CUACUGCUAUGUCAGGGAU | 5426 |
| CCCUGACAUAGCAGUAGCU | 5427 | AGCUACUGCUAUGUCAGGG | 5428 |
| CCUGACAUAGCAGUAGCUU | 5429 | AAGCUACUGCUAUGUCAGG | 5430 |
| CUGACAUAGCAGUAGCUUG | 5431 | CAAGCUACUGCUAUGUCAG | 5432 |
| UGACAUAGCAGUAGCUUGU | 5433 | ACAAGCUACUGCUAUGUCA | 5434 |
| ACAUAGCAGUAGCUUGUCU | 5435 | AGACAAGCUACUGCUAUGU | 5436 |
| CAUAGCAGUAGCUUGUCUU | 5437 | AAGACAAGCUACUGCUAUG | 5438 |
| GCAGUAGCUUGUCUUUUCC | 5439 | GGAAAAGACAAGCUACUGC | 5440 |
| CAGUAGCUUGUCUUUUCCA | 5441 | UGGAAAAGACAAGCUACUG | 5442 |
| AGUAGCUUGUCUUUUCCAC | 5443 | GUGGAAAAGACAAGCUACU | 5444 |
| GUAGCUUGUCUUUUCCACA | 5445 | UGUGGAAAAGACAAGCUAC | 5446 |
| CUUGUCUUUUCCACAUGAU | 5447 | AUCAUGUGGAAAAGACAAG | 5448 |
| UUGUCUUUUCCACAUGAUU | 5449 | AAUCAUGUGGAAAAGACAA | 5450 |
| CUUUUCCACAUGAUUUGUC | 5451 | GACAAAUCAUGUGGAAAAG | 5452 |
| UUUUCCACAUGAUUUGUCU | 5453 | AGACAAAUCAUGUGGAAAA | 5454 |
| UUUCCACAUGAUUUGUCUG | 5455 | CAGACAAAUCAUGUGGAAA | 5456 |
| UUCCACAUGAUUUGUCUGU | 5457 | ACAGACAAAUCAUGUGGAA | 5458 |
| GCUUAGGCUAUGUGAGGGC | 5459 | GCCCUCACAUAGCCUAAGC | 5460 |
| AGGCUAUGUGAGGGCAAAA | 5461 | UUUUGCCCUCACAUAGCCU | 5462 |
| AGGAGUGAAGGAGGCAGGU | 5463 | ACCUGCCUCCUUCACUCCU | 5464 |
| GGAGUGAAGGAGGCAGGUG | 5465 | CACCUGCCUCCUUCACUCC | 5466 |

TABLE 6-continued

| Sense Sequence | SEQ ID NO: | Antisense Sequence | SEQ ID NO: |
|---|---|---|---|
| GAGUGAAGGAGGCAGGUGG | 5467 | CCACCUGCCUCCUUCACUC | 5468 |
| AAUUAUCUUGAGUCUACAC | 5469 | GUGUAGACUCAAGAUAAUU | 5470 |
| ACUCCAGGGCACUGCAUCU | 5471 | AGAUGCAGUGCCCUGGAGU | 5472 |
| CUCCAGGGCACUGCAUCUG | 5473 | CAGAUGCAGUGCCCUGGAG | 5474 |
| AGGGCACUGCAUCUGGCGA | 5475 | UCGCCAGAUGCAGUGCCCU | 5476 |
| GGGCACUGCAUCUGGCGAU | 5477 | AUCGCCAGAUGCAGUGCCC | 5478 |
| GGCACUGCAUCUGGCGAUC | 5479 | GAUCGCCAGAUGCAGUGCC | 5480 |
| GCACUGCAUCUGGCGAUCA | 5481 | UGAUCGCCAGAUGCAGUGC | 5482 |
| CCCUGCUCGCCUUGGUCAU | 5483 | AUGACCAAGGCGAGCAGGG | 5484 |
| CCUGCUCGCCUUGGUCAUG | 5485 | CAUGACCAAGGCGAGCAGG | 5486 |
| CUGCUCGCCUUGGUCAUGU | 5487 | ACAUGACCAAGGCGAGCAG | 5488 |
| UGCUCGCCUUGGUCAUGUA | 5489 | UACAUGACCAAGGCGAGCA | 5490 |
| AUGAAGCACCAGCAGGAGG | 5491 | CCUCCUGCUGGUGCUUCAU | 5492 |
| UGAAGCACCAGCAGGAGGU | 5493 | ACCUCCUGCUGGUGCUUCA | 5494 |
| CAGCAGGAGGUGGACAGAG | 5495 | CUCUGUCCACCUCCUGCUG | 5496 |
| AGCAGGAGGUGGACAGAGU | 5497 | ACUCUGUCCACCUCCUGCU | 5498 |
| GCAGGAGGUGGACAGAGUC | 5499 | GACUCUGUCCACCUCCUGC | 5500 |
| CAGGAGGUGGACAGAGUCU | 5501 | AGACUCUGUCCACCUCCUG | 5502 |
| GGAGGUGGACAGAGUCUCU | 5503 | AGAGACUCUGUCCACCUCC | 5504 |
| AGGUGGACAGAGUCUCUCA | 5505 | UGAGAGACUCUGUCCACCU | 5506 |
| UGGACAGAGUCUCUCAUGG | 5507 | CCAUGAGAGACUCUGUCCA | 5508 |
| GGACAGAGUCUCUCAUGGA | 5509 | UCCAUGAGAGACUCUGUCC | 5510 |
| GACAGAGUCUCUCAUGGAU | 5511 | AUCCAUGAGAGACUCUGUC | 5512 |
| ACAGAGUCUCUCAUGGAUG | 5513 | CAUCCAUGAGAGACUCUGU | 5514 |
| GGAGCUUCCUUUUAAAUUU | 5515 | AAAUUUAAAAGGAAGCUCC | 5516 |
| AACUGAAGGUAGAUGGUGU | 5517 | ACACCAUCUACCUUCAGUU | 5518 |
| ACUGAAGGUAGAUGGUGUU | 5519 | AACACCAUCUACCUUCAGU | 5520 |
| CUGAAGGUAGAUGGUGUUA | 5521 | UAACACCAUCUACCUUCAG | 5522 |
| UGAAGGUAGAUGGUGUUAU | 5523 | AUAACACCAUCUACCUUCA | 5524 |
| GAAGGUAGAUGGUGUUAUA | 5525 | UAUAACACCAUCUACCUUC | 5526 |
| GUAGAUGGUGUUAUAGUUA | 5527 | UAACUAUAACACCAUCUAC | 5528 |
| UGUAAAUAAGCAUCUCACU | 5529 | AGUGAGAUGCUUAUUUACA | 5530 |
| AUAAGCAUCUCACUUUGUA | 5531 | UACAAAGUGAGAUGCUUAU | 5532 |

In some embodiments, the siRNA molecules comprise or consist of the nucleotide sequences (sense and antisense strands) shown in Table 7 and Table 8.

TABLE 7

| Sense Sequence 5' to 3' | SEQ ID NO: | Antisense Sequence 5' to 3' | SEQ ID NO: |
|---|---|---|---|
| ACACUUCCUUGUGUCUAUAGA | 5533 | UCUAUAGACACAAGGAAGUGUCG | 5534 |
| GUACCAGAAGAACUACCGAAA | 5535 | UUUCGGUAGUUCUUCUGGUACAG | 5536 |
| UACCAGAAGAACUACCGAAUA | 5537 | UAUUCGGUAGUUCUUCUGGUACA | 5538 |
| CUGUGACAUGGAAACUUCAGA | 5539 | UCUGAAGUUUCCAUGUCACAGAA | 5540 |
| CAGAAGAACUACCGAAUCUCA | 5541 | UGAGAUUCGGUAGUUCUUCUGGU | 5542 |
| AGAAGAACUACCGAAUCUCUA | 5543 | UAGAGAUUCGGUAGUUCUUCUGG | 5544 |
| GACAGUAUAAGCAAGGGUUUA | 5545 | UAAACCCUUGCUUAUACUGUCUC | 5546 |
| GAAGAACUACCGAAUCUCUGA | 5547 | UCAGAGAUUCGGUAGUUCUUCUG | 5548 |
| UGUGACAUGGAAACUUCAGGA | 5549 | UCCUGAAGUUUCCAUGUCACAGA | 5550 |
| GUCUCCUUCUACCAAGACUGA | 5551 | UCAGUCUUGGUAGAAGGAGACAA | 5552 |
| ACUCUGAGAUGAACAACCAGA | 5553 | UCUGGUUGUUCAUCUCAGAGUAC | 5554 |
| AGACAGUAUAAGCAAGGGUUA | 5555 | UAACCCUUGCUUAUACUGUCUCC | 5556 |
| ACAGUAUAAGCAAGGGUUUGA | 5557 | UCAAACCCUUGCUUAUACUGUCU | 5558 |
| UUGGGCAAUGAACUGAACAGA | 5559 | UCUGUUCAGUUCAUUGCCCAACG | 5560 |
| GCCAACUAUUCCCUCAAACGA | 5561 | UCGUUUGAGGGAAUAGUUGGCUC | 5562 |
| CCGAGCAAGUACUCUGAGA | 5563 | UCUCAGAGUACUUGCUCUCGGCA | 5564 |
| CAUAACAACACCGUCUUCAGA | 5565 | UCUGAAGACGGUGUUGUUAUGGU | 5566 |
| UGUACCAGAAGAACUACCGA | 5567 | UUCGGUAGUUCUUCUGGUACAGG | 5568 |
| UGACAUGGAAACUUCAGGAGA | 5569 | UCUCCUGAAGUUUCCAUGUCACA | 5570 |

TABLE 7-continued

| Sense Sequence 5' to 3' | SEQ ID NO: | Antisense Sequence 5' to 3' | SEQ ID NO: |
|---|---|---|---|
| CUGCAGAAGCCUCAUAAACGA | 5571 | UCGUUUAUGAGGCUUCUGCAGCC | 5572 |
| GCAGAAGCCUCAUAAACGCAA | 5573 | UUGCGUUUAUGAGGCUUCUGCAG | 5574 |
| UGCCGAGAGCAAGUACUCUGA | 5575 | UCAGAGUACUUGCUCUCGGCAGU | 5576 |

TABLE 8

| Sense Sequence 5' to 3' | SEQ ID NO: | Antisense Sequence 5' to 3' | SEQ ID NO: |
|---|---|---|---|
| CUUGGAAGGAAAGCUAUAGGU | 5577 | ACCUAUAGCUUUCCUUCCAAGCC | 5578 |
| UAUAGGCUACCCAUUCAGCUU | 5579 | AAGCUGAAUGGGUAGCCUAUAGC | 5580 |
| GAGACUCAAGCUUUGAGAAAU | 5581 | AUUUCUCAAAGCUUGAGUCUCUG | 5582 |
| GCUAGCAAAGAGCAAGGAAAU | 5583 | AUUUCCUUGCUCUUUGCUAGCCU | 5584 |
| AAGAGAGAAAACAACAAAGUU | 5585 | AACUUUGUUGUUUUCUCUCUUUC | 5586 |
| GUGGCGAGGCCCUCAGAGUGU | 5587 | ACACUCUGAGGGCCUCGCCACUU | 5588 |
| CAGAGUGAAAGCGUAAGGUUU | 5589 | AAACCUUACGCUUUCACUCUGAG | 5590 |
| CGUAAGGUUCAGUCAGCCUGU | 5591 | ACAGGCUGACUGAACCUUACGCU | 5592 |
| CUGCAGCUUUGCAGACCUCAU | 5593 | AUGAGGUCUGCAAAGCUGCAGCA | 5594 |
| CUCAGCUGGGCAUCUCCAGAU | 5595 | AUCUGGAGAUGCCCAGCUGAGGU | 5596 |
| UGAAGGAAGAGCCUUCCUCAU | 5597 | AUGAGGAAGGCUCUUCCUUCAGG | 5598 |
| CACCCAAACCCACAAAAGAU | 5599 | AAUCUUUGUGGGUUUGGGUGAG | 5600 |
| GCCUCUCUCAGCUGUGACCUU | 5601 | AAGGUCACAGCUGAGAGAGGCUU | 5602 |
| UGGCUCUGCAUUUUCAUCGUU | 5603 | AACGAUGAAAAUGCAGAGCCAGG | 5604 |

TABLE 8-continued

| Sense Sequence 5' to 3' | SEQ ID NO: | Antisense Sequence 5' to 3' | SEQ ID NO: |
|---|---|---|---|
| UUUCAUCGUGGCCUUUGUCAU | 5605 | AUGACAAAGGCCACGAUGAAAU | 5606 |
| CUGCAGAAGCUCUCUAAGCAU | 5607 | AUGCUUAGAGAGCUUCUGCAGCC | 5608 |
| AAGCACAAGACACCAGCACAU | 5609 | AUGUGCUGGUGUCUUGUGCUUAG | 5610 |
| CCAGCACAGCCACAGCUCAAU | 5611 | AUUGAGCUGUGGCUGUGCUGGUG | 5612 |
| CAGCUCAAAGCGGCCAACUGU | 5613 | ACAGUUGGCCGCUUUGAGCUGUG | 5614 |
| GCCAACUGCUGUGAGGAGGUU | 5615 | AACCUCCUCACAGCAGUUGGCCG | 5616 |
| GAGGAGGUGAAGGAGCUCAAU | 5617 | AUUGAGCUCCUUCACCUCCUCAC | 5618 |
| GGAGCUCAAGGCCCAAGUUGU | 5619 | ACAACUUGGGCCUUGAGCUCCUU | 5620 |
| CCAAGUUGCCAACCUUAGCAU | 5621 | AUGCUAAGGUUGGCAACUUGGGC | 5622 |
| CUUAGCAGCCUGCUGAGUGAU | 5623 | AUCACUCAGCAGGCUGCUAAGGU | 5624 |
| GCUGAGUGAACUGAACAAGAU | 5625 | AUCUUGUUCAGUUCACUCAGCAG | 5626 |
| UGAACAAGAAGCAGGAGAGGU | 5627 | ACCUCUCCUGCUUCUUGUUCAGU | 5628 |
| GACUGGGUCAGCGUGGUCAUU | 5629 | AAUGACCACGCUGACCCAGUCCC | 5630 |
| GUGGUCAUGCAGGUGAUGGAU | 5631 | AUCCAUCACCUGCAUGACCACGC | 5632 |
| GUGAUGGAGCUGGAGAGCAAU | 5633 | AUUGCUCUCCAGCUCCAUCACCU | 5634 |
| GGAGAGCAACAGCAAGCGCAU | 5635 | AUGCGCUUGCUGUUGCUCUCCAG | 5636 |
| AUGGAGUCGCGGCUCACAGAU | 5637 | AUCUGUGAGCCGCGACUCCAUGC | 5638 |
| CUCACAGAUGCUGAGAGCAAU | 5639 | AUUGCUCUCAGCAUCUGUGAGCC | 5640 |
| GAGCAAGUACUCCGAGAUGAU | 5641 | AUCAUCUCGGAGUACUUGCUCUC | 5642 |

TABLE 8-continued

| Sense Sequence 5' to 3' | SEQ ID NO: | Antisense Sequence 5' to 3' | SEQ ID NO: |
|---|---|---|---|
| CGAGAUGAACAACCAAAUUGU | 5643 | ACAAUUUGGUUGUUCAUCUCGGA | 5644 |
| ACCAAAUUGACAUCAUGCAGU | 5645 | ACUGCAUGAUGUCAAUUUGGUUG | 5646 |
| CAGCUGCAGGCAGCACAGACU | 5647 | AGUCUGUGCUGCCUGCAGCUGCA | 5648 |
| AGCACAGACGGUCACUCAGAU | 5649 | AUCUGAGUGACCGUCUGUGCUGC | 5650 |
| UCACUCAGACCUCCGCAGAUU | 5651 | AAUCUGCGGAGGUCUGAGUGACC | 5652 |
| CGCAGAUGCCAUCUACGACUU | 5653 | AAGUCGUAGAUGGCAUCUGCGGA | 5654 |
| UACGACUGCUCUUCCCUCUAU | 5655 | AUAGAGGGAAGAGCAGUCGUAGA | 5656 |
| UCCCUCUACCAGAAGAACUAU | 5657 | AUAGUUCUUCUGGUAGAGGGAAG | 5658 |
| GAAGAACUACCGCAUCUCUGU | 5659 | ACAGAGAUGCGGUAGUUCUUCUG | 5660 |
| UCUCUGGAGUGUAUAAGCUUU | 5661 | AAAGCUUAUACACUCCAGAGAUG | 5662 |
| CUUCCUCCUGAUGACUUCCUU | 5663 | AAGGAAGUCAUCAGGAGGAAGCU | 5664 |
| AGCCCUGAACUGGAGGUGUUU | 5665 | AAACACCUCCAGUUCAGGGCUGC | 5666 |
| GGAGGUGUUCUGUGACAUGGU | 5667 | ACCAUGUCACAGAACACCUCCAG | 5668 |
| GUGACAUGGAGACUUCAGGCU | 5669 | AGCCUGAAGUCUCCAUGUCACAG | 5670 |
| UCAGGCGGAGGCUGGACCAUU | 5671 | AAUGGUCCAGCCUCCGCCUGAAG | 5672 |
| GACCAUCAUCCAGAGACGAAU | 5673 | AUUCGUCUCUGGAUGAUGGUCCA | 5674 |
| GUGGCCUUGUCUCCUUCUACU | 5675 | AGUAGAAGGAGACAAGGCCACUU | 5676 |
| UCCUUCUACCGGGACUGGAAU | 5677 | AUUCCAGUCCCGGUAGAAGGAGA | 5678 |
| GGACUGGAAGCAGUACAAGCU | 5679 | AGCUUGUACUGCUUCCAGUCCCG | 5680 |
| GGGCUUUGGCAGCAUCCGUGU | 5681 | ACACGGAUGCUGCCAAAGCCCUG | 5682 |
| AACGAACACAUCCACCGGCUU | 5683 | AAGCCGGUGGAUGUGUUCGUUCC | 5684 |
| CCGGCUCUCCAGACAGCCAAU | 5685 | AUUGGCUGUCUGGAGAGCCGGUG | 5686 |
| AGCCAACCCGGCUGCGUGUAU | 5687 | AUACACGCAGCCGGGUUGGCUGU | 5688 |
| CUGCGUGUAGAGAUGGAGGAU | 5689 | AUCCUCCAUCUCUACACGCAGCC | 5690 |
| GAGGACUGGGAGGGCAACCUU | 5691 | AAGGUUGCCCUCCCAGUCCUCCA | 5692 |
| GGCAACCUGCGCUACGCUGAU | 5693 | AUCAGCUAGCGCAGGUUGCCCU | 5694 |
| UACGCUGAGUAUAGCCACUUU | 5695 | AAAGUGGCUAUACUCAGCGUAGC | 5696 |
| UAGCCACUUUGUUUUGGGCAU | 5697 | AUGCCCAAAACAAAGUGGCUAUA | 5698 |
| UUUGGGCAAUGAACUCAACAU | 5699 | AUGUUGAGUUCAUUGCCCAAAAC | 5700 |
| AACAGCUAUCGCCUCUUCCUU | 5701 | AAGGAAGAGGCGAUAGCUGUUGA | 5702 |
| GAACUACACUGGCAAUGUGGU | 5703 | ACCACAUUGCCAGUGUAGUUCCC | 5704 |
| CCUCCAGUAUCAUAACAACAU | 5705 | AUGUUGUUAUGAUACUGGAGGC | 5706 |
| AGCCUUCAGCACCAAGGACAU | 5707 | AUGUCCUUGGUGCUGAAGGCUGU | 5708 |
| AAGGACAAGGACAAUGACAAU | 5709 | AUUGUCAUUGUCCUUGUCCUUGG | 5710 |
| UGACAACUGCUUGGACAAGUU | 5711 | AACUUGUCCAAGCAGUUGUCAUU | 5712 |
| UGGACAAGUGUGCACAGCUCU | 5713 | AGAGCUGUGCACACUUGUCCAAG | 5714 |
| GCUCCGCAAAGGUGGCUACUU | 5715 | AAGUAGCCACCUUUGCGGAGCUG | 5716 |
| UGGCUACUGGUACAACUGCUU | 5717 | AAGCAGUUGUACCAGUAGCCACC | 5718 |

TABLE 8-continued

| Sense Sequence 5' to 3' | SEQ ID NO: | Antisense Sequence 5' to 3' | SEQ ID NO: |
|---|---|---|---|
| GCACAGACUCCAACCUCAAUU | 5719 | AAUUGAGGUUGGAGUCUGUGCAG | 5720 |
| AACCUCAAUGGAGUGUACUAU | 5721 | AUAGUACACUCCAUUGAGGUUGG | 5722 |
| ACUACCGCCUGGGUGAGCACU | 5723 | AGUGCUCACCCAGGCGGUAGUAC | 5724 |
| GGUGAGCACAAUAAGCACCUU | 5725 | AAGGUGCUUAUUGUGCUCACCCA | 5726 |
| UGGAUGGCAUCACCUGGUAUU | 5727 | AAUACCAGGUGAUGCCAUCCAGG | 5728 |
| ACCUGGUAUGGCUGGCAUGGU | 5729 | ACCAUGCCAGCCAUACCAGGUGA | 5730 |
| CUGGCAUGGAUCUACCUACUU | 5731 | AAGUAGGUAGAUCCAUGCCAGCC | 5732 |
| UACCUACUCCCUCAAACGGGU | 5733 | ACCCGUUUGAGGGAGUAGGUAGA | 5734 |
| ACGGGUGGAGAUGAAAAUCCU | 5735 | AGGAUUUUCAUCUCCACCCGUUU | 5736 |
| CCCAGAAGACUUCAAGCCUUU | 5737 | AAAGGCUUGAAGUCUUCUGGGCG | 5738 |
| UCAAGCCUUAAAAGGAGGCUU | 5739 | AAGCCUCCUUUUAAGGCUUGAAG | 5740 |
| AGCACGGAUACAGAAACUGAU | 5741 | AUCAGUUUCUGUAUCCGUGCUCC | 5742 |
| GAGACACGUGGAGACUGGAUU | 5743 | AAUCCAGUCUCCACGUGUCUCAG | 5744 |
| AGACUGGAUGAGGGCAGAUGU | 5745 | ACAUCUGCCCUCAUCCAGUCUCC | 5746 |
| GGCAGAUGAGGACAGGAAGAU | 5747 | AUCUUCCUGUCCUCAUCUGCCCU | 5748 |
| CAGGAAGAGAGUGUUAGAAAU | 5749 | AUUUCUAACACUCUCUUCCUGUC | 5750 |
| GAAAGGGUAGGACUGAGAAAU | 5751 | AUUUCUCAGUCCUACCCUUUCUA | 5752 |
| ACUGAGAAACAGCCUAUAAUU | 5753 | AAUUAUAGGCUGUUUCUCAGUCC | 5754 |
| UCUCCAAAGAAAGAAUAAGUU | 5755 | AACUUAUUCUUUCUUUGGAGAUU | 5756 |
| UAAGUCUCCAAGGAGCACAAU | 5757 | AUUGUGCUCCUUGGAGACUUAUU | 5758 |
| UCAUAUGUACCAAGGAUGUUU | 5759 | AAACAUCCUUGGUACAUAUGAUU | 5760 |
| AAGGAUGUUACAGUAAACAGU | 5761 | ACUGUUUACUGUAACAUCCUUGG | 5762 |
| ACAGGAUGAACUAUUUAAACU | 5763 | AGUUUAAAUAGUUCAUCCUGUUU | 5764 |
| AUUUAAACCCACUGGGUCCUU | 5765 | AAGGACCCAGUGGGUUUAAAUAG | 5766 |
| UGCCACAUCCUUCUCAAGGUU | 5767 | AACCUUGAGAAGGAUGUGGCAGG | 5768 |
| UCUCAAGGUGUAGACUGAGU | 5769 | ACUCAGUCUACCACCUUGAGAAG | 5770 |
| UCUCUCUGCCCAAGAUCCCUU | 5771 | AAGGGAUCUUGGGCAGAGAGACC | 5772 |
| UCCCUGACAUAGCAGUAGCUU | 5773 | AAGCUACUGCUAUGUCAGGGAUC | 5774 |
| GCAGUAGCUUGUCUUUUCCAU | 5775 | AUGGAAAAGACAAGCUACUGCUA | 5776 |
| UCUUUUCCACAUGAUUUGUCU | 5777 | AGACAAAUCAUGUGGAAAGACA | 5778 |
| AUUUGUCUGUGAAAGAAAAUU | 5779 | AAUUUUCUUUCACAGACAAAUCA | 5780 |
| AGAUCGUUUUAUCUAUUUUCU | 5781 | AGAAAAUAGAUAAAACGAUCUCA | 5782 |
| UCUACGGCUUAGGCUAUGUGU | 5783 | ACACAUAGCCUAAGCCGUAGAGA | 5784 |
| GUGAGGGCAAAACACAAAUCU | 5785 | AGAUUUGUGUUUUGCCCUCACAU | 5786 |
| ACACAAAUCCCUUUGCUAAAU | 5787 | AUUUAGCAAAGGGAUUUGUGUUU | 5788 |
| ACCAUAUUAUUUUGAUUCUCU | 5789 | AGAGAAUCAAAAUAAUAUGGUUC | 5790 |
| CUCAAAGGAUAGGCCUUUGAU | 5791 | AUCAAGGCCUAUCCUUUGAGAA | 5792 |
| GCCUUUGAGUGUUAGAGAAAU | 5793 | AUUUCUCUAACACUCAAAGGCCU | 5794 |

TABLE 8-continued

| Sense Sequence 5' to 3' | SEQ ID NO: | Antisense Sequence 5' to 3' | SEQ ID NO: |
|---|---|---|---|
| GAGAAAGGAGUGAAGGAGGCU | 5795 | AGCCUCCUUCACUCCUUUCUCUA | 5796 |
| AGGUGGGAAAUGGUAUUUCUU | 5797 | AAGAAAUACCAUUUCCCACCUGC | 5798 |
| CAGUGAAAUUAUCUUGAGUCU | 5799 | AGACUCAAGAUAAUUCACUGGA | 5800 |
| UUGAGUCUACACAUUAUUUUU | 5801 | AAAAAUAAUGUGUAGACUCAAGA | 5802 |
| AAUUGUUCGGCUGGAACUGAU | 5803 | AUCAGUUCCAGCCGAACAAUUUU | 5804 |
| UGACCCAGGCUGGACUUGCGU | 5805 | ACGCAAGUCCAGCCUGGGUCAGU | 5806 |
| GAGGAAACUCCAGGGCACUGU | 5807 | ACAGUGCCCUGGAGUUUCCUCCC | 5808 |
| GCACUGCAUCUGGCGAUCAGU | 5809 | ACUGAUCGCCAGAUGCAGUGCCC | 5810 |
| GCGAUCAGACUCUGAGCACUU | 5811 | AAGUGCUCAGAGUCUGAUCGCCA | 5812 |
| CGCCUUGGUCAUGUACAGCAU | 5813 | AUGCUGUACAUGACCAAGGCGAG | 5814 |
| CAGCACUGAAAGGAAUGAAGU | 5815 | ACUUCAUUCCUUUCAGUGCUGUA | 5816 |
| GGAAUGAAGCACCAGCAGGAU | 5817 | AUCCUGCUGGUGCUUCAUUCCUU | 5818 |
| CAGCAGGAGGUGGACAGAGUU | 5819 | AACUCUGUCCACCUCCUGCUGGU | 5820 |
| GGACAGAGUCUCUCAUGGAUU | 5821 | AAUCCAUGAGAGACUCUGUCCAC | 5822 |
| CUCAUGGAUGCCGGCACAAAU | 5823 | AUUUGUGCCGGCAUCCAUGAGAG | 5824 |
| GCACAAACUGCCUUAAAAUU | 5825 | AAUUUUAAGGCAGUUUGUGCCG | 5826 |
| UAGUUAUACAGGUAUAUCUU | 5827 | AAGAUAUACCUGUAUUAACUAUG | 5828 |
| CUUUGUAAGAAACAAGCUCAU | 5829 | AUGAGCUUGUUUCUUACAAAGUA | 5830 |
| GGAGCUUCCUUUUAAAUUUUU | 5831 | AAAAAUUUAAAAGGAAGCUCCUU | 5832 |
| CUGUAGGAAAUGGUUGAAAAU | 5833 | AUUUUCAACCAUUUCCUACAGAC | 5834 |
| GUUGAAACUGAAGGUAGAUU | 5835 | AAUCUACCUUCAGUUUUCAACCA | 5836 |
| AAGGUAGAUGGUGUUAUAGUU | 5837 | AACUAUAACACCAUCUACCUUCA | 5838 |
| GUAAAUAAGCAUCUCACUUUU | 5839 | AAAAGUGAGAUGCUUAUUUACAG | 5840 |
| UGGUUUUGUUUUAAACAUUCU | 5841 | AGAAUGUUUAAAACAAAACCACA | 5842 |
| AACAUUCAACGUUUCUUUUCU | 5843 | AGAAAAGAAACGUUGAAUGUUUA | 5844 |
| CUUUUCCUUCUACAAUAAACU | 5845 | AGUUUAUUGUAGAAGGAAAAGAA | 5846 |

The inhibitory nucleic acid molecules disclosed herein can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules disclosed herein can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:
Sense: mN*mN*/i2FN/mN/i2FN/mN/i2FN/mN/i2FN/mN/i2FN/mN/i2FN/mN/i2FN/mN/i2FN/*mN*/32FN/
Antisense: /52FN/*/i2FN/*mN/i2FN/mN/i2FN/mN/i2FN/mN/i2FN/mN/i2FN/mN/i2FN/mN/i2FN/mN*N*N
wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules disclosed herein. In some embodiments, the vectors comprise any one or more of the inhibitory nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules disclosed herein. In some embodiments, the composition is a pharmaceutical composition. In some embodiments, the compositions comprise a carrier and/or excipient. Examples of carriers include, but are not limited to, poly (lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the ANGPTL7 inhibitor comprises an anti-ANGPTL7 antibody. Antibodies that are specific to ANGPTL7 are described, for example, in U.S. Patent Application Publication Nos. US 2013/0022983 and US 2020/0399640, and in Comes et al., Genes Cells., 2011, 16, 243-259; Xu et al., FASEB J., 2020, 34, 13548-13560, and Kuchtey et al., Invest. Ophthalmol. Vis. Sci., 2008, 49, 3438-3448.

In some embodiments, the ANGPTL7 inhibitor comprises a nuclease agent that induces one or more nicks or double-strand breaks at a recognition sequence(s) or a DNA-binding protein that binds to a recognition sequence within an ANGPTL7 genomic nucleic acid molecule. The recognition sequence can be located within a coding region of the ANGPTL7 gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the ANGPTL7 gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify an ANGPTL7 genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of ANGPTL7 nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an ANGPTL7 genomic nucleic acid molecule or it can be a nickase that creates a single-strand break in an ANGPTL7 genomic nucleic acid molecule. Additional examples of Cas proteins include, but are not limited to, Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of an ANGPTL7 genomic nucleic acid molecules can be generated by contacting a cell with a Cas protein and one or more gRNAs that hybridize to one or more gRNA recognition sequences within a target genomic locus in the ANGPTL7 genomic nucleic acid molecule. For example, a gRNA recognition sequence can be located within a region of SEQ ID NO:1. The gRNA recognition sequence can also include or be proximate to a position corresponding to: position 4,291, position 4,287, position 4,243, position 4,325, or position 4,336 according to SEQ ID NO:1. For example, the gRNA recognition sequence can be located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 4,291, position 4,287, position 4,243, position 4,325, or position 4,336 according to SEQ ID NO:1. The gRNA recognition sequence can include or be proximate to the start codon of an ANGPTL7 genomic nucleic acid molecule or the stop codon of an ANGPTL7 genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in an ANGPTL7 genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an ANGPTL7 genomic nucleic acid molecule. An exemplary gRNA is a gRNA effective to direct a Cas enzyme to bind to or cleave an ANGPTL7 genomic nucleic acid molecule, wherein the gRNA comprises a DNA-targeting segment that hybridizes to a gRNA recognition sequence within the ANGPTL7 genomic nucleic acid molecule that includes or is proximate to a position corresponding to: position 4,291, position 4,287, position 4,243, position 4,325, or position 4,336 according to SEQ ID NO:1. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of a position corresponding to: position 4,291, position 4,287, position 4,243, position 4,325, or position 4,336 according to SEQ ID NO:1. Other exemplary gRNAs comprise a DNA-targeting segment that hybridizes to a gRNA recognition sequence present within an ANGPTL7 genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the ANGPTL7 reference gene are set forth in Tables 9-17 as SEQ ID NOs:25-165.

TABLE 9

Guide RNA Recognition Sequences Near ANGPTL7 Arg177Stop Variation

| Strand | Guide RNA Recognition Sequence | SEQ ID NO: |
|---|---|---|
| + | CTGCAGGGACAGGAACAGGTTGG | 25 |
| + | CAGAGTATCCCCTCTGCTTCAGG | 26 |
| + | GGCTCTGCAGGGACAGGAACAGG | 27 |
| + | GCTTCAGGTGTTCTGTGACATGG | 28 |
| + | TGCAGGGACAGGAACAGGTTGGG | 29 |
| + | TCTACTGGCTCTGCAGGGACAGG | 30 |
| − | CCTTCTACCGGGACTGGAAGCAG | 31 |
| − | CCGTGGGGACTTCTGGCTGGGGA | 32 |
| − | CCGGGACTGGAAGCAGTACAAGC | 33 |
| − | CCTTGTCTCCTTCTACCGGGACT | 34 |
| − | CCACCGGCTCTCCAGACAGCCAA | 35 |
| − | CCGGCTCTCCAGACAGCCAACCC | 36 |
| + | TGGAGACTTCAGGCGGAGGCTGG | 37 |
| + | TGTGACATGGAGACTTCAGGCGG | 38 |
| + | TTCTGTGACATGGAGACTTCAGG | 39 |
| + | GACATGGAGACTTCAGGCGGAGG | 40 |
| − | CCATGACTGGACCAGTGCCACCA | 41 |
| − | CCCGGCTGCGTGTAGAGATGGAG | 42 |
| − | CCGGCTGCGTGTAGAGATGGAGG | 43 |
| − | CCAACCCGGCTGCGTGTAGAGAT | 44 |
| − | CCAGGGGCCCCATGACTGGACCA | 45 |
| − | CCCCATGACTGGACCAGTGCCAC | 46 |

TABLE 10

Guide RNA Recognition Sequences Near ANGPTL7 Gln175His Variation

| Strand | Guide RNA Recognition Sequence | SEQ ID NO: |
|---|---|---|
| − | CTGCTTCCAGTCCCGGTAGAAGG | 47 |
| + | TTGTCTCCTTCTACCGGGACTGG | 48 |
| + | GCGGGAGTGCACACATCTACTGG | 49 |
| + | GGACTGGAAGCAGTACAAGCAGG | 50 |
| + | GACATGGAGACTTCAGGCGGAGG | 40 |
| + | GTGGCCTTGTCTCCTTCTACCGG | 51 |
| + | TGGAGACTTCAGGCGGAGGCTGG | 37 |
| − | TACTCTGGTGAGGGACTTGCAGG | 52 |
| − | ACTCTGGTGAGGGACTTGCAGGG | 53 |
| − | GCTTGTACTGCTTCCAGTCCCGG | 53 |
| − | AGTCCCGGTAGAAGGAGACAAGG | 55 |
| + | CACACATCTACTGGCTCTGCAGG | 56 |
| − | CAAGGCCACTTTTTCGTCTATGG | 57 |
| + | GACTGGAAGCAGTACAAGCAGGG | 58 |
| − | GCAGAGGGGATACTCTGGTGAGG | 59 |
| + | CAGAGTATCCCCTCTGCTTCAGG | 26 |
| + | TTCTGTGACATGGAGACTTCAGG | 39 |
| − | CTCTGGTGAGGGACTTGCAGGGG | 60 |
| − | CAGAGGGGATACTCTGGTGAGGG | 61 |
| − | ACTTTTTCGTCTATGGATGATGG | 62 |
| + | TGGCCTTGTCTCCTTCTACCGGG | 63 |
| + | AAGCAGTACAAGCAGGGCTTTGG | 64 |
| + | GCTTCAGGTGTTCTGTGACATGG | 28 |
| − | CTGAAGCAGAGGGGATACTCTGG | 65 |
| − | TCACAGAACACCTGAAGCAGAGG | 66 |
| + | ACACATCTACTGGCTCTGCAGGG | 67 |
| + | ATCATCCATAGACGAAAAAGTGG | 68 |
| + | TGTGACATGGAGACTTCAGGCGG | 38 |
| + | TCTACTGGCTCTGCAGGGACAGG | 30 |

TABLE 11

Guide RNA Recognition Sequences Near ANGPTL7 Arg220His Variation

| Strand | Guide RNA Recognition Sequence | SEQ ID NO: |
|---|---|---|
| + | ATGACCGCGTACAACTCCGGGGG | 69 |
| + | CATGACCGCGTACAACTCCGGGG | 70 |
| − | GGCACCCCCGGAGTTGTACGCGG | 71 |
| − | GAGTTGTACGCGGTCATGTGTGG | 72 |

TABLE 11-continued

Guide RNA Recognition Sequences Near ANGPTL7 Arg220His Variation

| Strand | Guide RNA Recognition Sequence | SEQ ID NO: |
|---|---|---|
| + | ACATGACCGCGTACAACTCCGGG | 73 |
| + | CACATGACCGCGTACAACTCCGG | 74 |
| − | TTGTACGCGGTCATGTGTGGTGG | 75 |
| + | TTGTCTCCTTCTACCGGGACTGG | 48 |
| − | CTGCTTCCAGTCCCGGTAGAAGG | 47 |
| + | TGGGGAACGAACACATCCACCGG | 76 |
| + | GGACTGGAAGCAGTACAAGCAGG | 50 |
| − | GGTGGCACTGGTCCAGTCATGGG | 77 |
| − | CAGAATAGGAATGGCACCCCCGG | 78 |
| − | GTGGCACTGGTCCAGTCATGGGG | 79 |
| − | GCGGTCATGTGTGGTGGCACTGG | 80 |
| − | TGGTGGCACTGGTCCAGTCATGG | 81 |
| + | GTGGCCTTGTCTCCTTCTACCGG | 51 |
| + | GCAGCATCCGTGGGGACTTCTGG | 82 |
| + | CATCCGTGGGGACTTCTGGCTGG | 83 |
| − | GCTTGTACTGCTTCCAGTCCCGG | 54 |
| − | AGTCCCGGTAGAAGGAGACAAGG | 55 |
| + | GGCTCTCCAGACAGCCAACCCGG | 84 |
| + | ATCCGTGGGGACTTCTGGCTGGG | 85 |
| + | GACTGGAAGCAGTACAAGCAGGG | 58 |
| − | TTGGCTGTCTGGAGAGCCGGTGG | 86 |
| − | TGGTCCAGTCATGGGGCCCCTGG | 86 |
| − | GATTTGTCTTGAATCAGAATAGG | 88 |
| + | AACCCGGCTGCATGTAGAGATGG | 89 |
| − | CTCCATCTCTACATGCAGCCGGG | 90 |
| + | TGGCCTTGTCTCCTTCTACCGGG | 63 |
| + | AAGCAGTACAAGCAGGGCTTTGG | 64 |
| + | TAGAGATGGAGGTAAGCACAAGG | 91 |
| + | TCCGTGGGGACTTCTGGCTGGGG | 92 |

TABLE 12

Guide RNA Recognition Sequences Near ANGPTL7 Arg220Cys Variation

| Strand | Guide RNA Recognition Sequence | SEQ ID NO: |
|---|---|---|
| + | ATGACCGCGTACAACTCCGGGGG | 69 |
| + | CATGACCGCGTACAACTCCGGGG | 70 |
| − | GGCACCCCCGGAGTTGTACGCGG | 71 |

TABLE 12-continued

Guide RNA Recognition Sequences Near ANGPTL7 Arg220Cys Variation

| Strand | Guide RNA Recognition Sequence | SEQ ID NO: |
|---|---|---|
| − | GAGTTGTACGCGGTCATGTGTGG | 72 |
| + | ACATGACCGCGTACAACTCCGGG | 73 |
| + | CACATGACCGCGTACAACTCCGG | 74 |
| − | TTGTACGCGGTCATGTGTGGTGG | 75 |
| + | TTGTCTCCTTCTACCGGGACTGG | 48 |
| − | CTGCTTCCAGTCCCGGTAGAAGG | 47 |
| + | TGGGGAACGAACACATCCACCGG | 76 |
| + | GGACTGGAAGCAGTACAAGCAGG | 50 |
| − | GGTGGCACTGGTCCAGTCATGGG | 77 |
| − | CAGAATAGGAATGGCACCCCCGG | 78 |
| − | GTGGCACTGGTCCAGTCATGGGG | 79 |
| − | GCGGTCATGTGTGGTGGCACTGG | 80 |
| − | TGGTGGCACTGGTCCAGTCATGG | 81 |
| + | CATCCGTGGGGACTTCTGGCTGG | 83 |
| + | GCAGCATCCGTGGGGACTTCTGG | 82 |
| + | GTGGCCTTGTCTCCTTCTACCGG | 51 |
| − | GCTTGTACTGCTTCCAGTCCCGG | 54 |
| + | GGCTCTCCAGACAGCCAACCCGG | 84 |
| − | AGTCCCGGTAGAAGGAGACAAGG | 55 |
| + | ATCCGTGGGGACTTCTGGCTGGG | 85 |
| + | GACTGGAAGCAGTACAAGCAGGG | 58 |
| − | TGGTCCAGTCATGGGGCCCCTGG | 87 |
| − | TTGGCTGTCTGGAGAGCCGGTGG | 86 |
| − | GATTTGTCTTGAATCAGAATAGG | 88 |
| − | ATCTCTACACACAGCCGGGTTGG | 93 |
| + | AAGCAGTACAAGCAGGGCTTTGG | 64 |
| + | TGGCCTTGTCTCCTTCTACCGGG | 63 |
| + | TAGAGATGGAGGTAAGCACAAGG | 91 |
| + | TCCGTGGGGACTTCTGGCTGGGG | 92 |
| + | AACCCGGCTGTGTGTAGAGATGG | 94 |
| − | CCTCCATCTCTACACACAGCCGG | 95 |

TABLE 13

Guide RNA Recognition Sequences Near ANGPTL7 Asn302Lys Variation

| Strand | Guide RNA Recognition Sequence | SEQ ID NO: |
|---|---|---|
| + | CAATGGAGTGTACTACCGCCTGG | 96 |
| + | AATGGAGTGTACTACCGCCTGGG | 97 |

TABLE 13-continued

Guide RNA Recognition Sequences Near ANGPTL7 Asn302Lys Variation

| Strand | Guide RNA Recognition Sequence | SEQ ID NO: |
|---|---|---|
| + | TACCTACTCCCTCAAACGGTGG | 98 |
| − | TTTCATCTCCACCCGTTTGAGGG | 99 |
| + | ACAGTCAACTTACTAGCACTGGG | 100 |
| − | TTTTCATCTCCACCCGTTTGAGG | 101 |
| + | GGGTGAGCACAATAAGCACCTGG | 102 |
| + | ATGGCATCACCTGGTATGGCTGG | 103 |
| − | CTCCACCCGTTTGAGGGAGTAGG | 104 |
| − | GGTGCTTATTGTGCTCACCCAGG | 105 |
| + | CTAACTCCTTACCTGATGTCTGG | 106 |
| + | CACAGTCAACTTACTAGCACTGG | 107 |
| − | CAGTTGTACCAGTAGCCACCTGG | 108 |
| − | GATAGACCAGACATCAGGTAAGG | 109 |
| − | TCAGGTAAGGAGTTAGAGCCAGG | 110 |
| + | GATCTACCTACTCCCTCAAACGG | 111 |
| − | AGATCCATGCCAGCCATACCAGG | 112 |
| − | GCTTATTGTGCTCACCCAGGCGG | 113 |
| − | CATACCAGGTGATGCCATCCAGG | 114 |
| + | ATCTACCTACTCCCTCAAACGGG | 115 |
| − | ACTGTGATAGACCAGACATCAGG | 116 |
| + | TTCTCATGCCAGGTGGCTACTGG | 117 |
| + | CTGGATGGCATCACCTGGTATGG | 118 |
| + | AGCACCTGGATGGCATCACCTGG | 119 |
| + | ATCACCTGGTATGGCTGGCATGG | 120 |
| − | GTAGTACACTCCATTGAGTTTGG | 121 |
| + | GAGCACAATAAGCACCTGGATGG | 122 |
| − | CAGGTAAGGAGTTAGAGCCAGGG | 123 |
| + | CTGGGTCTGTTTCTCATGCCAGG | 124 |
| + | TTTGGTATTCTTTCTGACCCTGG | 125 |
| − | GTCAGAAAGAATACCAAAACCGG | 126 |
| + | GGTCTGTTTCTCATGCCAGGTGG | 127 |

TABLE 14

Guide RNA Recognition Sequences Near ANGPTL7 Arg340His Variation

| Strand | Guide RNA Recognition Sequence | SEQ ID NO: |
|---|---|---|
| + | CAATGGAGTGTACTACCGCCTGG | 96 |
| + | AATGGAGTGTACTACCGCCTGGG | 97 |

TABLE 14-continued

Guide RNA Recognition Sequences
Near ANGPTL7 Arg340His Variation

| Strand | Guide RNA Recognition Sequence | SEQ ID NO: |
|---|---|---|
| − | GGCGGTAGTACACTCCATTGAGG | 128 |
| + | TACCTACTCCCTCAAACGGGTGG | 98 |
| − | GTAGTACACTCCATTGAGGTTGG | 129 |
| − | TTTCATCTCCACCCGTTTGAGGG | 99 |
| − | TTTTCATCTCCACCCGTTTGAGG | 101 |
| + | GGGTGAGCACAATAAGCACCTGG | 102 |
| + | ATGGCATCACCTGGTATGGCTGG | 103 |
| − | GGTGCTTATTGTGCTCACCCAGG | 105 |
| − | CTCCACCCGTTTGAGGGAGTAGG | 104 |
| − | GTTTCTGTATCCGTGCTCCACGG | 130 |
| + | AAACTGAGACACGTGGAGACTGG | 131 |
| − | GCTTATTGTGCTCACCCAGGCGG | 113 |
| + | GATCTACCTACTCCCTCAAACGG | 111 |
| − | AGATCCATGCCAGCCATACCAGG | 112 |
| + | GCCTTAAAAGGAGGCTGCCGTGG | 132 |
| − | CATACCAGGTGATGCCATCCAGG | 114 |
| + | ATCTACCTACTCCCTCAAACGGG | 115 |
| + | GACACGTGGAGACTGGATGAGGG | 133 |
| − | TCCACGGCAGCCTCCTTTTAAGG | 134 |
| + | CTGGATGGCATCACCTGGTATGG | 118 |
| + | AGCACCTGGATGGCATCACCTGG | 119 |
| + | ATCACCTGGTATGGCTGGCATGG | 120 |
| + | TGCACAGACTCCAACCTCAATGG | 135 |
| + | GAGCACAATAAGCACCTGGATGG | 122 |
| + | AGACACGTGGAGACTGGATGAGG | 136 |
| + | AGACTTCAAGCCTTAAAAGGAGG | 137 |
| − | TTTAAGGCTTGAAGTCTTCTGGG | 138 |
| − | AAGGCTTGAAGTCTTCTGGGTGG | 139 |
| − | TTTTAAGGCTTGAAGTCTTCTGG | 140 |
| + | GATACAGAAACTGAGACACGTGG | 141 |
| + | AAGGAGGCTGCCGTGGAGCACGG | 142 |
| + | AGAAGACTTCAAGCCTTAAAAGG | 143 |

TABLE 15

Guide RNA Recognition Sequences
Near ANGPTL7 Phe161Ile Variation

| Strand | Guide RNA Recognition Sequence | SEQ ID NO: |
|---|---|---|
| − | ACAGAACACCTGAAGCAGAGGGG | 144 |
| − | ACAGAACACCTGAAGCAGAGGGG | 145 |
| − | CACAGAACACCTGAAGCAGAGGG | 146 |
| + | CAGAGTATCCCCTCTGCTTCAGG | 147 |
| − | ACTCTGGTGAGGGACTTGCAGGG | 148 |
| − | TACTCTGGTGAGGGACTTGCAGG | 149 |
| − | GCAGAGGGGATACTCTGGTGAGG | 150 |
| + | GCTTCAGGTGTTCTGTGACATGG | 151 |
| − | CAGAGGGGATACTCTGGTGAGGG | 152 |

TABLE 16

Guide RNA Recognition Sequences
Near ANGPTL7 Trp188STOP Variation

| Strand | Guide RNA Recognition Sequence | SEQ ID NO: |
|---|---|---|
| + | TTGTCTCCTTCTACCGGGACTGG | 153 |
| + | GTGGCCTTGTCTCCTTCTACCGG | 154 |
| + | TGGCCTTGTCTCCTTCTACCGGG | 155 |
| + | GACTGGAAGCAGTACAAGCAGGG | 156 |
| + | GGACTGGAAGCAGTACAAGCAGG | 157 |
| − | CTGCTTCCAGTCCCGGTAGAAGG | 158 |
| − | GCTTGTACTGCTTCCAGTCCCGG | 159 |
| − | AGTCCCGGTAGAAGGAGACAAGG | 160 |

TABLE 17

Guide RNA Recognition Sequences
Near ANGPTL7 Lys192Gln Variation

| Strand | Guide RNA Recognition Sequence | SEQ ID NO: |
|---|---|---|
| + | GACTGGAAGCAGTACAAGCAGGG | 156 |
| + | GGACTGGAAGCAGTACAAGCAGG | 157 |
| − | GGACTGGAAGCAGTACAAGC | 159 |
| + | AAGCAGTACAAGCAGGGCTTTGG | 161 |
| + | CAGGGCTTTGGCAGCATCCGTGG | 162 |
| + | AGGGCTTTGGCAGCATCCGTGGG | 163 |
| + | GGGCTTTGGCAGCATCCGTGGGG | 164 |
| − | TCCCCAGCCAGAAGTCCCCACGG | 165 |

The Cas protein and the gRNA form a complex, and the Cas protein cleaves the target ANGPTL7 genomic nucleic acid molecule. The Cas protein can cleave the nucleic acid molecule at a site within or outside of the nucleic acid sequence present in the target ANGPTL7 genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the ANGPTL7 genomic nucleic acid molecule to which a DNA-targeting segment of a gRNA will bind.

Such methods can result, for example, in an ANGPTL7 genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the ANGPTL7 genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

In any of the embodiments described herein, the subject can also be treated with a therapeutic agent that treats or inhibits an ophthalmic condition. Such therapeutic agents include, but are not limited to, a prostaglandin, a beta blocker, an alpha-adrenergic agonist, a carbonic anhydrase inhibitor, a rho kinase inhibitor, or a miotic or cholinergic agent. In some embodiments, the therapeutic agent that treats or inhibits the ophthalmic condition is a prostaglandin. In some embodiments, the prostaglandin is XALATAN® (latanoprost), TRAVATAN Z® (travoprost), ZIOPTAN® (tafluprost), LUMIGAN® (bimatoprost), or VYZULTA® (latanoprostene bunod). In some embodiments, the prostaglandin is latanoprost, travoprost, tafluprost, bimatoprost, or latanoprostene bunod. In some embodiments, the therapeutic agent that treats or inhibits the ophthalmic condition is a beta blocker. In some embodiments, the beta blocker is BETIMOL®, ISTALOL®, or TIMOPTIC® (timolol) or BETOPTIC® (betaxolol). In some embodiments, the beta blocker is timolol or betaxolol. In some embodiments, the therapeutic agent that treats or inhibits the ophthalmic condition is an alpha-adrenergic agonist. In some embodiments, the alpha-adrenergic agonist is IOPIDINE® (apraclonidine) or ALPHAGAN® or QOLIANA® (brimonidine). In some embodiments, the alpha-adrenergic agonist is apraclonidine or brimonidine. In some embodiments, the therapeutic agent that treats or inhibits the ophthalmic condition is a carbonic anhydrase inhibitor. In some embodiments, the carbonic anhydrase inhibitor is TRUSOPT® (dorzolamide) or AZOPT® (brinzolamide). In some embodiments, the carbonic anhydrase inhibitor is dorzolamide or brinzolamide. In some embodiments, the therapeutic agent that treats or inhibits the ophthalmic condition is a rho kinase inhibitor. In some embodiments, the rho kinase inhibitor is RHOPRESSA® (netarsudil). In some embodiments, the rho kinase inhibitor is netarsudil. In some embodiments, the therapeutic agent that treats or inhibits the ophthalmic condition is a miotic or cholinergic agent. In some embodiments, the miotic or cholinergic agent is ISOPTO® Carpine (pilocarpine). In some embodiments, the miotic or cholinergic agent is pilocarpine.

In some embodiments, the methods of treatment further comprise detecting the presence or absence of an ANGPTL7 predicted loss-of-function variant nucleic acid molecule encoding an ANGPTL7 polypeptide in a biological sample from the subject. As used throughout the present disclosure, "an ANGPTL7 predicted loss-of-function variant nucleic acid molecule" is any ANGPTL7 nucleic acid molecule (such as, for example, genomic nucleic acid molecule, mRNA molecule, or cDNA molecule) encoding an ANGPTL7 polypeptide having a partial loss-of-function, a complete loss-of-function, a predicted partial loss-of-function, or a predicted complete loss-of-function.

The present disclosure also provides methods of treating a subject undergoing glucocorticoid treatment. In some embodiments, the subject is suffering from inflammation. In some embodiments, the methods comprise determining whether the subject has an ANGPTL7 predicted loss-of-function variant nucleic acid molecule encoding an ANGPTL7 polypeptide. In some embodiments, the determining step comprises obtaining or having obtained a biological sample from the subject, and performing or having performed a sequence analysis on the biological sample to determine if the subject has a genotype comprising the ANGPTL7 predicted loss-of-function variant nucleic acid molecule. In some embodiments, the methods comprise administering or continuing to administer to a subject that is ANGPTL7 reference the glucocorticoid in a standard dosage amount, and administering an ANGPTL7 inhibitor to the subject. In some embodiments, the methods comprise administering or continuing to administer to a subject that is heterozygous for the ANGPTL7 predicted loss-of-function variant the glucocorticoid in an amount that is the same as or higher than a standard dosage amount, and administering an ANGPTL7 inhibitor to the subject. In some embodiments, the methods comprise administering or continuing to administer to a subject that is homozygous for the ANGPTL7 predicted loss-of-function variant the glucocorticoid in an amount that is the same as or higher than a standard dosage amount. The presence of a genotype having the ANGPTL7 predicted loss-of-function variant nucleic acid molecule encoding the ANGPTL7 polypeptide indicates the subject has a decreased risk of developing a glucocorticoid-induced ophthalmic condition. In some embodiments, the subject is ANGPTL7 reference. In some embodiments, the subject is heterozygous for the ANGPTL7 predicted loss-of-function variant.

In some embodiments, the subject is ANGPTL7 reference, and the subject is administered or continued to be administered the glucocorticoid in a standard dosage amount, and is administered an ANGPTL7 inhibitor. In some embodiments, the subject is heterozygous for an ANGPTL7 predicted loss-of-function variant, and the subject is administered or continued to be administered the glucocorticoid in an amount that is the same as or higher than a standard dosage amount, and is administered an ANGPTL7 inhibitor. In some embodiments, the subject is homozygous for an ANGPTL7 predicted loss-of-function variant, and the subject is administered or continued to be administered the glucocorticoid in an amount that is the same as or higher than a standard dosage amount.

Detecting the presence or absence of an ANGPTL7 predicted loss-of-function variant nucleic acid molecule in a biological sample from a subject and/or determining whether a subject has an ANGPTL7 predicted loss-of-function variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

The present disclosure also provides methods of treating a subject undergoing glucocorticoid treatment. In some embodiments, the subject is suffering from inflammation. In some embodiments, the methods comprise determining whether the subject has an ANGPTL7 predicted loss-of-function variant polypeptide. In some embodiments, the determining step comprises obtaining or having obtained a biological sample from the subject, and performing or having performed an assay on the biological sample to determine if the subject has an ANGPTL7 predicted loss-of-function variant polypeptide. In some embodiments, the methods comprise administering or continuing to administer to a subject that does not have an ANGPTL7 predicted loss-of-function variant polypeptide the glucocorticoid in a standard dosage amount, and administering an ANGPTL7 inhibitor to the subject. In some embodiments, the methods comprise administering or continuing to administer to a subject that has the ANGPTL7 predicted loss-of-function variant polypeptide the glucocorticoid in an amount that is the same as or higher than a standard dosage amount. The presence of an ANGPTL7 predicted loss-of-function variant polypeptide indicates the subject does not have an increased risk of developing a glucocorticoid-induced ophthalmic condition. In some embodiments, the subject has an ANGPTL7 predicted loss-of-function variant polypeptide. In some embodiments, the subject does not have an ANGPTL7 predicted loss-of-function variant polypeptide.

Detecting the presence or absence of an ANGPTL7 predicted loss-of-function polypeptide in a biological sample from a subject and/or determining whether a subject has an ANGPTL7 predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the subject.

In some embodiments, the dose of the glucocorticoids can be increased by about 10%, by about 20%, by about 30%, by about 40%, by about 50%, by about 60%, by about 70%, by about 80%, or by about 90% for subjects that are heterozygous or homozygous for an ANGPTL7 predicted loss-of-function variant (i.e., a higher than the standard dosage amount) compared to subjects that are ANGPTL7 reference (who may receive a standard dosage amount). In some embodiments, the dose of the glucocorticoids can be increased by about 10%, by about 20%, by about 30%, by about 40%, or by about 50%. In addition, the dose of glucocorticoids in subjects that are heterozygous or homozygous for an ANGPTL7 predicted loss-of-function variant can be administered more frequently compared to subjects that are ANGPTL7 reference.

Administration of the glucocorticoids and/or ANGPTL7 inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the glucocorticoids and/or ANGPTL7 inhibitors can occur by any suitable route including, but not limited to, parenteral, intravenous, oral, subcutaneous, intraarterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

Administration of the glucocorticoids and/or ANGPTL7 inhibitors can be administered in a single dosage form or as separate dosage forms. When administered as separate dosage forms, the glucocorticoids can be administered concurrently with or sequentially to ANGPTL7 inhibitors. In some embodiments, the glucocorticoids and ANGPTL7 inhibitors are administered concurrently. In some embodiments, the glucocorticoids and ANGPTL7 inhibitors are administered sequentially. For example, in some embodiments, the glucocorticoids can be administered prior to the ANGPTL7 inhibitors. In some embodiments, the ANGPTL7 inhibitors are administered prior to the glucocorticoids.

The terms "treat", "treating", and "treatment" and "prevent", "preventing", and "prevention" as used herein referring to inflammation, refer to eliciting the desired biological response, such as a therapeutic and prophylactic effect, respectively. In some embodiments, a therapeutic effect comprises one or more of a decrease/reduction in inflammation, a decrease/reduction in the severity of inflammation (such as, for example, a reduction or inhibition of development of inflammation), a decrease/reduction in symptoms and inflammation-related effects, delaying the onset of symptoms and inflammation-related effects, reducing the severity of symptoms of inflammation-related effects, reducing the severity of an acute episode, reducing the number of symptoms and inflammation-related effects, reducing the latency of symptoms and inflammation-related effects, an amelioration of symptoms and inflammation-related effects, reducing secondary symptoms, reducing secondary infections, preventing relapse to inflammation, decreasing the number or frequency of relapse episodes, increasing latency between symptomatic episodes, increasing time to sustained progression, speeding recovery, and/or increasing efficacy of or decreasing resistance to alternative therapeutics, following administration of the glucocorticoid or composition comprising the glucocorticoid. A prophylactic effect may comprise a complete or partial avoidance/inhibition or a delay of inflammation development/progression (such as, for example, a complete or partial avoidance/inhibition or a delay) following administration of a therapeutic protocol. Treatment of inflammation encompasses the treatment of subjects already diagnosed as having any form of inflammation at any clinical stage or manifestation, the delay of the onset or evolution or aggravation or deterioration of the symptoms or signs of inflammation, and/or preventing and/or reducing the severity of inflammation.

The terms "treat", "treating", and "treatment" and "prevent", "preventing", and "prevention" as used herein referring to glucocorticoid-induced ophthalmic conditions, refer to eliciting the desired biological response, such as a therapeutic and prophylactic effect, respectively. In some embodiments, a therapeutic effect comprises one or more of a decrease/reduction in a glucocorticoid-induced ophthalmic condition, a decrease/reduction in the severity of a glucocorticoid-induced ophthalmic condition (such as, for example, a reduction or inhibition of development of a glucocorticoid-induced ophthalmic condition), a decrease/reduction in symptoms and a glucocorticoid-induced ophthalmic condition-related effects, delaying the onset of symptoms and a glucocorticoid-induced ophthalmic condition-related effects, reducing the severity of symptoms of a glucocorticoid-induced ophthalmic condition-related effects, reducing the severity of an acute episode, reducing the number of symptoms and a glucocorticoid-induced ophthalmic condition-related effects, reducing the latency of symptoms and a glucocorticoid-induced ophthalmic condition-related effects, an amelioration of symptoms and a glucocorticoid-induced ophthalmic condition-related effects, reducing secondary symptoms, preventing relapse to a glucocorticoid-induced ophthalmic condition, decreasing the number or frequency of relapse episodes, increasing latency between symptomatic episodes, increasing time to sustained progression, speeding recovery, and/or increasing efficacy of or decreasing resistance to alternative therapeutics, following administration of the ANGPTL7 inhibitor or composition comprising the ANGPTL7 inhibitor. A prophylactic effect may comprise a complete or partial avoidance/inhibition or a delay of a glucocorticoid-induced ophthalmic condition development/progression (such as, for example, a complete or partial avoidance/inhibition or a delay) following administration of an ANGPTL7 inhibitor. Treatment of a glucocorticoid-induced ophthalmic condition encompasses the treatment of subjects already diagnosed as having any form of a glucocorticoid-induced ophthalmic condition at any clinical stage or manifestation, the delay of the onset or evolution or aggravation or deterioration of the symptoms or signs of a glucocorticoid-induced ophthalmic condition, and/or preventing and/or reducing the severity of a glucocorticoid-induced ophthalmic condition.

The present disclosure also provides methods of identifying a subject undergoing glucocorticoid treatment having an increased risk for developing a glucocorticoid-induced ophthalmic condition. In some embodiments, the methods comprise determining or having determined the presence or absence of an ANGPTL7 predicted loss-of-function variant nucleic acid molecule encoding an ANGPTL7 polypeptide in a biological sample obtained from the subject. When the subject is ANGPTL7 reference, then the subject has an increased risk for developing the glucocorticoid-induced ophthalmic condition. When the subject is heterozygous or homozygous for an ANGPTL7 predicted loss-of-function variant, then the subject does not have an increased risk for developing the glucocorticoid-induced ophthalmic condition.

Having a single copy of an ANGPTL7 predicted loss-of-function variant nucleic acid molecule is more protective of a subject undergoing glucocorticoid treatment from developing a glucocorticoid-induced ophthalmic condition than having no copies of an ANGPTL7 predicted loss-of-function variant nucleic acid molecule. Without intending to be limited to any particular theory or mechanism of action, it is believed that a single copy of an ANGPTL7 predicted loss-of-function variant nucleic acid molecule (i.e., heterozygous for an ANGPTL7 predicted loss-of-function variant) is protective of a subject undergoing glucocorticoid treatment from developing a glucocorticoid-induced ophthalmic condition, and it is also believed that having two copies of an ANGPTL7 predicted loss-of-function variant nucleic acid molecule (i.e., homozygous for an ANGPTL7 predicted loss-of-function variant nucleic acid molecule) may be more protective of a subject undergoing glucocorticoid treatment from developing a glucocorticoid-induced ophthalmic condition, relative to a subject with a single copy. Thus, in some embodiments, a single copy of an ANGPTL7 predicted loss-of-function variant nucleic acid molecule may not be completely protective, but instead, may be partially or incompletely protective of a subject undergoing glucocorticoid treatment from developing a glucocorticoid-induced ophthalmic condition. While not desiring to be bound by any particular theory, there may be additional factors or molecules involved in the development of a glucocorticoid-induced ophthalmic condition that are still present in a subject having a single copy of an ANGPTL7 predicted loss-of-function variant nucleic acid molecule, thus resulting in less than complete protection from the development of a glucocorticoid-induced ophthalmic condition.

In some embodiments, the subject can have inflammation. In some embodiments, the inflammation can be acute inflammation or chronic inflammation. In some embodiments, the inflammation is acute inflammation. In some embodiments, the inflammation is chronic inflammation. In some embodiments, the inflammation is associated with rheumatoid arthritis, associated with Grave's disease, or is ophthalmic inflammation. In some embodiments, the inflammation is associated with rheumatoid arthritis. In some embodiments, the inflammation is associated with Grave's disease. In some embodiments, the inflammation is ophthalmic inflammation. In some embodiments, the ophthalmic inflammation is chosen from uveitis, juvenile idiopathic arthritis uveitis, scleritis, blepharitis, conjunctivitis, iritis, and episcleritis, or any combination thereof. In some embodiments, the ophthalmic inflammation is uveitis. In some embodiments, the ophthalmic inflammation is juvenile idiopathic arthritis uveitis. In some embodiments, the ophthalmic inflammation is scleritis. In some embodiments, the ophthalmic inflammation is blepharitis. In some embodiments, the ophthalmic inflammation is conjunctivitis. In some embodiments, the ophthalmic inflammation is iritis. In some embodiments, the ophthalmic inflammation is episcleritis.

In some embodiments, the glucocorticoid-induced ophthalmic condition is chosen from ocular hypertension, increased intraocular pressure (IOP), pre-glaucoma, glaucoma, decreased corneal hysteresis, and posterior subcapsular cataracts, or any combination thereof. In some embodiments, the glucocorticoid-induced ophthalmic condition is ocular hypertension. In some embodiments, the glucocorticoid-induced ophthalmic condition is increased IOP. In some embodiments, the glucocorticoid-induced ophthalmic condition is pre-glaucoma. In some embodiments, the glucocorticoid-induced ophthalmic condition is glaucoma. In some embodiments, the glucocorticoid-induced ophthalmic condition is decreased corneal hysteresis. In some embodiments, the glucocorticoid-induced ophthalmic condition is posterior subcapsular cataracts.

In some embodiments, the glucocorticoid treatment is treatment with prednisone, prednisolone, methylprednisolone, dexamethasone, betamethasone, triamcinolone, beclometasone, fludrocortisone acetate, DOCA, aldosterone, budesonide, mometasone furoate, fluticasone propionate, hydrocortisone, cortisone acetate, or fluticasone furoate, difluprednate ophthalmic, fluorometholone, loteprednol etabonate, medrysone, rimexolone, fluocinolone acetonide, clobetasol, halobetasol, diflorasone, fluocinonide, flurandrenolide, Neo-Poly-Dex, tobramycin-dexamethasone, difluprednate, or any combination thereof. In some embodiments, the glucocorticoid treatment is treatment with prednisone. In some embodiments, the glucocorticoid treatment is treatment with prednisolone. In some embodiments, the glucocorticoid treatment is treatment with methylprednisolone. In some embodiments, the glucocorticoid treatment is treatment with dexamethasone. In some embodiments, the glucocorticoid treatment is treatment with betamethasone. In some embodiments, the glucocorticoid treatment is treatment with triamcinolone. In some embodiments, the glucocorticoid treatment is treatment with beclomethasone. In some embodiments, the glucocorticoid treatment is treatment with fludrocortisone acetate. In some embodiments, the glucocorticoid treatment is treatment with DOCA. In some embodiments, the glucocorticoid treatment is treatment with aldosterone. In some embodiments, the glucocorticoid treatment is treatment with budesonide. In some embodiments, the glucocorticoid treatment is treatment with mometasone furoate. In some embodiments, the glucocorticoid treatment is treatment with fluticasone propionate. In some embodiments, the glucocorticoid treatment is treatment with hydrocortisone. In some embodiments, the glucocorticoid treatment is treatment with cortisone acetate. In some embodiments, the glucocorticoid treatment is treatment with fluticasone furoate. In some embodiments, the glucocorticoid treatment is treatment with difluprednate ophthalmic. In some embodiments, the glucocorticoid treatment is treatment with fluorometholone. In some embodiments, the glucocorticoid treatment is treatment with loteprednol etabonate. In some embodiments, the glucocorticoid treatment is treatment with medrysone. In some embodiments, the glucocorticoid treatment is treatment with rimexolone. In some embodiments, the glucocorticoid treatment is treatment with fluocinolone acetonide. In some embodiments, the glucocorticoid treatment is treatment with clobetasol. In some embodiments, the glucocorticoid treatment is treatment with halobetasol. In some embodiments, the glucocorticoid treatment is treatment with diflorasone. In some embodiments, the glucocorticoid treatment is treatment with fluocinonide. In some embodiments, the glucocorticoid treatment is treatment with flurandrenolide. In some embodiments, the glucocorticoid treatment is treatment with Neo-Poly-Dex. In some embodiments, the glucocorticoid treatment is treatment with tobramycin-dexamethasone. In some embodiments, the glucocorticoid treatment is treatment with difluprednate.

Determining whether a subject has an ANGPTL7 predicted loss-of-function variant nucleic acid molecule in a biological sample from the subject and/or determining whether a subject has an ANGPTL7 predicted loss-of-function variant nucleic acid molecule can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing a glucocorticoid-induced ophthalmic condition, the subject is further treated with an ANGPTL7 inhibitor, as described herein. For example, when the subject is ANGPTL7 reference, and therefore has an increased risk for developing a glucocorticoid-induced ophthalmic condition, the subject is administered an ANGPTL7 inhibitor. In some embodiments, when the subject is heterozygous for an ANGPTL7 predicted loss-of-function variant nucleic acid molecule, the subject is administered an ANGPTL7 inhibitor. In some embodiments, the subject is ANGPTL7 reference. In some embodiments, the subject is heterozygous for an ANGPTL7 predicted loss-of-function variant.

The present disclosure also provides methods of detecting the presence or absence of an ANGPTL7 predicted loss-of-function variant genomic nucleic acid molecule in a biological sample from a subject, and/or an ANGPTL7 predicted loss-of-function variant mRNA molecule in a biological sample from a subject, and/or an ANGPTL7 predicted loss-of-function variant cDNA molecule produced from an mRNA molecule in a biological sample from a subject. It is understood that gene sequences within a population and mRNA molecules encoded by such genes can vary due to polymorphisms such as single-nucleotide polymorphisms. The sequences provided herein for the ANGPTL7 variant genomic nucleic acid molecule, ANGPTL7 variant mRNA molecule, and ANGPTL7 variant cDNA molecule are only exemplary sequences. Other sequences for the ANGPTL7 variant genomic nucleic acid molecule, variant mRNA molecule, and variant cDNA molecule are also possible.

The biological sample can be derived from any cell, tissue, or biological fluid from the subject. The biological sample may comprise any clinically relevant tissue such as, for example, a bone marrow sample, a tumor biopsy, a fine needle aspirate, or a sample of bodily fluid, such as blood, gingival crevicular fluid, plasma, serum, lymph, ascitic fluid, cystic fluid, or urine. In some embodiments, the sample comprises a buccal swab. The biological sample used in the methods disclosed herein can vary based on the assay format, nature of the detection method, and the tissues, cells, or extracts that are used as the sample. A biological sample can be processed differently depending on the assay being employed. For example, when detecting any ANGPTL7 variant nucleic acid molecule, preliminary processing designed to isolate or enrich the biological sample for the ANGPTL7 variant nucleic acid molecule can be employed. A variety of techniques may be used for this purpose. When detecting the level of any ANGPTL7 variant mRNA molecule, different techniques can be used enrich the biological sample with mRNA molecules. Various methods to detect the presence or level of an mRNA molecule or the presence of a particular variant genomic DNA locus can be used.

In some embodiments, detecting an ANGPTL7 predicted loss-of-function variant nucleic acid molecule in a subject comprises assaying or analyzing a biological sample obtained from the subject to determine whether an ANGPTL7 genomic nucleic acid molecule in the biological sample, an ANGPTL7 mRNA molecule in the biological sample, and/or an ANGPTL7 cDNA molecule produced from an mRNA molecule in the biological sample, comprises one or more variations that cause a loss-of-function (partial or complete) or are predicted to cause a loss-of-function (partial or complete).

In some embodiments, the methods of detecting the presence or absence of an ANGPTL7 predicted loss-of-function variant nucleic acid molecule (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the nucleotide sequence comprises: a thymine at a position corresponding to position 4,291 according to SEQ ID NO:2 (for genomic nucleic acid molecules); a uracil at a position corresponding to position 529 according to SEQ ID NO:8 (for mRNA molecules); or a thymine at a position corresponding to position 529 according to SEQ ID NO:14 (for cDNA molecules obtained from mRNA molecules).

In some embodiments, the nucleotide sequence comprises: a thymine at a position corresponding to position 4,287 according to SEQ ID NO:3 (for genomic nucleic acid molecules); a uracil at a position corresponding to position 525 according to SEQ ID NO:9 (for mRNA molecules); or a thymine at a position corresponding to position 525 according to SEQ ID NO:15 (for cDNA molecules obtained from mRNA molecules).

In some embodiments, the nucleotide sequence comprises: an adenine at a position corresponding to position 4,243 according to SEQ ID NO:4 (for genomic nucleic acid molecules); an adenine at a position corresponding to position 481 according to SEQ ID NO:10 (for mRNA molecules); or an adenine at a position corresponding to position 481 according to SEQ ID NO:16 (for cDNA molecules obtained from mRNA molecules).

In some embodiments, the nucleotide sequence comprises: an adenine at a position corresponding to position 4,325 according to SEQ ID NO:5 (for genomic nucleic acid molecules); an adenine at a position corresponding to position 563 according to SEQ ID NO:11 (for mRNA molecules); or an adenine at a position corresponding to position 563 according to SEQ ID NO:17 (for cDNA molecules obtained from mRNA molecules).

In some embodiments, the nucleotide sequence comprises: a cytosine at a position corresponding to position 4,336 according to SEQ ID NO:6 (for genomic nucleic acid molecules); a cytosine at a position corresponding to position 574 according to SEQ ID NO:12 (for mRNA molecules); or a cytosine at a position corresponding to position 574 according to SEQ ID NO:18 (for cDNA molecules obtained from mRNA molecules).

In some embodiments, the nucleotide sequence comprises: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof.

In some embodiments, the nucleotide sequence comprises: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof.

In some embodiments, the nucleotide sequence comprises: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof.

In some embodiments, the biological sample comprises a cell or cell lysate. Such methods can further comprise, for example, obtaining a biological sample from the subject comprising an ANGPTL7 genomic nucleic acid molecule or mRNA molecule, and if mRNA, optionally reverse transcribing the mRNA into cDNA. Such assays can comprise, for example determining the identity of these positions of the particular ANGPTL7 nucleic acid molecule. In some embodiments, the method is an in vitro method.

In some embodiments, the determining step, detecting step, or sequence analysis comprises sequencing at least a portion of the nucleotide sequence of the ANGPTL7 genomic nucleic acid molecule, the ANGPTL7 mRNA molecule, or the ANGPTL7 cDNA molecule produced from the mRNA molecule in the biological sample, wherein the sequenced portion comprises one or more variations that cause a loss-of-function (partial or complete) or are predicted to cause a loss-of-function (partial or complete).

In some embodiments, the determining step, detecting step, or sequence analysis comprises sequencing at least a portion of: the nucleotide sequence of the ANGPTL7 genomic nucleic acid molecule in the biological sample, wherein the sequenced portion comprises a position corresponding to position 4,291 according to SEQ ID NO:2, or the complement thereof; the nucleotide sequence of the ANGPTL7 mRNA molecule in the biological sample, wherein the sequenced portion comprises a position corresponding to position 529 according to SEQ ID NO:8, or the complement thereof; and/or the nucleotide sequence of the ANGPTL7 cDNA molecule produced from the mRNA in the biological sample, wherein the sequenced portion comprises a position corresponding to position 529 according to SEQ ID NO:14, or the complement thereof. When the sequenced portion of the ANGPTL7 nucleic acid molecule in the biological sample comprises: a thymine at a position corresponding to position 4,291 according to SEQ ID NO:2, a uracil at a position corresponding to position 529 according to SEQ ID NO:8, or a thymine at a position corresponding to position 529 according to SEQ ID NO:14, then the ANGPTL7 nucleic acid molecule in the biological sample is an ANGPTL7 predicted loss-of-function variant nucleic acid molecule.

In some embodiments, the determining step, detecting step, or sequence analysis comprises sequencing at least a portion of: the nucleotide sequence of the ANGPTL7 genomic nucleic acid molecule in the biological sample, wherein the sequenced portion comprises a position corresponding to position 4,287 according to SEQ ID NO:3, or the complement thereof; the nucleotide sequence of the ANGPTL7 mRNA molecule in the biological sample, wherein the sequenced portion comprises a position corresponding to position 525 according to SEQ ID NO:9, or the complement thereof; and/or the nucleotide sequence of the ANGPTL7 cDNA molecule produced from the mRNA in the biological sample, wherein the sequenced portion comprises a position corresponding to position 525 according to SEQ ID NO:15, or the complement thereof. When the sequenced portion of the ANGPTL7 nucleic acid molecule in the biological sample comprises: a thymine at a position corresponding to position 4,287 according to SEQ ID NO:3, a uracil at a position corresponding to position 525 according to SEQ ID NO:9, or a thymine at a position corresponding to position 525 according to SEQ ID NO:15, then the ANGPTL7 nucleic acid molecule in the biological sample is an ANGPTL7 predicted loss-of-function variant nucleic acid molecule.

In some embodiments, the determining step, detecting step, or sequence analysis comprises sequencing at least a portion of: the nucleotide sequence of the ANGPTL7 genomic nucleic acid molecule in the biological sample, wherein the sequenced portion comprises a position corresponding to position 4,243 according to SEQ ID NO:4, or the complement thereof; the nucleotide sequence of the ANGPTL7 mRNA molecule in the biological sample, wherein the sequenced portion comprises a position corresponding to position 481 according to SEQ ID NO:10, or the complement thereof; and/or the nucleotide sequence of the ANGPTL7 cDNA molecule produced from the mRNA in the biological sample, wherein the sequenced portion comprises a position corresponding to position 481 according to SEQ ID NO:16, or the complement thereof. When the sequenced portion of the ANGPTL7 nucleic acid molecule in the biological sample comprises: an adenine at a position corresponding to position 4,243 according to SEQ ID NO:4, an adenine at a position corresponding to position 481 according to SEQ ID NO:10, or an adenine at a position corresponding to position 481 according to SEQ ID NO:16, then the ANGPTL7 nucleic acid molecule in the biological sample is an ANGPTL7 predicted loss-of-function variant nucleic acid molecule.

In some embodiments, the determining step, detecting step, or sequence analysis comprises sequencing at least a portion of: the nucleotide sequence of the ANGPTL7 genomic nucleic acid molecule in the biological sample, wherein the sequenced portion comprises a position corresponding to position 4,325 according to SEQ ID NO:5, or the complement thereof; the nucleotide sequence of the ANGPTL7 mRNA molecule in the biological sample, wherein the sequenced portion comprises a position corresponding to position 563 according to SEQ ID NO:11, or the complement thereof; and/or the nucleotide sequence of the ANGPTL7 cDNA molecule produced from the mRNA in the biological sample, wherein the sequenced portion comprises a position corresponding to position 563 according to SEQ ID NO:17, or the complement thereof. When the sequenced portion of the ANGPTL7 nucleic acid molecule in the biological sample comprises: an adenine at a position corresponding to position 4,325 according to SEQ ID NO:5, an adenine at a position corresponding to position 563 according to SEQ ID NO:11, or an adenine at a position corresponding to position 563 according to SEQ ID NO:17, then the ANGPTL7 nucleic acid molecule in the biological sample is an ANGPTL7 predicted loss-of-function variant nucleic acid molecule.

In some embodiments, the determining step, detecting step, or sequence analysis comprises sequencing at least a portion of: the nucleotide sequence of the ANGPTL7 genomic nucleic acid molecule in the biological sample, wherein the sequenced portion comprises a position corresponding to position 4,336 according to SEQ ID NO:6, or the complement thereof; the nucleotide sequence of the ANGPTL7 mRNA molecule in the biological sample, wherein the sequenced portion comprises a position corresponding to position 574 according to SEQ ID NO:12, or the complement thereof; and/or the nucleotide sequence of the ANGPTL7 cDNA molecule produced from the mRNA in the biological sample, wherein the sequenced portion comprises a position corresponding to position 574 according to SEQ ID NO:18, or the complement thereof. When the sequenced portion of the ANGPTL7 nucleic acid molecule in the biological sample comprises: a cytosine at a position corresponding to position 4,336 according to SEQ ID NO:6, a cytosine at a position corresponding to position 574 according to SEQ ID NO:12, or a cytosine at a position corresponding to position 574 according to SEQ ID NO:18, then the ANGPTL7 nucleic acid molecule in the biological sample is an ANGPTL7 predicted loss-of-function variant nucleic acid molecule.

In some embodiments, the determining step, detecting step, or sequence analysis comprises sequencing at least a portion of the nucleotide sequence of the ANGPTL7 genomic nucleic acid molecule in the biological sample, wherein the sequenced portion comprises a position corresponding to: position 4,291 according to SEQ ID NO:2, or the complement thereof; position 4,287 according to SEQ ID NO:3, or the complement thereof; position 4,243 according to SEQ ID NO:4, or the complement thereof; position 4,325 according to SEQ ID NO:5, or the complement thereof; or position 4,336 according to SEQ ID NO:6, or the complement thereof. When the sequenced portion of the ANGPTL7 nucleic acid molecule in the biological sample comprises: i) a thymine at a position corresponding to position 4,291 according to SEQ ID NO:2, a thymine at a position corresponding to position 4,287 according to SEQ ID NO:3, an adenine at a position corresponding to position 4,243 according to SEQ ID NO:4, an adenine at a position corresponding to position 4,325 according to SEQ ID NO:5, or a cytosine at a position corresponding to position 4,336 according to SEQ ID NO:6, then the ANGPTL7 nucleic acid molecule in the biological sample is an ANGPTL7 predicted loss-of-function variant nucleic acid molecule.

In some embodiments, the determining step, detecting step, or sequence analysis comprises sequencing at least a portion of the nucleotide sequence of the ANGPTL7 mRNA molecule in the biological sample, wherein the sequenced portion comprises a position corresponding to: position 529 according to SEQ ID NO:8, or the complement thereof; position 525 according to SEQ ID NO:9, or the complement thereof; position 481 according to SEQ ID NO:10, or the complement thereof; position 563 according to SEQ ID NO:11, or the complement thereof; or position 574 according to SEQ ID NO:12, or the complement thereof. When the sequenced portion of the ANGPTL7 nucleic acid molecule in the biological sample comprises: a uracil at a position corresponding to position 529 according to SEQ ID NO:8, a uracil at a position corresponding to position 525 according to SEQ ID NO:9, an adenine at a position corresponding to position 481 according to SEQ ID NO:10, an adenine at a position corresponding to position 563 according to SEQ ID NO:11, or a cytosine at a position corresponding to position 574 according to SEQ ID NO:12, then the ANGPTL7 nucleic acid molecule in the biological sample is an ANGPTL7 predicted loss-of-function variant nucleic acid molecule.

In some embodiments, the determining step, detecting step, or sequence analysis comprises sequencing at least a portion of the nucleotide sequence of the ANGPTL7 cDNA molecule produced from the mRNA molecule in the biological sample, wherein the sequenced portion comprises a position corresponding to: position 529 according to SEQ ID NO:14, or the complement thereof; position 525 according to SEQ ID NO:15, or the complement thereof; position 481 according to SEQ ID NO:16, or the complement thereof; position 563 according to SEQ ID NO:17, or the complement thereof; or position 574 according to SEQ ID NO:18, or the complement thereof. When the sequenced portion of the ANGPTL7 nucleic acid molecule in the biological sample comprises: a thymine at a position corresponding to position 529 according to SEQ ID NO:14, a thymine at a position corresponding to position 525 according to SEQ ID NO:15, an adenine at a position corresponding to position 481 according to SEQ ID NO:16, an adenine at a position corresponding to position 563 according to SEQ ID NO:17, or a cytosine at a position corresponding to position 574 according to SEQ ID NO:18, then the ANGPTL7 nucleic acid molecule in the biological sample is an ANGPTL7 predicted loss-of-function variant nucleic acid molecule.

In some embodiments, the determining step, detecting step, or sequence analysis comprises: a) contacting the biological sample with a primer hybridizing to a portion of the nucleotide sequence of the ANGPTL7: genomic nucleic acid molecule that is proximate to a position corresponding to position 4,291 according to SEQ ID NO:2; mRNA molecule that is proximate to a position corresponding to position 529 according to SEQ ID NO:8; and/or cDNA molecule that is proximate to a position corresponding to position 529 according to SEQ ID NO:14; b) extending the primer at least through the position of the nucleotide sequence of the ANGPTL7: genomic nucleic acid molecule corresponding to position 4,291 according to SEQ ID NO:2; mRNA molecule corresponding to position 529 according to SEQ ID NO:8; and/or cDNA molecule corresponding to position 529 according to SEQ ID NO:14; and c) determining whether the extension product of the primer comprises: a thymine at a position corresponding to position 4,291 according to SEQ ID NO:2, a uracil at a position corresponding to position 529 according to SEQ ID NO:8, and/or a thymine at a position corresponding to position 529 according to SEQ ID NO:14.

In some embodiments, the determining step, detecting step, or sequence analysis comprises: a) contacting the biological sample with a primer hybridizing to a portion of the nucleotide sequence of the ANGPTL7: genomic nucleic acid molecule that is proximate to a position corresponding to position 4,287 according to SEQ ID NO:3; mRNA molecule that is proximate to a position corresponding to position 525 according to SEQ ID NO:9; and/or cDNA molecule that is proximate to a position corresponding to position 525 according to SEQ ID NO:15; b) extending the primer at least through the position of the nucleotide sequence of the ANGPTL7: genomic nucleic acid molecule corresponding to position 4,287 according to SEQ ID NO:3; mRNA molecule corresponding to position 525 according to SEQ ID NO:9; and/or cDNA molecule corresponding to position 525 according to SEQ ID NO:15; and c) determining whether the extension product of the primer comprises: a thymine at a position corresponding to position 4,287 according to SEQ ID NO:3, a uracil at a position corresponding to position 525 according to SEQ ID NO:9, and/or a thymine at a position corresponding to position 525 according to SEQ ID NO:15.

In some embodiments, the determining step, detecting step, or sequence analysis comprises: a) contacting the biological sample with a primer hybridizing to a portion of the nucleotide sequence of the ANGPTL7: genomic nucleic acid molecule that is proximate to a position corresponding to position 4,243 according to SEQ ID NO:4; mRNA molecule that is proximate to a position corresponding to position 481 according to SEQ ID NO:10; and/or cDNA molecule that is proximate to a position corresponding to position 481 according to SEQ ID NO:16; b) extending the primer at least through the position of the nucleotide sequence of the ANGPTL7: genomic nucleic acid molecule corresponding to position 4,243 according to SEQ ID NO:4; mRNA molecule corresponding to position 481 according to SEQ ID NO:10; and/or cDNA molecule corresponding to position 481 according to SEQ ID NO:16; and c) determining whether the extension product of the primer comprises: an adenine at a position corresponding to position 4,243 according to SEQ ID NO:4, an adenine at a position corresponding to position 481 according to SEQ ID NO:10, and/or an adenine at a position corresponding to position 481 according to SEQ ID NO:16.

In some embodiments, the determining step, detecting step, or sequence analysis comprises: a) contacting the biological sample with a primer hybridizing to a portion of the nucleotide sequence of the ANGPTL7: genomic nucleic acid molecule that is proximate to a position corresponding to position 4,325 according to SEQ ID NO:5; mRNA molecule that is proximate to a position corresponding to position 563 according to SEQ ID NO:11; and/or cDNA molecule that is proximate to a position corresponding to position 563 according to SEQ ID NO:17; b) extending the primer at least through the position of the nucleotide sequence of the ANGPTL7: genomic nucleic acid molecule corresponding to position 4,325 according to SEQ ID NO:5; mRNA molecule corresponding to position 563 according to SEQ ID NO:11; and/or cDNA molecule corresponding to position 563 according to SEQ ID NO:17; and c) determining whether the extension product of the primer comprises: an adenine at a position corresponding to position 4,325 according to SEQ ID NO:5, an adenine at a position corresponding to position 563 according to SEQ ID NO:11, and/or an adenine at a position corresponding to position 563 according to SEQ ID NO:17.

In some embodiments, the determining step, detecting step, or sequence analysis comprises: a) contacting the biological sample with a primer hybridizing to a portion of the nucleotide sequence of the ANGPTL7: genomic nucleic acid molecule that is proximate to a position corresponding to position 4,336 according to SEQ ID NO:6; mRNA molecule that is proximate to a position corresponding to position 574 according to SEQ ID NO:12; and/or cDNA molecule that is proximate to a position corresponding to position 574 according to SEQ ID NO:18; b) extending the primer at least through the position of the nucleotide sequence of the ANGPTL7: genomic nucleic acid molecule corresponding to position 4,336 according to SEQ ID NO:6; mRNA molecule corresponding to position 574 according to SEQ ID NO:12; and/or cDNA molecule corresponding to position 574 according to SEQ ID NO:18; and c) determining whether the extension product of the primer comprises: a cytosine at a position corresponding to position 4,336 according to SEQ ID NO:6, a cytosine at a position corresponding to position 574 according to SEQ ID NO:12, and/or a cytosine at a position corresponding to position 574 according to SEQ ID NO:18.

In some embodiments, the determining step, detecting step, or sequence analysis comprises: a) contacting the biological sample with a primer hybridizing to a portion of the nucleotide sequence of the ANGPTL7 genomic nucleic acid molecule that is proximate to a position corresponding to: position 4,291 according to SEQ ID NO:2, position 4,287 according to SEQ ID NO:3, position 4,243 according to SEQ ID NO:4, position 4,325 according to SEQ ID NO:5, or position 4,336 according to SEQ ID NO:6; b) extending the primer at least through the position of the nucleotide sequence of the ANGPTL7 genomic nucleic acid molecule corresponding to: position 4,291 according to SEQ ID NO:2, position 4,287 according to SEQ ID NO:3, position 4,243 according to SEQ ID NO:4, position 4,325 according to SEQ ID NO:5, or position 4,336 according to SEQ ID NO:6; and c) determining whether the extension product of the primer comprises: a thymine at a position corresponding to position 4,291 according to SEQ ID NO:2, a thymine at a position corresponding to position 4,287 according to SEQ ID NO:3, an adenine at a position corresponding to position 4,243 according to SEQ ID NO:4, an adenine at a position corresponding to position 4,325 according to SEQ ID NO:5, or a cytosine at a position corresponding to position 4,336 according to SEQ ID NO:6.

In some embodiments, the determining step, detecting step, or sequence analysis comprises: a) contacting the biological sample with a primer hybridizing to a portion of the nucleotide sequence of the ANGPTL7 mRNA molecule that is proximate to a position corresponding to: position 529 according to SEQ ID NO:8, position 525 according to SEQ ID NO:9, position 481 according to SEQ ID NO:10; position 563 according to SEQ ID NO:11, or position 574 according to SEQ ID NO:12; b) extending the primer at least through the position of the nucleotide sequence of the ANGPTL7 mRNA molecule corresponding to: position 529 according to SEQ ID NO:8, position 525 according to SEQ ID NO:9, position 481 according to SEQ ID NO:10, position 563 according to SEQ ID NO:11, or position 574 according to SEQ ID NO:12; and c) determining whether the extension product of the primer comprises: a uracil at a position corresponding to position 529 according to SEQ ID NO:8, a uracil at a position corresponding to position 525 according to SEQ ID NO:9, an adenine at a position corresponding to position 481 according to SEQ ID NO:10, an adenine at a position corresponding to position 563 according to SEQ ID NO:11, or a cytosine at a position corresponding to position 574 according to SEQ ID NO:12.

In some embodiments, the determining step, detecting step, or sequence analysis comprises: a) contacting the biological sample with a primer hybridizing to a portion of the nucleotide sequence of the ANGPTL7 cDNA molecule that is proximate to a position corresponding to: position 529 according to SEQ ID NO:14, position 525 according to SEQ ID NO:15, position 481 according to SEQ ID NO:16, position 563 according to SEQ ID NO:17, or position 574 according to SEQ ID NO:18; b) extending the primer at least through the position of the nucleotide sequence of the ANGPTL7 cDNA molecule corresponding to: position 529 according to SEQ ID NO:14, position 525 according to SEQ ID NO:15, position 481 according to SEQ ID NO:16, position 563 according to SEQ ID NO:17, or position 574 according to SEQ ID NO:18, and c) determining whether the extension product of the primer comprises: a thymine at a position corresponding to position 529 according to SEQ ID NO:14, a thymine at a position corresponding to position 525 according to SEQ ID NO:15, an adenine at a position corresponding to position 481 according to SEQ ID NO:16, an adenine at a position corresponding to position 563 according to SEQ ID NO:17, or a cytosine at a position corresponding to position 574 according to SEQ ID NO:18.

In some embodiments, the assay comprises sequencing the entire nucleic acid molecule. In some embodiments, only an ANGPTL7 genomic nucleic acid molecule is analyzed. In some embodiments, only an ANGPTL7 mRNA is analyzed. In some embodiments, only an ANGPTL7 cDNA obtained from ANGPTL7 mRNA is analyzed.

In some embodiments, the determining step, detecting step, or sequence analysis comprises: a) amplifying at least a portion of the nucleic acid molecule that encodes the ANGPTL7 polypeptide, wherein the amplified portion comprises: a thymine at a position corresponding to position 4,291 according to SEQ ID NO:2, or the complement thereof; a uracil at a position corresponding to position 529 according to SEQ ID NO:8, or the complement thereof; and/or a thymine at a position corresponding to position 529 according to SEQ ID NO:14, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a thymine at a position corresponding to position 4,291 according to SEQ ID NO:2, or the complement thereof; a uracil at a position corresponding to position 529 according to SEQ ID NO:8, or the complement thereof; and/or a thymine at a position corresponding to position 529 according to SEQ ID NO:14, or the complement thereof; and d) detecting the detectable label.

In some embodiments, the determining step, detecting step, or sequence analysis comprises: a) amplifying at least a portion of the nucleic acid molecule that encodes the ANGPTL7 polypeptide, wherein the amplified portion comprises: a thymine at a position corresponding to position 4,287 according to SEQ ID NO:3, or the complement thereof; a uracil at a position corresponding to position 525 according to SEQ ID NO:9, or the complement thereof; and/or a thymine at a position corresponding to position 525 according to SEQ ID NO:15, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a thymine at a position corresponding to position 4,287 according to SEQ ID NO:3, or the complement thereof; a uracil at a position corresponding to position 525 according to SEQ ID NO:9, or the complement thereof; and/or a thymine at a position corresponding to position 525 according to SEQ ID NO:15, or the complement thereof; and d) detecting the detectable label.

In some embodiments, the determining step, detecting step, or sequence analysis comprises: a) amplifying at least a portion of the nucleic acid molecule that encodes the ANGPTL7 polypeptide, wherein the amplified portion comprises: an adenine at a position corresponding to position 4,243 according to SEQ ID NO:4, or the complement thereof; an adenine at a position corresponding to position 481 according to SEQ ID NO:10, or the complement thereof; and/or an adenine at a position corresponding to position 481 according to SEQ ID NO:16, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 4,243 according to SEQ ID NO:4, or the complement thereof; an adenine at a position corresponding to position 481 according to SEQ ID NO:10, or the complement thereof; and/or an adenine at a position corresponding to position 481 according to SEQ ID NO:16, or the complement thereof; and d) detecting the detectable label.

In some embodiments, the determining step, detecting step, or sequence analysis comprises: a) amplifying at least a portion of the nucleic acid molecule that encodes the ANGPTL7 polypeptide, wherein the amplified portion comprises: an adenine at a position corresponding to position 4,325 according to SEQ ID NO:5, or the complement thereof; an adenine at a position corresponding to position 563 according to SEQ ID NO:11, or the complement thereof; and/or an adenine at a position corresponding to position 563 according to SEQ ID NO:17, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: an adenine at a position corresponding to position 4,325 according to SEQ ID NO:5, or the complement thereof; an adenine at a position corresponding to position 563 according to SEQ ID NO:11, or the complement thereof; and/or an adenine at a position corresponding to position 563 according to SEQ ID NO:17, or the complement thereof; and d) detecting the detectable label.

In some embodiments, the determining step, detecting step, or sequence analysis comprises: a) amplifying at least a portion of the nucleic acid molecule that encodes the ANGPTL7 polypeptide, wherein the amplified portion comprises: a cytosine at a position corresponding to position 4,336 according to SEQ ID NO:6, or the complement thereof; a cytosine at a position corresponding to position 574 according to SEQ ID NO:12, or the complement thereof; and/or a cytosine at a position corresponding to position 574 according to SEQ ID NO:18, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a cytosine at a position corresponding to position 4,336 according to SEQ ID NO:6, or the complement thereof; a cytosine at a position corresponding to position 574 according to SEQ ID NO:12, or the complement thereof; and/or a cytosine at a position corresponding to position 574 according to SEQ ID NO:18, or the complement thereof; and d) detecting the detectable label.

In some embodiments, the determining step, detecting step, or sequence analysis comprises: a) amplifying at least a portion of the nucleic acid molecule that encodes the ANGPTL7 polypeptide, wherein the amplified portion comprises: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof; and d) detecting the detectable label.

In some embodiments, the determining step, detecting step, or sequence analysis comprises: a) amplifying at least a portion of the nucleic acid molecule that encodes the ANGPTL7 polypeptide, wherein the amplified portion comprises: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof; and d) detecting the detectable label.

In some embodiments, the determining step, detecting step, or sequence analysis comprises: a) amplifying at least a portion of the nucleic acid molecule that encodes the ANGPTL7 polypeptide, wherein the amplified portion comprises: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the nucleic acid sequence of the amplified nucleic acid molecule comprising: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a thymine at a position corresponding to position 4,291 according to SEQ ID NO:2, or the complement thereof; a uracil at a position corresponding to position 529 according to SEQ ID NO:8, or the complement thereof; and/or a thymine at a position corresponding to position 529 according to SEQ ID NO:14, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a thymine at a position corresponding to position 4,287 according to SEQ ID NO:3, or the complement thereof; a uracil at a position corresponding to position 525 according to SEQ ID NO:9, or the complement thereof; and/or a thymine at a position corresponding to position 525 according to SEQ ID NO:15, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 4,243 according to SEQ ID NO:4, or the complement thereof; an adenine at a position corresponding to position 481 according to SEQ ID NO:10, or the complement thereof; and/or an adenine at a position corresponding to position 481 according to SEQ ID NO:16, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: an adenine at a position corresponding to position 4,325 according to SEQ ID NO:5, or the complement thereof; an adenine at a position corresponding to position 563 according to SEQ ID NO:11, or the complement thereof; and/or an adenine at a position corresponding to position 563 according to SEQ ID NO:17, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a cytosine at a position corresponding to position 4,336 according to SEQ ID NO:6, or the complement thereof; a cytosine at a position corresponding to position 574 according to SEQ ID NO:12, or the complement thereof; and/or a cytosine at a position corresponding to position 574 according to SEQ ID NO:18, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof; and detecting the detectable label.

In some embodiments, the determining step, detecting step, or sequence analysis comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule comprising: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof; and detecting the detectable label.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to an ANGPTL7 variant genomic sequence, variant mRNA sequence, or variant cDNA sequence and not the corresponding ANGPTL7 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an ANGPTL7 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

In some embodiments, to determine whether an ANGPTL7 nucleic acid molecule (genomic nucleic acid molecule, mRNA molecule, or cDNA molecule), or complement thereof, within a biological sample comprises a nucleotide sequence comprising a thymine at a position corresponding to position 4,291 according to SEQ ID NO:2 (genomic nucleic acid molecule), a uracil at a position corresponding to position 529 according to SEQ ID NO:8 (mRNA molecule), or a thymine at a position corresponding to position 529 according to SEQ ID NO:14 (cDNA molecule), the biological sample can be subjected to an amplification method using a primer pair that includes a first primer derived from the 5' flanking sequence adjacent to a thymine at a position corresponding to position 4,291 according to SEQ ID NO:2, a uracil at a position corresponding to position 529 according to SEQ ID NO:8, or a thymine at a position corresponding to position 529 according to SEQ ID NO:14, and a second primer derived from the 3' flanking sequence adjacent to a thymine at a position corresponding to position 4,291 according to SEQ ID NO:2, a uracil at a position corresponding to position 529 according to SEQ ID NO:8, or a thymine at a position corresponding to position 529 according to SEQ ID NO:14 to produce an amplicon that is indicative of the presence of the SNP at positions encoding a thymine at a position corresponding to position 4,291 according to SEQ ID NO:2, a uracil at a position corresponding to position 529 according to SEQ ID NO:8, or a thymine at a position corresponding to position 529 according to SEQ ID NO:14. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 4,291 according to SEQ ID NO:2, a uracil at a position corresponding to position 529 according to SEQ ID NO:8, or a thymine at a position corresponding to position 529 according to SEQ ID NO:14, and at least 1, 2, 3, 4, 5, 6, 7, 8, 9, 10, or more nucleotides on each side of positions comprising a thymine at a position corresponding to position 4,291 according to SEQ ID NO:2, a uracil at a position corresponding to position 529 according to SEQ ID NO:8, or a thymine at a position corresponding to position 529 according to SEQ ID NO:14.

In some embodiments, to determine whether an ANGPTL7 nucleic acid molecule (genomic nucleic acid molecule, mRNA molecule, or cDNA molecule), or complement thereof, within a biological sample comprises a nucleotide sequence comprising a thymine at a position corresponding to position 4,287 according to SEQ ID NO:3 (genomic nucleic acid molecule), a uracil at a position corresponding to position 525 according to SEQ ID NO:9 (mRNA molecule), or a thymine at a position corresponding to position 525 according to SEQ ID NO:15 (cDNA molecule), the biological sample can be subjected to an amplification method using a primer pair that includes a first primer derived from the 5' flanking sequence adjacent to a thymine at a position corresponding to position 4,287 according to SEQ ID NO:3, a uracil at a position corresponding to position 525 according to SEQ ID NO:9, or a thymine at a position corresponding to position 525 according to SEQ ID NO:15, and a second primer derived from the 3' flanking sequence adjacent to a thymine at a position corresponding to position 4,287 according to SEQ ID NO:3, a uracil at a position corresponding to position 525 according to SEQ ID NO:9, or a thymine at a position corresponding to position 525 according to SEQ ID NO:15 to produce an amplicon that is indicative of the presence of the SNP at positions encoding a thymine at a position corresponding to position 4,287 according to SEQ ID NO:3, a uracil at a position corresponding to position 525 according to SEQ ID NO:9, or a thymine at a position corresponding to position 525 according to SEQ ID NO:15. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a thymine at a position corresponding to position 4,287 according to SEQ ID NO:3, a uracil at a position corresponding to position 525 according to SEQ ID NO:9, or a thymine at a position corresponding to position 525 according to SEQ ID NO:15, and at least 1, 2, 3, 4, 5, 6, 7, 8, 9, 10, or more nucleotides on each side of positions comprising a thymine at a position corresponding to position 4,287 according to SEQ ID NO:3, a uracil at a position corresponding to position 525 according to SEQ ID NO:9, or a thymine at a position corresponding to position 525 according to SEQ ID NO:15.

In some embodiments, to determine whether an ANGPTL7 nucleic acid molecule (genomic nucleic acid molecule, mRNA molecule, or cDNA molecule), or complement thereof, within a biological sample comprises a nucleotide sequence comprising an adenine at a position corresponding to position 4,243 according to SEQ ID NO:4 (genomic nucleic acid molecule), an adenine at a position corresponding to position 481 according to SEQ ID NO:10 (mRNA molecule), or an adenine at a position corresponding to position 481 according to SEQ ID NO:16 (cDNA molecule), the biological sample can be subjected to an amplification method using a primer pair that includes a first primer derived from the 5' flanking sequence adjacent to an adenine at a position corresponding to position 4,243 according to SEQ ID NO:4, an adenine at a position corresponding to position 481 according to SEQ ID NO:10, or an adenine at a position corresponding to position 481 according to SEQ ID NO:16, and a second primer derived from the 3' flanking sequence adjacent to an adenine at a position corresponding to position 4,243 according to SEQ ID NO:4, an adenine at a position corresponding to position 481 according to SEQ ID NO:10, or an adenine at a position corresponding to position 481 according to SEQ ID NO:16 to produce an amplicon that is indicative of the presence of the SNP at positions encoding an adenine at a position corresponding to position 4,243 according to SEQ ID NO:4, an adenine at a position corresponding to position 481 according to SEQ ID NO:10, or an adenine at a position corresponding to position 481 according to SEQ ID NO:16. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 4,243 according to SEQ ID NO:4, an adenine at a position corresponding to position 481 according to SEQ ID NO:10, or an adenine at a position corresponding to position 481 according to SEQ ID NO:16, and at least 1, 2, 3, 4, 5, 6, 7, 8, 9, 10, or more nucleotides on each side of positions comprising an adenine at a position corresponding to position 4,243 according to SEQ ID NO:4, an adenine at a position corresponding to position 481 according to SEQ ID NO:10, or an adenine at a position corresponding to position 481 according to SEQ ID NO:16.

In some embodiments, to determine whether an ANGPTL7 nucleic acid molecule (genomic nucleic acid molecule, mRNA molecule, or cDNA molecule), or complement thereof, within a biological sample comprises a nucleotide sequence comprising an adenine at a position corresponding to position 4,325 according to SEQ ID NO:5 (genomic nucleic acid molecule), an adenine at a position corresponding to position 563 according to SEQ ID NO:11 (mRNA molecule), or an adenine at a position corresponding to position 563 according to SEQ ID NO:17 (cDNA molecule), the biological sample can be subjected to an amplification method using a primer pair that includes a first primer derived from the 5' flanking sequence adjacent to an adenine at a position corresponding to position 4,325 according to SEQ ID NO:5, an adenine at a position corresponding to position 563 according to SEQ ID NO:11, or an adenine at a position corresponding to position 563 according to SEQ ID NO:17, and a second primer derived from the 3' flanking sequence adjacent to an adenine at a position corresponding to position 4,325 according to SEQ ID NO:5, an adenine at a position corresponding to position 563 according to SEQ ID NO:11, or an adenine at a position corresponding to position 563 according to SEQ ID NO:17 to produce an amplicon that is indicative of the presence of the SNP at positions encoding an adenine at a position corresponding to position 4,325 according to SEQ ID NO:5, an adenine at a position corresponding to position 563 according to SEQ ID NO:11, or an adenine at a position corresponding to position 563 according to SEQ ID NO:17. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising an adenine at a position corresponding to position 4,325 according to SEQ ID NO:5, an adenine at a position corresponding to position 563 according to SEQ ID NO:11, or an adenine at a position corresponding to position 563 according to SEQ ID NO:17, and at least 1, 2, 3, 4, 5, 6, 7, 8, 9, 10, or more nucleotides on each side of positions comprising an adenine at a position corresponding to position 4,325 according to SEQ ID NO:5, an adenine at a position corresponding to position 563 according to SEQ ID NO:11, or an adenine at a position corresponding to position 563 according to SEQ ID NO:17.

In some embodiments, to determine whether an ANGPTL7 nucleic acid molecule (genomic nucleic acid molecule, mRNA molecule, or cDNA molecule), or complement thereof, within a biological sample comprises a nucleotide sequence comprising a cytosine at a position corresponding to position 4,336 according to SEQ ID NO:6 (genomic nucleic acid molecule), a cytosine at a position corresponding to position 574 according to SEQ ID NO:12 (mRNA molecule), or a cytosine at a position corresponding to position 574 according to SEQ ID NO:18 (cDNA molecule), the biological sample can be subjected to an amplification method using a primer pair that includes a first primer derived from the 5' flanking sequence adjacent to a cytosine at a position corresponding to position 4,336 according to SEQ ID NO:6, a cytosine at a position corresponding to position 574 according to SEQ ID NO:12, or a cytosine at a position corresponding to position 574 according to SEQ ID NO:18, and a second primer derived from the 3' flanking sequence adjacent to a cytosine at a position corresponding to position 4,336 according to SEQ ID NO:6, a cytosine at a position corresponding to position 574 according to SEQ ID NO:12, or a cytosine at a position corresponding to position 574 according to SEQ ID NO:18 to produce an amplicon that is indicative of the presence of the SNP at positions encoding a cytosine at a position corresponding to position 4,336 according to SEQ ID NO:6, a cytosine at a position corresponding to position 574 according to SEQ ID NO:12, or a cytosine at a position corresponding to position 574 according to SEQ ID NO:18. In some embodiments, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including positions comprising a cytosine at a position corresponding to position 4,336 according to SEQ ID NO:6, a cytosine at a position corresponding to position 574 according to SEQ ID NO:12, or a cytosine at a position corresponding to position 574 according to SEQ ID NO:18, and at least 1, 2, 3, 4, 5, 6, 7, 8, 9, 10, or more nucleotides on each side of positions comprising a cytosine at a position corresponding to position 4,336 according to SEQ ID NO:6, a cytosine at a position corresponding to position 574 according to SEQ ID NO:12, or a cytosine at a position corresponding to position 574 according to SEQ ID NO:18.

Similar amplicons can be generated from the mRNA and/or cDNA sequences. PCR primer pairs can be derived from a known sequence, for example, by using computer programs intended for that purpose, such as the PCR primer analysis tool in Vector NTI version 10 (Informax Inc., Bethesda Md.); PrimerSelect (DNASTAR Inc., Madison, Wis.); and Primer3 (Version 0.4.0.COPYRGT., 1991, Whitehead Institute for Biomedical Research, Cambridge, Mass.). Additionally, the sequence can be visually scanned and primers manually identified using known guidelines.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneously with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of an ANGPTL7 predicted loss-of-function polypeptide comprising performing an assay on a biological sample obtained from the subject to determine whether an ANGPTL7 polypeptide in the subject contains one or more variations that causes the polypeptide to have a loss-of-function (partial or complete) or predicted loss-of-function (partial or complete). The ANGPTL7 predicted loss-of-function polypeptide can be any of the ANGPTL7 variant polypeptides described herein. In some embodiments, the methods detect the presence of ANGPTL7 Arg177STOP, Gln175His, Phe161Ile, Trp188STOP, Lys192Gln, Arg340His, Arg220His, Asn302Lys, or Arg220Cys. In some embodiments, the methods detect the presence of ANGPTL7 Arg177STOP, Gln175His, Phe161Ile, Trp188STOP, or Lys192Gln.

In some embodiments, the methods comprise performing an assay on a sample obtained from a subject to determine whether an ANGPTL7 polypeptide in the sample terminates at position 176 and does not comprise amino acids at positions corresponding to positions 177 to 346 according to SEQ ID NO:19. In some embodiments, the methods comprise performing an assay on a sample obtained from a subject to determine whether an ANGPTL7 polypeptide in the sample comprises a histidine at a position corresponding to position 175 according to SEQ ID NO:21. In some embodiments, the methods comprise performing an assay on a sample obtained from a subject to determine whether an ANGPTL7 polypeptide in the sample comprises an isoleucine at a position corresponding to position 161 according to SEQ ID NO:22. In some embodiments, the methods comprise performing an assay on a sample obtained from a subject to determine whether an ANGPTL7 polypeptide in the sample comprises terminates at position 187 and does not comprise amino acids at positions corresponding to positions 188 to 346 according to SEQ ID NO:19. In some embodiments, the methods comprise performing an assay on a sample obtained from a subject to determine whether an ANGPTL7 polypeptide in the sample comprises a glutamine at a position corresponding to position 192 according to SEQ ID NO:24.

In some embodiments, the determining step comprises sequencing at least a portion of the polypeptide that comprises a position corresponding to position 175 according to SEQ ID NO:21 or SEQ ID NO:19. In some embodiments, the determining step comprises sequencing at least a portion of the polypeptide that comprises a position corresponding to position 161 according to SEQ ID NO:22 or SEQ ID NO:19. In some embodiments, the determining step comprises sequencing at least a portion of the polypeptide that comprises a position corresponding to position 192 according to SEQ ID NO:24 or SEQ ID NO:19.

In some embodiments, the determining step comprises sequencing at least a portion of the ANGPTL7 polypeptide that may comprise positions corresponding to any positions that are C-terminal to position 176 according to SEQ ID NO:20. If amino acids are detected in the ANGPTL7 polypeptide at positions corresponding to positions 177 to 346 according to SEQ ID NO:19, then such ANGPTL7 polypeptide is an NGPTL7 reference polypeptide. An absence of positions 177 to 346 according to SEQ ID NO:19 in the ANGPTL7 polypeptide indicates that the ANGPTL7 polypeptide terminates at position 176 according to SEQ ID NO:20 and is an ANGPTL7 predicted loss-of-function polypeptide.

In some embodiments, the determining step comprises sequencing at least a portion of the ANGPTL7 polypeptide that may comprise positions corresponding to any positions that are C-terminal to position 187 according to SEQ ID NO:23. If amino acids are detected in the ANGPTL7 polypeptide at positions corresponding to positions 188 to 346 according to SEQ ID NO:19, then such ANGPTL7 polypeptide is an NGPTL7 reference polypeptide. An absence of positions 188 to 346 according to SEQ ID NO:19 in the ANGPTL7 polypeptide indicates that the ANGPTL7 polypeptide terminates at position 187 according to SEQ ID NO:23 and is an ANGPTL7 predicted loss-of-function polypeptide.

In some embodiments, the determining step comprises an immunoassay for detecting at least a portion of the polypeptide that comprises a position corresponding to position 175 according to SEQ ID NO:21 or SEQ ID NO:19. In some embodiments, the determining step comprises an immunoassay for detecting at least a portion of the polypeptide that comprises a position corresponding to position 161 according to SEQ ID NO:22 or SEQ ID NO:19. In some embodiments, the determining step comprises an immunoassay for detecting at least a portion of the polypeptide that comprises a position corresponding to position 192 according to SEQ ID NO:24 or SEQ ID NO:19.

In some embodiments, the determining step comprises an immunoassay for detecting at least a portion of the ANGPTL7 polypeptide that may comprise positions corresponding to any positions that are C-terminal to position 176 according to SEQ ID NO:20. If amino acids are detected in the ANGPTL7 polypeptide at positions corresponding to positions 177 to 346 according to SEQ ID NO:19, then such ANGPTL7 polypeptide is an NGPTL7 reference polypeptide. An absence of positions 177 to 346 according to SEQ ID NO:19 in the ANGPTL7 polypeptide indicates that the ANGPTL7 polypeptide terminates at position 176 according to SEQ ID NO:20 and is an ANGPTL7 predicted loss-of-function polypeptide.

In some embodiments, the determining step comprises an immunoassay for detecting at least a portion of the ANGPTL7 polypeptide that may comprise positions corresponding to any positions that are C-terminal to position 187 according to SEQ ID NO:23. If amino acids are detected in the ANGPTL7 polypeptide at positions corresponding to positions 188 to 346 according to SEQ ID NO:19, then such ANGPTL7 polypeptide is an NGPTL7 reference polypeptide. An absence of positions 188 to 346 according to SEQ ID NO:19 in the ANGPTL7 polypeptide indicates that the ANGPTL7 polypeptide terminates at position 187 according to SEQ ID NO:23 and is an ANGPTL7 predicted loss-of-function polypeptide.

In some embodiments, when the subject does not have an ANGPTL7 predicted loss-of-function polypeptide, the subject has an increased risk for developing a glucocorticoid-induced ophthalmic condition. In some embodiments, when the subject has an ANGPTL7 predicted loss-of-function polypeptide, the subject has a decreased risk for developing a glucocorticoid-induced ophthalmic condition.

The present disclosure also provides isolated nucleic acid molecules that hybridize to ANGPTL7 variant genomic nucleic acid molecules, ANGPTL7 variant mRNA molecules, and/or ANGPTL7 variant cDNA molecules (such as any of the genomic variant nucleic acid molecules, mRNA variant molecules, and cDNA variant molecules disclosed herein). In some embodiments, the isolated nucleic acid molecules hybridize to a portion of the ANGPTL7 nucleic acid molecule that includes a position corresponding to: position 4,291 according to SEQ ID NO:2, position 529 according to SEQ ID NO:8, or position 529 according to SEQ ID NO:14. In some embodiments, the isolated nucleic acid molecules hybridize to a portion of the ANGPTL7 nucleic acid molecule that includes a position corresponding to: position 4,287 according to SEQ ID NO:3, position 525 according to SEQ ID NO:9, or position 525 according to SEQ ID NO:15. In some embodiments, the isolated nucleic acid molecules hybridize to a portion of the ANGPTL7 nucleic acid molecule that includes a position corresponding: to position 4,243 according to SEQ ID NO:4, position 481 according to SEQ ID NO:10, or position 481 according to SEQ ID NO:16. In some embodiments, the isolated nucleic acid molecules hybridize to a portion of the ANGPTL7 nucleic acid molecule that includes a position corresponding to: position 4,325 according to SEQ ID NO:5, position 563 according to SEQ ID NO:11, or position 563 according to SEQ ID NO:17. In some embodiments, the isolated nucleic acid molecules hybridize to a portion of the ANGPTL7 nucleic acid molecule that includes a position corresponding to: position 4,336 according to SEQ ID NO:6, position 574 according to SEQ ID NO:12, or position 574 according to SEQ ID NO:18.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to ANGPTL7 variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to ANGPTL7 variant genomic nucleic acid molecules, ANGPTL7 variant mRNA molecules, and/or ANGPTL7 variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding an ANGPTL7 polypeptide, wherein the portion comprises a position corresponding to: position 4,291 according to SEQ ID NO:2, or the complement thereof; position 529 according to SEQ ID NO:8, or the complement thereof; or position 529 according to SEQ ID NO:14, or the complement thereof. In some embodiments, the alteration-specific probe or alteration-specific primer comprises a nucleotide sequence which is complementary to a portion of a nucleotide sequence comprising positions corresponding to: positions 4,291 to 4,293 according to SEQ ID NO:2, or the complement thereof; positions 529 to 531 according to SEQ ID NO:8, or the complement thereof; and/or positions 529 to 531 according to SEQ ID NO:14, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding an ANGPTL7 polypeptide, wherein the portion comprises a position corresponding to: position 4,287 according to SEQ ID NO:3, or the complement thereof; position 525 according to SEQ ID NO:9, or the complement thereof; or position 525 according to SEQ ID NO:15, or the complement thereof. In some embodiments, the alteration-specific probe or alteration-specific primer comprises a nucleotide sequence which is complementary to a portion of a nucleotide sequence comprising positions corresponding to: positions 4,285 to 4,287 according to SEQ ID NO:3, or the complement thereof; positions 523 to 525 according to SEQ ID NO:9, or the complement thereof; and/or positions 523 to 525 according to SEQ ID NO:15, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding an ANGPTL7 polypeptide, wherein the portion comprises a position corresponding to: position 4,243 according to SEQ ID NO:4, or the complement thereof; position 481 according to SEQ ID NO:10, or the complement thereof; or position 481 according to SEQ ID NO:16, or the complement thereof. In some embodiments, the alteration-specific probe or alteration-specific primer comprises a nucleotide sequence which is complementary to a portion of a nucleotide sequence comprising positions corresponding to: positions 4,243 to 4,245 according to SEQ ID NO:4, or the complement thereof; positions 481 to 483 according to SEQ ID NO:10, or the complement thereof; and/or positions 481 to 483 according to SEQ ID NO:16, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding an ANGPTL7 polypeptide, wherein the portion comprises a position corresponding to: position 4,325 according to SEQ ID NO:5, or the complement thereof; position 563 according to SEQ ID NO:11, or the complement thereof; or position 563 according to SEQ ID NO:17, or the complement thereof. In some embodiments, the alteration-specific probe or alteration-specific primer comprises a nucleotide sequence which is complementary to a portion of a nucleotide sequence comprising positions corresponding to: positions 4,324 to 4,326 according to SEQ ID NO:5, or the complement thereof; positions 562 to 564 according to SEQ ID NO:11, or the complement thereof; and/or positions 562 to 564 according to SEQ ID NO:17, or the complement thereof.

In some embodiments, the isolated alteration-specific probes or alteration-specific primers comprise at least about 15 nucleotides, wherein the alteration-specific probe or alteration-specific primer comprises a nucleotide sequence which is complementary to a portion of a nucleotide sequence encoding an ANGPTL7 polypeptide, wherein the portion comprises a position corresponding to: position 4,336 according to SEQ ID NO:6, or the complement thereof; position 574 according to SEQ ID NO:12, or the complement thereof; or position 574 according to SEQ ID NO:18, or the complement thereof. In some embodiments, the alteration-specific probe or alteration-specific primer comprises a nucleotide sequence which is complementary to a portion of a nucleotide sequence comprising positions corresponding to: positions 4,336 to 4,338 according to SEQ ID NO:6, or the complement thereof; positions 574 to 576 according to SEQ ID NO:12, or the complement thereof; and/or positions 574 to 576 according to SEQ ID NO:18, or the complement thereof.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the ANGPTL7 variant genomic nucleic acid molecules, ANGPTL7 variant mRNA molecules, and/or ANGPTL7 variant cDNA molecules disclosed herein. The primers described herein can be used to amplify the ANGPTL7 variant genomic nucleic acid molecules, ANGPTL7 variant mRNA molecules, or ANGPTL7 variant cDNA molecules, or a fragment thereof.

The present disclosure also provides pairs of primers comprising any of the primers described above. For example, if one of the primers' 3'-ends hybridizes to a cytosine at a position corresponding to position 4,291 according to SEQ ID NO:1 (rather than a thymine) in a particular ANGPTL7 nucleic acid molecule, then the presence of the amplified fragment would indicate the presence of an ANGPTL7 reference genomic nucleic acid molecule. Conversely, if one of the primers' 3'-ends hybridizes to a thymine at a position corresponding to position 4,291 according to SEQ ID NO:2 (rather than a cytosine) in a particular ANGPTL7 nucleic acid molecule, then the presence of the amplified fragment would indicate the presence of the ANGPTL7 variant genomic nucleic acid molecule. In some embodiments, the nucleotide of the primer complementary to the thymine at a position corresponding to position 4,291 according to SEQ ID NO:2 can be at the 3' end of the primer. In addition, if one of the primers' 3'-ends hybridizes to a cytosine at a position corresponding to position 529 according to SEQ ID NO:7 (rather than a uracil) in a particular ANGPTL7 nucleic acid molecule, then the presence of the amplified fragment would indicate the presence of an ANGPTL7 reference mRNA molecule. Conversely, if one of the primers' 3'-ends hybridizes to a uracil at a position corresponding to position 529 according to SEQ ID NO:8 (rather than a cytosine) in a particular ANGPTL7 mRNA molecule, then the presence of the amplified fragment would indicate the presence of the ANGPTL7 variant mRNA molecule. In some embodiments, the nucleotide of the primer complementary to the uracil at a position corresponding to position 529 according to SEQ ID NO:8 can be at the 3' end of the primer. In addition, if one of the primers' 3'-ends hybridizes to a cytosine at a position corresponding to position 529 according to SEQ ID NO:13 (rather than a thymine) in a particular ANGPTL7 nucleic acid molecule, then the presence of the amplified fragment would indicate the presence of an ANGPTL7 reference cDNA molecule. Conversely, if one of the primers' 3'-ends hybridizes to a thymine at a position corresponding to position 529 according to SEQ ID NO:14 (rather than a cytosine) in a particular ANGPTL7 cDNA molecule, then the presence of the amplified fragment would indicate the presence of the ANGPTL7 variant cDNA molecule. In some embodiments, the nucleotide of the primer complementary to the thymine at a position corresponding to position 529 according to SEQ ID NO:14 can be at the 3' end of the primer.

The present disclosure also provides pairs of primers comprising any of the primers described above. For example, if one of the primers' 3'-ends hybridizes to a guanine at a position corresponding to position 4,287 according to SEQ ID NO:1 (rather than a thymine) in a particular ANGPTL7 nucleic acid molecule, then the presence of the amplified fragment would indicate the presence of an ANGPTL7 reference genomic nucleic acid molecule. Conversely, if one of the primers' 3'-ends hybridizes to a thymine at a position corresponding to position 4,287 according to SEQ ID NO:3 (rather than a guanine) in a particular ANGPTL7 nucleic acid molecule, then the presence of the amplified fragment would indicate the presence of the ANGPTL7 variant genomic nucleic acid molecule. In some embodiments, the nucleotide of the primer complementary to the thymine at a position corresponding to position 4,287 according to SEQ ID NO:3 can be at the 3' end of the primer. In addition, if one of the primers' 3'-ends hybridizes to a guanine at a position corresponding to position 525 according to SEQ ID NO:7 (rather than a uracil) in a particular ANGPTL7 nucleic acid molecule, then the presence of the amplified fragment would indicate the presence of an ANGPTL7 reference mRNA molecule. Conversely, if one of the primers' 3'-ends hybridizes to a uracil at a position corresponding to position 525 according to SEQ ID NO:9 (rather than a guanine) in a particular ANGPTL7 mRNA molecule, then the presence of the amplified fragment would indicate the presence of the ANGPTL7 variant mRNA molecule. In some embodiments, the nucleotide of the primer complementary to the uracil at a position corresponding to position 525 according to SEQ ID NO:9 can be at the 3' end of the primer. In addition, if one of the primers' 3'-ends hybridizes to a guanine at a position corresponding to position 525 according to SEQ ID NO:13 (rather than a thymine) in a particular ANGPTL7 nucleic acid molecule, then the presence of the amplified fragment would indicate the presence of an ANGPTL7 reference cDNA molecule. Conversely, if one of the primers' 3'-ends hybridizes to a thymine at a position corresponding to position 525 according to SEQ ID NO:15 (rather than a guanine) in a particular ANGPTL7 cDNA molecule, then the presence of the amplified fragment would indicate the presence of the ANGPTL7 variant cDNA molecule. In some embodiments, the nucleotide of the primer complementary to the thymine at a position corresponding to position 525 according to SEQ ID NO:15 can be at the 3' end of the primer.

The present disclosure also provides pairs of primers comprising any of the primers described above. For example, if one of the primers' 3'-ends hybridizes to a thymine at a position corresponding to position 4,243 according to SEQ ID NO:1 (rather than an adenine) in a particular ANGPTL7 nucleic acid molecule, then the presence of the amplified fragment would indicate the presence of an ANGPTL7 reference genomic nucleic acid molecule.

Conversely, if one of the primers' 3'-ends hybridizes to an adenine at a position corresponding to position 4,243 according to SEQ ID NO:4 (rather than a thymine) in a particular ANGPTL7 nucleic acid molecule, then the presence of the amplified fragment would indicate the presence of the ANGPTL7 variant genomic nucleic acid molecule. In some embodiments, the nucleotide of the primer complementary to the adenine at a position corresponding to position 4,243 according to SEQ ID NO:4 can be at the 3' end of the primer. In addition, if one of the primers' 3'-ends hybridizes to a uracil at a position corresponding to position 481 according to SEQ ID NO:7 (rather than an adenine) in a particular ANGPTL7 nucleic acid molecule, then the presence of the amplified fragment would indicate the presence of an ANGPTL7 reference mRNA molecule. Conversely, if one of the primers' 3'-ends hybridizes to an adenine at a position corresponding to position 481 according to SEQ ID NO:10 (rather than a uracil) in a particular ANGPTL7 mRNA molecule, then the presence of the amplified fragment would indicate the presence of the ANGPTL7 variant mRNA molecule. In some embodiments, the nucleotide of the primer complementary to the adenine at a position corresponding to position 481 according to SEQ ID NO:10 can be at the 3' end of the primer. In addition, if one of the primers' 3'-ends hybridizes to a thymine at a position corresponding to position 481 according to SEQ ID NO:13 (rather than an adenine) in a particular ANGPTL7 nucleic acid molecule, then the presence of the amplified fragment would indicate the presence of an ANGPTL7 reference cDNA molecule. Conversely, if one of the primers' 3'-ends hybridizes to an adenine at a position corresponding to position 481 according to SEQ ID NO:16 (rather than a thymine) in a particular ANGPTL7 cDNA molecule, then the presence of the amplified fragment would indicate the presence of the ANGPTL7 variant cDNA molecule. In some embodiments, the nucleotide of the primer complementary to the adenine at a position corresponding to position 481 according to SEQ ID NO:16 can be at the 3' end of the primer.

The present disclosure also provides pairs of primers comprising any of the primers described above. For example, if one of the primers' 3'-ends hybridizes to a guanine at a position corresponding to position 4,325 according to SEQ ID NO:1 (rather than an adenine) in a particular ANGPTL7 nucleic acid molecule, then the presence of the amplified fragment would indicate the presence of an ANGPTL7 reference genomic nucleic acid molecule. Conversely, if one of the primers' 3'-ends hybridizes to an adenine at a position corresponding to position 4,325 according to SEQ ID NO:5 (rather than a guanine) in a particular ANGPTL7 nucleic acid molecule, then the presence of the amplified fragment would indicate the presence of the ANGPTL7 variant genomic nucleic acid molecule. In some embodiments, the nucleotide of the primer complementary to the adenine at a position corresponding to position 4,325 according to SEQ ID NO:5 can be at the 3' end of the primer. In addition, if one of the primers' 3'-ends hybridizes to a guanine at a position corresponding to position 563 according to SEQ ID NO:7 (rather than an adenine) in a particular ANGPTL7 nucleic acid molecule, then the presence of the amplified fragment would indicate the presence of an ANGPTL7 reference mRNA molecule. Conversely, if one of the primers' 3'-ends hybridizes to an adenine at a position corresponding to position 563 according to SEQ ID NO:11 (rather than a guanine) in a particular ANGPTL7 mRNA molecule, then the presence of the amplified fragment would indicate the presence of the ANGPTL7 variant mRNA molecule. In some embodiments, the nucleotide of the primer complementary to the adenine at a position corresponding to position 563 according to SEQ ID NO:11 can be at the 3' end of the primer. In addition, if one of the primers' 3'-ends hybridizes to a guanine at a position corresponding to position 563 according to SEQ ID NO:13 (rather than an adenine) in a particular ANGPTL7 nucleic acid molecule, then the presence of the amplified fragment would indicate the presence of an ANGPTL7 reference cDNA molecule. Conversely, if one of the primers' 3'-ends hybridizes to an adenine at a position corresponding to position 563 according to SEQ ID NO:17 (rather than a guanine) in a particular ANGPTL7 cDNA molecule, then the presence of the amplified fragment would indicate the presence of the ANGPTL7 variant cDNA molecule. In some embodiments, the nucleotide of the primer complementary to the adenine at a position corresponding to position 563 according to SEQ ID NO:17 can be at the 3' end of the primer.

The present disclosure also provides pairs of primers comprising any of the primers described above. For example, if one of the primers' 3'-ends hybridizes to an adenine at a position corresponding to position 4,336 according to SEQ ID NO:1 (rather than a cytosine) in a particular ANGPTL7 nucleic acid molecule, then the presence of the amplified fragment would indicate the presence of an ANGPTL7 reference genomic nucleic acid molecule. Conversely, if one of the primers' 3'-ends hybridizes to a cytosine at a position corresponding to position 4,336 according to SEQ ID NO:6 (rather than an adenine) in a particular ANGPTL7 nucleic acid molecule, then the presence of the amplified fragment would indicate the presence of the ANGPTL7 variant genomic nucleic acid molecule. In some embodiments, the nucleotide of the primer complementary to the cytosine at a position corresponding to position 4,336 according to SEQ ID NO:6 can be at the 3' end of the primer. In addition, if one of the primers' 3'-ends hybridizes to an adenine at a position corresponding to position 574 according to SEQ ID NO:7 (rather than a cytosine) in a particular ANGPTL7 nucleic acid molecule, then the presence of the amplified fragment would indicate the presence of an ANGPTL7 reference mRNA molecule. Conversely, if one of the primers' 3'-ends hybridizes to a cytosine at a position corresponding to position 574 according to SEQ ID NO:12 (rather than an adenine) in a particular ANGPTL7 mRNA molecule, then the presence of the amplified fragment would indicate the presence of the ANGPTL7 variant mRNA molecule. In some embodiments, the nucleotide of the primer complementary to the cytosine at a position corresponding to position 574 according to SEQ ID NO:12 can be at the 3' end of the primer. In addition, if one of the primers' 3'-ends hybridizes to an adenine at a position corresponding to position 574 according to SEQ ID NO:13 (rather than a cytosine) in a particular ANGPTL7 nucleic acid molecule, then the presence of the amplified fragment would indicate the presence of an ANGPTL7 reference cDNA molecule. Conversely, if one of the primers' 3'-ends hybridizes to a cytosine at a position corresponding to position 574 according to SEQ ID NO:18 (rather than an adenine) in a particular ANGPTL7 cDNA molecule, then the presence of the amplified fragment would indicate the presence of the ANGPTL7 variant cDNA molecule. In some embodiments, the nucleotide of the primer complementary to the cytosine at a position corresponding to position 574 according to SEQ ID NO:18 can be at the 3' end of the primer.

In the context of the present disclosure "specifically hybridizes" means that the probe or primer (such as, for example, the alteration-specific probe or alteration-specific primer) does not hybridize to a nucleic acid sequence encoding an ANGPTL7 reference genomic nucleic acid molecule, an ANGPTL7 reference mRNA molecule, and/or an ANGPTL7 reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of an ANGPTL7 reference genomic nucleic acid molecule is set forth in SEQ ID NO:1. Referring to SEQ ID NO:1, position 4,291 is a cytosine. Referring to SEQ ID NO:1, position 4,287 is a guanine. Referring to SEQ ID NO:1, position 4,243 is a thymine. Referring to SEQ ID NO:1, position 4,325 is a guanine. Referring to SEQ ID NO:1, position 4,336 is an adenine.

A variant genomic nucleic acid molecule of ANGPTL7 exists, wherein the cytosine at position 4,291 is replaced with a thymine. The nucleotide sequence of this ANGPTL7 variant genomic nucleic acid molecule is set forth in SEQ ID NO:2.

Another variant genomic nucleic acid molecule of ANGPTL7 exists, wherein the guanine at position 4,287 is replaced with a thymine. The nucleotide sequence of this ANGPTL7 variant genomic nucleic acid molecule is set forth in SEQ ID NO:3.

Another variant genomic nucleic acid molecule of ANGPTL7 exists, wherein the thymine at position 4,243 is replaced with an adenine. The nucleotide sequence of this ANGPTL7 variant genomic nucleic acid molecule is set forth in SEQ ID NO:4.

Another variant genomic nucleic acid molecule of ANGPTL7 exists, wherein the guanine at position 4,325 is replaced with an adenine. The nucleotide sequence of this ANGPTL7 variant genomic nucleic acid molecule is set forth in SEQ ID NO:5.

Another variant genomic nucleic acid molecule of ANGPTL7 exists, wherein the adenine at position 4,336 is replaced with a cytosine. The nucleotide sequence of this ANGPTL7 variant genomic nucleic acid molecule is set forth in SEQ ID NO:6.

The nucleotide sequence of an ANGPTL7 reference mRNA molecule is set forth in SEQ ID NO:7. Referring to SEQ ID NO:7, position 529 is a cytosine. Referring to SEQ ID NO:7, position 525 is a guanine. Referring to SEQ ID NO:7, position 481 is a uracil. Referring to SEQ ID NO:7, position 563 is a guanine. Referring to SEQ ID NO:7, position 574 is an adenine.

A variant mRNA molecule of ANGPTL7 exists, wherein the cytosine at position 529 is replaced with a uracil. The nucleotide sequence of this ANGPTL7 variant mRNA molecule is set forth in SEQ ID NO:8.

Another variant mRNA molecule of ANGPTL7 exists, wherein the guanine at position 525 is replaced with a uracil. The nucleotide sequence of this ANGPTL7 variant mRNA molecule is set forth in SEQ ID NO:9.

Another variant mRNA molecule of ANGPTL7 exists, wherein the uracil at position 481 is replaced with an adenine. The nucleotide sequence of this ANGPTL7 variant mRNA molecule is set forth in SEQ ID NO:10.

Another variant mRNA molecule of ANGPTL7 exists, wherein the guanine at position 563 is replaced with an adenine. The nucleotide sequence of this ANGPTL7 variant mRNA molecule is set forth in SEQ ID NO:11.

Another variant mRNA molecule of ANGPTL7 exists, wherein the adenine at position 574 is replaced with a cytosine. The nucleotide sequence of this ANGPTL7 variant mRNA molecule is set forth in SEQ ID NO:12.

The nucleotide sequence of an ANGPTL7 reference cDNA molecule is set forth in SEQ ID NO:13. Referring to SEQ ID NO:13, position 529 is a cytosine. Referring to SEQ ID NO:13, position 525 is a guanine. Referring to SEQ ID NO:13, position 481 is a thymine. Referring to SEQ ID NO:13, position 563 is a guanine. Referring to SEQ ID NO:13, position 574 is an adenine. Referring to SEQ ID NO:13, position 574 is an adenine.

A variant cDNA molecule of ANGPTL7 exists, wherein the cytosine at position 529 is replaced with a thymine. The nucleotide sequence of this ANGPTL7 variant cDNA molecule is set forth in SEQ ID NO:14.

Another variant cDNA molecule of ANGPTL7 exists, wherein the guanine at position 525 is replaced with a thymine. The nucleotide sequence of this ANGPTL7 variant cDNA molecule is set forth in SEQ ID NO:15.

Another variant cDNA molecule of ANGPTL7 exists, wherein the thymine at position 481 is replaced with an adenine. The nucleotide sequence of this ANGPTL7 variant cDNA molecule is set forth in SEQ ID NO:16.

Another variant cDNA molecule of ANGPTL7 exists, wherein the guanine at position 563 is replaced with an adenine. The nucleotide sequence of this ANGPTL7 variant cDNA molecule is set forth in SEQ ID NO:17.

Another variant cDNA molecule of ANGPTL7 exists, wherein the adenine at position 574 is replaced with a cytosine. The nucleotide sequence of this ANGPTL7 variant cDNA molecule is set forth in SEQ ID NO:18.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

Also provided herein are functional polynucleotides that can interact with the disclosed nucleic acid molecules. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, $-O(CH_2)_n-ONH_2$, and $-O(CH_2)_nON[(CH_2)_nCH_3)]_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

Desired regulatory sequences for mammalian host cell expression can include, for example, viral elements that direct high levels of polypeptide expression in mammalian cells, such as promoters and/or enhancers derived from retroviral LTRs, cytomegalovirus (CMV) (such as, for example, CMV promoter/enhancer), Simian Virus 40 (SV40) (such as, for example, SV40 promoter/enhancer), adenovirus, (such as, for example, the adenovirus major late promoter (AdMLP)), polyoma and strong mammalian promoters such as native immunoglobulin and actin promoters. Methods of expressing polypeptides in bacterial cells or fungal cells (such as, for example, yeast cells) are also well known. A promoter can be, for example, a constitutively active promoter, a conditional promoter, an inducible promoter, a temporally restricted promoter (such as, for example, a developmentally regulated promoter), or a spatially restricted promoter (such as, for example, a cell-specific or tissue-specific promoter).

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the isolated nucleic acid molecules, genomic nucleic acid molecules, mRNA molecules, and/or cDNA molecules disclosed herein. In some embodiments, the composition is a pharmaceutical composition. In some embodiments, the compositions comprise a carrier and/or excipient. Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence (such as, for example, SEQ ID NO:1, SEQ ID NO:7, or SEQ ID NO:13). In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide sequence is made with respect to the reference sequence to which it has been aligned.

For example, a nucleic acid molecule comprising a nucleotide sequence encoding an ANGPTL7 polypeptide, wherein the nucleotide sequence comprises a thymine at a position corresponding to position 4,291 according to SEQ ID NO:2 means that if the nucleotide sequence of the ANGPTL7 genomic nucleic acid molecule is aligned to the sequence of SEQ ID NO:2, the ANGPTL7 sequence has a thymine residue at the position that corresponds to position 4,291 of SEQ ID NO:2. The same applies for mRNA molecules comprising a nucleotide sequence encoding an ANGPTL7 polypeptide, wherein the nucleotide sequence comprises a uracil at a position corresponding to position 529 according to SEQ ID NO:8, and cDNA molecules comprising a nucleotide sequence encoding an ANGPTL7 polypeptide, wherein the nucleotide sequence comprises a thymine at a position corresponding to position 529 according to SEQ ID NO:14. In other words, these phrases refer to a nucleic acid molecule encoding an ANGPTL7 polypeptide, wherein the genomic nucleic acid molecule has a nucleotide sequence that comprises a thymine residue that is homologous to the thymine residue at position 4,291 of SEQ ID NO:2 (or wherein the mRNA molecule has a nucleotide sequence that comprises a uracil residue that is homologous to the uracil residue at position 529 of SEQ ID NO:8, or wherein the cDNA molecule has a nucleotide sequence that comprises a thymine residue that is homologous to the thymine residue at position 529 of SEQ ID NO:14). Herein, the polypeptide produced from such nucleic acid molecules is referred to herein as "Arg177STOP."

As described herein, a position within an ANGPTL7 genomic nucleic acid molecule that corresponds to position 4,291 according to SEQ ID NO:2, for example, can be identified by performing a sequence alignment between the nucleotide sequence of a particular ANGPTL7 nucleic acid molecule and the nucleotide sequence of SEQ ID NO:2. A variety of computational algorithms exist that can be used for performing a sequence alignment to identify a nucleotide position that corresponds to, for example, position 4,291 in SEQ ID NO:2. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

The amino acid sequence of an ANGPTL7 reference polypeptide is set forth in SEQ ID NO:19. Referring to SEQ ID NO:19, the ANGPTL7 reference polypeptide is 346 amino acids in length. Referring to SEQ ID NO:19, position 175 is a glutamine. Referring to SEQ ID NO:19, position 177 is an arginine. Referring to SEQ ID NO:19, position 161 is a phenylalanine. Referring to SEQ ID NO:19, position 188 is a tryptophan. Referring to SEQ ID NO:19, position 192 is a lysine.

A variant polypeptide of ANGPTL7 exists (Arg177STOP), the amino acid sequence of which is set forth in SEQ ID NO:20. Referring to SEQ ID NO:20, the ANGPTL7 variant polypeptide terminates at position 176. Thus, this variant is 176 amino acids in length. Referring to SEQ ID NO:20, the ANGPTL7 variant polypeptide does not contain amino acids at positions corresponding to positions 177 to 346 of SEQ ID NO:19.

Another variant polypeptide of ANGPTL7 exists (Gln175His), the amino acid sequence of which is set forth in SEQ ID NO:21. Referring to SEQ ID NO:21, the ANGPTL7 variant polypeptide is 346 amino acids in length. Referring to SEQ ID NO:21, position 175 is a histidine.

Another variant polypeptide of ANGPTL7 exists (Phe161Ile), the amino acid sequence of which is set forth in SEQ ID NO:22. Referring to SEQ ID NO:22, the ANGPTL7 variant polypeptide is 346 amino acids in length. Referring to SEQ ID NO:22, position 161 is an isoleucine.

A variant polypeptide of ANGPTL7 exists (Trp188STOP), the amino acid sequence of which is set forth in SEQ ID NO:23. Referring to SEQ ID NO:23, the ANGPTL7 variant polypeptide terminates at position 187. Thus, this variant is 187 amino acids in length. Referring to SEQ ID NO:23, the ANGPTL7 variant polypeptide does not contain amino acids at positions corresponding to positions 188 to 346 of SEQ ID NO:19.

Another variant polypeptide of ANGPTL7 exists (Lys192Gln), the amino acid sequence of which is set forth in SEQ ID NO:24. Referring to SEQ ID NO:24, the ANGPTL7 variant polypeptide is 346 amino acids in length. Referring to SEQ ID NO:24, position 192 is a glutamine.

The present disclosure also provides combinations of a glucocorticoid and an ANGPTL7 inhibitor for use in the treatment of inflammation. The present disclosure also provides combinations of a glucocorticoid and an ANGPTL7 inhibitor for use in the preparation of a medicament for treating inflammation. In any of the embodiments described herein, the subject is identified as having any of the ANGPTL7 variant nucleic acid molecules and/or polypeptides described herein. The glucocorticoid can be any of the glucocorticoids described herein. The ANGPTL7 inhibitors can be any of the ANGPTL7 inhibitors described herein. The combinations of a glucocorticoid and an ANGPTL7 inhibitor can be used to treat or prevent a glucocorticoid-induced ophthalmic condition in a subject who is undergoing or will be undergoing glucocorticoid treatment, such as for inflammation.

The present disclosure also provides ANGPTL7 inhibitors for use in decreasing or preventing a glucocorticoid-induced ophthalmic condition in a subject undergoing glucocorticoid treatment. The present disclosure also provides ANGPTL7 inhibitors for use in the preparation of a medicament for decreasing or preventing a glucocorticoid-induced ophthalmic condition in a subject undergoing glucocorticoid treatment. In any of the embodiments described herein, the subject is identified as having any of the ANGPTL7 variant nucleic acid molecules and/or polypeptides described herein. The glucocorticoid treatment can be treatment with any of the glucocorticoids described herein. The ANGPTL7 inhibitors can be any of the ANGPTL7 inhibitors described herein. The glucocorticoid-induced ophthalmic condition can be any of the glucocorticoid-induced ophthalmic conditions described herein.

In any of the embodiments described herein, the subject is identified as having a genomic nucleic acid molecule having a nucleotide sequence encoding an ANGPTL7 polypeptide, wherein the nucleotide sequence comprises: a thymine at a position corresponding to position 4,291 according to SEQ ID NO:2, or the complement thereof; a thymine at a position corresponding to position 4,287 according to SEQ ID NO:3, or the complement thereof; an adenine at a position corresponding to position 4,243 according to SEQ ID NO:4, or the complement thereof; an adenine at a position corresponding to position 4,325 according to SEQ ID NO:5, or the complement thereof; or a cytosine at a position corresponding to position 4,336 according to SEQ ID NO:6, or the complement thereof. In any of the embodiments described herein, the subject is identified as having an mRNA molecule having a nucleotide sequence encoding an ANGPTL7 polypeptide, wherein the nucleotide sequence comprises: a uracil at a position corresponding to position 529 according to SEQ ID NO:8, or the complement thereof; a uracil at a position corresponding to position 525 according to SEQ ID NO:9, or the complement thereof; an adenine at a position corresponding to position 481 according to SEQ ID NO:10, or the complement thereof; an adenine at a position corresponding to position 563 according to SEQ ID NO:11, or the complement thereof; or a cytosine at a position corresponding to position 574 according to SEQ ID NO:12, or the complement thereof. In any of the embodiments described herein, the subject is identified as having a cDNA molecule having a nucleotide sequence encoding an ANGPTL7 polypeptide, wherein the nucleotide sequence comprises: a thymine at a position corresponding to position 529 according to SEQ ID NO:14, or the complement thereof; a thymine at a position corresponding to position 525 according to SEQ ID NO:15, or the complement thereof; an adenine at a position corresponding to position 481 according to SEQ ID NO:16, or the complement thereof; an adenine at a position corresponding to position 563 according to SEQ ID NO:17, or the complement thereof; or a cytosine at a position corresponding to position 574 according to SEQ ID NO:18, or the complement thereof.

In some embodiments, the subject can have inflammation. In some embodiments, the inflammation can be acute inflammation or chronic inflammation. In some embodiments, the inflammation is acute inflammation. In some embodiments, the inflammation is chronic inflammation. In some embodiments, the inflammation is associated with rheumatoid arthritis, associated with Grave's disease, or is ophthalmic inflammation. In some embodiments, the inflammation is associated with rheumatoid arthritis. In some embodiments, the inflammation is associated with Grave's disease. In some embodiments, the inflammation is ophthalmic inflammation. In some embodiments, the ophthalmic inflammation is chosen from uveitis, juvenile idiopathic arthritis uveitis, scleritis, blepharitis, conjunctivitis, iritis, and episcleritis, or any combination thereof. In some embodiments, the ophthalmic inflammation is uveitis. In some embodiments, the ophthalmic inflammation is juvenile idiopathic arthritis uveitis. In some embodiments, the ophthalmic inflammation is scleritis. In some embodiments, the ophthalmic inflammation is blepharitis. In some embodiments, the ophthalmic inflammation is conjunctivitis. In some embodiments, the ophthalmic inflammation is iritis. In some embodiments, the ophthalmic inflammation is episcleritis.

In some embodiments, the glucocorticoid-induced ophthalmic condition is chosen from ocular hypertension, increased intraocular pressure (IOP), pre-glaucoma, glaucoma, decreased corneal hysteresis, and posterior subcapsular cataracts, or any combination thereof. In some embodiments, the glucocorticoid-induced ophthalmic condition is ocular hypertension. In some embodiments, the glucocorticoid-induced ophthalmic condition is increased IOP. In some embodiments, the glucocorticoid-induced ophthalmic condition is pre-glaucoma. In some embodiments, the glucocorticoid-induced ophthalmic condition is glaucoma. In some embodiments, the glucocorticoid-induced ophthalmic condition is decreased corneal hysteresis. In some embodiments, the glucocorticoid-induced ophthalmic condition is posterior subcapsular cataracts.

In some embodiments, the glucocorticoid treatment is treatment with prednisone, prednisolone, methylprednisolone, dexamethasone, betamethasone, triamcinolone, beclometasone, fludrocortisone acetate, DOCA, aldosterone, budesonide, mometasone furoate, fluticasone propionate, hydrocortisone, cortisone acetate, or fluticasone furoate, difluprednate ophthalmic, fluorometholone, loteprednol etabonate, medrysone, rimexolone, fluocinolone acetonide, clobetasol, halobetasol, diflorasone, fluocinonide, flurandrenolide, Neo-Poly-Dex, tobramycin-dexamethasone, difluprednate, or any combination thereof. In some embodiments, the glucocorticoid treatment is treatment with prednisone. In some embodiments, the glucocorticoid treatment is treatment with prednisolone. In some embodiments, the glucocorticoid treatment is treatment with methylprednisolone. In some embodiments, the glucocorticoid treatment is treatment with dexamethasone. In some embodiments, the glucocorticoid treatment is treatment with betamethasone. In some embodiments, the glucocorticoid treatment is treatment with triamcinolone. In some embodiments, the glucocorticoid treatment is treatment with beclomethasone. In some embodiments, the glucocorticoid treatment is treatment with fludrocortisone acetate. In some embodiments, the glucocorticoid treatment is treatment with DOCA. In some embodiments, the glucocorticoid treatment is treatment with aldosterone. In some embodiments, the glucocorticoid treatment is treatment with budesonide. In some embodiments, the glucocorticoid treatment is treatment with mometasone furoate. In some embodiments, the glucocorticoid treatment is treatment with fluticasone propionate. In some embodiments, the glucocorticoid treatment is treatment with hydrocortisone. In some embodiments, the glucocorticoid treatment is treatment with cortisone acetate. In some embodiments, the glucocorticoid treatment is treatment with fluticasone furoate. In some embodiments, the glucocorticoid treatment is treatment with difluprednate ophthalmic. In some embodiments, the glucocorticoid treatment is treatment with fluorometholone. In some embodiments, the glucocorticoid treatment is treatment with loteprednol etabonate. In some embodiments, the glucocorticoid treatment is treatment with medrysone. In some embodiments, the glucocorticoid treatment is treatment with rimexolone. In some embodiments, the glucocorticoid treatment is treatment with fluocinolone acetonide. In some embodiments, the glucocorticoid treatment is treatment with clobetasol. In some embodiments, the glucocorticoid treatment is treatment with halobetasol. In some embodiments, the glucocorticoid treatment is treatment with diflorasone. In some embodiments, the glucocorticoid treatment is treatment with fluocinonide. In some embodiments, the glucocorticoid treatment is treatment with flurandrenolide. In some embodiments, the glucocorticoid treatment is treatment with Neo-Poly-Dex. In some embodiments, the glucocorticoid treatment is treatment with tobramycin-dexamethasone. In some embodiments, the glucocorticoid treatment is treatment with difluprednate.

In some embodiments, the ANGPTL7 inhibitor comprises an inhibitory nucleic acid molecule. In some embodiments, the inhibitory nucleic acid molecule comprises an antisense nucleic acid molecule, an siRNA, or an shRNA that hybridizes to an ANGPTL7 nucleic acid molecule. In some embodiments, the inhibitory nucleic acid molecule comprises an antisense nucleic acid molecule. In some embodiments, the inhibitory nucleic acid molecule comprises an siRNA. In some embodiments, the inhibitory nucleic acid molecule comprises an shRNA.

In some embodiments, the ANGPTL7 inhibitor comprises a Cas protein and gRNA that hybridizes to a gRNA recognition sequence within an ANGPTL7 genomic nucleic acid molecule. In some embodiments, the Cas protein is Cas9 or Cpf1. In some embodiments, the gRNA recognition sequence includes or is proximate to a position corresponding to: position 4,291 according to SEQ ID NO:1, position 4,287 according to SEQ ID NO:1, position 4,243 according to SEQ ID NO:1, position 4,325 according to SEQ ID NO:1, or position 4,336 according to SEQ ID NO:1. In some embodiments, the gRNA recognition sequence is located from about 1000, from about 500, from about 400, from about 300, from about 200, from about 100, from about 50, from about 45, from about 40, from about 35, from about 30, from about 25, from about 20, from about 15, from about 10, or from about 5 nucleotides of a position corresponding to: position 4,291 according to SEQ ID NO:1, position 4,287 according to SEQ ID NO:1, position 4,243 according to SEQ ID NO:1, position 4,325 according to SEQ ID NO:1, or position 4,336 according to SEQ ID NO:1. In some embodiments, a PAM sequence is about 2 to about 6 nucleotides downstream of the gRNA recognition sequence. In some embodiments, the gRNA comprises from about 17 nucleotides to about 23 nucleotides. In some embodiments, the gRNA recognition sequence comprises a nucleotide sequence according to any one of SEQ ID NOs:25-165.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in °C. or is at ambient temperature, and pressure is at or near atmospheric.

EXAMPLES

Example 1: ANGPTL7 KO Mice Inhibit DEX-Ac-Induced Ocular Hypertension in Mice

Weekly periocular CF injections of DEX-Ac in both eyes in ANGPTL7 WT mice significantly elevated IOP in (see, FIG. 1). IOP measurements of DEX-Ac-treated (n=18) versus vehicle-treated (n=6) mice show IOP elevation from week 1 to 6; $p<0.01$, *$p<0.001$, ****$p<0.0001$. In contrast, weekly periocular CF injections of DEX-Ac in both eyes in ANGPTL7 KO mice did not elevate IOP (see, FIG. 1). IOP measurements of DEX-Ac-treated (n=20) versus vehicle-treated (n=12) ANGPTL7 KO mice showed no effect in IOP elevation from week 1 to week 6.

Example 2: In Vivo Evaluation of ANGPTL7 siRNA in Wild-Type Mice dsRNA were assessed for their ability to reduce the level of ANGPTL7 RNAs and/or reduce IOP in vivo in wild-type mice.

Six different siRNAs targeting ANGPTL7 (siRNA #1-6; see below) were tested in C57BL/6J wild-type mice and IOP was monitored over time. C57BL/6J mice were each intravitreally injected with 15 μg of an siRNA or PBS control. Animals in the naïve group received no injection. Six weeks later, animals were sacrificed, eyes were collected, and limbal rings were carefully micro-dissected. qPCR was performed on limbal rings dissected from mouse eyes enriched for the travecular meshwork (TM) for ANGPTL7 expression. The data were expressed as percent message remaining relative to the baseline value, and presented as mean±standard error of the mean (SEM).

| Duplex # | sense strand sequence | antisense strand sequence |
|---|---|---|
| #1 | UUGGGCAAUGAACUGAACAGA (SEQ ID NO: 5559) | UCUGUUCAGUUCAUUGCCCAACG (SEQ ID NO: 5560) |
| #2 | GUACCAGAAGAACUACCGAAA (SEQ ID NO: 5535) | UUUCGGUAGUUCUUCUGGUACAG (SEQ ID NO: 5536) |
| #3 | AGACAGUAUAAGCAAGGGUUA (SEQ ID NO: 5555) | UAACCCUUGCUUAUACUGUCUCC (SEQ ID NO: 5556) |
| #4 | GCAGAAGCCUCAUAAACGCAA (SEQ ID NO: 5573) | UUGCGUUUAUGAGGCUUCUGCAG (SEQ ID NO: 5574) |
| #5 | ACACUUCCUUGUGUCUAUAGA (SEQ ID NO: 5533) | UCUAUAGACACAAGGAAGUGUCG (SEQ ID NO: 5534) |
| #6 | CUGCAGAAGCCUCAUAAACGA (SEQ ID NO: 5571) | UCGUUUAUGAGGCUUCUGCAGCC (SEQ ID NO: 5572) |

Figure 2:
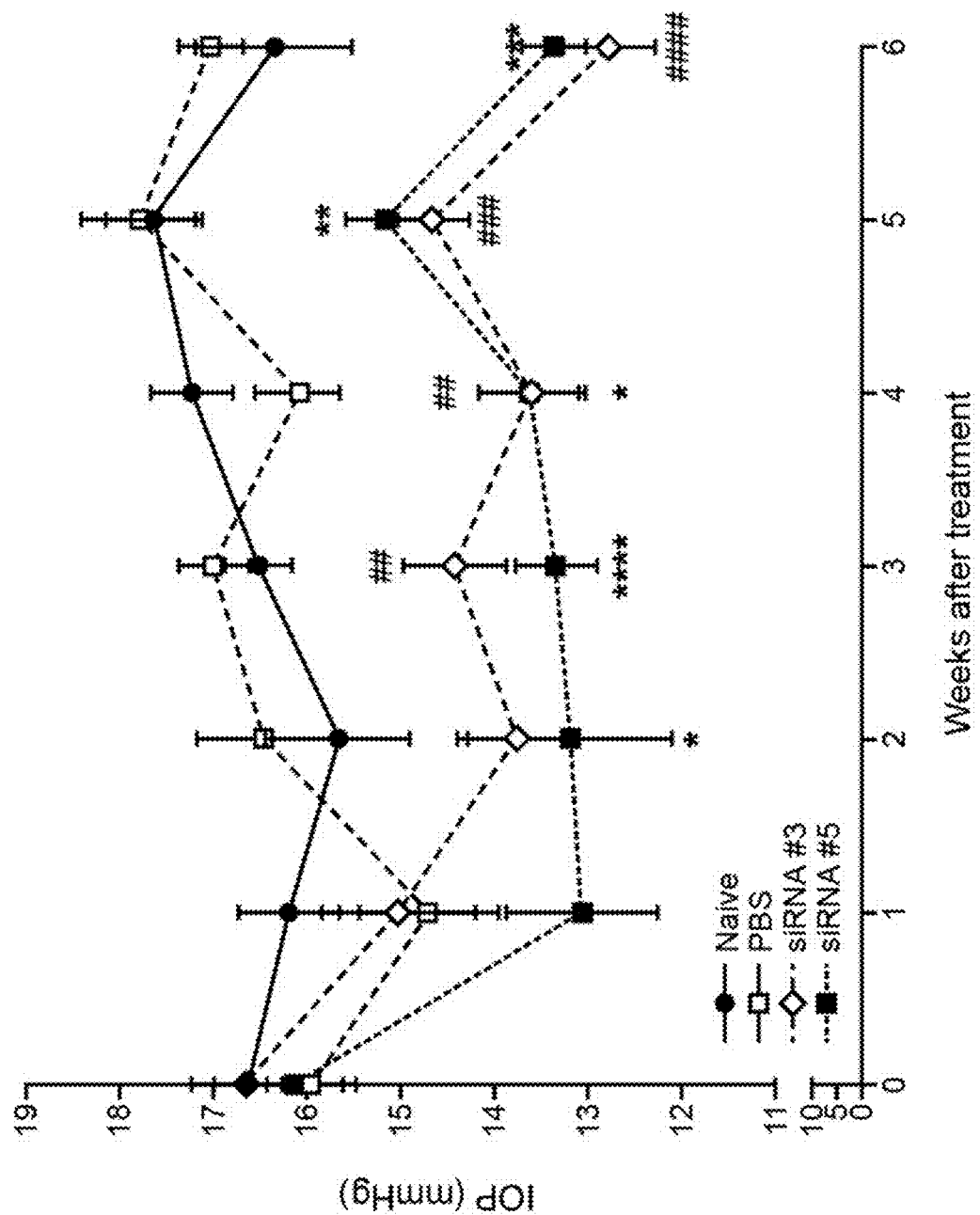
FIG. 2 depicts effect of ANGPTL7 siRNA on intraocular pressure (IOP) of wild-type mice. Intravitreal injection with 15 μg of ANGPTL7-siRNA significantly lowered IOP in two of six siRNAs tested (n=6-8/group) compared to the PBS-treated (n=6) and naïve (no injection, n=5) groups starting at week 2 and through the end of the study. Error bars represent standard error of the mean (SEM).
Figure 3:
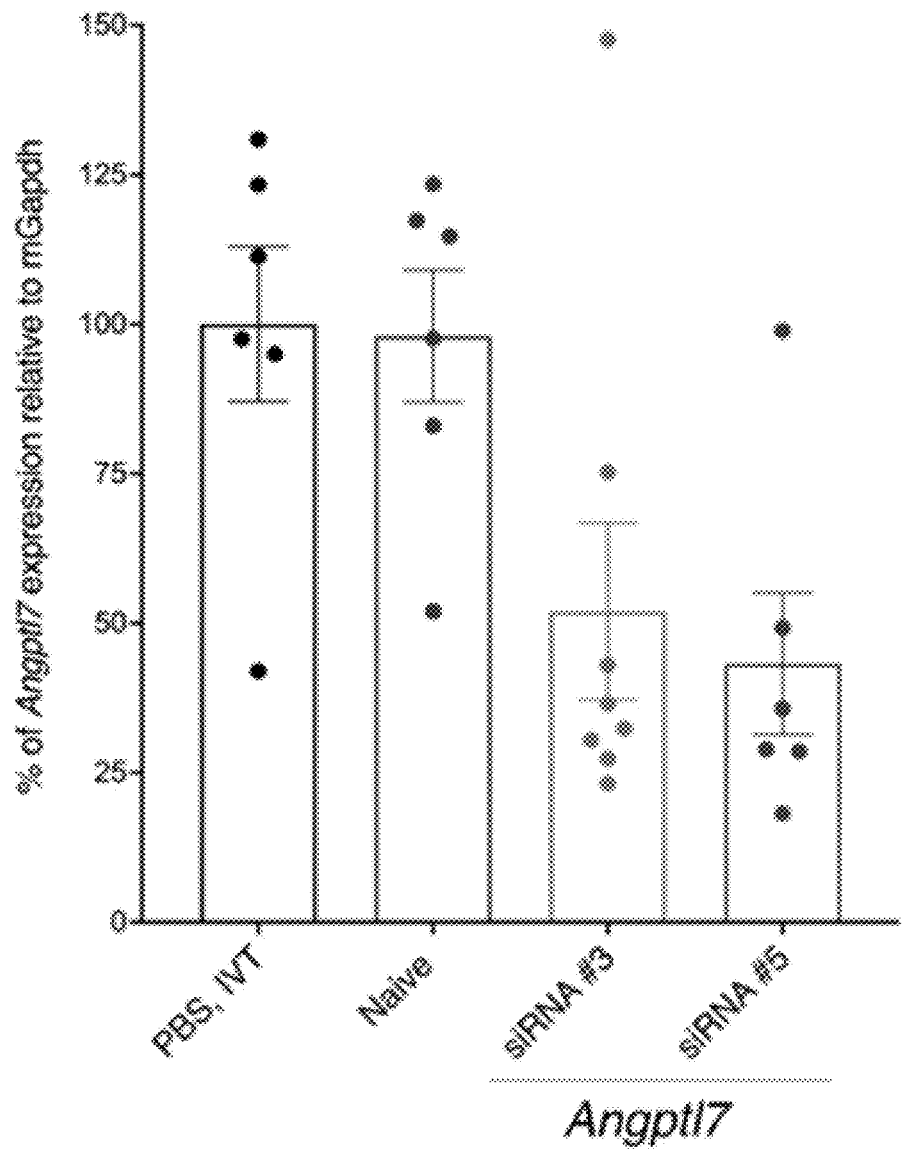
FIG. 3 depicts effect of ANGPTL7 siRNA on ANGPTL7 expression in the limbal ring of wild-type mice in vivo. qPCR results from micro-dissected limbal ring showed the highest level of knockdown (>50%) of ANGPTL7 mRNA with siRNAs #3 and #5 compared to PBS-treated or naïve (no injection) mice, which is consistent with the IOP lowering observed in mice injected with one of these two siRNAs (shown in FIG. 1). Error bars represent SEM.

The results of the in vivo evaluation are shown in FIGS. 2 and 3. As shown in FIG. 2, IOP was significantly lowered 2 weeks post-injection in mice treated with two of the six siRNAs (siRNA #3 and #5, n=6-8/group) compared to the PBS-treated (n=6) or naïve (no injection, n=5) groups. Naïve and PBS-treated animals maintained their IOPs at baseline for the duration of the study (weeks 0-6). In contrast, in mice treated with siRNA #3 and #5, IOP was lowered by 2-4 mmHg starting at week 2 compared to PBS-treated or naïve mice, and remained lowered through the end of the study (i.e., 6 weeks).

As shown in FIG. 3, in qPCR of the limbal ring tissue harvested at the end of the study (i.e., 6 weeks after the siRNA administration), the highest level of knockdown (>50%) of ANGPTL7 mRNA was observed with siRNAs #3 and #5 compared to PBS-treated or naïve mice. Such mRNA knockdown effect is consistent with the lowering of IOP observed in mice injected with one of these two siRNAs. The results suggest that inhibition of ANGPTL7 expression also lowers IOP, and demonstrate the ability of the exemplary dsRNA agents to reduce the ANGPTL7 expression and also lower IOP in vivo.

Figure 4:
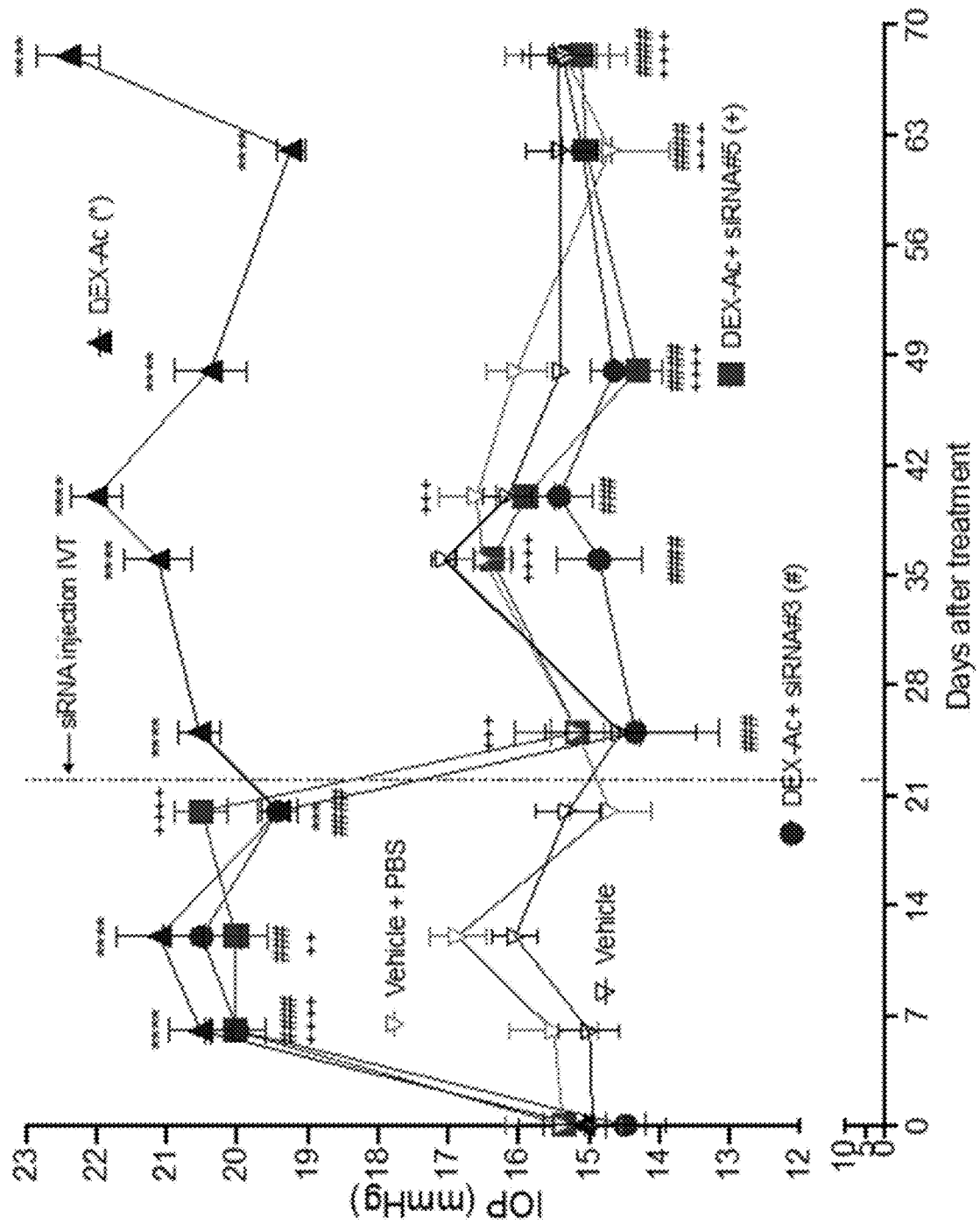
FIG. 4 depicts effect of ANGPTL7 siRNA on reducing dexamethasone-21-acetate (DEX-Ac)-induced ocular hypertension.

Example 3: In Vivo Knock Down of ANGPTL7 by siRNA in Wild Type Mice Inhibits Steroid-Induced and Other Types of TM-Stress Related IOP Elevation in Glaucoma dsRNA were further assessed for their ability to reduce steroid induced IOP in vivo in wild-type mice. Weekly periocular CF injections of DEX-Ac suspension to both eyes caused DEX-induced OHT with sustained and significantly elevated IOP in WT mice. Mice were divided into following groups as shown in FIG. 4: a) Vehicle (n=4), b) Vehicle+PBS (n=6), c) DEX-Ac (n=12), d) DEX-Ac+siRNA #3 (n=14), and e) DEX-Ac+siRNA #5 (n=14). IOP elevation was rapid and significantly higher in DEX-Ac-treated mice compared with vehicle-treated mice starting 6-days post-injection. DEX-Ac treated mice in group c developed DEX-induced OHT with sustained and significantly elevated IOP throughout the study. At Day 22, siRNA targeting ANGPTL7 (#3 and #5) were intravitreally injected into groups: d and e (DEX-Ac+siRNA #3 and DEX-Ac+siRNA #5) and IOP measurements continued to be recorded. In groups d and e, IOPs were significantly reduced and returned to baseline IOP within one week as compared with DEX-Ac treated group (c). The IOP remained at baseline throughout the study even though these mice continued to receive weekly DEX-Ac treatment.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

SEQUENCE LISTING

The patent contains a lengthy sequence listing. A copy of the sequence listing is available in electronic form from the USPTO web site (https://seqdata.uspto.gov/?pageRequest=docDetail&DocID=US11865134B2). An electronic copy of the sequence listing will also be available from the USPTO upon request and payment of the fee set forth in 37 CFR 1.19(b)(3).

What is claimed is:

1. A method of treating a subject having rheumatoid arthritis, Graves' disease, or ophthalmic inflammation, the method comprising administering an Angiopoietin-Like 7 (ANGPTL7) inhibitor and a glucocorticoid to the subject, wherein:
   the ANGPTL7 inhibitor is a double stranded ribonucleic acid (dsRNA) inhibitory nucleic acid molecule for inhibiting expression of ANGPTL7; and
   the dsRNA inhibitory nucleic acid molecule comprises a sense strand and an antisense strand forming a double stranded region; and
   the sense strand comprises a nucleotide sequence comprising AGACAGUAUAAGCAAGGGUUA (SEQ ID NO:5555) and wherein the antisense strand comprises a nucleotide sequence comprising UAACCCUUGCUUAUACUGUCUCC (SEQ ID NO:5556); and/or
   the sense strand comprises a nucleotide sequence comprising ACACUUCCUUGUGUCUAUAGA (SEQ ID NO:5533) and wherein the antisense strand comprises a nucleotide sequence comprising UCUAUAGACACAAGGAAGUGUCG (SEQ ID NO:5534).

2. A method of decreasing a glucocorticoid-induced ophthalmic condition in a subject treated with a glucocorticoid, the method comprising administering an Angiopoietin-Like 7 (ANGPTL7) inhibitor to the subject, wherein:
   the ANGPTL7 inhibitor is a double stranded ribonucleic acid (dsRNA) inhibitory nucleic acid molecule for inhibiting expression of ANGPTL7; and
   the dsRNA inhibitory nucleic acid molecule comprises a sense strand and an antisense strand forming a double stranded region; and
   the sense strand comprises a nucleotide sequence comprising AGACAGUAUAAGCAAGGGUUA (SEQ ID NO:5555) and wherein the antisense strand comprises a nucleotide sequence comprising UAACCCUUGCUUAUACUGUCUCC (SEQ ID NO:5556); and/or
   the sense strand comprises a nucleotide sequence comprising ACACUUCCUUGUGUCUAUAGA (SEQ ID NO:5533) and wherein the antisense strand comprises a nucleotide sequence comprising UCUAUAGACACAAGGAAGUGUCG (SEQ ID NO:5534).

3. A method of treating a subject having inflammation, rheumatoid arthritis, Graves' disease, or ophthalmic inflammation, and undergoing glucocorticoid treatment, the method comprising administering an Angiopoietin-Like 7 (ANGPTL7) inhibitor to the subject, wherein:
   the ANGPTL7 inhibitor is a double stranded ribonucleic acid (dsRNA) inhibitory nucleic acid molecule for inhibiting expression of ANGPTL7; and
   the dsRNA inhibitory nucleic acid molecule comprises a sense strand and an antisense strand forming a double stranded region; and
   the sense strand comprises a nucleotide sequence comprising AGACAGUAUAAGCAAGGGUUA (SEQ ID NO:5555) and wherein the antisense strand comprises a nucleotide sequence comprising UAACCCUUGCUUAUACUGUCUCC (SEQ ID NO:5556); and/or
   the sense strand comprises a nucleotide sequence comprising ACACUUCCUUGUGUCUAUAGA (SEQ ID NO:5533) and wherein the antisense strand comprises a nucleotide sequence comprising UCUAUAGACACAAGGAAGUGUCG (SEQ ID NO:5534).

\* \* \* \* \*